US010400220B2

(12) United States Patent
Wimmer et al.

(10) Patent No.: US 10,400,220 B2
(45) Date of Patent: Sep. 3, 2019

(54) ATTENUATED VIRUS HAVING MULTIPLE HOSTS

(71) Applicant: The Research Foundation for The State University of New York, Albany, NY (US)

(72) Inventors: Eckard Wimmer, East Setauket, NY (US); Steffen Mueller, Kings Point, NY (US); Bruce Futcher, Stony Brook, NY (US); Sam Shen, Iowa City, IA (US); Charles Stauft, Setauket, NY (US); Charles Ward, San Jose, CA (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 15/508,695

(22) PCT Filed: Sep. 8, 2015

(86) PCT No.: PCT/US2015/048985
§ 371 (c)(1),
(2) Date: Mar. 3, 2017

(87) PCT Pub. No.: WO2016/037187
PCT Pub. Date: Mar. 10, 2016

(65) Prior Publication Data

US 2019/0002837 A1 Jan. 3, 2019

Related U.S. Application Data

(60) Provisional application No. 62/050,638, filed on Sep. 15, 2014, provisional application No. 62/046,565, filed on Sep. 5, 2014.

(51) Int. Cl.

| | |
|---|---|
| ***C12N 7/00*** | (2006.01) |
| ***A61K 39/12*** | (2006.01) |
| ***C12N 7/04*** | (2006.01) |
| *A61K 39/00* | (2006.01) |

(52) U.S. Cl.

CPC ................ *C12N 7/00* (2013.01); *A61K 39/12* (2013.01); *C12N 7/04* (2013.01); *A61K 2039/5254* (2013.01); *C12N 2760/12221* (2013.01); *C12N 2760/12233* (2013.01); *C12N 2760/12234* (2013.01); *C12N 2760/12262* (2013.01); *C12N 2760/20062* (2013.01); *C12N 2770/24121* (2013.01); *C12N 2770/24122* (2013.01); *C12N 2770/24134* (2013.01); *C12N 2770/24162* (2013.01); *C12N 2800/22* (2013.01); *Y02A 50/386* (2018.01)

(58) Field of Classification Search
None
See application file for complete search history.

(56) References Cited

U.S. PATENT DOCUMENTS

| | | | |
|---|---|---|---|
| 2005/0010043 A1 | 1/2005 | Whitehead et al. |
| 2010/0209454 A1 | 8/2010 | Wimmer et al. |
| 2012/0282287 A1 | 11/2012 | Apt et al. |

FOREIGN PATENT DOCUMENTS

| | | |
|---|---|---|
| WO | 2006/042156 A2 | 4/2006 |
| WO | 2008/121992 A2 | 10/2008 |

OTHER PUBLICATIONS

Coleman, J. R. et al., “Virus Attenuation by Genome-Scale Changes in Condon Pair Bias”; Science (2008); vol. 320; pp. 1784-1787.
Federov, A. et al., “Regulatries of Context-Dependent Condon Bias in Eukaryotic Genes”; NAR (2002); vol. 30:5; pp. 1192-1197.
Gutman, G. A. et al., “Nonrandom Utilization of Condon Pairs in *Escherichia coli*”; PNAS (1989); vol. 86; pp. 3699-3703.
Moura G. et al. “Large Scale Comparative Codon-Pair Context Analysis Unveils General Rules that Fine-Tune Evolution of mRNA Primary Structure”; PLoS One (2007); vol. 2:9, pp. e847 (10 pgs).
Mueller, S. et al., “Live Attenuated Influenza Virus Vaccines by Computer-Aided Rational Design”; Nature Biotechnology (2010); vol. 28:7; pp. 723-727.
Nougairede; A., et al., “Random Condon Re-encoding Induces Stable Reduction of Replicative Fitness of Chikungunya Virus in Primate and Mosquito Cells”, PLoSOne (2013); vol. 9:2; e1003172 (18 ;gs).
Park, S. et al., “Advances in Computational Protein Design”; Current Opinion in Structual Biology (2004); vol. 14; pp. 487-494.
Shen, S. H. et al., “Large-Scale Recording of an Arbovirus Genome to Rebalance its Insect Versus Mammalian Preference” PNAS (2015); vol. 112:15; pp. 4749-4754.
Wimmer, E. et al., “Synthetic Poliovirus and Other Designer Viruses: What Have We Learned from Them?”; Annu. Rev. Microbiol. (2011); vol. 65; pp. 583-609.

*Primary Examiner* — Nicole Kinsey White
(74) *Attorney, Agent, or Firm* — Fox Rothschild LLP

(57) ABSTRACT

This invention provides an attenuated virus comprising a modified viral genome engineered to containing multiple nucleotide substitutions that reduce the codon pair bias of a virus protein encoding sequence relative to a first host while the codon pair bias relative to a second host is not substantially reduced. In another embodiment, the invention provides an attenuated virus comprising modified viral genome engineered to containing multiple nucleotide substitutions that reduce the codon pair bias of a virus protein-encoding sequence relative to a first host and a second host. The attenuated virus may be used in a vaccine composition for inducing a protective immune response in a subject. The invention also provides a method of synthesizing the attenuated virus. Further, this invention further provides a method for preventing a subject from becoming afflicted with a virus-associated disease comprising administering to the subject a prophylactically effective dose of a vaccine composition comprising the attenuated virus.

22 Claims, 8 Drawing Sheets

Specification includes a Sequence Listing.

C

| Virus | $LD_{50}$ (PFU/mL) |
|---|---|
| D2-syn | 5 |
| E*hmin* | 11,000 |
| NS3*hmin* | 730 |
| NS5*hmin* | 1,200 |

SEQUENCE LISTING

<160> NUMBER OF SEQ ID NOS: 5

<210> SEQ ID NO 1
<211> LENGTH: 10723
<212> TYPE: DNA
<213> ORGANISM: Dengue virus

<400> SEQUENCE: 1

```
agttgttagt ctacgtggac cgacaaagac agattctttg agggagctaa gctcaacgta     60

gttctaacag ttttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acacgtaacg gagaaccaca catgatcgtc    480

agcagacaag agaaagggaa aagtcttctg tttaaaacag aggatggcgt gaacatgtgt    540

accctcatgg ccatggacct tggtgaattg tgtgaagaca caatcacgta caagtgtccc    600

cttctcaggc agaatgagcc agaagacata gactgttggt gcaactctac gtccacgtgg    660

gtaacttatg ggacgtgtac caccatggga gaacatagaa gagaaaaaag atcagtggca    720

ctcgttccac atgtgggaat gggactggag acacgaactg aaacatggat gtcatcagaa    780

ggggcctgga aacatgtcca gagaattgaa acttggatct tgagacatcc aggcttcacc    840

atgatggcag caatcctggc atacaccata ggaacgacac atttccaaag agccctgatt    900

ttcatcttac tgacagctgt cactccttca atgacaatgc gttgcatagg aatgtcaaat    960

agagactttg tggaaggggt ttcaggagga agctgggttg acatagtctt agaacatgga   1020
```

```
agctgtgtga cgacgatggc aaaaaacaaa ccaacattgg attttgaact gataaaaaca   1080
gaagccaaac agcctgccac cctaaggaag tactgtatag aggcaaagct aaccaacaca   1140
acaacagaat ctcgctgccc aacacaaggg gaacccagcc taaatgaaga gcaggacaaa   1200
aggttcgtct gcaaacactc catggtagac agaggatggg gaaatggatg tggactattt   1260
ggaaagggag gcattgtgac ctgtgctatg ttcagatgca aaaagaacat ggaaggaaaa   1320
gttgtgcaac cagaaaactt ggaatacacc attgtgataa cacctcactc aggggaagag   1380
catgcagtcg gaaatgacac aggaaaacat ggcaaggaaa tcaaaataac accacagagt   1440
tccatcacag aagcagaatt gacaggttat ggcactgtca caatggagtg ctctccaaga   1500
acgggcctcg acttcaatga gatggtgttg ctgcagatgg aaaataaagc ttggctggtg   1560
cacaggcaat ggttcctaga cctgccgtta ccatggttgc ccggagcgga cacacaaggg   1620
tcaaattgga tacagaaaga gacattggtc actttcaaaa atccccatgc gaagaaacag   1680
gatgttgttg ttttaggatc ccaagaaggg gccatgcaca cagcacttac aggggccaca   1740
gaaatccaaa tgtcatcagg aaacttactc ttcacaggac atctcaagtg caggctgaga   1800
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat ccccttttgag ataatggatt tggaaaaaag acatgtctta   1980
ggtcgcctga ttacagtcaa cccaattgtg acagaaaaag atagcccagt caacatagaa   2040
gcagaacctc cattcggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagagggc   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
```

```
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgttcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
```

ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240
gaagaaaacg tggaagttga aatctggaca aaagaagggg aaaggaagaa attgaaaccc 6300
agatggttgg atgctaggat ctattctgac ccactggcgc taaaagaatt taaggaattt 6360
gcagccggaa gaaagtctct gaccctgaac ctaatcacag aaatgggtag gctcccaacc 6420
ttcatgactc agaaggcaag agacgcactg gacaacttag cagtgctgca cacggctgag 6480
gcaggtggaa gggcgtacaa ccatgctctc agtgaactgc cggagaccct ggagacattg 6540
cttttactga cacttctggc tacagtcacg ggagggatct tttttattctt gatgagcgga 6600 aggggcatag ggaagatgac cctgggaatg tgctgcataa tcacggctag catcctccta 6660
tggtacgcac aaatacagcc acactggata gcagcttcaa taatactgga gttttttctc 6720
atagttttgc ttattccaga acctgaaaaa cagagaacac cccaagacaa ccaactgacc 6780
tacgttgtca tagccatcct cacagtggtg gccgcaacca tggcaaacga gatgggtttc 6840
ctagaaaaaa cgaagaaaga tctcggattg ggaagcattg caacccagca acccgagagc 6900
aacatcctgg acatagatct acgtcctgca tcagcatgga cgctgtatgc cgtggccaca 6960
acatttgtta caccaatgtt gagacatagc attgaaaatt cctcagtgaa tgtgtcccta 7020
acagctatag ccaaccaagc cacagtgtta atgggtctcg ggaaaggatg gccattgtca 7080
aagatggaca tcggagttcc ccttctcgcc attggatgct actcacaagt caaccccata 7140
actctcacag cagctctttt cttattggta gcacattatg ccatcatagg gccaggactc 7200
caagcaaaag caaccagaga agctcagaaa agagcagcgg cgggcatcat gaaaaaccca 7260
actgtcgatg gaataacagt gattgaccta gatccaatac cttatgatcc aaagtttgaa 7320
aagcagttgg gacaagtaat gctcctagtc ctctgcgtga ctcaagtatt gatgatgagg 7380
actacatggg ctctgtgtga ggctttaacc ttagctaccg ggcccatctc cacattgtgg 7440
gaaggaaatc cagggaggtt ttggaacact accattgcgg tgtcaatggc taacattttt 7500
agagggagtt acttggccgg agctggactt ctcttttcta ttatgaagaa cacaaccaac 7560
acaagaaggg gaactggcaa cataggagag acgcttggag agaaatggaa aagccgattg 7620
aacgcattgg gaaaaagtga attccagatc tacaagaaaa gtggaatcca ggaagtggat 7680
agaaccttag caaaagaagg cattaaaaga ggagaaacgg accatcacgc tgtgtcgcga 7740
ggctcagcaa aactgagatg gttcgttgag agaaacatgg tcacaccaga agggaaagta 7800
gtggacctcg gttgtggcag aggaggctgg tcatactatt gtggaggact aaagaatgta 7860
agagaagtca aaggcctaac aaaaggagga ccaggacacg aagaacccat ccccatgtca 7920
acatatgggt ggaatctagt gcgtcttcaa agtggagttg acgttttctt catcccgcca 7980
gaaaagtgtg acacattatt gtgtgacata ggggagtcat caccaaatcc cacagtggaa 8040
gcaggacgaa cactcagagt ccttaactta gtagaaaatt ggttgaacaa caacactcaa 8100

-continued

```
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgaacaac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
gttctgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
```

-continued ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 2
<211> LENGTH: 10723
<212> TYPE: DNA
<213> ORGANISM: Artificial Sequence
<220> FEATURE:
<223> OTHER INFORMATION: Accession #U87411 containing new restriction sites

<400> SEQUENCE: 2
agttgttagt ctacgtggac cgacaaagac agattctttg agggagctaa gctcaacgta 60
gttctaacag ttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggatggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660
gtaacttatg ggacgtgtac caccatggga gaacatagaa gagaaaaaag atcagtggca 720
ctcgttccac atgtgggaat gggactggag acgcgtactg aaacatggat gtcatcagaa 780
ggggcctgga aacatgtcca gagaattgaa acttggatct tgagacatcc aggcttcacc 840
atgatggcag caatcctggc atacaccata ggaacgacac atttccaaag agccctgatt 900
ttcatcttac tgacagctgt cactccttca atgacaatgc gttgcatagg aatgtcaaat 960
agagactttg tggaaggggt ttcaggagga agctgggttg acatagtctt agaacatgga 1020
agctgtgtga cgacgatggc aaaaaacaaa ccaacattgg attttgaact gataaaaaca 1080
gaagccaaac agcctgccac cctaaggaag tactgtatag aggcaaagct aaccaacaca 1140
acaacagaat ctcgctgccc aacacaaggg gaacccagcc taaatgaaga gcaggacaaa 1200
aggttcgtct gcaaacactc catggtagac agaggatggg gaaatggatg tggactattt 1260
ggaaagggag gcattgtgac ctgtgctatg ttcagatgca aaaagaacat ggaaggaaaa 1320
gttgtgcaac cagaaaactt ggaatacacc attgtgataa cacctcactc aggggaagaa 1380
catgcagtcg gaaatgacac aggaaaacat ggcaaggaaa tcaaaataac accacagagt 1440
tccatcacag aagcagaatt gacaggttat ggcactgtca caatggagtg ctctccaaga 1500
acgggcctcg acttcaatga gatggtgttg ctgcagatgg aaaataaggc ttggctggtg 1560
cacaggcaat ggttcctaga cctgccgtta ccatggttgc ccggagcgga cacacaaggg 1620
tcaaattgga tacagaaaga gacattggtc actttcaaaa atccccatgc gaagaaacag 1680
gatgttgttg ttttaggatc ccaagaaggg gccatgcaca cagcacttac aggggccaca 1740
gaaatccaaa tgagctcagg aaacttactc ttcacaggac atctcaagtg caggctgaga 1800

-continued

```
atggacaagc tacagctcaa aggaatgtca tactctatgt gcacaggaaa gtttaaagtt   1860
gtgaaggaaa tagcagaaac acaacatgga acaatagtta tcagagtgca atatgaaggg   1920
gacggctctc catgcaagat ccccttttgag ataatggatt tggaaaaaag acatgtctta   1980
ggtcgcctga ttacagtcaa cccaattgtg acagaaaaag atagcccagt caacatagaa   2040
gcagaacctc cattcggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ttagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaag   2520
ttccaaccag aatccccttc aaaactagct tcagctatcc agaaagccca tgaagagggc   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggcttaa gttgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagcta   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcagt tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
```

-continued

```
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggcaga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aaccggtttg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgttcg tggaattccg gtcatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
```

-continued

```
cttttactga cacttctggc tacagtcacg ggagggatct tttattcttt gatgagcgga   6600
aggggcatag ggaagatgac cctgggaatg tgctgcataa tcacggcaag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gcctggcctg   7200
caggcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcgt   7740
ggctcagcaa aactgagatg gttcgttgag agaaacatgg tcacaccaga agggaaagta   7800
gtggacctcg gttgtggccg cggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaagag    8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
```

```
gaaaggaatc tccatcttga aggaaagtgt gaaacatgtg tgtacaacat gatgggaaaa   8940

agagagaaga agctagggga attcggcaag gcaaaaggca gcagagccat atggtacatg   9000

tggcttggag cacgcttctt agagtttgaa gccctaggat tcttaaatga agatcactgg   9060

ttctccagag agaactccct gagtggagtg gaaggagaag ggctgcacaa gctaggttac   9120

attctaagag acgtgagcaa gaaagaggga ggagcaatgt atgccgatga caccgcagga   9180

tgggatacaa gaatcacact agaagaccta aaaaatgaag aaatggtaac aaaccacatg   9240

gaaggagaac acaagaaact agccgaggcc attttcaaac taacgtacca aaacaaggtg   9300

gtgcgtgtgc aaagaccaac accaagaggc acagtaatgg acatcatatc gagaagagac   9360

caaagaggta gtggacaagt tggcacctat ggactcaata ctttcaccaa tatggaagcc   9420

caactaatca gacagatgga gggagaagga gtctttaaaa gcattcagca cctaacaatc   9480

acagaagaaa tcgctgtgca aaactggtta gcaagagtgg ggcgcgaaag gttatcaaga   9540

atggccatca gtggagatga ttgtgttgtg aaacctttag atgacaggtt cgcaagcgct   9600

ttaacagctc taaatgacat gggaaagatt aggaaagaca tacaacaatg ggaaccttca   9660

agaggatgga atgattggac acaagtgccc ttctgttcac accatttcca tgagttaatc   9720

atgaaagacg gtcgcgtact cgttgttcca tgtagaaacc aagatgaact gattggcaga   9780

gcccgaatct cccaaggagc agggtggtct ttgcgggaga cggcctgttt ggggaagtct   9840

tacgcccaaa tgtggagctt gatgtacttc cacagacgcg acctcaggct ggcggcaaat   9900

gctatttgct cggcagtacc atcacattgg gttccaacaa gtcgtacgac ctggtccata   9960

catgctaaac atgaatggat gacaacggaa gacatgctga cagtctggaa cagggtgtgg  10020

attcaagaaa acccatggat ggaagacaaa actccagtgg aatcatggga ggaaatccca  10080

tacttgggga aaagagaaga ccaatggtgc ggctcattga ttgggttaac aagcagggcc  10140

acctgggcaa agaacatcca agcagcaata aatcaagtta gatcccttat aggcaatgaa  10200

gaatacacag attacatgcc atccatgaaa agattcagaa gagaagagga agaagcagga  10260

gttctgtggt agaaagcaaa actaacatga aacaaggcta gaagtcaggt cggattaagc  10320

catagtacgg aaaaaactat gctacctgtg agccccgtcc aaggacgtta aaagaagtca  10380

ggccatcata aatgccatag cttgagtaaa ctatgcagcc tgtagctcca cctgagaagg  10440

tgtaaaaaat ccgggaggcc acaaaccatg gaagctgtac gcatggcgta gtggactagc  10500

ggttagagga gacccctccc ttacaaatcg cagcaacaat gggggcccaa ggcgagatga  10560

agctgtagtc tcgctggaag gactagaggt tagaggagac ccccccgaaa caaaaaacag  10620

catattgacg ctgggaaaga ccagagatcc tgctgtctcc tcagcatcat tccaggcaca  10680

gaacgccaga aaatggaatg gtgctgttga atcaacaggt tct                    10723
```

<210> SEQ ID NO 3
<211> LENGTH: 10723
<212> TYPE: DNA
<213> ORGANISM: Artificial Sequence
<220> FEATURE:
<223> OTHER INFORMATION: Recoded E
<220> FEATURE:
<221> NAME/KEY: misc_feature
<222> LOCATION: (937)..(2421)
<223> OTHER INFORMATION: deoptimized region

<400> SEQUENCE: 3

```
agttgttagt ctacgtggac cgacaaagac agattctttg agggagctaa gctcaacgta     60

gttctaacag tttttaatt agagagcaga tctctgatga ataaccaacg gaaaaaggcg    120
```

```
aaaaacacgc ctttcaatat gctgaaacgc gagagaaacc gcgtgtcgac tgtgcaacag    180
ctgacaaaga gattctcact tggaatgctg cagggacgag gaccattaaa actgttcatg    240
gccctggtgg cgttccttcg tttcctaaca atcccaccaa cagcagggat attgaagaga    300
tggggaacaa ttaaaaaatc aaaagctatt aatgttttga gagggttcag gaaagagatt    360
ggaaggatgc tgaacatctt gaataggaga cgcagatctg caggcatgat cattatgctg    420
attccaacag tgatggcgtt ccatttaacc acacgtaacg gagaaccaca catgatcgtc    480
agcagacaag agaaagggaa aagtcttctg tttaaaacag aggatggcgt gaacatgtgt    540
accctcatgg ccatggacct tggtgaattg tgtgaagaca caatcacgta caagtgtccc    600
cttctcaggc agaatgagcc agaagacata gactgttggt gcaactctac gtccacgtgg    660
gtaacttatg ggacgtgtac caccatggga gaacatagaa gagaaaaaag atcagtggca    720
ctcgttccac atgtgggaat gggactggag acgcgtactg aaacatggat gtcatcagaa    780
ggggcctgga aacatgtcca gagaattgaa acttggatct tgagacatcc aggcttcacc    840
atgatggcag caatcctggc atacaccata ggaacgacac atttccaaag agccctgatt    900
ttcatcttac tgacagctgt cactccttca atgacaatga gatgcatagg aatgagcaac    960
cgcgatttcg tcgaaggcgt ttccggaggg agttgggtcg acatagtgct cgaacacgga   1020
tcttgcgtta ccacaatggc caaaaataaa ccaacactcg actttgaact cataaaaacc   1080
gaagctaagc aaccggcaac acttaggaag tattgtatcg aagcgaaatt gactaacaca   1140
acaacagagt ctaggtgtcc aacacaaggc gaacctagct tgaacgaaga gcaagacaaa   1200
agattcgttt gcaaacattc tatggtcgat cgcggatggg gaaacggatg cggattgttc   1260
ggaaaggggg gaatcgttac atgcgctatg ttcagatgca aaaaaaacat ggagggaaag   1320
gtcgtgcaac ccgaaaatct ggagtataca atcgttataa caccacattc cggcgaagag   1380
catgccgtcg gaaacgacac gggtaagcac ggtaaggaaa tcaaaattac acctcaatct   1440
agcataaccg aagccgaact gacagggtac ggaacagtga caatggaatg ctcacctaga   1500
acagggttgg acttcaacga aatggtgcta ctgcaaatgg agaataaggc atggttagtg   1560
cataggcaat ggtttctcga tctgccacta ccatggttac ccggagccga tacacaggga   1620
tctaattgga tacagaagga aacattggtg acatttaaaa acccacacgc aaaaaaacag   1680
gacgtcgtcg ttctcggatc acaggaaggg gcaatgcata cagccctaac cggagcaacc   1740
gaaattcaga tgagctcagg gaatctatta tttacgggac atctgaaatg tagattgcgt   1800
atggacaaac tgcagttgaa gggaatgagc tattctatgt gtacaggtaa gtttaaggtc   1860
gttaaggaga tagccgaaac gcaacacgga acaatcgtaa ttagggtgca atacgaaggc   1920
gacggatcac cttgcaaaat accgtttgaa attatggacc tcgaaaaaag acacgtactc   1980
ggaagactga taacagtcaa tccaattgtg acagagaagg actcaccagt gaatatcgaa   2040
gccgaaccac cattcggaga tagctatatt ataatcggag tcgaacccgg acagttgaaa   2100
ctgaattggt ttaaaaaggg atcatcaatc ggacagatgt ttgaaacaac aatgcgcgga   2160
gcgaaaagaa tggcaatatt aggcgacact gcttgggact tcgggagctt agggggagtg   2220
tttacatcaa tcggaaaggc actacatcaa gtgttcggag cgatatacgg agccgcattt   2280
tccggagtga gttggactat gaagatactg atagggggtga taattacatg gatcggaatg   2340
aatagtaggt ctacatcact atccgttaca ttggtgttag tcggaatcgt tacattgtac   2400
ttaggcgtaa tggtgcaagc tgatagtggt tgcgttgtga gctggaaaaa caaagaactg   2460
```

-continued

```
aaatgtggca gtgggatttt catcacagac aacgtgcaca catggacaga acaatacaag   2520
ttccaaccag aatccccttc aaaactagct tcagctatcc agaaagccca tgaagagggc   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggcttaa gttgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagcta   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcagt tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggcaga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aaccggtttg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac catcatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
```

-continued

```
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tgacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgttcg tggaattccg gtcatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgga   6600
aggggcatag ggaagatgac cctgggaatg tgctgcataa tcacggcaag catcctccta   6660
tggtacgcac aaatacagcc acactggata gcagcttcaa taatactgga gtttttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gcctggcctg   7200
```

-continued

```
caggcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcgt   7740
ggctcagcaa aactgagatg gttcgttgag agaaacatgg tcacaccaga agggaaagta   7800
gtggacctcg gttgtggccg cggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
```

ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgtacgac ctggtccata 9960
catgctaaac atgaatggat gacaacggaa gacatgctga cagtctggaa cagggtgtgg 10020
attcaagaaa acccatggat ggaagacaaa actccagtgg aatcatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 4
<211> LENGTH: 10723
<212> TYPE: DNA
<213> ORGANISM: Artificial Sequence
<220> FEATURE:
<223> OTHER INFORMATION: Recoded NS3
<220> FEATURE:
<221> NAME/KEY: misc_feature
<222> LOCATION: (4522)..(6375)
<223> OTHER INFORMATION: deoptimized region

<400> SEQUENCE: 4
agttgttagt ctacgtggac cgacaaagac agattctttg agggagctaa gctcaacgta 60
gttctaacag ttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggatggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660
gtaacttatg ggacgtgtac caccatggga gaacatagaa gagaaaaaag atcagtggca 720
ctcgttccac atgtgggaat gggactggag acgcgtactg aaacatggat gtcatcagaa 780

```
ggggcctgga aacatgtcca gagaattgaa acttggatct tgagacatcc aggcttcacc     840
atgatggcag caatcctggc atacaccata ggaacgacac atttccaaag agccctgatt     900
ttcatcttac tgacagctgt cactccttca atgacaatgc gttgcatagg aatgtcaaat     960
agagactttg tggaaggggt ttcaggagga agctgggttg acatagtctt agaacatgga    1020
agctgtgtga cgacgatggc aaaaaacaaa ccaacattgg attttgaact gataaaaaca    1080
gaagccaaac agcctgccac cctaaggaag tactgtatag aggcaaagct aaccaacaca    1140
acaacagaat ctcgctgccc aacacaaggg gaacccagcc taaatgaaga gcaggacaaa    1200
aggttcgtct gcaaacactc catggtagac agaggatggg gaaatggatg tggactattt    1260
ggaaagggag gcattgtgac ctgtgctatg ttcagatgca aaaagaacat ggaaggaaaa    1320
gttgtgcaac cagaaaactt ggaatacacc attgtgataa cacctcactc aggggaagaa    1380
catgcagtcg gaaatgacac aggaaaacat ggcaaggaaa tcaaaataac accacagagt    1440
tccatcacag aagcagaatt gacaggttat ggcactgtca caatggagtg ctctccaaga    1500
acgggcctcg acttcaatga gatggtgttg ctgcagatgg aaaataaggc ttggctggtg    1560
cacaggcaat ggttcctaga cctgccgtta ccatggttgc ccggagcgga cacacaaggg    1620
tcaaattgga tacagaaaga gacattggtc actttcaaaa atccccatgc gaagaaacag    1680
gatgttgttg ttttaggatc ccaagaaggg gccatgcaca cagcacttac aggggccaca    1740
gaaatccaaa tgagctcagg aaacttactc ttcacaggac atctcaagtg caggctgaga    1800
atggacaagc tacagctcaa aggaatgtca tactctatgt gcacaggaaa gtttaaagtt    1860
gtgaaggaaa tagcagaaac acaacatgga acaatagtta tcagagtgca atatgaaggg    1920
gacggctctc catgcaagat ccctttgag ataatggatt tggaaaaaag acatgtctta    1980
ggtcgcctga ttacagtcaa cccaattgtg acagaaaaag atagcccagt caacatagaa    2040
gcagaacctc cattcggaga cagctacatc atcataggag tagagccggg acaactgaag    2100
ctcaactggt ttaagaaagg aagttctatc ggccaaatgt ttgagacaac aatgaggggg    2160
gcgaagagaa tggccatttt aggtgacaca gcctgggatt ttggatcctt gggaggagtg    2220
tttacatcta taggaaaggc tctccaccaa gtctttggag caatctatgg agctgccttc    2280
agtggggttt catggactat gaaaatcctc ataggagtca ttatcacatg gataggaatg    2340
aattcacgca gcacctcact gtctgtgaca ttagtattgg tgggaattgt gacactgtat    2400
ttgggagtca tggtgcaggc cgatagtggt tgcgttgtga gctggaaaaa caaagaactg    2460
aaatgtggca gtgggatttt catcacagac aacgtgcaca catggacaga acaatacaag    2520
ttccaaccag aatccccttc aaaactagct tcagctatcc agaaagccca tgaagagggc    2580
atttgtggaa tccgctcagt aacaagactg gagaatctga tgtggaaaca aataacacca    2640
gaattgaatc acattctatc agaaaatgag gtgaagttaa ctattatgac aggagacatc    2700
aaaggaatca tgcaggcagg aaaacgatct ctgcggcctc agcccactga gctgaagtat    2760
tcatggaaaa catggggcaa agcaaaaatg ctctctacag agtctcataa ccagaccttt    2820
ctcattgatg gccccgaaac agcagaatgc cccaacacaa atagagcttg gaattcgttg    2880
gaagttgaag actatggctt tggagtattc accaccaata tatggcttaa gttgaaagaa    2940
aaacaggatg tattctgcga ctcaaaactc atgtcagcgg ccataaaaga caacagagcc    3000
gtccatgccg atatgggtta ttggatagaa agtgcactca atgacacatg gaagatagag    3060
aaagcctctt tcattgaagt taaaaactgc cactggccaa aatcacacac cctctggagc    3120
aatggagtgc tagaaagtga gatgataatt ccaaagaatc tcgctggacc agtgtctcaa    3180
```

```
cacaactata gaccaggcta ccatacacaa ataacaggac catggcatct aggtaagcta   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcagt tggcagtgac tatcatggct atcttgtgcg tcccaaacgc agtgatatta   3960
caaaacgcat ggaaagtgag ttgcacaata ttggcagtgg tgtccgtttc cccactgctc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
aatgatattc ccatgacagg accattagtg gctggagggc tcctcactgt gtgctacgtg   4260
ctcactggac gatcggcaga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aaccggtttg   4440
ctggtgatct caggactttt tcctgtatca ataccaatca cggcagcagc atggtacctg   4500
tgggaagtga agaaacaacg ggccggagtt ttatgggacg ttccatctcc accaccaatg   4560
ggtaaggccg agctggaaga cggagcatat cggatcaaac agaagggaat actagggtat   4620
tctcaaatcg gagccggagt gtacaaagaa ggaacctttc atacaatgtg gcacgttact   4680
aggggagccg tactgatgca caagggtaag agaatcgaac ctagttgggc agacgttaag   4740
aaagacctaa tctcatacgg aggaggatgg aaactggaag gcgaatggaa agagggagaa   4800
gaggtgcagg tgcttgcact cgaacccggt aagaatccta gagcagtgca aacgaaaccc   4860
ggtctattca aaactaatgc cggaacaatc ggtgccgtaa gtttggactt tagtccagga   4920
actagcggat caccaattat cgacaaaaag ggtaaggtcg tcggattgta cggtaacgga   4980
gtcgttacga gatctggagc atacgttagc gctatagcgc aaaccgaaaa gtcaatcgaa   5040
gacaatcccg aaatcgaaga cgacattttt agaaaaagaa ggttaacgat tatggaccta   5100
catcccggag ccggtaagac taaacggtat ctgccagcaa tcgtgcgcga agcaatcaaa   5160
agggggttga gaacattgat tctagctcct actagggtag tcgcagccga gatggaagaa   5220
gcacttaggg ggttgccaat tagatatcag acacctgcta ttagggccga acataccgga   5280
agagagatag tcgatctgat gtgtcacgct acatttacga tgcgattgct atcaccagtt   5340
agagtgccta attacaatct gataattatg gacgaagcgc attttaccga tccagctagt   5400
atagccgcta ggggatacat atctactcga gtggaaatgg gcgaagctgc cggaattttt   5460
atgaccgcta cacctccagg atcaagagac ccatttccac aatctaacgc tccaattatc   5520
```

-continued

```
gacgaggaaa gagaaatacc ggagcggtca tggaattccg gacacgaatg ggttaccgat   5580
tttaagggta agaccgtttg gttcgtacct agtatcaaag ccggaaacga tatcgctgca   5640
tgccttagaa aaaacggtaa gaaagtgata cagctatcga gaaagacatt cgatagcgaa   5700
tacgttaaga ctagaacaaa cgattgggat ttcgtcgtta caaccgatat tagcgaaatg   5760
ggagctaatt ttaaggccga aagggtgatt gatcctagaa gatgtatgaa accagtgata   5820
cttaccgacg gagaggaaag agtgatacta gccggaccaa tgccagttac gcattctagt   5880
gcagctcaac gtagagggag aatcggacgt aatccgaaaa acgaaaacga tcagtatata   5940
tacatgggcg aaccactcga aaacgacgag gattgcgcac attggaagga agcgaaaatg   6000
ctattagaca atatcaatac acccgaaggg attataccat caatgttcga acccgagcgc   6060
gaaaaggtcg acgcaatcga cggagaatat agacttagag gcgaagctag aaagacattc   6120
gtcgatctga tgagaagggg ggatctgcca gtttggttgg catacagagt ggcagccgag   6180
gggataaact acgccgatag aagatggtgt ttcgacggag tgaaaaataa tcagatactc   6240
gaagaaaacg tcgaagtcga aatttggaca aaagaaggag aacgtaaaaa actgaaacct   6300
agatggttgg acgctaggat atattccgat ccacttgcac tgaaagaatt taaagagttc   6360
gcagccggaa gaaaatctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattctt gatgagcgga   6600
aggggcatag ggaagatgac cctgggaatg tgctgcataa tcacggcaag catcctccta   6660
tggtacgcac aaatacagcc acactggata gcagcttcaa taatactgga gtttttctc   6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gcctggcctg   7200
caggcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcgt   7740
ggctcagcaa aactgagatg gttcgttgag agaaacatgg tcacaccaga agggaaagta   7800
gtggacctcg gttgtggccg cggaggctgg tcatactatt gtggaggact aaagaatgta   7860
agagaagtca aaggcctaac aaaaggagga ccaggacacg aagaacccat ccccatgtca   7920
```

-continued

```
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt cgtccccatg   8580
gtgacacaga tggcaatgac agacacgact ccatttggac aacagcgcgt tttaaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
agagagaaga agctagggga attcggcaag gcaaaaggca gcagagccat atggtacatg   9000
tggcttggag cacgcttctt agagtttgaa gccctaggat tcttaaatga agatcactgg   9060
ttctccagag agaactccct gagtggagtg gaaggagaag ggctgcacaa gctaggttac   9120
attctaagag acgtgagcaa gaaagaggga ggagcaatgt atgccgatga caccgcagga   9180
tgggatacaa gaatcacact agaagaccta aaaaatgaag aaatggtaac aaaccacatg   9240
gaaggagaac acaagaaact agccgaggcc attttcaaac taacgtacca aaacaaggtg   9300
gtgcgtgtgc aaagaccaac accaagaggc acagtaatgg acatcatatc gagaagagac   9360
caaagaggta gtggacaagt tggcacctat ggactcaata ctttcaccaa tatggaagcc   9420
caactaatca gacagatgga gggagaagga gtctttaaaa gcattcagca cctaacaatc   9480
acagaagaaa tcgctgtgca aaactggtta gcaagagtgg ggcgcgaaag gttatcaaga   9540
atggccatca gtggagatga ttgtgttgtg aaacctttag atgacaggtt cgcaagcgct   9600
ttaacagctc taaatgacat gggaaagatt aggaaagaca tacaacaatg ggaaccttca   9660
agaggatgga atgattggac acaagtgccc ttctgttcac accatttcca tgagttaatc   9720
atgaaagacg gtcgcgtact cgttgttcca tgtagaaacc aagatgaact gattggcaga   9780
gcccgaatct cccaaggagc agggtggtct ttgcgggaga cggcctgttt ggggaagtct   9840
tacgcccaaa tgtggagctt gatgtacttc cacagacgcg acctcaggct ggcggcaaat   9900
gctatttgct cggcagtacc atcacattgg gttccaacaa gtcgtacgac ctggtccata   9960
catgctaaac atgaatggat gacaacggaa gacatgctga cagtctggaa cagggtgtgg  10020
attcaagaaa acccatggat ggaagacaaa actccagtgg aatcatggga ggaaatccca  10080
tacttgggga aaagagaaga ccaatggtgc ggctcattga ttgggttaac aagcagggcc  10140
acctgggcaa agaacatcca agcagcaata aatcaagtta gatcccttat aggcaatgaa  10200
gaatacacag attacatgcc atccatgaaa agattcagaa gagaagagga agaagcagga  10260
```

gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagagga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 5
<211> LENGTH: 10723
<212> TYPE: DNA
<213> ORGANISM: Artificial Sequence
<220> FEATURE:
<223> OTHER INFORMATION: Recoded NS5
<220> FEATURE:
<221> NAME/KEY: misc_feature
<222> LOCATION: (7570)..(10269)
<223> OTHER INFORMATION: deoptimized region
<400> SEQUENCE: 5
agttgttagt ctacgtggac cgacaaagac agattctttg agggagctaa gctcaacgta 60
gttctaacag ttttttaatt agagagcaga tctctgatga ataaccaacg gaaaaaggcg 120
aaaaacacgc ctttcaatat gctgaaacgc gagagaaacc gcgtgtcgac tgtgcaacag 180
ctgacaaaga gattctcact tggaatgctg cagggacgag gaccattaaa actgttcatg 240
gccctggtgg cgttccttcg tttcctaaca atcccaccaa cagcagggat attgaagaga 300
tggggaacaa ttaaaaaatc aaaagctatt aatgttttga gagggttcag gaaagagatt 360
ggaaggatgc tgaacatctt gaataggaga cgcagatctg caggcatgat cattatgctg 420
attccaacag tgatggcgtt ccatttaacc acacgtaacg gagaaccaca catgatcgtc 480
agcagacaag agaaagggaa aagtcttctg tttaaaacag aggatggcgt gaacatgtgt 540
accctcatgg ccatggacct tggtgaattg tgtgaagaca caatcacgta caagtgtccc 600
cttctcaggc agaatgagcc agaagacata gactgttggt gcaactctac gtccacgtgg 660
gtaacttatg ggacgtgtac caccatggga gaacatagaa gagaaaaaag atcagtggca 720
ctcgttccac atgtgggaat gggactggag acgcgtactg aaacatggat gtcatcagaa 780
ggggcctgga aacatgtcca gagaattgaa acttggatct tgagacatcc aggcttcacc 840
atgatggcag caatcctggc atacaccata ggaacgacac atttccaaag agccctgatt 900
ttcatcttac tgacagctgt cactccttca atgacaatgc gttgcatagg aatgtcaaat 960
agagactttg tggaaggggt ttcaggagga agctgggttg acatagtctt agaacatgga 1020
agctgtgtga cgacgatggc aaaaaacaaa ccaacattgg attttgaact gataaaaaca 1080
gaagccaaac agcctgccac cctaaggaag tactgtatag aggcaaagct aaccaacaca 1140
acaacagaat ctcgctgccc aacacaaggg gaacccagcc taaatgaaga gcaggacaaa 1200
aggttcgtct gcaaacactc catggtagac agaggatggg gaaatggatg tggactattt 1260
ggaaagggag gcattgtgac ctgtgctatg ttcagatgca aaaagaacat ggaaggaaaa 1320
gttgtgcaac cagaaaactt ggaatacacc attgtgataa cacctcactc aggggaagaa 1380
catgcagtcg gaaatgacac aggaaaacat ggcaaggaaa tcaaaataac accacagagt 1440
tccatcacag aagcagaatt gacaggttat ggcactgtca caatggagtg ctctccaaga 1500
acgggcctcg acttcaatga gatggtgttg ctgcagatgg aaaataaggc ttggctggtg 1560
cacaggcaat ggttcctaga cctgccgtta ccatggttgc ccggagcgga cacacaaggg 1620
tcaaattgga tacagaaaga gacattggtc actttcaaaa atccccatgc gaagaaacag 1680
gatgttgttg ttttaggatc ccaagaaggg gccatgcaca cagcacttac aggggccaca 1740
gaaatccaaa tgagctcagg aaacttactc ttcacaggac atctcaagtg caggctgaga 1800
atggacaagc tacagctcaa aggaatgtca tactctatgt gcacaggaaa gtttaaagtt 1860
gtgaaggaaa tagcagaaac acaacatgga acaatagtta tcagagtgca atatgaaggg 1920
gacggctctc catgcaagat cccttttgag ataatggatt tggaaaaaag acatgtctta 1980
ggtcgcctga ttacagtcaa cccaattgtg acagaaaaag atagcccagt caacatagaa 2040
gcagaacctc cattcggaga cagctacatc atcataggag tagagccggg acaactgaag 2100
ctcaactggt ttaagaaagg aagttctatc ggccaaatgt ttgagacaac aatgaggggg 2160
gcgaagagaa tggccatttt aggtgacaca gcctgggatt ttggatcctt gggaggagtg 2220
tttacatcta taggaaaggc tctccaccaa gtctttggag caatctatgg agctgccttc 2280
agtggggttt catggactat gaaaatcctc ataggagtca ttatcacatg gataggaatg 2340
aattcacgca gcacctcact gtctgtgaca ttagtattgg tgggaattgt gacactgtat 2400
ttgggagtca tggtgcaggc cgatagtggt tgcgttgtga gctggaaaaa caaagaactg 2460
aaatgtggca gtgggatttt catcacagac aacgtgcaca catggacaga acaatacaag 2520
ttccaaccag aatccccttc aaaactagct tcagctatcc agaaagccca tgaagagggc 2580
atttgtggaa tccgctcagt aacaagactg gagaatctga tgtggaaaca aataacacca 2640
gaattgaatc acattctatc agaaaatgag gtgaagttaa ctattatgac aggagacatc 2700
aaaggaatca tgcaggcagg aaaacgatct ctgcggcctc agcccactga gctgaagtat 2760
tcatggaaaa catggggcaa agcaaaaatg ctctctacag agtctcataa ccagaccttt 2820
ctcattgatg gccccgaaac agcagaatgc cccaacacaa atagagcttg gaattcgttg 2880
gaagttgaag actatggctt tggagtattc accaccaata tatggcttaa gttgaaagaa 2940
aaacaggatg tattctgcga ctcaaaactc atgtcagcgg ccataaaaga caacagagcc 3000
gtccatgccg atatgggtta ttggatagaa agtgcactca atgacacatg gaagatagag 3060
aaagcctctt tcattgaagt taaaaactgc cactggccaa aatcacacac cctctggagc 3120
aatggagtgc tagaaagtga gatgataatt ccaaagaatc tcgctggacc agtgtctcaa 3180
cacaactata gaccaggcta ccatacacaa ataacaggac catggcatct aggtaagcta 3240
gagatggact ttgatttctg tgatggaaca acagtggtag tgactgagga ctgcggaaat 3300
agaggaccct ctttgagaac aaccactgcc tctggaaaac tcataacaga atggtgctgc 3360
cgatcttgca cattaccacc gctaagatac agaggtgagg atgggtgctg gtacgggatg 3420
gaaatcagac cattgaagga gaaagaagag aatttggtca actccttggt cacagctgga 3480
catgggcagg tcgacaactt ttcactagga gtcttgggaa tggcattgtt cctggaggaa 3540
atgcttagga cccgagtagg aacgaaacat gcaatactac tagttgcagt ttcttttgtg 3600
acattgatca cagggaacat gtcctttaga gacctgggaa gagtgatggt tatggtaggc 3660
gccactatga cggatgacat aggtatgggc gtgacttatc ttgccctact agcagccttc 3720
aaagtcagac caacttttgc agctggacta ctcttgagaa agctgacctc caaggaattg 3780
atgatgacta ctataggaat tgtactcctc tcccagagca ccataccaga gaccattctt 3840

-continued gagttgactg atgcgttagc cttaggcatg atggtcctca aaatggtgag aaatatggaa 3900
aagtatcagt tggcagtgac tatcatggct atcttgtgcg tcccaaacgc agtgatatta 3960
caaaacgcat ggaaagtgag ttgcacaata ttggcagtgg tgtccgtttc cccactgctc 4020
ttaacatcct cacagcaaaa aacagattgg ataccattag cattgacgat caaaggtctc 4080
aatccaacag ctatttttct aacaaccctc tcaagaacca gcaagaaaag gagctggcca 4140
ttaaatgagg ctatcatggc agtcgggatg gtgagcattt tagccagttc tctcctaaaa 4200
aatgatattc ccatgacagg accattagtg gctggagggc tcctcactgt gtgctacgtg 4260
ctcactggac gatcggcaga tttggaactg gagagagcag ccgatgtcaa atgggaagac 4320
caggcagaga tatcaggaag cagtccaatc ctgtcaataa caatatcaga agatggtagc 4380
atgtcgataa aaaatgaaga ggaagaacaa acactgacca tactcattag aaccggtttg 4440
ctggtgatct caggactttt tcctgtatca ataccaatca cggcagcagc atggtacctg 4500
tgggaagtga agaaacaacg ggccggagta ttgtgggatg ttccttcacc cccacccatg 4560
ggaaaggctg aactggaaga tggagcctat agaattaagc aaaaagggat tcttggatat 4620
tcccagatcg gagccggagt ttacaaagaa ggaacattcc atacaatgtg gcatgtcaca 4680
cgtggcgctg ttctaatgca taaaggaaag aggattgaac catcatgggc ggacgtcaag 4740
aaagacctaa tatcatatgg aggaggctgg aagttagaag gagaatggaa ggaaggagaa 4800
gaagtccagg tattggcact ggagcctgga aaaaatccaa gagccgtcca aacgaaacct 4860
ggtcttttca aaaccaacgc cggaacaata ggtgctgtat ctctggactt ttctcctgga 4920
acgtcaggat ctccaattat cgacaaaaaa ggaaaagttg tgggtcttta tggtaatggt 4980
gttgttacaa ggagtggagc atatgtgagt gctatagccc agactgaaaa aagcattgaa 5040
gacaacccag agatcgaaga tgacattttc cgaaagagaa gactgaccat catggacctc 5100
cacccaggag cgggaaagac gaagagatac cttccggcca tagtcagaga agctataaaa 5160
cggggtttga gaacattaat cttggccccc actagagttg tggcagctga aatggaggaa 5220
gcccttagag gacttccaat aagataccag accccagcca tcagagctga gcacaccggg 5280
cgggagattg tggacctaat gtgtcatgcc acatttacca tgaggctgct atcaccagtt 5340
agagtgccaa actacaacct gattatcatg gacgaagccc atttcacaga cccagcaagt 5400
atagcagcta gaggatacat ctcaactcga gtggagatgg gtgaggcagc tgggattttt 5460
atgacagcca ctcccccggg aagcagagac ccatttcctc agagcaatgc accaatcata 5520
gatgaagaaa gagaaatccc tgaacgttcg tggaattccg gtcatgaatg ggtcacggat 5580
tttaaaggga agactgtttg gttcgttcca agtataaaag caggaaatga tatagcagct 5640
tgcctgagga aaaatggaaa gaaagtgata caactcagta ggaagacctt tgattctgag 5700
tatgtcaaga ctagaaccaa tgattgggac ttcgtggtta caactgacat ttcagaaatg 5760
ggtgccaatt tcaaggctga gagggttata gaccccagac gctgcatgaa accagtcata 5820
ctaacagatg gtgaagagcg ggtgattctg gcaggaccta tgccagtgac ccactctagt 5880
gcagcacaaa gaagagggag aataggaaga aatccaaaaa atgagaatga ccagtacata 5940
tacatggggg aacctctgga aaatgatgaa gactgtgcac actggaaaga agctaaaatg 6000
ctcctagata acatcaacac gccagaagga atcattccta gcatgttcga accagagcgt 6060
gaaaaggtgg atgccattga tggcgaatac cgcttgagag gagaagcaag gaaaaccttt 6120
gtagacttaa tgagaagagg agacctacca gtctggttgg cctacagagt ggcagctgaa 6180
ggcatcaact acgcagacag aaggtggtgt tttgatggag tcaagaacaa ccaaatccta 6240

-continued

```
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattctt gatgagcgga    6600
aggggcatag ggaagatgac cctgggaatg tgctgcataa tcacggcaag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gcctggcctg   7200
caggcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggaaa catcggcgaa acattaggcg aaaagtggaa gagtagattg   7620
aacgctctcg gtaagtctga attccaaatc tacaagaaat ccgggataca agaagttgat   7680
agaacactcg caaaagaggg aatcaaaaga ggcgaaaccg atcatcacgc cgttagcaga   7740
gggtccgcta aacttagatg gttcgtcgaa cgtaacatgg tgacacccga aggtaaggta   7800
gtcgatctcg gatgtggccg cggagggtgg tcatactatt gtggcggatt gaagaatgta   7860
cgcgaagtga aaggcctaac gaaaggcgga cccggacacg aggaaccaat cccaatgagt   7920
acatacggat ggaatctagt gagactgcaa tccggcgttg acgttttctt catacctccc   7980
gaaaagtgcg atacactgtt atgtgacatc ggcgaatcta gtcccaatcc gacagtcgaa   8040
gccggaagaa cacttagggt gcttaaccta gtcgagaatt ggttgaacaa caatacgcaa   8100
ttttgtataa aggtgcttaa cccatatatg ccaagcgtaa tcgaaaaaat ggaagcactg   8160
caacgtaagt acggaggggc attagtgaga aatcccctat cacgtaacag tacacacgaa   8220
atgtattggg tgtcaaacgc atccggaaac atagtgtcaa gcgtaaacat gataagcaga   8280
atgctaatca atagattcac aatgcgatac aaaaaagcga catacgaacc ggacgttgat   8340
ctcggaagcg gaacacgtaa tatcggaatc gaaagcgaaa ttccgaatct ggacataatc   8400
ggaaagagaa tcgaaaagat taagcaagag cacgaaacca gttggcatta cgatcaggac   8460
catccataca aaacatgggc ataccacggg tcatacgaaa ctaagcaaac cggatccgct   8520
agttcaatgg tgaacggagt ggttagacta ctaacgaaac cttgggacgt agtgccaatg   8580
```

-continued

```
gtgacacaaa tggcaatgac cgatacaaca ccattcggac agcagcgcgt attcaaagag   8640
aaggtcgata cgagaacaca ggaaccaaaa gagggaacga aaaaactgat gaagattact   8700
gccgaatggt tatggaaaga gttagggaaa aaaaagactc ccagaatgtg tacgagagag   8760
gaattcacac gaaaagtgag atcaaacgca gcactcggag caatattcac agacgaaaac   8820
aaatggaaat ccgcacgcga agccgttgag gacagtagat tttgggagtt agtcgacaaa   8880
gagagaaatc tgcatctcga agggaaatgc gaaacatgcg tttacaatat gatgggtaag   8940
agagagaaaa agttaggcga attcggaaag gctaaggggt caagggcaat ttggtatatg   9000
tggttagggg ctagatttct cgaatttgaa gccctaggat tccttaacga agaccattgg   9060
tttagcagag agaatagtct atccggagtc gaaggcgaag ggttacacaa actagggtat   9120
atactgagag acgtctcgaa aaaagaggga ggcgcaatgt acgccgacga tacagccgga   9180
tgggacacta ggattacact cgaagatctg aaaaacgaag agatggttac gaaccatatg   9240
gaaggcgaac acaaaaaact agccgaagcc atattcaaac taacatacca aaacaaagtg   9300
gttagggtgc aacgaccaac acctagagga accgttatgg acataatatc gagaagggac   9360
caacgaggat ccggacaagt cggaacatac ggattgaaca cttttacgaa tatggaagcc   9420
caactgatta ggcaaatgga aggcgaagga gtgttcaaat caatccaaca cctaacgatt   9480
accgaagaga ttgccgttca gaattggtta gctagagtgg gacgcgaacg gttaagcaga   9540
atggcaatat ccggagacga ttgcgtagtg aaaccattgg acgatagatt cgcaagcgca   9600
ctaaccgcat tgaacgatat gggtaagatt agaaaggaca tacagcaatg ggaaccatca   9660
agggggtgga acgattggac acaagtgcca ttctgttcac atcattttca cgagttgatt   9720
atgaaagacg gaagggtgtt agtggtgcca tgtagaaacc aagacgaatt gatcggaagg   9780
gcacgtatat cgcaaggggc cggatggtca cttagggaaa cagcatgttt agggaaatca   9840
tacgctcaaa tgtggtcact gatgtatttc catagaaggg accttagatt ggcagcaaac   9900
gcaatttgtt ccgccgtacc atcacattgg gtgccaacat cacgtacgac atggtcaata   9960
cacgctaagc acgaatggat gacaaccgaa gacatgctaa ccgtttggaa tagggtttgg  10020
atacaagaga atccatggat ggaagacaaa acacccgtcg aaagttggga ggaaattcca  10080
tacctcggta agagagagga ccaatggtgt ggatcgctaa tcgggttgac tagcagagca  10140
acatgggcaa aaaacataca agccgcaatc aatcaggtta ggtcactaat cggaaacgaa  10200
gagtatactg actatatgcc atcaatgaaa agattcagac gcgaagagga ggaagccgga  10260
gtgttgtggt agaaagcaaa actaacatga aacaaggcta gaagtcaggt cggattaagc  10320
catagtacgg aaaaaactat gctacctgtg agccccgtcc aaggacgtta aaagaagtca  10380
ggccatcata aatgccatag cttgagtaaa ctatgcagcc tgtagctcca cctgagaagg  10440
tgtaaaaaat ccgggaggcc acaaaccatg gaagctgtac gcatggcgta gtggactagc  10500
ggttagagga gacccctccc ttacaaatcg cagcaacaat gggggcccaa ggcgagatga  10560
agctgtagtc tcgctggaag gactagaggt tagaggagac ccccccgaaa caaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

ATTENUATED VIRUS HAVING MULTIPLE HOSTS

CROSS REFERENCE TO RELATED APPLICATIONS

This application claims priority to U.S. Application No. 62/046,565 filed Sep. 5, 2014, and U.S. Application No. 62/050,638 filed Sep. 15, 2014, which are incorporated herein by reference in their entireties.

FEDERAL FUNDING

This invention was made with government support under Grant Nos. AI07521901 and GM098400 awarded by the National Institute of Health. The government has certain rights in the invention.

COPYRIGHT NOTICE

A portion of the disclosure of this patent document contains material which is subject to copyright protection. The copyright owner has no objection to the facsimile reproduction by anyone of the patent document or patent disclosure as it appears in the Patent and Trademark Office patent file or records, but otherwise reserves all copyright rights whatsoever.

FIELD OF THE INVENTION

The present invention provides attenuated viruses, methods for making attenuated viruses, and vaccine compositions comprising one or more attenuated viruses, wherein the attenuated virus comprises a modified viral genome containing a plurality of nucleotide substitutions that result in the rearrangement of codons of one or more virus protein encoding sequences and changes in codon pair bias compared to one or more viral hosts. The attenuated viruses enable production of improved vaccines and are used to elicit protective immune response.

BACKGROUND OF THE INVENTION

Viruses that infect multiple phylogenetically distant hosts, for example hosts from different kingdoms, phyla, or classes, must accommodate the differences in the hosts so that the virus can efficiently replicate in hosts with different biochemical and molecular processes. These host differences include, for example, thermoregulation, protein glycosylation patterns, biochemical features of cell membranes, and CpG dinucleotide frequencies. Arboviruses, for example, have the ability to infect vertebrate and arthropod hosts.

The term arbovirus (arthropod-borne virus) applies to any virus that is transmitted to humans and/or other vertebrates by certain species of blood-feeding arthropods, chiefly insects (flies and mosquitoes) and arachnids (ticks). Families in the current classification system that have some arbovirus members include Bunyaviridae (comprising the bunyaviruses, phleboviruses, nairoviruses, and hantaviruses), Flaviviridae (comprising only the flaviviruses), Reoviridae (comprising the coltiviruses and orbiviruses), and Togaviridae (comprising the alphaviruses). Birds are often reservoirs for arboviruses, which are transmitted by mosquitoes to horses, other domestic animals, and humans. Certain arboviruses are transmissible by humans, including dengue fever, yellow fever, and chikungunya disease, which can be transmitted from person to person via mosquitoes.

Dengue virus (DENV) is an enveloped, plus stranded RNA arbovirus (genome ~11 kb) of the genus *Flavivirus* of the Flaviviridae family. DENV is primarily transmitted by the urban-adapted *Aedes aegypti* mosquito vector that has become widely distributed in tropical and subtropical regions. The diseases resulting from DENV infection include self-limiting dengue fever (DF), life-threatening dengue shock syndrome (DSS), and dengue hemorrhagic fever (DHF) characterized by increased vascular permeability and thrombo-cytopenia. DENV infections are one of the leading causes of arthropod-borne human diseases in the world. Each year there is an estimated 50-200 million DENV infections world-wide, resulting in 500,000 cases of DHF/DSS, and over 20,000 deaths, with 3.6 billion people at risk.

There are five antigenically distinct serotypes of DENV. Infection with one serotype induces immunity against that serotype and some degree of cross-protection against the other serotypes. However, the cross-protective immunity typically persists only for a relatively short time. Also, cross-reactive antibodies may bind to, but not neutralize other serotypes, leading to more severe secondary infections. An effective dengue vaccine would preferably be protective against all known serotypes. Currently, there are no marketable vaccines available capable of preventing human infection by any of the DENV serotypes.

Codon pair preference, or codon pair bias, refers to a phenomenon in which certain pairs of adjacent codons are used more frequently or less frequently in a particular host than expected after accounting for the frequency of usage of the individual codons (Gutman & Hatfield, 1989; Moura et al., 2007; Coleman et al., 2008). Every codon pair can be assigned a codon pair score (CPS), which is the natural logarithm of the ratio of the observed frequency of the codon pair to the expected frequency of the codon pair (i.e., CPS=ln(Observed/Expected) (Coleman et al., 2008).

SUMMARY OF THE INVENTION

In one aspect the invention provides an attenuated virus containing a viral genome having one or more modified virus protein-encoding sequences wherein the codon pair bias, relative to a first host, of at least one virus protein-encoding sequence is less than the codon pair bias of the parent nucleic acid sequence from which it is derived, and wherein the codon pair bias of the one or more modified virus protein-encoding sequences is not substantially reduced relative to that of a second host. In one embodiment, the codon pair bias of the one or more modified virus protein-encoding sequences in the attenuated virus is reduced relative to the first host by at least 0.05, at least 0.1, at least 0.2, at least 0.3, or at least 0.4. In a further embodiment, the codon pair bias of the one or more modified virus protein-encoding sequences is within 0.002, 0.005, 0.010, 0.020, or 0.050 of the parent nucleic acid from which it is derived relative to the second host. In one embodiment, the codon pair bias of the one or more modified virus protein-encoding sequences is reduced relative to the first host by codon rearrangement of the parent nucleic acid without substantially changing the codon usage.

In another aspect, the invention provides an attenuated virus comprising a viral genome having one or more modified virus protein-encoding sequences wherein the codon pair bias, relative to a first host and a second host, of at least one virus protein-encoding sequence is less than the codon pair bias of the parent nucleic acid from which it is derived. In one embodiment, the codon pair bias of the one or more modified virus protein-encoding sequences is reduced relative to the first host and second host independently by at least 0.05, at least 0.1, at least 0.2, at least 0.3, or at least 0.4.

In one aspect, the invention provides a method of making an attenuated virus genome comprising the steps: (a) obtaining an virus protein-encoding sequence; (b) rearranging synonymous codons of the protein-encoding sequence to obtain a modified protein-encoding sequence that (i) encodes the same amino acid sequence as the unrearranged protein-encoding sequence, (ii) has a reduced codon pair bias relative to a first host compared to the protein-encoding nucleotide sequence, (iii) has a substantially similar codon pair bias relative to a second host compared to the unrearranged nucleotide sequence; and (c) substituting all or part of the modified nucleotide sequence into the unrearranged genome of a parent virus. In one embodiment, the codon pair bias of the modified protein encoding sequence relative to the first host is reduced by at least 0.05, at least 0.1, at least 0.2, at least 0.3, or at least 0.4 compared to the unrearranged protein encoding nucleotide sequence. In one embodiment, the codon pair bias of the modified protein encoding sequence relative to the second host is within 0.002, 0.005, 0.010, 0.020, or 0.050 of the unrearranged nucleotide sequence. In one embodiment, an attenuated virus is made by inserting the attenuated viral genome into a cell line.

In another aspect, the invention provides a method of making an attenuated virus genome comprising the steps: (a) obtaining an virus protein-encoding sequence; (b) rearranging synonymous codons of the protein-encoding sequence to obtain a modified protein-encoding sequence that (i) encodes the same amino acid sequence as the unrearranged protein-encoding sequence, (ii) has a reduced codon pair bias relative to a first host compared to the protein-encoding nucleotide sequence, (iii) has a substantially reduced codon pair bias relative to a second host compared to the unrearranged nucleotide sequence; and (c) substituting all or part of the modified nucleotide sequence into the unrearranged genome of a parent virus. In one embodiment, the codon pair bias of the modified protein encoding sequence relative to the first host and second host is independently reduced by at least 0.05, at least 0.1, at least 0.2, at least 0.3, or at least 0.4 compared to the unrearranged protein encoding nucleotide sequence. In one embodiment, an attenuated virus is made by inserting the attenuated viral genome into a cell line.

In one embodiment of the invention, the first host is a vertebrate. In a further embodiment the first host in a mammal. In a further embodiment the first host is a human. In one embodiment, the second host is an arthropod. In further embodiment the second host is an arachnid. In one embodiment the second host is a tick. In one embodiment the second host is an insect. In one embodiment the second host is a mosquito.

In one embodiment, the virus is attenuated in the first host, but replicates efficiently in the second host and cell lines derived from the second host. In one embodiment, the codon pair bias of the one or more modified virus protein-encoding sequences is increased relative to the second host.

In one embodiment, the attenuated virus is an arbovirus. In a further embodiment, the attenuated arbovirus is selected from the group consisting of Bunyaviridae (comprising the bunyaviruses, phleboviruses, nairoviruses, and hantaviruses), Flaviviridae (comprising only the flaviviruses), Reoviridae (comprising the coltiviruses and orbiviruses), and Togaviridae (comprising the alphaviruses). In one embodiment, the attenuated virus is a flavavirus. In one embodiment, the attenuated virus is a dengue virus.

In one embodiment, the one or more modified virus protein-encoding sequences is derived from the nucleic acid sequence encoding the dengue virus protein-encoding sequence, or a portion thereof, selected from one or more of the group consisting of C; prM; E; NS1; 2A; 2B; NS3; 4A; 4B, and NS5. In one embodiment, the modified virus protein-encoding sequence is derived from the nucleic acid sequence encoding the E structural glycoprotein. In one embodiment, the modified virus protein-encoding sequence is derived from the nucleic acid sequence encoding the NS3 multi-functional protease. In one embodiment, the modified virus protein-encoding sequence is derived from the nucleic acid sequence encoding the NS5 multifunctional RNA polymerase.

In one aspect, the invention provides a vaccine composition for inducing a protective immune response in a subject, wherein the vaccine composition comprises an attenuated virus described herein. In one embodiment, the vaccine composition induces a protective immune response in a subject comprising an attenuated arbovirus described herein, wherein the protective immune response is against one or more Dengue virus serotypes selected from the group consisting of dengue virus serotypes 1 to 5. In one aspect the invention provides a method of eliciting a protective immune response in a subject comprising administering to the subject a prophylactically or therapeutically effective dose of the vaccine composition comprising an attenuated virus as described herein.

DETAILED DESCRIPTION OF THE INVENTION

Figure 1:
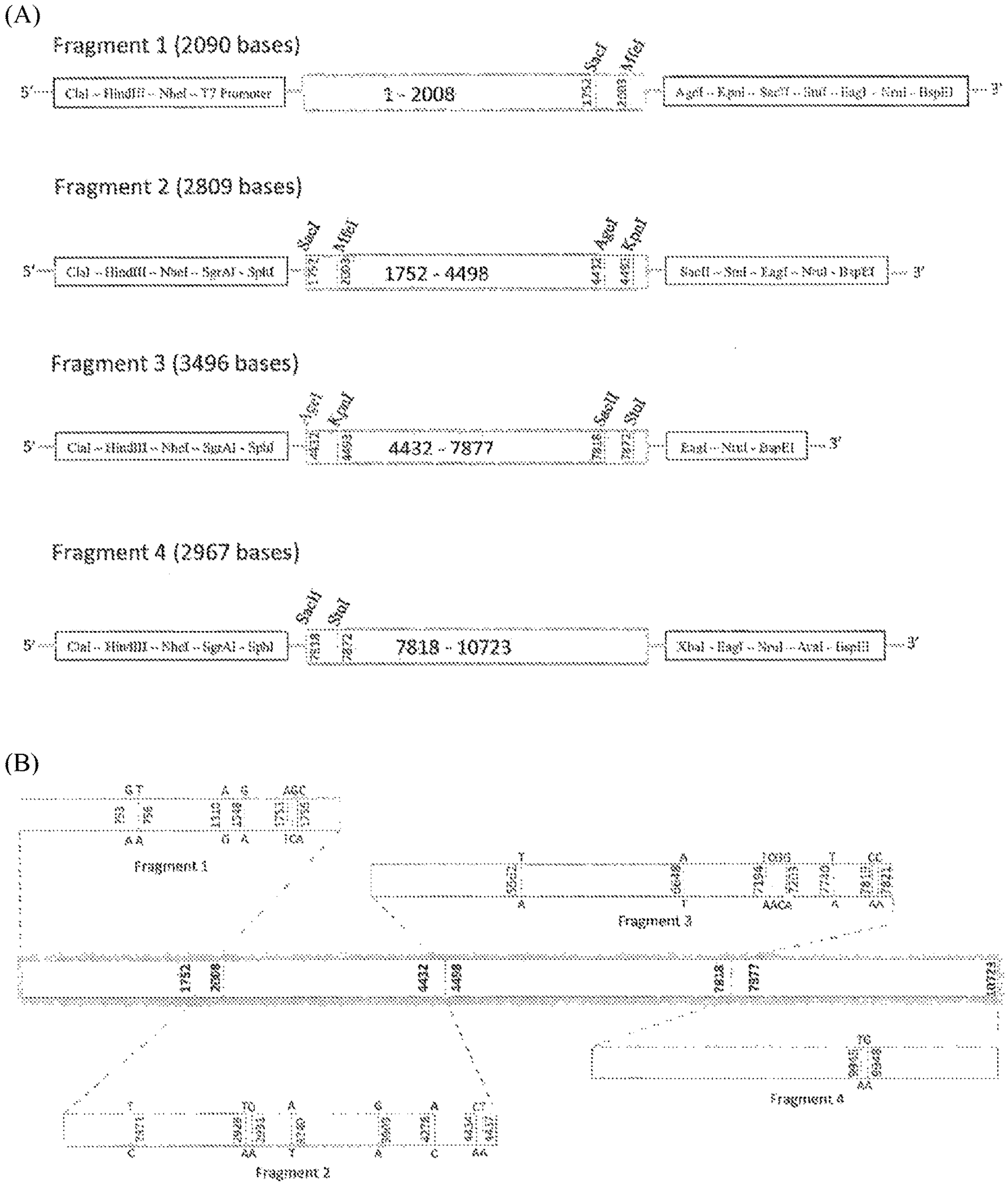
FIG. 1. Construction of a synthetic wild-type dengue serotype 2 virus. (A) A synthetic wild-type DENV-2 virus was designed based on strain 16681 genome (Accession# U87411) and divided into four fragments incorporating 26 silent mutations (listed in Table 4). Fragment 1 contained an upstream T7 promoter with no extraneous 5' G nt inserted between the T7 promoter and the 5'-terminal A nt of the genomic cDNA. Each fragment was designed with different sets of restriction sites at the 5' and 3' ends to facilitate ligation, synthesized by GenScript, and placed into a high-copy pUC57 plasmid. (B) To construct full-length DENV-2 genome, each fragment was ligated into the low-copy pBR322 plasmid in the following order using specified restriction enzymes: Fragment 4 (AvaI/SphI), Fragment 3 (ClaI/StuI), Fragment 2 (NheI/KpnI), and Fragment 1 (ClaI/SacI).

Arboviruses exhibit life cycles that involve both vertebrates and arthropods. In order to infect and replicate in these two very different types of hosts, the virus must be able to adapt to growth conditions that are very different, including temperature, host factors, cell membrane thickness and composition, and even differences in genome synonymous codon usage and codon pair bias. All species have preferences in the ways they encode proteins in nucleic acids and then translate them. Provided the degeneracy of the genetic code, different organisms have evolved diverging preferences for encoding proteins reflected by differences in codon bias (or codon usage) and codon pair bias (CPB). CPB is the preferential use of certain codon pairings to encode adjacent amino acids compared to what would be expected based on the codon usage of each of the two synonymous codons encoding the amino acid pair. WO 08/121992, which is incorporated by reference, provides a description of codon-pair bias.

It has been discovered that CPB diverges dramatically with increasing evolutionary distance such as between mammals and insects. For example, adjacent codon pairs under- or over-represented in humans tend to be under- or over-represented in other mammals, and adjacent codon pairs under- or over-represented in *Aedes aegypti* (an insect vector for certain arboviruses) tend to be under- or over-represented in certain other insects, but there is little such similarity in codon pair preference between insects and mammals.

The present invention relates to attenuated viruses comprising a viral genome that has been engineered to contain one or more modified virus protein encoding sequences that have a codon pair bias that is less than the nucleic acid sequence from which it was derived relative to a first viral host, while not substantially reducing the codon pair bias of the modified sequence relative to a second host. In this embodiment, the virus is designed to be attenuated in one host while maintaining the virus's ability to grow efficiently in the second host.

In another embodiment, the invention relates to an attenuated virus comprising a viral genome that has been engineered to contain one or more modified virus protein-encoding sequences that have a codon pair bias that is less than the codon pair bias of the parent nucleic acid from which it is derived, relative to a first host and a second host. In this embodiment, the virus is designed to be attenuated in both hosts.

The invention utilizes the differences in codon-pair bias between phylogenetically distant organisms to (i) deoptimize a virus for growth in one host while optimizing (or leaving unchanged) growth in another host; (ii) deoptimize the virus for growth in both hosts; or (iii) optimize the virus for growth in both hosts. In one embodiment of the invention, the differences in codon-pair bias between insects and mammals is used to design and synthesize a live arbovirus (e.g., dengue virus) that is attenuated in a mammalian host, but replicates efficiently in insects and insect-derived cell lines. In another embodiment, an arbovirus is designed that is attenuated in both mammalian and insect hosts. The methods described herein can be applied to make other arboviruses besides dengue, that are attenuated in mammals or other vertebrate hosts, in a phylum-specific manner.

The present invention relates to the production of attenuated virus that can be used in vaccines to protect against viral infection and disease. Accordingly, the invention provides an attenuated virus, which comprises a modified viral genome containing nucleotide substitutions engineered in one or more virus protein encoding sequences, wherein the substitutions introduce a plurality of rearranged synonymous codons into the genome. In one embodiment, the order of existing codons is changed, as compared to a reference (e.g., a wild type) viral sequence, while maintaining the reference amino acid sequence. The change in codon order alters the occurrence of codon pairs, and consequently, alters codon pair bias relative to at least one viral host.

Most amino acids are encoded by more than one codon. See the genetic code in Table 1. Alanine, for example, is encoded by four codons: GCU, GCC, GCA, and GCG. Three amino acids (Leu, Ser, and Arg) are encoded by six different codons, while only Trp and Met have unique codons. "Synonymous" codons are codons that encode the same amino acid. Thus, for example, CUU, CUC, CUA, CUG, UUA, and UUG are synonymous codons that code for Leu. Synonymous codons are not used with equal frequency. In general, the most frequently used codons in a particular organism are those for which the cognate tRNA is abundant, and the use of these codons enhances the rate and/or accuracy of protein translation. Conversely, tRNAs for the rarely used codons are found at relatively low levels, and the use of rare codons is thought to reduce translation rate and/or accuracy. To replace a given codon in a nucleic acid by a synonymous but less frequently used codon is to substitute a "deoptimized" codon into the nucleic acid.

TABLE 1

| Genetic Code[a] | | | | | |
|---|---|---|---|---|---|
| | U | C | A | G | |
| U | Phe | Ser | Tyr | Cys | U |
| | Phe | Ser | Tyr | Cys | C |
| | Leu | Ser | STOP | STOP | A |
| | Leu | Ser | STOP | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

[a]The first nucleotide in each codon encoding a particular amino acid is shown in the left-most column; the second nucleotide is shown in the top row; and the third nucleotide is shown in the right-most column.

Codon Bias

As used herein, a "rare" codon is one of at least two synonymous codons encoding a particular amino acid that is present in an mRNA at a significantly lower frequency than the most frequently used codon for that amino acid. Thus, the rare codon may be present at about a 2-fold lower frequency than the most frequently used codon. Preferably, the rare codon is present in at least a 3-fold, more preferably at least a 5-fold, lower frequency than the most frequently used codon for the amino acid. Conversely, a "frequent" codon is one of at least two synonymous codons encoding a particular amino acid that is present in an mRNA at a significantly higher frequency than the least frequently used codon for that amino acid. The frequent codon may be present at about a 2-fold, preferably at least a 3-fold, more preferably at least a 5-fold, higher frequency than the least frequently used codon for the amino acid. For example, human genes use the leucine codon CTG 40% of the time, but use the synonymous CTA only 7% of the time (see Table 2). Thus, CTG is a frequent codon in humans, whereas CTA is a rare codon. Roughly consistent with these frequencies of usage, there are 6 copies in the human genome for the gene for the tRNA recognizing CTG, whereas there are only 2 copies of the gene for the tRNA recognizing CTA. Similarly, human genes use the frequent codons TCT and TCC for serine 18% and 22% of the time, respectively, but the rare codon TCG only 5% of the time. TCT and TCC are read, via wobble, by the same tRNA, which has 10 copies of its gene in the human genome, while TCG is read by a tRNA with only 4 copies. It is well known that those mRNAs that are very actively translated are strongly biased to use only the most frequent codons. This includes genes for ribosomal proteins and glycolytic enzymes. On the other hand, mRNAs for relatively non-abundant proteins may use the rare codons.

TABLE 2

Codon usage in *Homo sapiens* (source: http://www.kazusa.or.jp/codon/)

| Amino Acid | Codon | Number | /1000 | Fraction |
|---|---|---|---|---|
| Gly | GGG | 636457.00 | 16.45 | 0.25 |
| Gly | GGA | 637120.00 | 16.47 | 0.25 |
| Gly | GGT | 416131.00 | 10.76 | 0.16 |
| Gly | GGC | 862557.00 | 22.29 | 0.34 |
| Glu | GAG | 1532589.00 | 39.61 | 0.58 |
| Glu | GAA | 1116000.00 | 28.84 | 0.42 |
| Asp | GAT | 842504.00 | 21.78 | 0.46 |
| Asp | GAC | 973377.00 | 25.16 | 0.54 |
| Val | GTG | 1091853.00 | 28.22 | 0.46 |
| Val | GTA | 273515.00 | 7.07 | 0.12 |
| Val | GTT | 426252.00 | 11.02 | 0.18 |
| Val | GTC | 562086.00 | 14.53 | 0.24 |
| Ala | GCG | 286975.00 | 7.42 | 0.11 |
| Ala | GCA | 614754.00 | 15.89 | 0.23 |
| Ala | GCT | 715079.00 | 18.48 | 0.27 |
| Ala | GCC | 1079491.00 | 27.90 | 0.40 |
| Arg | AGG | 461676.00 | 11.93 | 0.21 |
| Arg | AGA | 466435.00 | 12.06 | 0.21 |

TABLE 2-continued

Codon usage in *Homo sapiens* (source: http://www.kazusa.or.jp/codon/)

| Amino Acid | Codon | Number | /1000 | Fraction |
|---|---|---|---|---|
| Ser | AGT | 469641.00 | 12.14 | 0.15 |
| Ser | AGC | 753597.00 | 19.48 | 0.24 |
| Lys | AAG | 1236148.00 | 31.95 | 0.57 |
| Lys | AAA | 940312.00 | 24.30 | 0.43 |
| Asn | AAT | 653566.00 | 16.89 | 0.47 |
| Asn | AAC | 739007.00 | 19.10 | 0.53 |
| Met | ATG | 853648.00 | 22.06 | 1.00 |
| Ile | ATA | 288118.00 | 7.45 | 0.17 |
| Ile | ATT | 615699.00 | 15.91 | 0.36 |
| Ile | ATC | 808306.00 | 20.89 | 0.47 |
| Thr | ACG | 234532.00 | 6.06 | 0.11 |
| Thr | ACA | 580580.00 | 15.01 | 0.28 |
| Thr | ACT | 506277.00 | 13.09 | 0.25 |
| Thr | ACC | 732313.00 | 18.93 | 0.36 |
| Trp | TGG | 510256.00 | 13.19 | 1.00 |
| End | TGA | 59528.00 | 1.54 | 0.47 |
| Cys | TGT | 407020.00 | 10.52 | 0.45 |
| Cys | TGC | 487907.00 | 12.61 | 0.55 |
| End | TAG | 30104.00 | 0.78 | 0.24 |
| End | TAA | 38222.00 | 0.99 | 0.30 |
| Tyr | TAT | 470083.00 | 12.15 | 0.44 |
| Tyr | TAC | 592163.00 | 15.30 | 0.56 |
| Leu | TTG | 498920.00 | 12.89 | 0.13 |
| Leu | TTA | 294684.00 | 7.62 | 0.08 |
| Phe | TTT | 676381.00 | 17.48 | 0.46 |
| Phe | TTC | 789374.00 | 20.40 | 0.54 |
| Ser | TCG | 171428.00 | 4.43 | 0.05 |
| Ser | TCA | 471469.00 | 12.19 | 0.15 |
| Ser | TCT | 585967.00 | 15.14 | 0.19 |
| Ser | TCC | 684663.00 | 17.70 | 0.22 |
| Arg | CGG | 443753.00 | 11.47 | 0.20 |
| Arg | CGA | 239573.00 | 6.19 | 0.11 |
| Arg | CGT | 176691.00 | 4.57 | 0.08 |
| Arg | CGC | 405748.00 | 10.49 | 0.18 |
| Gln | CAG | 1323614.00 | 34.21 | 0.74 |
| Gln | CAA | 473648.00 | 12.24 | 0.26 |
| His | CAT | 419726.00 | 10.85 | 0.42 |
| His | CAC | 583620.00 | 15.08 | 0.58 |
| Leu | CTG | 1539118.00 | 39.78 | 0.40 |
| Leu | CTA | 276799.00 | 7.15 | 0.07 |
| Leu | CTT | 508151.00 | 13.13 | 0.13 |
| Leu | CTC | 759527.00 | 19.63 | 0.20 |
| Pro | CCG | 268884.00 | 6.95 | 0.11 |
| Pro | CCA | 653281.00 | 16.88 | 0.28 |
| Pro | CCT | 676401.00 | 17.48 | 0.29 |
| Pro | CCC | 767793.00 | 19.84 | 0.32 |

The propensity for highly expressed genes to use frequent codons is called "codon bias." A gene for a ribosomal protein might use only the 20 to 25 most frequent of the 61 codons, and have a high codon bias (a codon bias close to 1), while a poorly expressed gene might use all 61 codons, and have little or no codon bias (a codon bias close to 0). It is thought that the frequently used codons are codons where larger amounts of the cognate tRNA are expressed, and that use of these codons allows translation to proceed more rapidly, or more accurately, or both. The PV capsid protein is very actively translated, and has a high codon bias.

Codon Pair Bias

In addition to codon bias, a given organism has a preference for the nearest codon neighbor of a given codon, referred to as bias in codon pair utilization. A change in codon pair bias, without changing the existing codons, can influence the rate of protein synthesis and production of a protein.

Codon pair bias may be illustrated by considering the amino acid pair Ala-Glu, which can be encoded by 8 different codon pairs. If no factors other than the frequency of each individual codon (as shown in Table 2) are responsible for the frequency of the codon pair, the expected frequency of each of the 8 encodings can be calculated by multiplying the frequencies of the two relevant codons. For example, by this calculation in humans the codon pair GCA-GAA would be expected to occur at a frequency of 0.097 out of all Ala-Glu coding pairs (0.23×0.42; based on the frequencies in Table 2). In order to relate the expected (hypothetical) frequency of each codon pair to the actually observed frequency in the human genome the Consensus CDS (CCDS) database of consistently annotated human coding regions, containing a total of 14,795 human genes, was used. Using this set of genes, the frequencies of codon usage were re-calculated by dividing the number of occurrences of a codon by the number of all synonymous codons coding for the same amino acid. As expected the frequencies correlated closely with previously published ones such as the ones given in Table 2. Slight frequency variations are possibly due to an oversampling effect in the data provided by the codon usage database at Kazusa DNA Research Institute (http://www.kazusa.or.jp/codon/codon.html) where 84949 human coding sequences were included in the calculation (far more than the actual number of human genes). The codon frequencies thus calculated were then used to calculate the expected codon-pair frequencies by first multiplying the frequencies of the two relevant codons with each other (see Table 3, expected frequency), and then multiplying this result with the observed frequency (in the entire CCDS data set) with which the amino acid pair encoded by the codon pair in question occurs. In the example of codon pair GCA-GAA, this second calculation gives an expected frequency of 0.098 (compared to 0.97 in the first calculation using the Kazusa dataset). Finally, the actual codon pair frequencies as observed in a set of 14,795 human genes was determined by counting the total number of occurrences of each codon pair in the set and dividing it by the number of all synonymous coding pairs in the set coding for the same amino acid pair (Table 3; observed frequency). Frequency and observed/expected values for the complete set of 3721 ($61^2$) codon pairs, based on the set of 14,795 human genes, are provided as Supplemental Table 1 in U.S. Pub. No. US2010/0209454 (Ser. No. 12/594,173) incorporated herein by reference.

TABLE 3

Codon Pair Scores Exemplified by the Amino Acid Pair Ala-Glu

| amino acid pair | codon pair | expected frequency | observed frequency | obs/exp ratio |
|---|---|---|---|---|
| AE | GCAGAA | 0.098 | 0.163 | 1.65 |
| AE | GCAGAG | 0.132 | 0.198 | 1.51 |
| AE | GCCGAA | 0.171 | 0.031 | 0.18 |
| AE | GCCGAG | 0.229 | 0.142 | 0.62 |
| AE | GCGGAA | 0.046 | 0.027 | 0.57 |
| AE | GCGGAG | 0.062 | 0.089 | 1.44 |
| AE | GCTGAA | 0.112 | 0.145 | 1.29 |
| AE | GCTGAG | 0.150 | 0.206 | 1.37 |
| Total | | 1.000 | 1.000 | |

If the ratio of observed frequency/expected frequency of the codon pair is greater than one, the codon pair is said to be overrepresented. If the ratio is smaller than one, it is said to be underrepresented. In Table 3, the codon pair GCA-GAA is overrepresented 1.65 fold while the coding pair GCC-GAA is more than 5-fold underrepresented.

Many other codon pairs show very strong bias in humans; some pairs are under-represented, while other pairs are over-represented. For instance, the codon pairs GCCGAA (AlaGlu) and GATCTG (AspLeu) are three- to six-fold under-represented in humans (the preferred pairs being GCAGAG and GACCTG, respectively), while the codon pairs GCCAAG (AlaLys) and AATGAA (AsnGlu) are about two-fold over-represented in humans. It is noteworthy that codon pair bias has nothing to do with the frequency of pairs of amino acids, nor with the frequency of individual codons. For instance, the under-represented pair GATCTG (AspLeu) happens to use the most frequent Leu codon, (CTG).

It has been discovered that codon pair bias diverges dramatically with increasing evolutionary distance such as between mammals and insects. For example, adjacent codon pairs under- or over-represented in humans tend to be under- or over-represented in other mammals, and adjacent codon pairs under- or over-represented in *Aedes aegypti* (an insect vector for certain arboviruses) tend to be under- or over-represented in certain other insects, but there is little such similarity between insects and mammals. The analysis disclosed herein revealed that codon pair preferences in insects and mammals are very different and almost uncorrelated with each other (compare FIG. 4A with FIG. 4B). For example, in mammals the CPS of GCG GGC (Ala Gly) is +0.655, whereas in insects it is −0.651; in contrast, the CPS of CTT CCC (Leu Pro) in mammals is −0.021, whereas in insects it is +0.615. A negative codon pair score denotes that the pair is under-represented (Coleman et al., 2008), suggesting that these pairs are unfavorable for the organism. Indeed; recoding a segment of poliovirus with under-represented codon pairs yielded a dead virus (Coleman et al., 2008) even though the receded region contained the exact same synonymous codons and translated into exactly the same protein.

Codon pair observed and expected values and codon pair scores for the complete set of 3721 codon pairs in mosquito are provided in Supplemental Table 1 and are available at http://www.pnas.org/content/suppl/2015/03/24/1502864112.DCSupplemental/pnas.1502864112. sd01.pdf.

As discussed more fully below, codon pair bias takes into account the score for each codon pair in a coding sequence averaged over the entire length of the coding sequence. Codon pair bias is determined by $$CPB = \sum_{i=1}^{k} \frac{CPSi}{k-1}.$$

Accordingly, similar codon pair bias for a coding sequence can be obtained, for example, by minimized codon pair scores over a subsequence or moderately diminished codon pair scores over the full length of the coding sequence.

Calculation of Codon Pair Bias.

Every individual codon pair of the possible 3721 non-"STOP" containing codon pairs (e.g., GTT-GCT) carries an assigned "codon pair score," or "CPS" that is specific for a given "training set" of genes in a particular organism. The CPS of a given codon pair is defined as the log ratio of the observed number of occurrences over the number that would have been expected in this set of genes (in this example the human genome). Determining the actual number of occurrences of a particular codon pair (or in other words the likelihood of a particular amino acid pair being encoded by a particular codon pair) is simply a matter of counting the actual number of occurrences of a codon pair in a particular set of coding sequences. Determining the expected number, however, requires additional calculations. The expected number is calculated so as to be independent of both amino acid frequency and codon bias similarly to Gutman and Hatfield (1989). That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome.

To perform these calculations within the human context, the most recent Consensus CDS (CCDS) database of consistently annotated human coding regions, containing a total of 14,795 genes, was used. This data set provided codon and codon pair, and thus amino acid and amino-acid pair frequencies on a genomic scale.

The paradigm of Federov et al. (2002), was used to further enhanced the approach of Gutman and Hatfield (1989). This allowed calculation of the expected frequency of a given codon pair independent of codon frequency and non-random associations of neighboring codons encoding a particular amino acid pair.

$$S(P_{ij}) = \ln\left(\frac{N_O(P_{ij})}{N_E(P_{ij})}\right) = \ln\left(\frac{N_O(P_{ij})}{F(C_i)F(C_j)N_O(X_{ij})}\right)$$

In the calculation, $P_{ij}$ is a codon pair occurring with a frequency of $N_O(P_{ij})$ in its synonymous group. $C_i$ and $C_j$ are the two codons comprising $P_{ij}$, occurring with frequencies $F(C_i)$ and $F(C_j)$ in their synonymous groups respectively. More explicitly, $F(C_i)$ is the frequency that corresponding amino acid $X_i$ is coded by codon $C_i$ throughout all coding regions and $F(C_i)=N_O(C_i)/N_O(X_i)$, where $N_O(C_i)$ and $N_O(X_i)$ are the observed number of occurrences of codon $C_i$ and amino acid $X_i$ respectively. $F(C_j)$ is calculated accordingly. Further, $N_O(X_{ij})$ is the number of occurrences of amino acid pair $X_{ij}$throughout all coding regions. The codon pair bias score $S(P_{ij})$ of $P_{ij}$ was calculated as the log-odds ratio of the observed frequency $N_o(P_{ij})$ over the expected number of occurrences of $N_e(P_{ij})$.

Using the formula above, it is then determined whether individual codon pairs in individual coding sequences are over- or under-represented when compared to the corresponding genomic $N_e(P_{ij})$ values that were calculated by using the entire human CCDS data set (or data set from another host). This calculation provides positive $S(P_{ij})$ score values for over-represented and negative values for under-represented codon pairs in the human coding regions.

The "combined" codon pair bias of an individual coding sequence is calculated by averaging all codon pair scores according to the following formula:

$$S(P_{ij}) = \sum_{i=1}^{k} \frac{S(Pij)l}{k-1}$$

The codon pair bias of an entire coding region is thus calculated by adding all of the individual codon pair scores comprising the region and dividing this sum by the length of the coding sequence.

Calculation of Codon Pair Bias, Implementation of Algorithm to Produce Codon Pair Deoptimized Sequences (Relative to a Single Host).

An algorithm was developed to quantify codon pair bias. Every possible individual codon pair was given a "codon pair score," or "CPS". CPS is defined as the natural log of the ratio of the observed over the expected number of occurrences of each codon pair over all coding regions in a particular organism.

$$CPS = \ln\left(\frac{F(AB)o}{\frac{F(A)\times F(B)}{F(X)\times F(Y)}\times F(XY)}\right)$$

Although the calculation of the observed occurrences of a particular codon pair is straightforward (the actual count within the gene set), the expected number of occurrences of a codon pair requires additional calculation. This expected number is calculated to be independent both of amino acid frequency and of codon bias, similar to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome.

Using these calculated CPSs, any coding region can then be rated as using over- or under-represented codon pairs by taking the average of the codon pair scores, thus giving a Codon Pair Bias (CPB) for the entire coding sequence.

$$CPB = \sum_{i=1}^{k} \frac{CPSi}{k-1}$$

Accordingly, similar codon pair bias for a coding sequence can be obtained, for example, by minimized codon pair scores over a subsequence or moderately diminished codon pair scores over the full length of the coding sequence.

Codon pair bias, which is a measure of codon pair usage, can be evaluated for a coding sequence, whether or not codon substitutions are made as described below. In addition to the above example of CPB relative to humans, CPB relative to other organisms can be calculated utilizing the reference genome sequence for that organism.

Virus Attenuation by Optimization/Deoptimization Codon Pair Bias Relative to Two Hosts The present invention utilizes the differences in codon pair bias between two viral hosts that are phlogenetically distinct to recode one or more virus protein-encoding sequences by manipulating the codon pair bias of the sequence(s) relative to the two hosts. The one or more virus protein-encoding sequences are recoded to (i) deoptimize the virus for growth in one host while optimizing (or leaving unchanged) growth in another host; (ii) deoptimize the virus for growth in both hosts; or (iii) optimize the virus for growth in both hosts. The methods of the present invention are used to generate one or more modified virus protein-encoding sequences wherein the codon pair bias, relative to a first host, is less than the codon pair bias of the parent nucleic acid from which it is derived (e.g., the wild-type sequence), and wherein the codon pair bias of the one or more modified virus protein-encoding sequences is not substantially reduced relative to that of a second host. The methods of the present invention are also used to generate one or more modified virus protein-encoding sequences wherein the codon pair bias, relative to both hosts, is less than the codon pair bias of the parent nucleic acid from which it is derived (e.g., the wild-type sequence).

In one embodiment, the virus comprises a protein encoding nucleic acid sequence that is recoded to deoptimize the sequence with respect to replication in a mammalian host or cell, while optimizing its replication properties in an insect host or cell. In another embodiment, a protein encoding nucleic acid sequence is recoded to deoptimize the sequence with respect to expression in a mammalian host of cell, and its replication properties in an insect host or cell are also deoptimized. Similarly, in other embodiments, protein encoding nucleic acid sequences can be recoded to maintain or optimize replication in a mammalian host or cell while deoptimizing, maintaining, or optimizing replication properties in an insect host or cell.

According to the invention, viruses can be described, by their replication properties. Maintaining replicative properties in a particular host means viral titers obtained for the recoded virus at levels similar to, e.g., within 2× or 5× of viral titers of the parent virus. Deoptimizing a virus with respect to a host means reducing viral titers by 5× or more, for example 10×, 50×, 100×, 500×, or 1000× or more. Likewise, optimizing a virus with respect to a host means increasing viral titers by 5× or more, for example 10×, 50×, 100×, 500×, or 1000× or more.

According to the invention, codon pair bias can be altered independently of codon usage. For example, in a protein encoding sequence of interest, codon pair bias can be altered simply by directed rearrangement of its codons. In particular, the same codons that appear in the parent sequence, which can be of varying frequency in the host organisms, are used in the altered sequence, but in different positions. In the simplest form, because the same codons are used as in the parent sequence, codon usage over the protein coding region being considered remains unchanged (as does the encoded amino acid sequence). Nevertheless, certain codons appear in new contexts, that is, preceded by and/or followed by codons that encode the same amino acid as in the parent sequence, but employing a different nucleotide triplet.

The rearrangement of a codon may result in two codon pairs that are both less frequent in a host than in the parent sequence. In practice, rearranging codons often results in a less frequent codon pair at one location and a more frequent pair at a second location. By judicious rearrangement of codons, the codon pair usage bias over a given length of coding sequence can be reduced relative to the parent sequence. Alternatively, the codons could be rearranged so as to produce a sequence that makes use of codon pairs which are more frequent in the host than in the parent sequence.

Codon pair bias is evaluated by considering each codon pair in turn, scoring each pair according to the frequency that the codon pair is observed in protein coding sequences of a host, and then determining the codon pair bias for the sequence, as disclosed herein. It will be appreciated that one can create many different sequences that have the same codon pair bias. Also, codon pair bias can be altered to a greater or lesser extent, depending on the way in which codons are rearranged. The codon pair bias of a coding sequence can be altered by recoding the entire coding sequence, or by recoding one or more subsequences. As used herein, "codon pair bias" is evaluated over the length of a coding sequence, even though only a portion of the sequence may be mutated. Because codon pairs are scored in the context of codon usage of the host organism, a codon pair bias value can be assigned to wild type viral sequences and mutant viral sequences. A virus can be attenuated by recoding all or portions of the protein encoding sequences of the virus so as to reduce its codon pair bias.

Codon pair bias is a quantitative property determined from codon pair usage of a host. Accordingly, absolute codon pair bias values may be determined for any given viral protein coding sequence for a given host. And a viral protein encoding sequence may have different absolute codon pair bias values relative to different hosts, in particular when the different hosts are phylogenetically distinct (for example the hosts are from different kingdoms phyla, or classes). Alternatively, relative changes in codon pair bias values can be determined that relate a deoptimized viral protein coding sequence to a "parent" sequence from which it is derived. As viruses come in a variety of types (i.e., types I to VII by the Baltimore classification), and natural (i.e., virulent) isolates of different viruses yield different values of absolute codon pair bias, it is relative changes in codon pair bias that are usually more relevant to determining desired levels of attenuation for a given host. Accordingly, the invention provides attenuated viruses and methods of making such, wherein the attenuated viruses comprise viral genomes in which one or more protein encoding nucleotide sequences have codon pair bias reduced by mutation. In viruses that encode only a single protein (i.e., a polyprotein), all or part of the polyprotein can be mutated to a desired degree to reduce codon pair bias, and all or a portion of the mutated sequence can be provided in a recombinant viral construct. For a virus that separately encodes multiple proteins, one can reduce the codon pair bias of all of the protein encoding sequences simultaneously, or select only one or a few of the protein encoding sequences for modification. The reduction in codon pair bias is determined over the length of a protein encoding sequences, and is at least about 0.05, or at least about 0.1, or at least about 0.15, or at least about 0.2, or at least about 0.3, or at least about 0.4. Depending on the virus, the absolute codon pair bias, based on codon pair usage of the host, can be about −0.05 or less, or about 0.1 or less, or about −0.15 or less, or about −0.2 or less, or about −0.3 or less, or about −0.4 or less.

Viruses of the invention can be described by shifts in codon-pair preference or codon pair bias. As describe herein, codon-pair score (CPS) and codon-pair bias (CPB) relate to the observed vs. expected frequency of adjacent codon pairs in a host. For viruses of the invention, which replicate in more than one host, CPS and CPB are evaluated independently for each host. Virus protein encoding nucleic acid sequences that are deoptimized for a particular host can have reduced CPB, in other words CPB values that are substantially more negative than the parent virus protein encoding sequence evaluated for that host. For example, the attenuated virus can have CPB scores that are at least, 0.05, at least 0.1, at least 0.2, at least 0.3, at least 0.4, from 0.5 to 0.1, from 0.1 to 0.2, from 0.2 to 0.3, from 0.3 to 0.4, or from 0.5 to 0.5 more negative than parent viruses evaluated for that host. According to the invention, a nucleic acid sequence may be deoptimized and have a CPB that is reduced for one host, without a substantial change in CPB for a second host. For example, the CPB with respect to the second host can be within 0.002, 0.005, 0.010, 0.020, or 0.050 of the parent virus with respect to the second host. The above values are not strict limitations on changes in CPB values, as effects on replication may vary depending on which coding sequences of the virus are modified. While in certain embodiments, changes in CPB compared to a parent virus result from rearrangement, or shuffling, of the parent virus codons, in other embodiments, the recoded virus can also contain synonymous codon substitutions and/or encode amino acid substitutions.

It will be apparent that codon pair bias can also be superimposed on other sequence variation. For example, a coding sequence can be altered to encode a protein or polypeptide which contains one or more amino acid changes and also has been recoded by shuffling synonymous codons in order to alter codon pair bias. Also, one may shuffle codons to maintain exactly the same codon usage profile in a codon pair bias reduced protein encoding sequence as in a parent protein encoding sequence. Alternatively, codon selection can result in an overall change in codon usage in a coding sequence.

According to the invention, viral attenuation can be accomplished by changes in codon pair bias as well as codon bias. Both deoptimized codon bias, and deoptimized codon pair bias, separately create non-viable viruses probably by causing inefficient translation of the recoded sequence. However, it is expected that adjusting codon pair bias is particularly advantageous. For example, attenuating a virus through codon bias generally requires elimination of common codons, and so the complexity of the nucleotide sequence is reduced. In contrast, codon pair bias reduction or minimization can be accomplished while maintaining far greater sequence diversity, and consequently greater control over nucleic acid secondary structure, annealing temperature, and other physical and biochemical properties. The work disclosed herein includes attenuated codon pair bias-reduced or -minimized sequences in which codons are shuffled, but the codon usage profile is unchanged or substantially unchanged.

During recoding, essential nucleic acid signals in the viral genome are preserved, but the efficiency of protein translation in one or both hosts is systematically reduced by deoptimizing codon pair bias. Other parameters may also be deoptimized such as codon bias, RNA secondary structure and CpG dinucleotide content, C+G content, translation frameshift sites, translation pause sites, or any combination thereof. This deoptimization may involve hundreds or thousands of changes, each with a small effect. Generally, deoptimization is performed to a point at which the virus can still be grown in some cell lines (including lines specifically engineered to be permissive for a particular virus), but where the virus is avirulent in one or more host. Such avirulent viruses are excellent candidates for either a killed or live vaccine since they encode exactly the same proteins as the fully virulent virus and accordingly provoke exactly the same immune response as the fully virulent virus. In addition, the present invention offers the prospect for fine tuning the level of attenuation in each host; that is, it provides the capacity to design synthetic viruses that are deoptimized to a roughly predictable extent in one or more hosts. Design, synthesis, and production of viral particles is achievable in a timeframe of weeks once the genome sequence is known, which has important advantages for the production of vaccines in potential emergencies. Furthermore, the attenuated viruses are expected to have virtually no potential to revert to virulence because of the extremely large numbers of deleterious nucleotide changes involved.

The extent and intensity of recoding of a virus can be varied depending on the length of the protein encoding nucleic acid, whether all or a portion can be recoded, and the desired reduction of codon pair bias. In an embodiment of the invention, a protein encoding sequence is modified over a length of at least about 100 nucleotides, or at least about 200 nucleotides, or at least about 300 nucleotides, or at least about 500 nucleotides, or at least about 1000 nucleotides.

A attenuated virus according to the present invention has been modified to reduce pathogenicity in one or more hosts. The attenuated virus has reduced virulence in one or more hosts, but can stimulate an immune response in a subject. Viral attenuation can be confirmed in ways that are well known to one of ordinary skill in the art. Non-limiting examples include plaque assays, growth measurements, and reduced lethality in test animals. The instant application demonstrates that the attenuated viruses are capable of inducing protective immune responses in a host.

The term "parent" virus or "parent" protein encoding sequence is used herein to refer to viral genomes and protein encoding sequences from which new sequences, which may be more or less attenuated, are derived. Parent viruses and sequences are usually "wild type" or "naturally occurring" prototypes or isolates of variants for which it is desired to obtain a more highly attenuated virus. However, parent viruses also include mutants specifically created or selected in the laboratory on the basis of real or perceived desirable properties. Accordingly, parent viruses that are candidates for attenuation include mutants of wild type or naturally occurring viruses that have deletions, insertions, amino acid substitutions and the like, and also include mutants which have codon substitutions. In one embodiment, such a parent sequence differs from a natural isolate by about 30 amino acids or fewer. In another embodiment, the parent sequence differs from a natural isolate by about 20 amino acids or fewer. In yet another embodiment, the parent sequence differs from a natural isolate by about 10 amino acids or fewer.

The description of a virus as having a first host and a second host is not meant to imply order of infection or any relative value of the two hosts. Rather, the use of the terms first host and second host identifies viral hosts that are phylogenetically distant and thus have sufficiently different codon pair preferences that the viral sequence can be manipulated to, for example, simultaneously favor one host over the other. In one embodiment the first host and second host are from different kingdoms. In another embodiment, the first host and second host are from different phyla. In another embodiment first host and second host are from different classes.

Algorithm to Produce Recoded Sequences with CPB Rebalanced Relative to Two Hosts.

As exemplified herein, a computer-based algorithm can be used to manipulate the codon pair bias of any coding region relative to two hosts. The algorithm has the ability to shuffle existing codons and to evaluate the resulting CPB relative to two hosts, and then to reshuffle the sequence, optionally locking in particularly "valuable" codon pairs. The algorithm also employs a form of "simulated annealing" so as not to get stuck in local minima. Other parameters, such as the free energy of folding of RNA, may optionally be under the control of the algorithm as well, in order to avoid creation of undesired secondary structures. The algorithm can be used to find a sequence with codon pair bias that is independently minimized, maximized, or substantially unchanged, relative to two unrelated hosts. In the event that such a sequence does not provide a viable virus, the algorithm can be adjusted to find sequences with reduced, but not minimized biases.

Choosing a random codon and swapping it with another randomly chosen synonymous codon, the heuristic works over a particular sequence in several hundred thousand iterations. If the codon change is "good", the change is retained, while if the change is "bad," it may still be retained, with a probability dependent on a specified "temperature" (hence the analogy to metallurgical annealing). Unlike the codon pair deoptimization for a single host described previously, in this case there is a non-trivial bi-criteria optimization problem, in which, for example, the cumulative score of codon pairs is minimized according to the human codon pair bias table, while not allowing the cumulative score according to the insect table to drift substantially. Combining both criteria into a single function:

$$\min(a*\text{human\_score}+b*\text{abs}(\text{insect\_score}-\text{insect\_score\_wt})^{c})$$

where a, b, and c are coefficients. By varying a, b, and c, one can, for example, control the importance of minimizing the human score (a), and limiting the variation of the insect score from wild-type (b and c). The same approach may be used to simultaneously reduce the codon pair score relative to both hosts to produce a virus that is attenuated in, for example, both humans and insects.

Sequence optimization/deoptimization relative to two hosts may be performed with or without the aid of a computer, using, for example, a gradient descent, or simulated annealing, or other minimization routine. An example of the procedure that rearranges codons present in a starting sequence can be represented by the following steps:

(1) Obtain parent (e.g., wild-type) viral genome sequence.

(2) Select protein encoding sequence(s) to target for attenuated design.

(3) Lock down known or conjectured DNA segments with non-coding functions.

(4) Select heuristic function coefficients to determine relative importance of minimizing CPB score relative to a first host versus keeping neutral CPB score relative to a second host; or alternatively minimizing CPB scores relative to a first host and relative to a second host.

(5) Perform random shuffle of at least two synonymous unlocked codon positions and calculate two codon-pair bias scores relative to a first and second host.

(6) Compute the resulting change in heuristic function (e.g., by simulated annealing) and keep or reject the synonymous codon shuffle.

(7) Repeat steps (5) and (6) for desired number of iterations.

In addition to the above steps, one or more of the following steps may be performed to generate a virus that has altered growth properties relative to at least one of two hosts:

(8) Inspect resulting design for excessive secondary structure and unwanted restriction site:

if yes->go to step (5) or correct the design by replacing problematic regions with wildtype sequences and go to step (9).

(9) Synthesize DNA sequence corresponding to virus design.

(10) Create viral construct and assess viral phenotype:

if too attenuated, prepare subclone construct and go to 10;

if insufficiently attenuated, go to 2.

Using the formulas above, a computer based algorithm was developed to manipulate the CPB of any coding region with respect to two hosts having divergent codon pair preferences while maintaining the original amino acid sequence. The algorithm has the ability to maintain the codon usage of the selected sequence (i.e. preserve the frequency of use of each existing codon) but "shuffle" the existing codons so that the CPB can be increased, decreased, or remain substantially unchanged relative to each of the two hosts. The algorithm uses simulated annealing, a mathematical process suitable for full-length optimization (Park, et al., 2004). Other parameters are also under the control of this algorithm; for instance, the free energy of the folding of the RNA. This free energy is maintained within a narrow range, to prevent large changes in secondary structure as a consequence of codon re-arrangement. The optimization process specifically excludes the creation of any regions with large secondary structures, such as hairpins or stem loops, which could otherwise arise in the customized RNA. Using this computer software the user simply needs to input the cDNA sequence of a given gene and the CPB of the gene can be customized as the experimenter sees fit.

Alternatively, one can devise a procedure which allows each pair of amino acids to be deoptimized by choosing a codon pair without a requirement that the codons be swapped out from elsewhere in the protein encoding sequence.

This invention provides a method of making an attenuated virus genome, the method comprising: (a) obtaining an virus protein-encoding sequence; (b) rearranging synonymous codons of the nucleotide sequences to obtain modified nucleotide sequences that (i) encodes the same amino acid sequence as the unrearranged nucleotide sequence, (ii) has a reduced codon pair bias relative to a first host compared to the unrearranged nucleotide sequence, (iii) has a substantially similar codon pair bias or a reduced codon pair bias relative to a second host compared to the unrearranged nucleotide sequence; and (c) substituting all or part of the modified nucleotide sequence into the unrearranged genome of a parent virus.

In certain embodiments of the instant methods, step (b) is guided by a computer-based algorithm described above that permits design of a viral genome by varying specified pattern sets of deoptimized codon distribution and/or deoptimized codon-pair distribution within preferred limits. The invention also provides a method wherein, the pattern sets alternatively or additionally comprise, density of deoptimized codons and deoptimized codon pairs, RNA secondary structure, CpG dinucleotide content, C+G content, overlapping coding frames, restriction site distribution, frameshift sites, or any combination thereof.

In one embodiments, the recoded viral protein encoding sequence is generated by de novo synthesis of DNA containing the synonymous codons and/or codon pairs.

Attenuated Arboviruses

Arboviruses, for example, exhibit life cycles that involve both vertebrates and arthropods as hosts. In order to infect and replicate in these two very different types of hosts, the virus must be able to adapt to growth conditions that are very different, including temperature, host factors, cell membrane thickness and composition, and even differences in genome synonymous codon usage and codon pair bias.

One aspect of the present invention involves "recoding" of arbovirus genomes including but not limited to DENV so as to alter or disrupt the finely balanced use of codon pairs that permits the virus to efficiently use both insect and mammalian translational machineries. In one embodiment, codon pairings are utilized that are similarly favorable as the wild-type virus for expression in insects (thus allowing for vaccine production in insect cell culture) while, at the same time, being detrimental for expression in human host (attenuation). In another embodiment, the disclosed technique can be used to produce arboviruses that are attenuated in both host as vaccine candidates.

In one embodiment, the attenuated virus of the present invention is an arbovirus. Families in the current classification system that have some arbovirus members include Bunyaviridae (comprising the bunyaviruses, phleboviruses, nairoviruses, and hantaviruses), Flaviviridae (comprising only the flaviviruses), Reoviridae (comprising the coltiviruses and orbiviruses), and Togaviridae (comprising the alphaviruses). Birds are often reservoirs for arboviruses, which are transmitted by mosquitoes to horses, other domestic animals, and humans. Certain arboviruses are transmissible by humans, including dengue fever, yellow fever, and chikungunya disease, which can be transmitted from person to person via mosquitoes.

In one embodiment of the invention the arbovirus is yellow fever virus, West Nile virus, dengue virus, chikungunya virus, African swine fever virus, Japanese encephalitis virus, Rift Valley fever virus, tick-borne encephalitis virus, Crimean-Congo hemorrhagic fever virus, Bunyamwera virus, California encephalitis virus, Jamestown Canyon virus, La Crosse encephalitis, Toscana virus, heartland virus, Kyasanur forest disease virus, Murray Valley encephalitis virus, St. Louis encephalitis virus, African horse sickness virus, bluetongue disease virus, equine encephalosis virus, banna virus, Coltivirus Colorado tick fever virus, Eastern equine encephalitis virus, Ross River virus, Venezuelan equine encephalitis virus, and Western equine encephalitis virus.

In one embodiment the arbovirus is dengue virus. There are four dengue virus serotypes (DENV 1-4) that commonly infect humans. A fifth DENV serotype has recently been reported in Malaysia, although only one human infection has been documented.

According to the invention, one or more virus protein-encoding nucleic acid sequences, or portions thereof, may be modified. In this regard, for example, dengue virus encodes several proteins in an open reading frame: C; prM; E; NS1; 2A; 2B; NS3; 4A; 4B, and NS5. DENV C is a capsid protein; the DENV E (envelope) protein is found on the viral surface and is important in the initial attachment of the viral particle to the host cell; the DENV prM (membrane) protein is important in the formation and maturation of the viral particle; DENV NS3 is a serine protease, as well as an RNA helicase and RTPase/NTPase; DENV NS5 is a 900 residue peptide with a methyltransferase domain at its N-terminal end and a RNA-dependent RNA polymerase (RdRp) at its C-terminal end; NS4B it is a small hydrophobic protein which may block phosphorylation of STAT1 and inhibit interferon signaling; NS5 inactivates and degrades STAT2.

The invention is exemplified by recoding of the E structural glycoprotein (SEQ ID NO:3, recoded E), NS3 multifunctional protease (SEQ ID NO:4, recoded NS3), and NS5 multifunctional RNA polymerase (SEQ ID NO:5, recoded NS5) of the DENV serotype 2 (strain 16681; SEQ ID NO:1). As exemplified, a DENV serotype 2 virus genome based on the 16681 strain was synthesized ab initio with 26 silent nucleotide changes to provide convenient restriction sites (SEQ ID NO:2) (referred to herein as "D2-syn" and also called D2SAM1). The growth characteristics of the synthesized virus in monkey and mosquito cells are indistinguishable from the 16681 strain. The virus genome was recoded in silico to produce three recoded open reading frames having strongly negative human codon pair scores compared to wild-type, but mosquito codon pair scores similar to wild-type.

Accordingly, the invention provides arboviruses adapted for use in vaccines, as well as methods of making and using such viruses. According to the invention, protein encoding sequences of the virus can be recoded to alter replication properties in one or more of its mammalian and insect hosts. In one embodiment, the virus comprises a protein encoding nucleic acid sequence that is recoded to deoptimize the sequence with respect to replication in a mammalian host or cell, while maintaining its replication properties in an insect host or cell. In one embodiment, the invention provides an arbovirus that is attenuated in a human, and can be produced at high titers in cells of a second, evolutionarily distant, host. For example, existing synonymous codons of an arbovirus are rearranged so as to replace existing adjacent codon pairs with pairs that are unfavorable in humans and favorable in insects.

Large-Scale DNA Assembly

In recent years, the plunging costs and increasing quality of oligonucleotide synthesis have made it practical to assemble large segments of DNA (at least up to about 10 kb) from synthetic oligonucleotides. Commercial vendors such as Blue Heron Biotechnology, Inc. (Bothwell, Wash.) (and also many others) currently synthesize, assemble, clone, sequence-verify, and deliver a large segment of synthetic DNA of known sequence for the relatively low price of about $1.50 per base. Thus, purchase of synthesized viral genomes from commercial suppliers is a convenient and cost-effective option, and prices continue to decrease rapidly. Furthermore, new methods of synthesizing and assembling very large DNA molecules at extremely low costs are emerging (Tian et al., 2004). The Church lab has pioneered a method that uses parallel synthesis of thousands of oligonucleotides (for instance, on photo-programmable microfluidics chips, or on microarrays available from Nimblegen Systems, Inc., Madison, Wis., or Agilent Technologies, Inc., Santa Clara, Calif.), followed by error reduction and assembly by overlap PCR. These methods have the potential to reduce the cost of synthetic large DNAs to less than 1 cent per base. The improved efficiency and accuracy, and rapidly declining cost, of large-scale DNA synthesis provides an impetus for the development and broad application of the creation of attenuated virus by the strategies disclosed herein.

Vaccine Compositions

The present invention provides a vaccine composition for inducing the production of neutralizing antibodies in a subject. In one embodiment, the present invention provides a vaccine composition for inducing a protective immune response in a subject comprising any of the attenuated viruses described herein and a pharmaceutically acceptable carrier. In one aspect of the invention the attenuated virus is an arbovirus. In a further embodiment the attenuated virus is a dengue virus. In one aspect of the invention, vaccine composition comprises an attenuated DENV and is affective at inducing protective immunity against one or more DENV serotypes. In one aspect, the vaccine composition comprises one or more DENV serotypes. In one embodiment, the attenuated arbovirus is a chimeric construct (see Caufour et al, 2001; Osorio et al., 2011; Durbin et al., 2011) used to develop a multivalent (e.g., tetravalent) vaccine.

In an embodiment of the invention, a vaccine composition is provided for inducing a protective immune response in a subject, wherein the vaccine composition comprises an arbovirus as set forth above. In an embodiment of the invention, the vaccine composition further comprises at least one adjuvant. The invention provides a method of eliciting a protective immune response in a subject comprising administering to the subject a prophylactically or therapeutically effective dose of a vaccine composition set forth above.

It should be understood that an attenuated virus of the invention, where used to elicit a protective immune response in a subject or to prevent a subject from becoming afflicted with a virus-associated disease, is administered to the subject in the form of a composition additionally comprising a pharmaceutically acceptable carrier. Pharmaceutically acceptable carriers are well known to those skilled in the art and include, but are not limited to, one or more of 0.01-0.1M and preferably 0.05M phosphate buffer, phosphate-buffered saline (PBS), or 0.9% saline. Such carriers also include aqueous or non-aqueous solutions, suspensions, and emulsions. Aqueous carriers include water, alcoholic/aqueous solutions, emulsions or suspensions, saline and buffered media. Examples of non-aqueous solvents are propylene glycol, polyethylene glycol, vegetable oils such as olive oil, and injectable organic esters such as ethyl oleate. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of C6 to C22 fatty acids or natural glycerides, and a propellant. Additional carriers such as lecithin may be included to facilitate intranasal delivery. Pharmaceutically acceptable carriers can further comprise minor amounts of auxiliary substances such as wetting or emulsifying agents, preservatives and other additives, such as, for example, antimicrobials, antioxidants and chelating agents, which enhance the shelf life and/or effectiveness of the active ingredients. The instant compositions can, as is well known in the art, be formulated so as to provide quick, sustained or delayed release of the active ingredient after administration to a subject.

In various embodiments of the instant vaccine composition, the attenuated virus (i) does not substantially alter the synthesis and processing of viral proteins in an infected cell; (ii) produces similar amounts of virions per infected cell as wild-type virus; and/or (iii) exhibits substantially lower virion-specific infectivity than wild-type virus. In further embodiments, the attenuated virus induces a substantially similar immune response in a host animal as the corresponding wt virus.

This invention also provides a modified host cell line specially isolated or engineered to be permissive for an attenuated virus that is inviable in a wild type host cell or otherwise not efficiently replicated in cell culture. Since the attenuated virus cannot grow in normal (wild type) host cells, it is dependent on the specific helper cell line for growth. This provides a very high level of safety for the generation of virus for vaccine production. Various embodiments of the instant modified cell line permit the growth of an attenuated virus, wherein the genome of said cell line has been altered to increase the number of genes encoding rare tRNAs.

In addition, the present invention provides a method for eliciting a protective immune response in a subject comprising administering to the subject a prophylactically or therapeutically effective dose of any of the vaccine compositions described herein. This invention also provides a method for preventing a subject from becoming afflicted with a virus-associated disease comprising administering to the subject a prophylactically effective dose of any of the instant vaccine compositions. In embodiments of the above methods, the subject has been exposed to a pathogenic virus. "Exposed" to a pathogenic virus means contact with the virus such that infection could result.

The invention further provides a method for delaying the onset, or slowing the rate of progression, of a virus-associated disease in a virus-infected subject comprising administering to the subject a therapeutically effective dose of any of the instant vaccine compositions.

As used herein, "administering" means delivering using any of the various methods and delivery systems known to those skilled in the art. Administering can be performed, for example, intraperitoneally, intracerebrally, intravenously, orally, transmucosally, subcutaneously, transdermally, intradermally, intramuscularly, topically, parenterally, via implant, intrathecally, intralymphatically, intralesionally, pericardially, or epidurally. An agent or composition may also be administered in an aerosol, such as for pulmonary and/or intranasal delivery. Administering may be performed, for example, once, a plurality of times, and/or over one or more extended periods.

Eliciting a protective immune response in a subject can be accomplished, for example, by administering a primary dose of a vaccine to a subject, followed after a suitable period of time by one or more subsequent administrations of the vaccine. A suitable period of time between administrations of the vaccine may readily be determined by one skilled in the art, and is usually on the order of several weeks to months. The present invention is not limited, however, to any particular method, route or frequency of administration.

A "subject" means any animal or artificially modified animal. Animals include, but are not limited to, humans, non-human primates, cows, horses, sheep, pigs, dogs, cats, rabbits, ferrets, rodents such as mice, rats and guinea pigs, and birds. In a preferred embodiment, the subject is a human.

A "prophylactically effective dose" is any amount of a vaccine that, when administered to a subject prone to viral infection or prone to affliction with a virus-associated disorder, induces in the subject an immune response that protects the subject from becoming infected by the virus or afflicted with the disorder. "Protecting" the subject means either reducing the likelihood of the subject's becoming infected with the virus, or lessening the likelihood of the disorder's onset in the subject, by at least two-fold, preferably at least ten-fold. For example, if a subject has a 1% chance of becoming infected with a virus, a two-fold reduction in the likelihood of the subject becoming infected with the virus would result in the subject having a 0.5% chance of becoming infected with the virus. Most preferably, a "prophylactically effective dose" induces in the subject an immune response that completely prevents the subject from becoming infected by the virus or prevents the onset of the disorder in the subject entirely.

As used herein, a "therapeutically effective dose" is any amount of a vaccine that, when administered to a subject afflicted with a disorder against which the vaccine is effective, induces in the subject an immune response that causes the subject to experience a reduction, remission or regression of the disorder and/or its symptoms. In preferred embodiments, recurrence of the disorder and/or its symptoms is prevented. In other preferred embodiments, the subject is cured of the disorder and/or its symptoms.

Certain embodiments of any of the instant immunization and therapeutic methods further comprise administering to the subject at least one adjuvant. An "adjuvant" shall mean any agent suitable for enhancing the immunogenicity of an antigen and boosting an immune response in a subject. Numerous adjuvants, including particulate adjuvants, suitable for use with both protein- and nucleic acid-based vaccines, and methods of combining adjuvants with antigens, are well known to those skilled in the art. Suitable adjuvants for nucleic acid based vaccines include, but are not limited to, Quil A, imiquimod, resiquimod, and interleukin-12 delivered in purified protein or nucleic acid form. Adjuvants suitable for use with protein immunization include, but are not limited to, alum, Freund's incomplete adjuvant (FIA), saponin, Quil A, and QS-21.

The invention also provides a kit for immunization of a subject with an attenuated virus of the invention. The kit comprises the attenuated virus, a pharmaceutically acceptable carrier, an applicator, and an instructional material for the use thereof. In further embodiments, the attenuated virus may be one or more poliovirus, one or more rhinovirus, one or more influenza virus, etc. More than one virus may be preferred where it is desirable to immunize a host against a number of different isolates of a particular virus. The invention includes other embodiments of kits that are known to those skilled in the art. The instructions can provide any information that is useful for directing the administration of the attenuated viruses.

Throughout this application, various publications, reference texts, textbooks, technical manuals, patents, and patent applications have been referred to. The teachings and disclosures of these publications, patents, patent applications and other documents in their entireties are hereby incorporated by reference into this application to more fully describe the state of the art to which the present invention pertains. However, the citation of a reference herein should not be construed as an acknowledgement that such reference is prior art to the present invention.

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. Detailed descriptions of conventional methods, such as those employed in the construction of recombinant plasmids, transfection of host cells with viral constructs, polymerase chain reaction (PCR), and immunological techniques can be obtained from numerous publications, including Sambrook et al. (1989) and Coligan et al. (1994). All references mentioned herein are incorporated in their entirety by reference into this application.

EXAMPLES

Example 1

Comparison of Codon Pair Bias Between Insects, Mammals, and Plants

Figure 3:
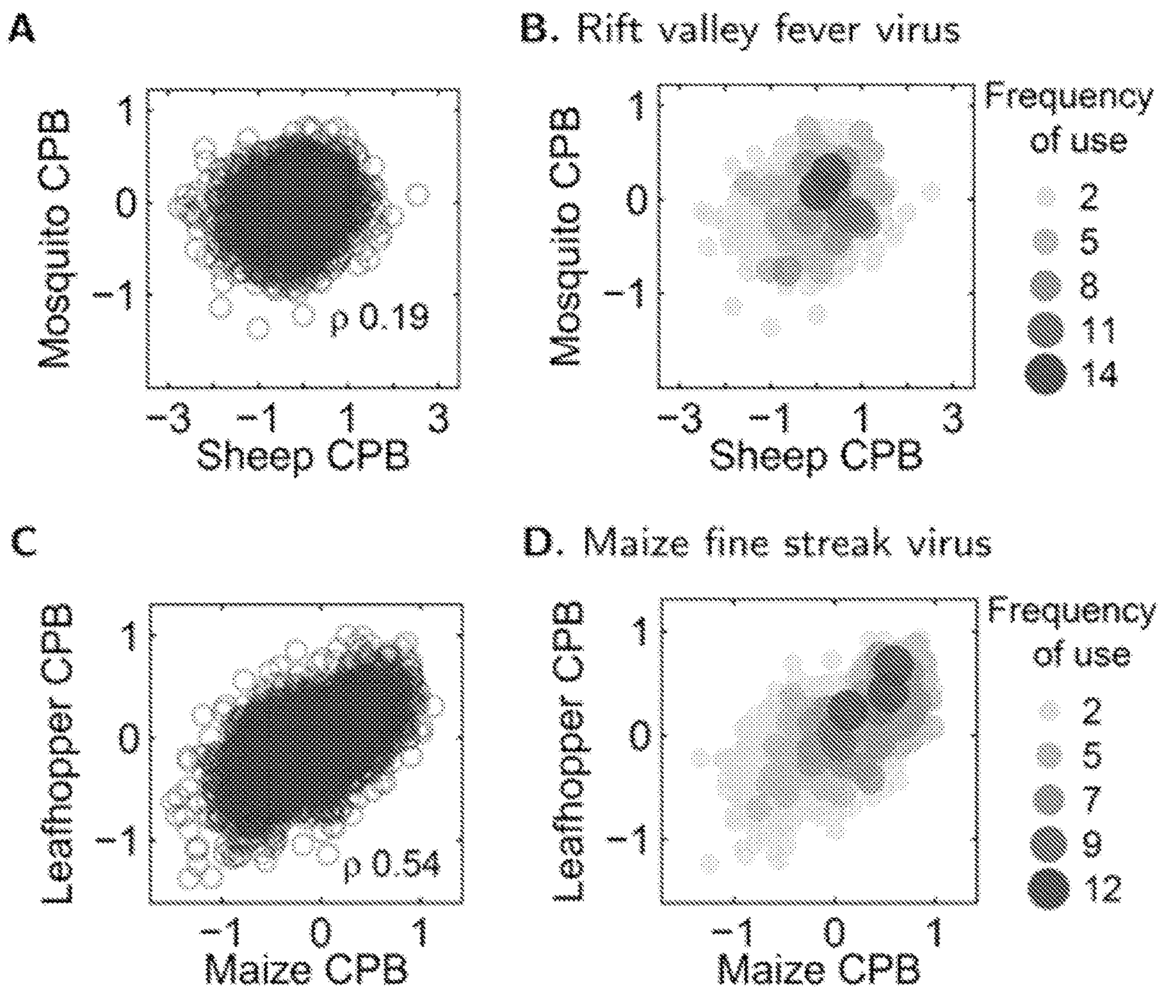
FIG. 3. Codon pair use by two arthropod vector transmitted viruses infecting either plant or animal primary hosts. (A) Correlation of codon pair use frequency between sheep (*O. aries*) and mosquito (*A. aegypti*) genomes and (B) the frequency at which these codon pairs are used in the Rift Valley fever virus genome. (C) A similar comparison between maize (*Z. mays*) and leafhopper (*G. nigrifronts*) which are host to (D) Maize fine streak virus. Coding DNA sequences for the leafhopper were generated using transcriptome data from NCBI Bioproject PRGNA200322 and the Augustus gene prediction program.

Rift Valley fever virus (RVFV) is a negative-stranded RNA virus of Bunyaviridae, which infects mosquitoes and sheep (and other mammals). A comparison of the codon pair bias of mosquito to that of sheep shows poor correlation between the codon pair preferences between sheep and mosquitoes (FIG. 3A). The codon pairs in the genome of RVFV, a negative-stranded RNA virus of Bunyaviridae, were compared to the codon pairs used by its two hosts, mosquitoes and sheep. The codon pairs used by RVFV were found to be strongly biased toward the relatively small set of codon pairs that have high codon pairs scores (i.e., which are preferred) in both sheep and mosquitoes (FIG. 3B).

Insect-borne transmission of viruses is widespread also in the Plantae kingdom (12). An example is maize fine streak virus (MFSV), a nucleorhabdovirus that infects leafhoppers (an insect) and is transmitted to *Zea mays* (corn, a plant) and other plants. A similar comparison was performed examining codon pairs used by maize (*Z. mays*) and leafhopper (*G. nigrifronts*). Coding DNA sequences for the leafhopper were generated using transcriptome data from NCBI Bioproject PRGNA200322 and the Augustus gene prediction program. A comparison between leafhopper and maize codon pair bias revealed poor correlation in codon pair preference between the two hosts (FIG. 3C). The codon pairs present in the MFSV genome were strongly biased toward those pairs having high codon pair scores in both leafhoppers and corn (FIG. 3D).

Figure 4:
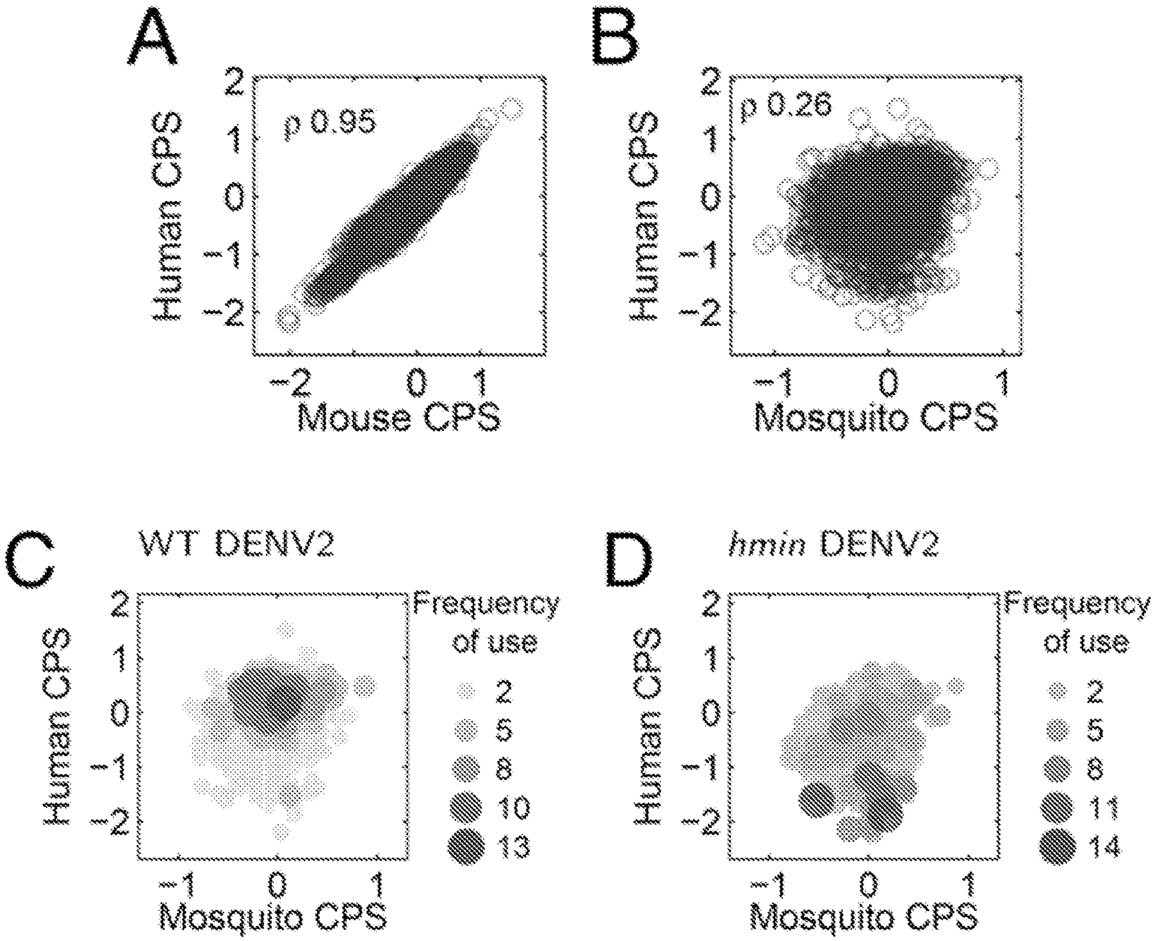
FIG. 4. Codon pair bias in humans and mosquitoes. (A) Codon pair preferences are well-correlated (Spearman rho=0.95) between humans and mice. (B) Codon pair preferences are poorly correlated (Spearman rho=0.26) between humans and mosquitoes. Each circle represents one of the 3,721 possible codon pairs. (C) Codon pairs actually used by natural wild-type dengue virus, type 2 (16681). The more times a particular codon pair is used by the virus, the bigger and darker the dot. (D) Codon pairs used by an in silico recoded dengue virus designed to have a good codon pair score in mosquitoes but a bad (negative) codon pair score in humans (dots). "hmin" signifies a human minimized virus.
Figure 5:
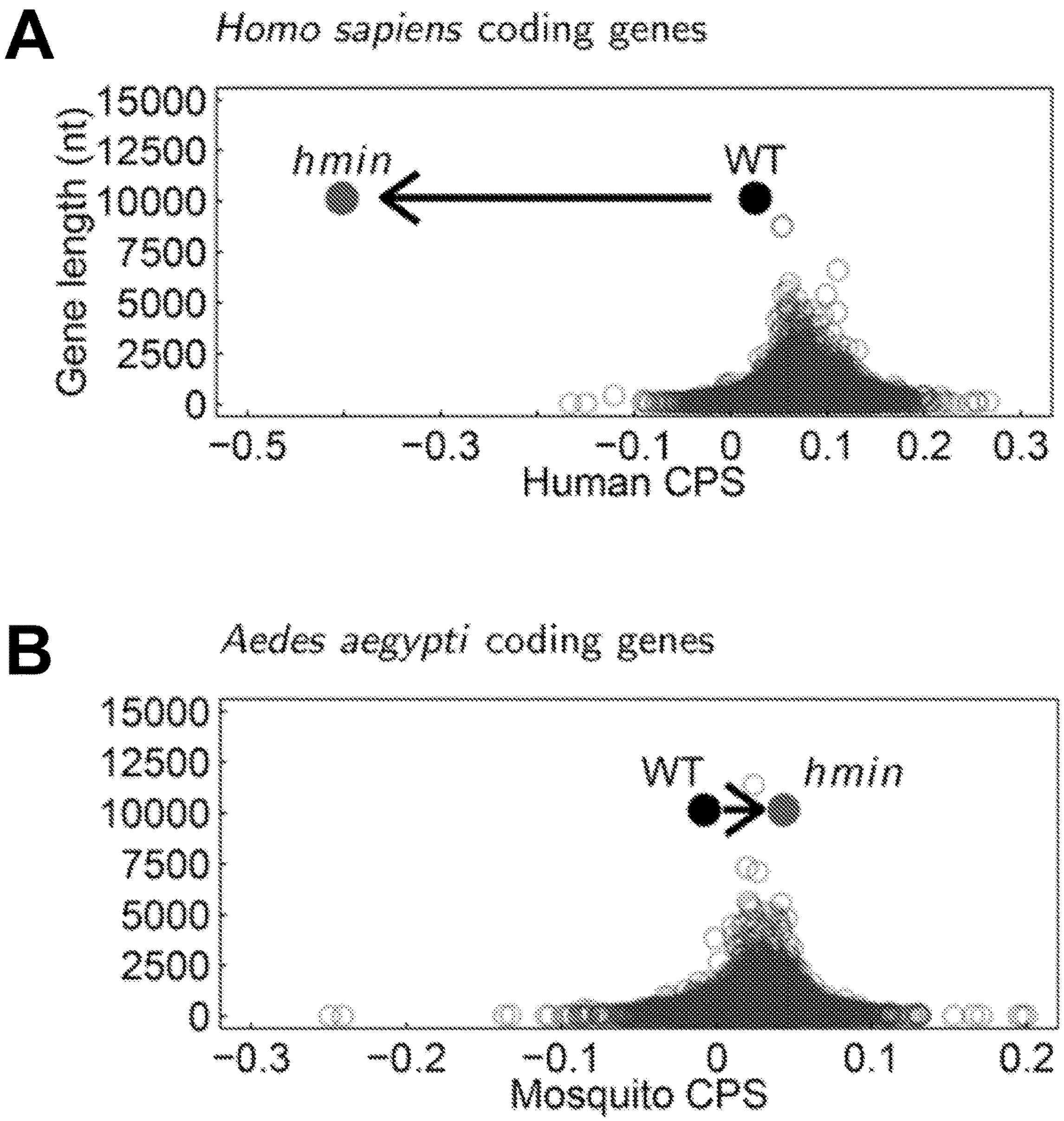
FIG. 5. (A) The average human codon pair score of the in silico hmin virus (grey dot) compared with WT (black dot) and the average codon pair scores of >14,000 human coding genes. (B) The same two viruses as in E (grey and black dots) evaluated using mosquito codon pair scores and compared with all *Aedes aegypti* mosquito coding genes. The in silico hmin virus demonstrates that it is possible to design a synthetic dengue virus drastically deoptimized in humans but optimized in mosquitoes.

Codon pair preferences are well correlated between human and mouse, but are poorly correlated between humans and mosquitoes (FIGS. 4 A-B). Human codon pair preferences were calculated as described before (Coleman et al., 2008) and those for insects were calculated using genomic sequences of *Aedes aegypti*. Dengue virus (DENV), a positive-stranded RNA virus of Flaviviridae, which infects mosquitoes and humans, has a bias toward codon pairs with high scores in both hosts (FIG. 4C). These results suggested that viruses with multiple hosts that have differing codon pair preferences use a restricted, balanced set of codon pairs to compromise between their hosts.

Example 2

Construction of a Synthetic Wild-Type Dengue Virus

A synthetic infectious cDNA, 10,723 nt long, was designed based on the sequence of dengue virus, type 2 (strain 16681) (accession no. U87411, SEQ ID NO:1). The cDNA was designed to contain 26 silent nucleotide changes (Table 4) downstream of the capsid coding region and upstream of the 3' UTR. These changes place convenient (unique) restriction sites every 1 kb and provide watermarks for identification (see FIG. 1B). These mutations do not lead to amino acid changes in the polyprotein. In addition, no new *E. coli* promoters were created by these 26 mutations as determined by the Neural Network promoter program from the Berkeley *Drosophila* Genome Project (http:/ jwww.fruitfly.org/seq_tools/promoter.html).

TABLE 4 list of 26 silent nucleotide changes in the synthetic wild-type virus

| Mutation | Effect |
|---|---|
| A753G | +MluI |
| A756T | |
| G1310A | −SphI |
| A1548G | −HindIII |
| T1753A | +SacI |
| C1754G | |
| A1755C | |
| C2371T | −SpeI |
| A2928T | +AflII |
| A2931G | |
| T3240A | −HindIII |
| A3909G | −MfeI |
| C4278A | −EagI |
| A4434C | +AgeI |
| A4437T | |
| A5562T | −BspEI |
| T6648A | −NheI |
| A7194T | −StuI** |
| A7197C | +SbfI |
| C7200G | |
| A7203G | |
| A7740T | −NruI |
| A7819C | +SacII |
| A7821C | |
| A9945T | BsiWI |
| A9948G | |

**StuI site formed as a result of the engineered SbfI site

The dengue virus serotype 2 (DENV2) genome was divided into four fragments starting at the 5' end, each encompassing 2,008 nt, 2,490 nt, 3,379 nt, and 2,846 nt (DENV2 F1-4, respectively). Each fragment was designed to carry an overlap region and a multiple cloning site at each end of the fragment to facilitate ligation of each fragment into a low-copy bacterial plasmid, pBR322, independent of order. (FIG. 1A). The full-length infectious clone was assembled by ligating in order fragments 4-3-2-1 as shown in FIG. 1B and verified by sequence analysis. This synthetic dengue virus is referred to as "D2-syn" (or alternatively as D2SAM1) (SEQ ID NO:2).

Figure 2:
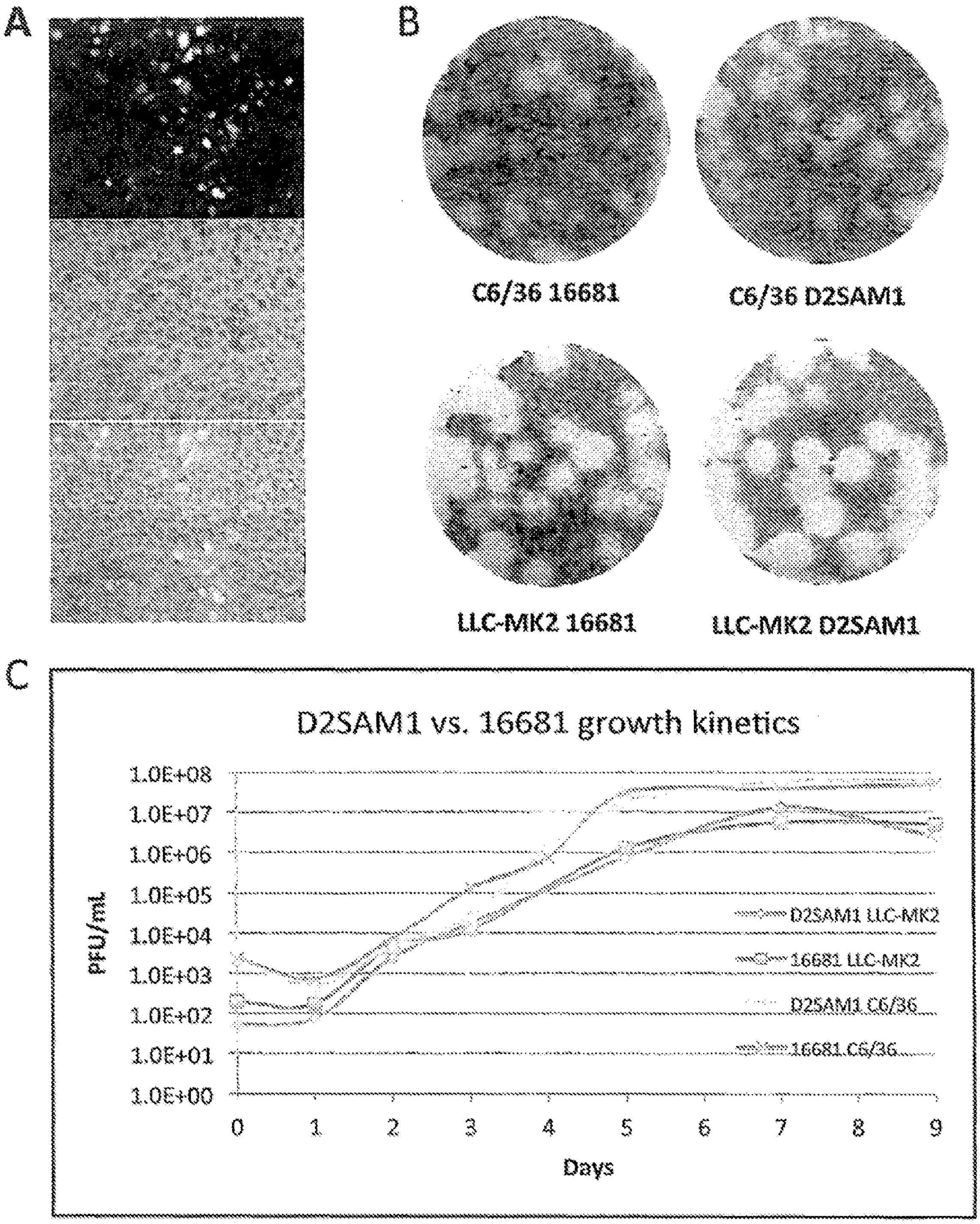
FIG. 2. (A) Growth of synthetic wild-type (D2-syn) compared to DENV strain 16681. Infectivity of RNA transcripts was verified by indirect immunofluorescence using culture media collected from the third or fourth blind passages, 7-9 days post-infection. (B) To verify that the 26 silent mutations did not alter the growth phenotype and kinetics of D2-syn compared to the wild-type 16681 virus, plaque titrations were performed in both C6/36 and LLC-MK2 rhesus monkey kidney cells at a MOI of 0.01. Plaque sizes and phenotype were found to be similar between D2-syn and 16681 viruses. (C) Growth kinetics was also found to be similar, with D2-syn and 16681 reaching maximal titers of $1.3\times10^7$ PFU/mL and $5.5\times10^6$ PFU/mL respectively in LLC-MK2 cells at Day 7 and $6\times10^7$ PFU/mL and $5\times10^7$ PFU/mL respectively in C6/36 cells at Day 9.

The synthetic dengue cDNA was linearized, in vitro transcribed, and transfected into C6/36 mosquito cells. Infectivity of RNA transcripts was verified by indirect immunofluorescence using culture media collected from the third or fourth blind passages, 7-9 days post-infection (FIG. 2A). To further verify that this virus was derived from transfected permissive cells, the complete genomic viral RNA was extracted, analyzed by RT-PCR and DNA sequencing, and verified to contain all 26 silent mutations.

To verify that the 26 silent mutations did not alter the growth phenotype and kinetics of D2-Syn compared to the 16681 virus, plaque titrations were performed in both C6/36 (CRL-1660;ATCC) and LLC-MK2 rhesus monkey kidney cells at a MOI of 0.01. Viruses were grown in C6/36 in Eagle's minimum essential medium (MEM) and 10% fetal bovine serum (FBS). Plaque assays were performed in baby hamster kidney (BHK-21) grown in Dulbecco's modified Eagle medium (DMEM) plus 10% bovine calf serum (BCS). Viral growth was also evaluated in LLC-MK2 (CCL-7; ATCC) maintained in Medium 199 plus 1% horse serum. All cells were maintained at 37° C. and 5% $CO_2$ except for C6/36 which was maintained at 28° C. and 5% $CO_2$.

As shown in FIG. 2B, plaque sizes and phenotype were found to be similar between D2-syn and 16681 viruses. The plaque assays for C6/36 and LLC-MK2 were performed separately and therefore are not comparable. Growth kinetics was also found to be similar, with D2-syn and 16681 reaching maximal titers of 1.3x107 PFU/mL and $5.5\times10^6$ PFU/mL respectively in LLC-MK2 cells at Day 7 and $6\times10^7$ PFU/mL and $5\times10^7$ PFU/mL respectively in C6/36 cells at Day 9, as shown in FIG. 2C. Thus, the growth phenotypes of the synthetic wild-type dengue virus, "D2-syn," in monkey LLC-MK2 and mosquito C6/36 cells was indistinguishable from those of the natural wildtype serotype 2 strain 16681.

Example 3

Design and Construction of Codon Pair-Deoptimized Dengue Virus

The open reading frames of three dengue proteins, E, NS3, and NS5 were independently recoded by rearranging existing synonymous dengue codons thereby replacing existing codon pairs (that are acceptable in both humans and insects) with pairs that are unfavorable in humans and favorable in insects. These recodings, while changing codon pairs, neither altered the encoded polypeptide sequence, nor the codon usage. The three dengue proteins selected for recoding, E, NS3, and NS5, play multiple roles in the replicative cycle of DENV. The E glycoprotein functions in viral attachment, entry, and membrane fusion; NS3 is a multifunctional enzyme with serine protease/helicase/NTPase activity; and NS5 is the RNA-dependent RNA polymerase crucial for viral genome replication that also harbors methyltransferase activity. The three recoded ORFs each harbor more than 300 nucleotide changes and have strongly negative human codon pair scores but are similar to wild-type with respect to mosquito codon pair scores (FIG. 2A and Table 1). Each of the three recoded segments was synthesized and cloned, separately, into the synthetic wild-type D2-syn to create three new viruses, referred to as $E^{hmin}$, $NS3^{hmin}$, and $NS5^{hmin}$, where "hmin" signifies a human minimized codon pair score, whereas the codon pair score for insect mRNA is maintained.

The designs of CP-deoptimized (with maintained wild-type CPB) of E, NS3, and NS5 were obtained in silica by simulated annealing methods similar to the previously reported SAVE implementations (Coleman et al., 2008; Meuller et al., 2010). In brief, simulated annealing is a heuristic search through a solution space of genetic sequences attempting to find a good solution as defined by a given heuristic function. In contrast to previous works, here two criteria were used to optimize, namely minimizing the codon pair bias according to the human codon pair bias table, while maintaining closely the wild-type codon pair bias according to the insect table. Calculated codon pair scores (CPS) for all 3721 possible codon pair combinations (excluding Stop codons) in the insect ORFeome are shown in Supplemental Table 1. Human and insect codon-pair biases are sufficiently different that many good approximate solutions were possible.

A simulated annealing heuristic was implemented to design synthetic, recoded dengue viruses intended to be attenuated in humans. Each codon was swapped with a randomly chosen synonymous codon with a certain probability of retaining the change even if an increase in CPS occurs during deoptimization to reach a global minimum CPS. This process was iterated several hundred thousand times over a particular sequence. If the codon change is good, the change is retained, whereas if the change is bad, it may still be retained, with a probability dependent on a specified temperature (hence the analogy to metallurgical annealing). In a nontrivial bicriteria optimization problem, the cumulative score of codon pairs was minimized according to the human codon pair bias table, while not allowing the cumulative score according to the insect table to drift too far. Combining both criteria into a single function, $$\min(a*\text{human\_score}+b*\text{abs}(\text{insect\_score}-\text{insect\_score\_wt})^{c}),$$

where a, b, and c are coefficients. By varying a, b, and c, it is possible to control the importance of minimizing the human score (a), and limiting the variation of the insect score from wild type (b and c).

The process of sequence design also entails controlling the folding energy of the RNA, thereby avoiding the formation of higher-order RNA structures.

TABLE 5

Recoded E, NS3, and NS5 Codon Pair Bias

| | Mosquito CBP | | Human CBP | | |
|---|---|---|---|---|---|
| Design | WT 16681 | D2-Syn | WT 16681 | D2-Syn | Δ(NT) |
| DENV2 | −0.008 | −0.008 | 0.0256 | 0.0253 | 26/10173* (0.26%) |
| $E^{hmin}$ | −0.016 | −0.018 | 0.052 | −0.360 | 334/1485 (22%) |
| $NS3^{hmin}$ | −0.010 | −0.015 | 0.038 | −0.362 | 402/1854 (22%) |
| $NS5^{hmin}$ | −0.003 | −0.019 | 0.019 | −0.378 | 565/2700 (21%) |

*entire coding region of dengue genome

As shown in Table 5, the changes to the CPB score for E, NS3 and NS5 with respect to the human system are highly significant whereas those for the mosquito are negligible. The differences in CPB between the synthetic D2-syn and 16681 wild-type DENVs for both the mosquito and human systems were also negligible. Each ORF (E, NS3, NS5) was CP-deoptimized separately.

Synthetic DNA fragments containing the CP-deoptimized sequences plus surrounding wild-type sequences were used to individually replace the corresponding sequence in D2-syn. Regions of recoding were limited by locations of unique restriction sites engineered into the D2-syn genome. Additionally, no RNA secondary structure important in viral proliferation are known to exist in these coding regions. The $NS3^{hmin}$ fragment was inserted into a pUC57 high-copy plasmid and ligated into D2-syn to produce $NS3^{hmin}$ virus. However, both the $E^{hmin}$ and $NS5^{hmin}$ fragments were highly unstable and therefore insertion into the inducible single-copy pCC1BAC vector was done. In addition, successful cloning of full-length D2-syn-$E^{hmin}$ and D2-syn-$NS5^{hmin}$ cDNA was accomplished using of *E. coli* strain BD1528, which has been used to stably amplify the full-length cDNA of a highly unstable DENV4 (Lai et al., 1991). High-quality cDNAs were then linearized, in vitro transcribed, and transfected into C6/36 mosquito cells. Infectivity of RNA transcripts was verified by indirect immunofluorescence using culture media collected from the third or fourth blind passages, 7-9 days post infection. The accuracy of the genotypes of all three viruses constructed ($E^{hmin}$, $NS3^{hmin}$, and $NS5^{hmin}$) was confirmed by sequencing.

The codon pair bias sequences described above have the following GenBank accession numbers: D2-syn, KP161064; $E^{hmin}$, KP161065; $NS3^{hmin}$, KP161066; and $NS5^{hmin}$, KP161067.

Example 4

Growth Kinetics of Wild-Type and Recoded Dengue Virus

DENV infections were carried out in culture media with partially depleted serum at room temperature with rocking for 1 hour (C6/36 in MEM+2.5% PBS and BHK in DMEM+2.5% FBS). Culture media for LLC-MK2 infections retained 1% horse serum. For growth kinetics and plaque phenotype, either C6/36 or LLC-MK2 (about 50-60% confluence) were infected with DENV at MOI of 0.01 (except $NS5^{hmin}$ at MOI of 1) and cell supernatant samples were collected every 24 hours for 9 days and stored at −80° C. with at most one freeze/thaw cycle. Plaque titrations of these samples were performed on BHK cells. Briefly, infections of a viral dilution series were carried out in PBS+1% FBS for 2 hours at room temperature with rocking. After 2 hours, a 1% agarose overlay (with final 5% FBS and 1× Modified Eagle Medium) was added directly to infected BHK cells grown to 60-90% confluence in 6-well plates. Cells were incubated at 37° C. and 5% $CO_2$ for 7 days. On Day 2, 1 mL of DMEM+10% BCS was added to each well to prevent drying out. After 7 days, agarose plugs were carefully extracted and cells stained with crystal violet overnight. A similar method was used for FFAs in A549, BHK, LLC-MK2, and Vero E6 cells. C6/36 cells were incubated for 7 d at 28° C., 5% CO2.

Cultured C6/36 mosquito cells or rhesus macaque LLC-MK2 cells were infected with D2-syn and the deoptimized viruses, and viral replication was followed using quantitative RT-PCR (FIG. 6B-C). Quantitative RT-PCR was performed on cell cultures that were separately infected with the indicated virus at 0.01 MOI in each cell line. Total RNA was extracted from infected cells after freeze-thaw. The RNA was then amplified using Roche's one step LightCycler RNA Amplification Kit SYBR Green I with an ABI StepOnePlus Real-Time PCR System, and a common dengue primer binding in the NS4 B region,

```
                                   (SEQ ID NO: 7)
F7050-AATGGGTCTCGGGAAAGGATG

                                   (SEQ ID NO: 7)
R7153-CTGCTGTGAGAGTTATGGGGT
```

Virus RNA concentration was quantitated using a standard curve made from serial 10 fold dilutions of a spectrophotometrically (NanoDrop) determined concentration of virus transcript. DENV RNA quantity at all time points was normalized relative to the zero time point for each growth curve.

As measured by quantitative RT-PCR in the C6/36 cell line, the three human deoptimized viruses $E^{hmin}$, $NS3^{hmin}$, and $NS5^{hmin}$ grew with the same kinetics as the D2-syn virus (to Day 3) (see FIG. 6B), demonstrating that replication in the insect cells correlates to a good codon pair score for mosquitoes. In contrast, when primate (rhesus macaque) LLC-MK2 cells were infected, the three mammalian deoptimized viruses grew distinctly less well than the D2-syn virus (FIG. 6C). Moreover, the degree of attenuation was in proportion to the length of the deoptimized region (compare FIGS. 6C to 6A).

Mammalian BHK (baby hamster kidney) cells were also infected with D2-syn and the deoptimized (hmin) viruses. Surprisingly, robust replication of all deoptimized variants resulted (FIG. 6D). BHK cells, however, have a defect in RIG-I signaling (Habjan, et al., 2008), leading to a defect in both interferon production and robust innate immune response. It is most likely due to these deficiencies that BHK cells have been found to be highly sensitive to dengue infections with the ability to produce relatively high viral titers (Malewicz & Jenkin, 1979). Possibly, these reasons also account for why the three human deoptimized viruses grew well in this cell type. Indeed, all four dengue variants gave relatively clear, well-defined plaques on BHK cells allowing us to determine titers in plaque-forming units (PFUs).

Plaque formation on BHK cell monolayers was compared using virus produced by infections of insect C6/36 cells and monkey LLC-MK2 cells. Results mirrored those obtained by the quantitative RT-PCR assay—that is, the three mammalian deoptimized viruses were specifically attenuated in LLC-MK2 cells, in proportion to the length of deoptimized sequence, but behaved like D2-syn and the natural wild-type in insect cells (FIG. 7A-F). Additional results suggest that the hmin viruses also grow similarly to the wild-type D2-syn in a different mosquito cell line, Aag-2. For these three hmin viruses, the ability to form a focus (suggesting virion formation and spread) was also attenuated in at least two other mammalian cell lines, Vero E6 and A549 cells (FIG. 7G).

Example 5

The Recoded Viruses Are Attenuated in Newborn Mice and Confer Protective Immunity Dengue is a disease of primates, and no other good animal model exists. However, neonatal mammals are more susceptible than adult mammals to infections. Newborn mice have often been used for studies of viral virulence for which proper animal models were not available [for example, coxsackie viruses (Dalldorf et al., 1949) or DENV (Lai, et al., 2007; Kinney et al., 1997). Therefore, analysis of D2-$syn^{hmin}$ variants for attenuation was performed by intracranial injection into newborn ICR mice (mice and humans have almost identical CPB; FIG. 4A).

Figure 8:
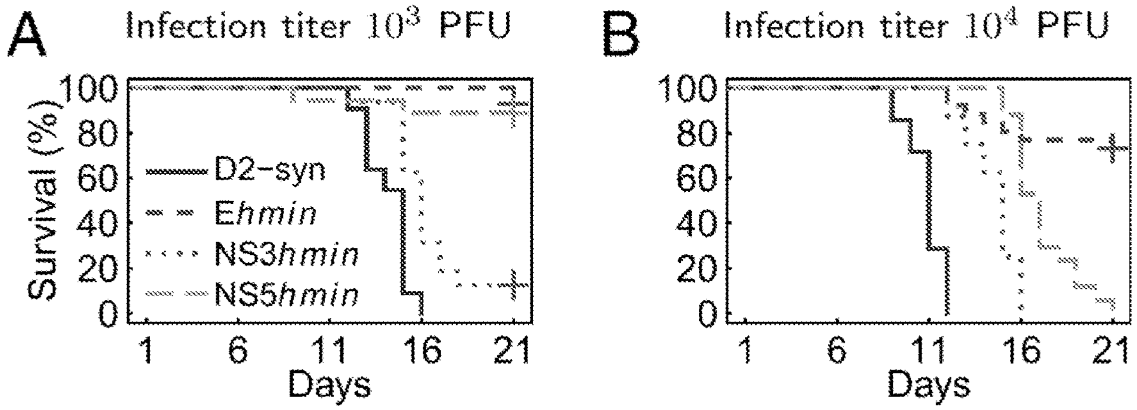
FIG. 8. Survival curves showing attenuation of the hmin viruses in newborn mice. (A and B) Attenuation of hmin viruses after intracerebral infection. Groups of newborn ICR mice (1-2 d old) were infected intracerebrally with $10^3$ (A) or $10^4$ PFU (B) of (D2-syn) or hmin viruses, respectively. (C) Median lethal dose ($LD_{50}$) values in newborn mice after intracerebral infection. (D) Maternal antibody $PRNT_{50}$ titer in juvenile mice born to mothers vaccinated (when they were newborn animals) with D2-syn or $E^{hmin}$ (*P value<0.05 by Wilcox rank sum test).
Figure 8:
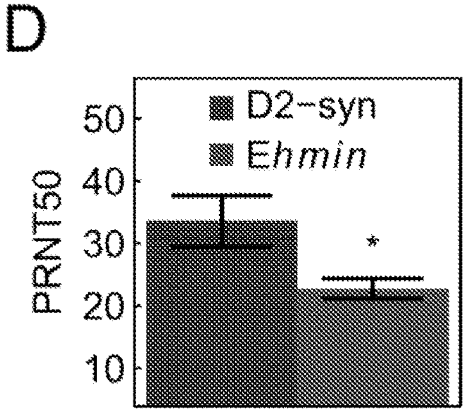

Intracranial Challenge of Newborn Mice. Newborn, 1-day old, or 2-day old, inbred ICR mice from a colony were challenged intracranially in groups of 5-12 depending upon litter size with $10^4$, $10^3$, $10^2$, $10^1$, or $10^0$ PFU of each virus (D2-syn, $E^{hmin}$, $NS3^{hmin}$, and $NS5^{hmin}$) diluted in 20 µL PBS (FIG. 8). Animals were monitored daily for mortality during the 5 weeks following infection. The lethal dose 50% ($LD_{50}$) for each virus was calculated using the method of Reed and Muench (Reed and Muench, 1938). Kaplan-Meier survival curves were created using GraphPad Prism version 6.03 for Windows, GraphPad Software, La Jolla Calif. USA, www.graphpad.com. The wild-type, D2-syn, was highly virulent in these neonatal ICR mice, with an $LD_{50}$ of 5 plaque-forming-units (PFU). Dramatic attenuation was observed with the codon pair deoptimized viruses (FIGS. 8 A and B), revealing 100-fold ($NS3^{hmin}$), 200-fold ($NS5^{hmin}$), and 2,000-fold ($E^{hmin}$) increases in $LD_{50}$ compared with D2-syn (FIG. 8C).

Many of the newborn mice inoculated with $10^3$ PFU of deoptimized viruses survived. At 35 days post infection, sera were collected and tested for virus neutralizing antibodies by a modified $PRNT_{50}$ assay. For the $PRNT_{50}$ assays, viral titers were measured by immune focus assay of D2-Syn in the presence of serial dilutions (1:20, 1:40, 1:80, 1:160, . . . ) of serum collected from survivors of $E^{hmin}$, $NS3^{hmin}$, or $NS5^{hmin}$ as neonates. Briefly, infections of BHK cells were carried out by rocking at room temperature for 30 minutes followed by incubation at 37° C., 5% $CO_2$ for 4 hours. After infection, a 1.2% Tragacanth gum overlay consisting of final concentration 1% FBS, 1× Penicillin/Streptomycin, and 1× Modified Eagle Medium was added directly to cells. Cells were incubated for 5 days before being fixed in 2% paraformaldehyde and 50% Methanol:Acetone. After fixation, dengue foci were developed using a primary mouse anti-dengue 2 IgG (4G2) antibody and secondary horseradish peroxidase (HRP) conjugated goat anti-mouse IgG and precipitating Vector VIP HRP substrate.

Strikingly, as measured by the $PRNT_{50}$ assay, all three deoptimized viruses induced high levels of neutralizing antibodies in adult survivors (Table 6).

TABLE 6

Induction of neutralizing antibodies by the hmin viruses

| Dose (PFU) | D2-syn | $E^{hmin}$ | $NS3^{hmin}$ | $NS5^{hmin}$ |
|---|---|---|---|---|
| $10^1$ | 533 ± 107 | — | — | — |
| $10^3$ | — | 427 ± 107 | 160 | 53 ± 13 |

Titers are presented as the reciprocal of serum dilution (e.g., 500 indicates a 1/500 dilution of serum)±SEM.

Since adult mice are not susceptible to DENV infection, whether the antibodies in these adult survivors were protective could not be directly assayed. To circumvent this problem the "vaccinated" females were bred after they had grown to maturity, and their newborn offspring (which received antisera from their mothers) were subjected to otherwise lethal challenges with D2-syn (sWT). Table 7 shows the result of one such experiment. Female newborns were "vaccinated" with $NS3^{hmin}$. When these females grew to maturity they had litters of mice, and these newborn mice were challenged with a viral dose 200 times $LD_{50}$ of D2-syn. Mice were observed daily for morbidity (weight loss) and mortality. Remarkably, these offspring of mothers that had survived intracranial DENV were highly resistant to intracranial injection of the synthetic wild-type virus (Table 7).

TABLE 7

Induction of protective antibodies by $NS3^{hmin}$

| Mother | Percent survival |
|---|---|
| Naive | 0 (0/6) |
| $NS3^{hmin}$ | 93 (13/14) |

This demonstrates that intracranial injection with attenuated virus induces neutralizing antibodies in newborn mice, and after these mice mature these antibodies can be transmitted to offspring and protect against DENV. The choice of the $NS3^{hmin}$ variant was based on available virus samples. Results with $E^{hmin}$ and $NS5^{hmin}$ variants have yielded results similar to those with the $NS3^{hmin}$ variant.

Burns et al reported in 2009 that replacement in the capsid coding region of poliovirus with unpreferred synonymous codons resulted in sharp virus attenuation and attributed the main mechanism of attenuation to an increase in CpG and UpA dinucleotide pair frequencies (Burns et al., 2009) rather than changes to codon bias or codon pair bias. An increase in frequencies of CpG and/or UpA has been found to correlate with a decline in viral fitness and both dinucleotides are normally suppressed not only in viral genomes, but in the genomes of most living organisms (Nussinov, 1984). In fact, it has been well documented from nearest neighbor analyses first performed in Arthur Kornberg's lab and continued by others, the deviation from random expectation of the occurrences of both the doublets CpG in the genomes of vertebrates and UpA in all genomes (including humans, insects, DNA/RNA viruses) (Nussinov, 1984; Josse et al, 1961; Swartz et al., 1962; Jabbari & Bernardi, 2004). Specifically relevant to DENV, CpG (while depleted in humans) are observed with predicted frequency and show no downward bias in insects though UpA are depleted in the genomes of both insects and humans (Simmen, 2008). These differences, particularly CpG frequencies, would impose contrasting selective pressures on DENV and other arboviruses which alternate replication in vertebrate and arthropod organisms (Lobo et al., 2009). In this study, CpG and UpA frequencies of the CP-deoptimized dengue viruses all increased as shown in Table 8. Both deoptimization of codon pair bias and codon bias would likely result in increased frequencies of CpG and UpA dinucleotides pairs as these dinucleotides are common in rare codons and are also more commonly found across codons in rare codon pairs. This increase was unavoidable and is very difficult to completely separate from changes in codon or codon pair bias.

TABLE 8

Changes to CpG and UpA frequencies*

| | $E^{hmin}$ | $NS3^{hmin}$ | $NS5^{hmin}$ |
|---|---|---|---|
| CpG | +67 | +84 | +98 |
| UpA | +31 | +48 | +49 |

*Total number of CpG's and UpA in the wild-type 16681 DENV is 233 and 439, respectively. The above numbers show increases in CpG and UpA formed at the junction of codons ($X_3$-$Y_1$ for the two codons, $X_1X_2X_3$-$Y_1Y_2Y_3$) as a result of CP-deoptimization.

Potential mechanisms of attenuation as a result of CpG and UpA overrepresentation can be found. CpG suppression is usually observed in CpGmethylating genomes, such as those of vertebrates (Bird, 1980), whereas organisms that do not methylate DNA, including mosquitoes, display no depletion in CpG (Lobo et al., 2009). Methylation of cytosines followed by spontaneous deamination results in the formation of thymines, which results in an over-representation of TpG and CpA in the genomes, as is observed (Jabbari & Bernardi, 2004). Other potential mechanisms include stimulation of the innate immune system by unmethylated DNA (Darn & Kippenberger, 2008) and potential DNA/RNA structural contraints (Shabalina et al., 2006). UpA depletion, which is common to both humans and insects, have been proposed to result from low thermodynamic stacking energy (Breslauer et al., 1986), the presence of Up A in regulatory sequences such as the TAT A box and the polyadenylation signal AA T AAA as well as in two of the three stop codons, UAA and UAG (depletion could prevent nonsense mutations) (Karlin & Mrazek, 1997), and the action of UpA-selective ribonucleases (Beutler, E., et al., 1989).

Figure 6:
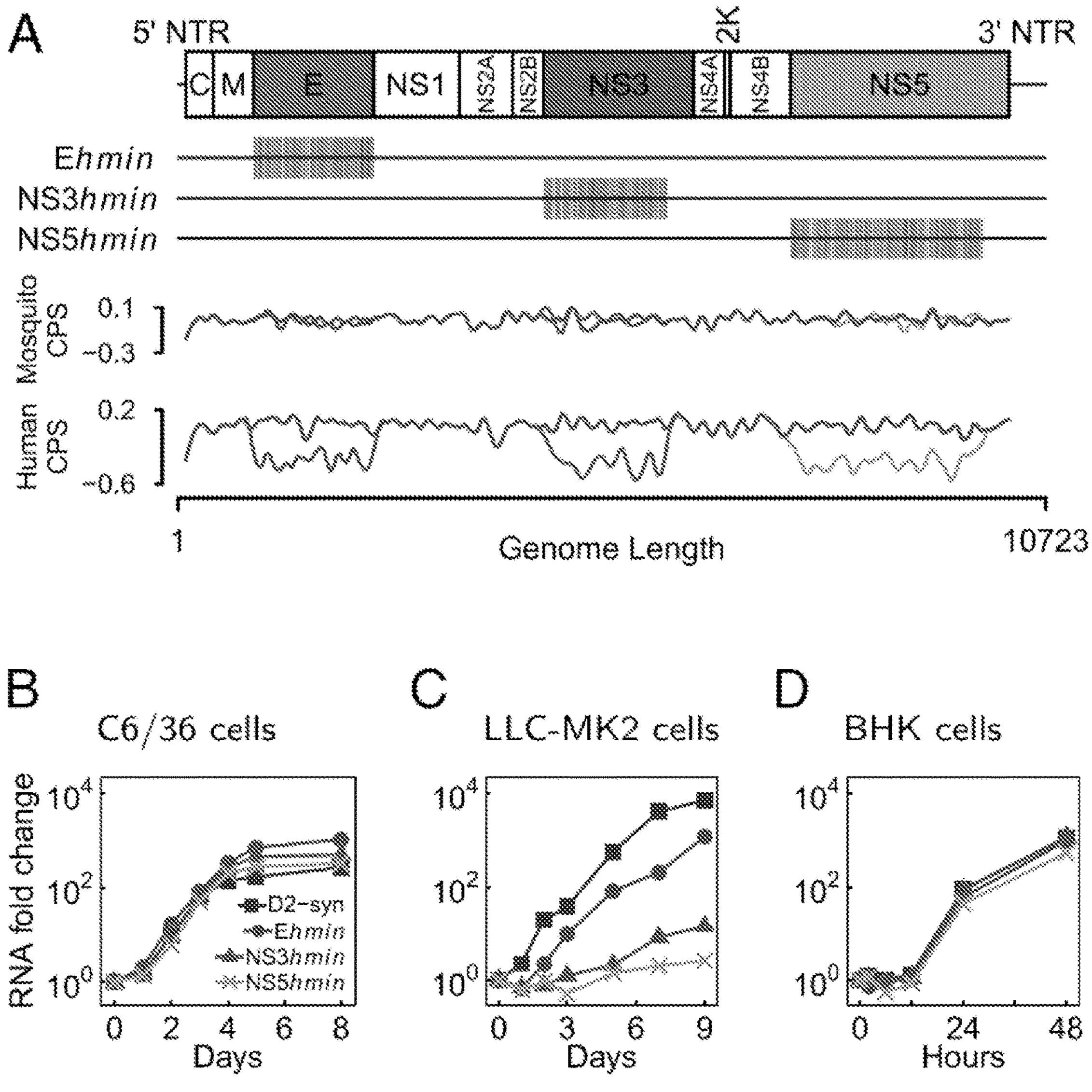
FIG. 6. Design and growth kinetics of WT (D2-syn) and three hmin dengue viruses in mammalian and mosquito cell lines. (A) (Top) Diagram of the DENV2 genome marks, the polyprotein coding region and the coding regions of polypeptides before proteolytic processing. The color-coded regions indicate regions recoded in the three novel hmin viruses. Full length genomes of the three hmin viruses ($E^{hmin}$, $NS3^{hmin}$, and $NS5^{hmin}$) are aligned to the WT (D2-syn) sequence, and point mutations generated by codon pair recoding are indicated by a barcode diagram. The two CPS line plots (Bottom) show how the codon pair score changes along the length of the genome for each virus relative to the mosquito and human CPBs. There are four overlapping loess curves: $E^{hmin}$, $NS3^{hmin}$, $NS5^{hmin}$, and D2-syn. (B-D) Virus growth curves in different cell lines produced by measuring the fold change in virus RNA concentration from time 0.
Figure 7:
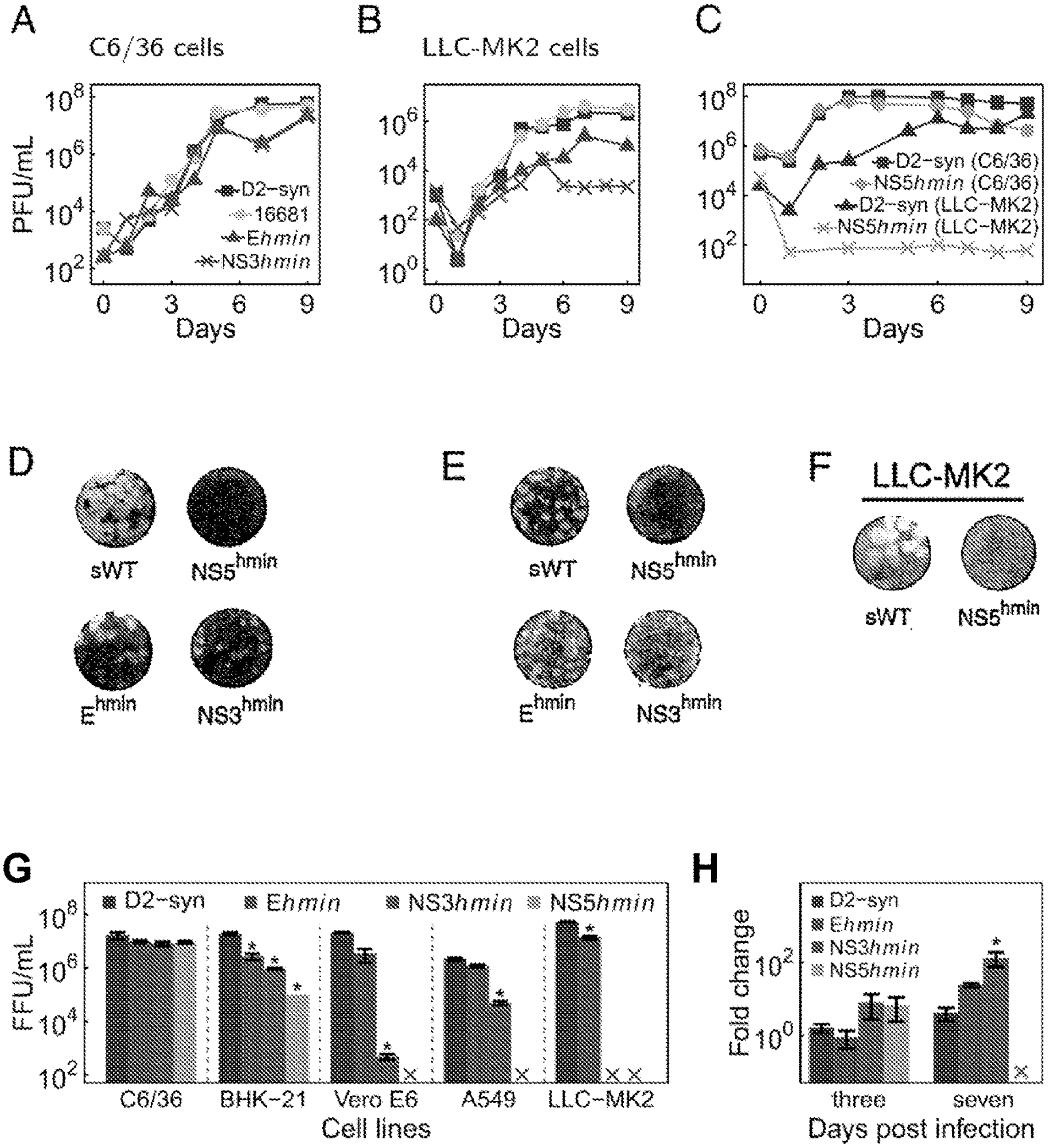
FIG. 7. Growth curves and plaque phenotypes of viruses grown in different cells. (A) Insect C6/36 cells or (B) mammalian LLC-MK2 cells were infected with virus variants at a multiplicity of infection (MOI) of 0.001. Virus titer was measured by plaque assay on BHK cells. (C) $NS5^{hmin}$ growth kinetics in different cells. C6/36 or LLC-MK2 cells were infected with $NS5^{hmin}$ at a MOI of 1. Virus titer was measured by plaque assay on BHK cells. (D) BHK cell plaque phenotypes using virus grown in LLC-MK2, or (E) C6/36 cells at 0.01 MOI. (F) Plaque phenotypes were more evident for $NS5^{hmin}$ using virus grown in C6/36 cells at 1 MOI. (G) Virus titers, measured by focus forming assays in C6/36, BHK-21, Vero E6, A549, or LLC-MK2 cell lines. (H) Effect of Jak inhibitor 1 treatment on virus titer. LLC-MK2 cells were pretreated with Jak inhibitor 1, and the fold change in virus titer relative to untreated cells was measured by a 50% tissue culture infectious dose ($TCID_{50}$) assay at three and seven days post infection. Significant differences from D2-syn in (G) and (H) are marked by *P value<0.05 by Wilcox rank sum test.

It is possible that these increases in CpG and UpA frequencies contribute to the attenuation observed in LLC-MK2 cells and newborn mice. The increase in CpG frequencies in the CP-deoptimized DENV did not seem to affect the growth kinetics in either C6/36 insect cells or the interferon-defective BHK cells, as shown in FIGS. 6 and 7. However, it is unclear what phenotype an increase in CpG dinucleotides in the insect system would manifest since CpG depletion does not occur in mosquitoes. On the other hand, UpA's are depleted in both humans and insects but an increase in UpA frequencies did not attenuate the DENV viruses in C6/36 cells with all three CP-deoptimized viruses growing similarly to the wild-type virus and exhibiting similar growth kinetics, as shown in FIGS. 6 and 7. These results suggest that the observed attenuation, at least in cell culture, and likely in mice was a result of CP-deoptimization rather than increases in UpA frequencies.

These examples described a profound difference by which insects of Arthropoda and mammals of Chordata, two distantly related Phyla of the Animal Kingdom, encode mRNA. This difference is the unexpected preference in insect vs mammalian cells for synonymous codon pairs (codon pair bias) that yields severe phenotypes of expression when disturbed by large scale recoding. Arboviruses that proliferate in cells of both Phyla have evolved to successfully balance codon pair bias. Using DENV as example, these examples show that the balance can be shifted towards insect bias thereby attenuating DENV in mammalian cells. Despite attenuated virulence, the recoded viruses induced high levels of neutralizing antibodies in mice, and these antibodies were protective against disease. Recoding can be tailored allowing different degrees of attenuation with little chance of reversion to virulence.

REFERENCES

Beutler, E., et al., Evolution of the genome and the genetic code: selection at the dinucleotide level by methylation and polyribonucleotide cleavage. Proc Natl Acad Sci US A, 1989. 86(1): 192-6.

Bird, A. P., DNA methylation and the frequency of CpG in animal DNA. Nucleic Acids Res, 1980. 8(7):1499-504.

Breslauer, K., et al., Predicting DNA duplex stability from the base sequence. Proc Natl Acad Sci US A, 1986. 83(11): 3746-50.

Burns, C. C., et al., Genetic inactivation of poliovirus infectivity by increasing the frequencies of CpG and UpA dinucleotides within and across synonymous capsid region codons. J Viral, 2009. 83(19):9957-69.

Caufour, P. S., et al., Construction, characterization and immunogenicity of recombinant yellow fever 17D-dengue type 2 viruses. Virus Res, 2001. 79(1-2):1-14.

Coligan, J., A. Kruisbeek, D. Margulies, E. Shevach, and W. Strober, eds. (1994) Current Protocols in Immunology, Wiley & Sons, Inc., New York.

Coleman J R, et al. (2008) Virus attenuation by genome-scale changes in codon pair bias. Science 320(5884):1784-87

Dalldorf G, et al. (1949) A virus recovered from the feces of poliomyelitis patients pathogenic for suckling mice. J Exp Med 89(6):567-582.

Darn, A. and S. Kippenberger, Clinical application of CpG-, non-CpG-, and antisense oligodeoxynucleotides as immunomodulators. Curr Opin Mol Ther, 2008. 10(1):10-20.

Durbin, A. P., et al., Development and clinical evaluation of multiple investigational monovalent DENV vaccines to identify components for inclusion in a live attenuated tetravalent DENV vaccine. Vaccine, 2011. 29(42):7242-50.

Fedorov, A., S. Saxonov, and W. Gilbert. 2002. Regularities of context-dependent codon bias in eukaryotic genes. Nucl. Acids Res. 30:1192-97.

Gutman, G A & Hatfield, G W, Nonrandom utilization of codon pairs in *Escherichia coli*. Proceedings of the National Academy of Sciences of the United States of America 86:3699-3703 (1989).

Habjan, M. et al., T7 RNA polymerase-dependent and -independent systems for eDNA-based rescue of Rift Valley fever virus. The Journal of General Virology 89, 2157-2166 (2008).

Jabbari, K. and G. Bernardi, Cytosine methylation and CpG, TpG (CpA] and TpA frequencies. Gene, 2004. 333: 143-9.

Josse, J., A. D. Kaiser, and A. Kornberg, Enzymatic synthesis of deoxyribonucleic acid. VIII. Frequencies of nearest neighbor base sequences in deoxyribonucleic acid. J Bioi Chern, 1961. 236:864-75.

Karlin, S. and J. Mrazek, Compositional differences within and between eukaryoticgenomes. Proc Natl Acad Sci US A, 1997. 94(19):10227-32.

Kinney R M, et al. (1997) Construction of infectious cDNA clones for dengue 2 virus: Strain 16681 and its attenuated vaccine derivative, strain PDK-53. Virology 230 (2):300-308.

Lai, C. J., et al., Infectious RNA transcribed from stably cloned full-length cDNA of dengue type 4 virus. Proceedings of the National Academy of Sciences of the United States of America, 1991. 88(12): 5139-43.

Lai C J, et al. (2007) Epitope determinants of a chimpanzee dengue virus type 4 (DENV-4)-neutralizing antibody and protection against DENV-4 challenge in mice and rhesus monkeys by passively transferred humanized antibody. J Virol 81(23):12766-12774.

Lobo, F. P., et al., Virus-host coevolution: common patterns of nucleotide motif usage in Flaviviridae and their hosts. PLoS One, 2009. 4(7): e6282.

Malewicz, B. & Jenkin, H. M. Cultivation of dengue virus type 2 in baby hamster kidney cells in serum-free medium. The American journal of tropical medicine and hygiene 28, 918-920 (1979).

Moura, M. et al., Large scale comparative codon-pair context analysis unveils general rules that fine-tune evolution of mRNA primary structure. PloS one 2, e847 (2007).

Mueller, S., et al., Live attenuated influenza virus vaccines by computer-aided rational design. Nature biotechnology, 2010. 28(7):723-6.

Nussinov, R., Doublet frequencies in evolutionary distinct groups. Nucleic Acids Res, 1984. 12 (3):1749-63.

Osorio, J. E., et al., Development of DENVax: a chimeric dengue-2 PDK-53-based tetravalent vaccine for protection against dengue fever. Vaccine, 2011. 29(42): 7251-60.

Park, S., X. Yang, and J. G. Saven. 2004. Advances in computational protein design. Curr Opin Struct Biol 14:487-94.

Reed L J, Muench H (1938) A simple method of estimating fifty percent endpoints. Am J Hyg 27(3):493-497.

Sambrook, J., E. F. Fritsch, and T. Maniatis. (1989) Molecular Cloning: A Laboratory Manual, 2nd ed., Cold Spring Harbor Laboratory Press, Cold Spring Harbor, N.Y.

Simmen, M. W., Genome-scale relationships between cytosine methylation and dinucleotide abundances in animals. Genomics, 2008. 92(1):33-40.

Shabalina, S. A., A. Y. Ogurtsov, and N. A. Spiridonov, A periodic pattern of mRNA secondary structure created by the genetic code. Nucleic Acids Res, 2006. 34(8):2428-37.

Swartz, M. N., T. A. Trautner, and A. Kornberg, Enzymatic synthesis of deoxyribonucleic acid. XI. Further studies on nearest neighbor base sequences in deoxyribonucleic acids. J Bioi Chern, 1962.237:1961-7.

Dataset SI. Mosquito codon pair scores.

| AA pair | Codon Pair | Expected | Ob-served | Observed/ Expected | CPS |
|---|---|---|---|---|---|
| KK | AAAAAA | 11107.25 | 8499 | 0.765 | -0.268 |
| KN | AAAAAC | 7236.19 | 5958 | 0.823 | -0.194 |
| KK | AAAAAG | 10553.09 | 8710 | 0.825 | -0.192 |
| KN | AAAAAT | 6251.78 | 7057 | 1.129 | 0.121 |
| KT | AAAACA | 3956.19 | 5211 | 1.317 | 0.275 |
| KT | AAAACC | 4701.74 | 5375 | 1.143 | 0.134 |
| KT | AAAACG | 4628.08 | 5623 | 1.215 | 0.195 |
| KT | AAAACT | 3409.99 | 4924 | 1.444 | 0.367 |
| KR | AAAAGA | 3256.67 | 3426 | 1.052 | 0.051 |
| KS | AAAAGC | 4094.87 | 4083 | 0.997 | -0.003 |
| KR | AAAAGG | 2419.14 | 2325 | 0.961 | -0.040 |
| KS | AAAAGT | 3747.56 | 4873 | 1.300 | 0.263 |
| KI | AAAATA | 3638.01 | 5003 | 1.375 | 0.319 |
| KI | AAAATC | 7060.51 | 6842 | 0.969 | -0.031 |
| KM | AAAATG | 6446.31 | 6761 | 1.049 | 0.048 |
| KI | AAAATT | 6112.35 | 6422 | 1.051 | 0.049 |
| KQ | AAACAA | 6406.38 | 5937 | 0.927 | -0.076 |
| KH | AAACAC | 3941.79 | 3286 | 0.834 | -0.182 |
| KQ | AAACAG | 6293.94 | 5550 | 0.882 | -0.126 |
| KH | AAACAT | 3861.88 | 4030 | 1.044 | 0.043 |
| KP | AAACCA | 4312.47 | 5078 | 1.178 | 0.163 |
| KP | AAACCC | 2633.42 | 2983 | 1.133 | 0.125 |
| KP | AAACCG | 4563.95 | 5541 | 1.214 | 0.194 |
| KP | AAACCT | 2603.73 | 3137 | 1.205 | 0.186 |
| KR | AAACGA | 4315.66 | 4961 | 1.150 | 0.139 |
| KR | AAACGC | 2788.65 | 2793 | 1.002 | 0.002 |
| KR | AAACGG | 3658.09 | 3954 | 1.081 | 0.078 |
| KR | AAACGT | 2934.05 | 3157 | 1.076 | 0.073 |
| KL | AAACTA | 2890 | 3538 | 1.224 | 0.202 |
| KL | AAACTC | 3383.62 | 2854 | 0.843 | -0.170 |
| KL | AAACTG | 7480.52 | 7160 | 0.957 | -0.044 |
| KL | AAACTT | 3397.83 | 3501 | 1.030 | 0.030 |
| KE | AAAGAA | 9693.38 | 7743 | 0.799 | -0.225 |
| KD | AAAGAC | 5251.56 | 3944 | 0.751 | -0.286 |
| KE | AAAGAG | 6511.87 | 4990 | 0.766 | -0.266 |
| KD | AAAGAT | 6943.15 | 5683 | 0.819 | -0.200 |
| KA | AAAGCA | 3857.86 | 4274 | 1.108 | 0.102 |
| KA | AAAGCC | 4531.97 | 3873 | 0.855 | -0.157 |
| KA | AAAGCG | 3157.53 | 3446 | 1.091 | 0.087 |
| KA | AAAGCT | 3765.64 | 3858 | 1.025 | 0.024 |
| KG | AAAGGA | 4016.54 | 4075 | 1.015 | 0.014 |
| KG | AAAGGC | 2588.45 | 2450 | 0.947 | -0.055 |
| KG | AAAGGG | 1544.1 | 1497 | 0.969 | -0.031 |
| KG | AAAGGT | 2679.54 | 2773 | 1.035 | 0.034 |
| KV | AAAGTA | 2768.8 | 3105 | 1.121 | 0.115 |
| KV | AAAGTC | 3383.86 | 2532 | 0.748 | -0.290 |
| KV | AAAGTG | 5037.7 | 5315 | 1.055 | 0.054 |
| KV | AAAGTT | 4354.94 | 4440 | 1.020 | 0.019 |

-continued

Dataset SI. Mosquito codon pair scores.

| AA pair | Codon Pair | Expected | Ob-served | Observed/ Expected | CPS |
|---|---|---|---|---|---|
| KY | AAATAC | 5274.74 | 3893 | 0.738 | -0.304 |
| KY | AAATAT | 3908.86 | 4532 | 1.159 | 0.148 |
| KS | AAATCA | 3298.06 | 4467 | 1.354 | 0.303 |
| KS | AAATCC | 3889.33 | 4397 | 1.131 | 0.123 |
| KS | AAATCG | 4661.05 | 5463 | 1.172 | 0.159 |
| KS | AAATCT | 2688.4 | 3764 | 1.400 | 0.337 |
| KC | AAATGC | 3633.44 | 3038 | 0.836 | -0.179 |
| KW | AAATGG | 3350.07 | 3311 | 0.988 | -0.012 |
| KC | AAATGT | 3362.59 | 3862 | 1.149 | 0.138 |
| KL | AAATTA | 2809.15 | 3004 | 1.069 | 0.067 |
| KF | AAATTC | 6074.78 | 4702 | 0.774 | -0.256 |
| KL | AAATTG | 5907.72 | 4595 | 0.778 | -0.251 |
| KF | AAATTT | 4650.78 | 4940 | 1.062 | 0.060 |
| NK | AACAAA | 6679.1 | 8525 | 1.276 | 0.244 |
| NN | AACAAC | 7216.32 | 9807 | 1.359 | 0.307 |
| NK | AACAAG | 6345.86 | 7247 | 1.142 | 0.133 |
| NN | AACAAT | 6234.61 | 7567 | 1.214 | 0.194 |
| NT | AACACA | 2861.06 | 2950 | 1.031 | 0.031 |
| NT | AACACC | 3400.23 | 4210 | 1.238 | 0.214 |
| NT | AACACG | 3346.96 | 2983 | 0.891 | -0.115 |
| NT | AACACT | 2466.05 | 2804 | 1.137 | 0.128 |
| NR | AACAGA | 2698.03 | 2383 | 0.883 | -0.124 |
| NS | AACAGC | 3635.74 | 5331 | 1.466 | 0.383 |
| NR | AACAGG | 2004.16 | 1700 | 0.848 | -0.165 |
| NS | AACAGT | 3327.38 | 4821 | 1.449 | 0.371 |
| NI | AACATA | 2939.57 | 2647 | 0.900 | -0.105 |
| NI | AACATC | 5705.01 | 7247 | 1.270 | 0.239 |
| NM | AACATG | 4450.2 | 5042 | 1.133 | 0.125 |
| NI | AACATT | 4938.87 | 5874 | 1.189 | 0.173 |
| NQ | AACCAA | 5045.18 | 4351 | 0.862 | -0.148 |
| NH | AACCAC | 3282.81 | 2913 | 0.887 | -0.120 |
| NQ | AACCAG | 4956.64 | 4117 | 0.831 | -0.186 |
| NH | AACCAT | 3216.26 | 2928 | 0.910 | -0.094 |
| NP | AACCCA | 3558.38 | 2458 | 0.691 | -0.370 |
| NP | AACCCC | 2172.93 | 1490 | 0.686 | -0.377 |
| NP | AACCCG | 3765.89 | 2531 | 0.672 | -0.397 |
| NP | AACCCT | 2148.44 | 1460 | 0.680 | -0.386 |
| NR | AACCGA | 3575.35 | 3333 | 0.932 | -0.070 |
| NR | AACCGC | 2310.29 | 2035 | 0.881 | -0.127 |
| NR | AACCGG | 3030.59 | 2984 | 0.985 | -0.015 |
| NR | AACCGT | 2430.74 | 2466 | 1.015 | 0.014 |
| NL | AACCTA | 2336.52 | 1846 | 0.790 | -0.236 |
| NL | AACCTC | 2735.61 | 2288 | 0.836 | -0.179 |
| NL | AACCTG | 6047.9 | 4579 | 0.757 | -0.273 |
| NL | AACCTT | 2747.1 | 2291 | 0.834 | -0.182 |
| NE | AACGAA | 7667.18 | 8429 | 1.099 | 0.095 |
| ND | AACGAC | 4726.78 | 5466 | 1.156 | 0.145 |
| NE | AACGAG | 5150.7 | 6062 | 1.177 | 0.163 |
| ND | AACGAT | 6249.32 | 7350 | 1.176 | 0.162 |
| NA | AACGCA | 3376.31 | 2699 | 0.799 | -0.224 |
| NA | AACGCC | 3966.27 | 3502 | 0.883 | -0.124 |
| NA | AACGCG | 2763.4 | 1745 | 0.631 | -0.460 |
| NA | AACGCT | 3295.6 | 2737 | 0.831 | -0.186 |
| NG | AACGGA | 5785.17 | 5427 | 0.938 | -0.064 |
| NG | AACGGC | 3728.25 | 3306 | 0.887 | -0.120 |
| NG | AACGGG | 2224.03 | 2152 | 0.968 | -0.033 |
| NG | AACGGT | 3859.45 | 3769 | 0.977 | -0.024 |
| NV | AACGTA | 2652.91 | 2411 | 0.909 | -0.096 |
| NV | AACGTC | 3242.22 | 3197 | 0.986 | -0.014 |
| NV | AACGTG | 4826.84 | 4538 | 0.940 | -0.062 |
| NV | AACGTT | 4172.66 | 3853 | 0.923 | -0.080 |
| NY | AACTAC | 4547.26 | 5612 | 1.234 | 0.210 |
| NY | AACTAT | 3369.76 | 3797 | 1.127 | 0.119 |
| NS | AACTCA | 2928.28 | 2190 | 0.748 | -0.291 |
| NS | AACTCC | 3453.25 | 3006 | 0.870 | -0.139 |
| NS | AACTCG | 4138.44 | 3704 | 0.895 | -0.111 |
| NS | AACTCT | 2386.97 | 1927 | 0.807 | -0.214 |
| NC | AACTGC | 3176.95 | 3446 | 1.085 | 0.081 |
| NW | AACTGG | 2839.12 | 3170 | 1.117 | 0.110 |
| NC | AACTGT | 2940.13 | 3146 | 1.070 | 0.068 |
| NL | AACTTA | 2271.16 | 1384 | 0.609 | -0.495 |
| NF | AACTTC | 5542.41 | 5797 | 1.046 | 0.045 |
| NL | AACTTG | 4776.32 | 3358 | 0.703 | -0.352 |

-continued

Dataset SI. Mosquito codon pair scores.

| AA pair | Codon Pair | Expected | Ob-served | Observed/ Expected | CPS |
|---|---|---|---|---|---|
| NF | AACTTT | 4243.21 | 4151 | 0.978 | -0.022 |
| KK | AAGAAA | 10553.09 | 11257 | 1.067 | 0.065 |
| KN | AAGAAC | 6875.16 | 7555 | 1.099 | 0.094 |
| KK | AAGAAG | 10026.57 | 13774 | 1.374 | 0.318 |
| KN | AAGAAT | 5939.86 | 5733 | 0.965 | -0.035 |
| KT | AAGACA | 3758.81 | 2511 | 0.668 | -0.403 |
| KT | AAGACC | 4467.16 | 3145 | 0.704 | -0.351 |
| KT | AAGACG | 4397.17 | 3249 | 0.739 | -0.303 |
| KT | AAGACT | 3239.86 | 2521 | 0.778 | -0.251 |
| KR | AAGAGA | 3094.19 | 2276 | 0.736 | -0.307 |
| KS | AAGAGC | 3890.57 | 3776 | 0.971 | -0.030 |
| KR | AAGAGG | 2298.45 | 1869 | 0.813 | -0.207 |
| KS | AAGAGT | 3560.59 | 3018 | 0.848 | -0.165 |
| KI | AAGATA | 3456.5 | 2659 | 0.769 | -0.262 |
| KI | AAGATC | 6708.25 | 6442 | 0.960 | -0.040 |
| KM | AAGATG | 6124.69 | 5810 | 0.949 | -0.053 |
| KI | AAGATT | 5807.39 | 5415 | 0.932 | -0.070 |
| KQ | AAGCAA | 6086.75 | 6370 | 1.047 | 0.045 |
| KH | AAGCAC | 3745.13 | 4245 | 1.133 | 0.125 |
| KQ | AAGCAG | 5979.93 | 6910 | 1.156 | 0.145 |
| KH | AAGCAT | 3669.2 | 3657 | 0.997 | -0.003 |
| KP | AAGCCA | 4097.32 | 3589 | 0.876 | -0.132 |
| KP | AAGCCC | 2502.03 | 2152 | 0.860 | -0.151 |
| KP | AAGCCG | 4336.25 | 3162 | 0.729 | -0.316 |
| KP | AAGCCT | 2473.83 | 1881 | 0.760 | -0.274 |
| KR | AAGCGA | 4100.34 | 4358 | 1.063 | 0.061 |
| KR | AAGCGC | 2649.52 | 2769 | 1.045 | 0.044 |
| KR | AAGCGG | 3475.58 | 3276 | 0.943 | -0.059 |
| KR | AAGCGT | 2787.66 | 2614 | 0.938 | -0.064 |
| KL | AAGCTA | 2745.81 | 3133 | 1.141 | 0.132 |
| KL | AAGCTC | 3214.8 | 3211 | 0.999 | -0.001 |
| KL | AAGCTG | 7107.3 | 9255 | 1.302 | 0.264 |
| KL | AAGCTT | 3228.31 | 3264 | 1.011 | 0.011 |
| KE | AAGGAA | 9209.76 | 11217 | 1.218 | 0.197 |
| KD | AAGGAC | 4989.55 | 6612 | 1.325 | 0.282 |
| KE | AAGGAG | 6186.98 | 7652 | 1.237 | 0.213 |
| KD | AAGGAT | 6596.74 | 7542 | 1.143 | 0.134 |
| KA | AAGGCA | 3665.38 | 3614 | 0.986 | -0.014 |
| KA | AAGGCC | 4305.86 | 4268 | 0.991 | -0.009 |
| KA | AAGGCG | 3000 | 3397 | 1.132 | 0.124 |
| KA | AAGGCT | 3577.77 | 3132 | 0.875 | -0.133 |
| KG | AAGGGA | 3816.14 | 3546 | 0.929 | -0.073 |
| KG | AAGGGC | 2459.31 | 2885 | 1.173 | 0.160 |
| KG | AAGGGG | 1467.06 | 1188 | 0.810 | -0.211 |
| KG | AAGGGT | 2545.85 | 2703 | 1.062 | 0.060 |
| KV | AAGGTA | 2630.66 | 2200 | 0.836 | -0.179 |
| KV | AAGGTC | 3215.03 | 3518 | 1.094 | 0.090 |
| KV | AAGGTG | 4786.36 | 5269 | 1.101 | 0.096 |
| KV | AAGGTT | 4137.66 | 3936 | 0.951 | -0.050 |
| KY | AAGTAC | 5011.57 | 5670 | 1.131 | 0.123 |
| KY | AAGTAT | 3713.84 | 3814 | 1.027 | 0.027 |
| KS | AAGTCA | 3133.52 | 2109 | 0.673 | -0.396 |
| KS | AAGTCC | 3695.28 | 2895 | 0.783 | -0.244 |
| KS | AAGTCG | 4428.5 | 2892 | 0.653 | -0.426 |
| KS | AAGTCT | 2554.27 | 1905 | 0.746 | -0.293 |
| KC | AAGTGC | 3452.16 | 3599 | 1.043 | 0.042 |
| KW | AAGTGG | 3182.93 | 3222 | 1.012 | 0.012 |
| KC | AAGTGT | 3194.82 | 3144 | 0.984 | -0.016 |
| KL | AAGTTA | 2668.99 | 2168 | 0.812 | -0.208 |
| KF | AAGTTC | 5771.7 | 6472 | 1.121 | 0.115 |
| KL | AAGTTG | 5612.97 | 4764 | 0.849 | -0.164 |
| KF | AAGTTT | 4418.74 | 4802 | 1.087 | 0.083 |
| NK | AATAAA | 5770.47 | 5527 | 0.958 | -0.043 |
| NN | AATAAC | 6234.61 | 3208 | 0.515 | -0.664 |
| NK | AATAAG | 5482.57 | 2979 | 0.543 | -0.610 |
| NN | AATAAT | 5386.45 | 4490 | 0.834 | -0.182 |
| NT | AATACA | 2471.84 | 2436 | 0.986 | -0.015 |
| NT | AATACC | 2937.66 | 2375 | 0.808 | -0.213 |
| NT | AATACG | 2891.64 | 2679 | 0.926 | -0.076 |
| NT | AATACT | 2130.57 | 2069 | 0.971 | -0.029 |
| NR | AATAGA | 2330.99 | 1588 | 0.681 | -0.384 |
| NS | AATAGC | 3141.14 | 2265 | 0.721 | -0.327 |
| NR | AATAGG | 1731.52 | 989 | 0.571 | -0.560 |
| NS | AATAGT | 2874.72 | 2607 | 0.907 | -0.098 |

-continued

Dataset SI. Mosquito codon pair scores.

| AA pair | Codon Pair | Expected | Ob-served | Observed/ Expected | CPS |
|---|---|---|---|---|---|
| NI | AATATA | 2539.67 | 2470 | 0.973 | -0.028 |
| NI | AATATC | 4928.9 | 3207 | 0.651 | -0.430 |
| NM | AATATG | 3844.8 | 3253 | 0.846 | -0.167 |
| NI | AATATT | 4266.99 | 3874 | 0.908 | -0.097 |
| NQ | AATCAA | 4358.84 | 5724 | 1.313 | 0.272 |
| NH | AATCAC | 2836.22 | 2991 | 1.055 | 0.053 |
| NQ | AATCAG | 4282.34 | 4451 | 1.039 | 0.039 |
| NH | AATCAT | 2778.72 | 3282 | 1.181 | 0.166 |
| NP | AATCCA | 3074.3 | 4099 | 1.333 | 0.288 |
| NP | AATCCC | 1877.33 | 2724 | 1.451 | 0.372 |
| NP | AATCCG | 3253.57 | 4277 | 1.315 | 0.273 |
| NP | AATCCT | 1856.16 | 2668 | 1.437 | 0.363 |
| NR | AATCGA | 3088.96 | 4106 | 1.329 | 0.285 |
| NR | AATCGC | 1996 | 2579 | 1.292 | 0.256 |
| NR | AATCGG | 2618.3 | 2856 | 1.091 | 0.087 |
| NR | AATCGT | 2100.06 | 2896 | 1.379 | 0.321 |
| NL | AATCTA | 2018.66 | 2962 | 1.467 | 0.383 |
| NL | AATCTC | 2363.46 | 3062 | 1.296 | 0.259 |
| NL | AATCTG | 5225.14 | 5801 | 1.110 | 0.105 |
| NL | AATCTT | 2373.39 | 2999 | 1.264 | 0.234 |
| NE | AATGAA | 6624.13 | 5993 | 0.905 | -0.100 |
| ND | AATGAC | 4083.74 | 2970 | 0.727 | -0.318 |
| NE | AATGAG | 4449.99 | 3408 | 0.766 | -0.267 |
| ND | AATGAT | 5399.16 | 4673 | 0.866 | -0.144 |
| NA | AATGCA | 2916.99 | 3705 | 1.270 | 0.239 |
| NA | AATGCC | 3426.7 | 4182 | 1.220 | 0.199 |
| NA | AATGCG | 2387.47 | 2725 | 1.141 | 0.132 |
| NA | AATGCT | 2847.27 | 3685 | 1.294 | 0.258 |
| NG | AATGGA | 4998.16 | 5297 | 1.060 | 0.058 |
| NG | AATGGC | 3221.06 | 3493 | 1.084 | 0.081 |
| NG | AATGGG | 1921.47 | 2451 | 1.276 | 0.243 |
| NG | AATGGT | 3334.41 | 3177 | 0.953 | -0.048 |
| NV | AATGTA | 2292.01 | 2641 | 1.152 | 0.142 |
| NV | AATGTC | 2801.15 | 2678 | 0.956 | -0.045 |
| NV | AATGTG | 4170.2 | 4649 | 1.115 | 0.109 |
| NV | AATGTT | 3605.01 | 3796 | 1.053 | 0.052 |
| NY | AATTAC | 3928.65 | 2399 | 0.611 | -0.493 |
| NY | AATTAT | 2911.33 | 2949 | 1.013 | 0.013 |
| NS | AATTCA | 2529.91 | 2717 | 1.074 | 0.071 |
| NS | AATTCC | 2983.47 | 2897 | 0.971 | -0.029 |
| NS | AATTCG | 3575.45 | 3154 | 0.882 | -0.125 |
| NS | AATTCT | 2062.25 | 2418 | 1.173 | 0.159 |
| NC | AATTGC | 2744.76 | 2091 | 0.762 | -0.272 |
| NW | AATTGG | 2452.88 | 2122 | 0.865 | -0.145 |
| NC | AATTGT | 2540.16 | 2719 | 1.070 | 0.068 |
| NL | AATTTA | 1962.19 | 2985 | 1.521 | 0.420 |
| NF | AATTTC | 4788.42 | 4244 | 0.886 | -0.121 |
| NL | AATTTG | 4126.54 | 5429 | 1.316 | 0.274 |
| NF | AATTTT | 3665.96 | 4048 | 1.104 | 0.099 |
| TK | ACAAAA | 3709.77 | 4702 | 1.267 | 0.237 |
| TN | ACAAAC | 3300.4 | 3479 | 1.054 | 0.053 |
| TK | ACAAAG | 3524.69 | 2794 | 0.793 | -0.232 |
| TN | ACAAAT | 2851.41 | 3363 | 1.179 | 0.165 |
| TT | ACAACA | 2474.47 | 3418 | 1.381 | 0.323 |
| TT | ACAACC | 2940.79 | 2999 | 1.020 | 0.020 |
| TT | ACAACG | 2894.72 | 3221 | 1.113 | 0.107 |
| TT | ACAACT | 2132.84 | 2837 | 1.330 | 0.285 |
| TR | ACAAGA | 1251.76 | 2183 | 1.744 | 0.556 |
| TS | ACAAGC | 2178.04 | 2036 | 0.935 | -0.067 |
| TR | ACAAGG | 929.84 | 1564 | 1.682 | 0.520 |
| TS | ACAAGT | 1993.31 | 2000 | 1.003 | 0.003 |
| TI | ACAATA | 1706.82 | 2074 | 1.215 | 0.195 |
| TI | ACAATC | 3312.53 | 3104 | 0.937 | -0.065 |
| TM | ACAATG | 2772.13 | 2676 | 0.965 | -0.035 |
| TI | ACAATT | 2867.69 | 2743 | 0.957 | -0.044 |
| TQ | ACACAA | 2197.73 | 2464 | 1.121 | 0.114 |
| TH | ACACAC | 1532.28 | 1623 | 1.059 | 0.058 |
| TQ | ACACAG | 2159.16 | 1742 | 0.807 | -0.215 |
| TH | ACACAT | 1501.21 | 1775 | 1.182 | 0.168 |
| TP | ACACCA | 2180.12 | 2589 | 1.188 | 0.172 |
| TP | ACACCC | 1331.29 | 1377 | 1.034 | 0.034 |
| TP | ACACCG | 2307.25 | 2652 | 1.149 | 0.139 |
| TP | ACACCT | 1316.28 | 1583 | 1.203 | 0.185 |

-continued

Dataset SI. Mosquito codon pair scores.

| AA pair | Codon Pair | Expected | Ob-served | Observed/Expected | CPS |
|---|---|---|---|---|---|
| TR | ACACGA | 1658.8 | 1401 | 0.845 | -0.169 |
| TR | ACACGC | 1071.87 | 823 | 0.768 | -0.264 |
| TR | ACACGG | 1406.05 | 999 | 0.711 | -0.342 |
| TR | ACACGT | 1127.75 | 983 | 0.872 | -0.137 |
| TL | ACACTA | 1180.41 | 1140 | 0.966 | -0.035 |
| TL | ACACTC | 1382.03 | 1200 | 0.868 | -0.141 |
| TL | ACACTG | 3055.39 | 2595 | 0.849 | -0.163 |
| TL | ACACTT | 1387.83 | 1627 | 1.172 | 0.159 |
| TE | ACAGAA | 4104.01 | 3207 | 0.781 | -0.247 |
| TD | ACAGAC | 2334.13 | 1445 | 0.619 | -0.480 |
| TE | ACAGAG | 2757.01 | 1668 | 0.605 | -0.503 |
| TD | ACAGAT | 3085.97 | 2314 | 0.750 | -0.288 |
| TA | ACAGCA | 2197.92 | 2909 | 1.324 | 0.280 |
| TA | ACAGCC | 2581.97 | 1682 | 0.651 | -0.429 |
| TA | ACAGCG | 1798.92 | 1713 | 0.952 | -0.049 |
| TA | ACAGCT | 2145.38 | 2209 | 1.030 | 0.029 |
| TG | ACAGGA | 2770.23 | 2001 | 0.722 | -0.325 |
| TG | ACAGGC | 1785.27 | 895 | 0.501 | -0.691 |
| TG | ACAGGG | 1064.98 | 716 | 0.672 | -0.397 |
| TG | ACAGGT | 1848.09 | 1184 | 0.641 | -0.445 |
| TV | ACAGTA | 1550.25 | 1560 | 1.006 | 0.006 |
| TV | ACAGTC | 1894.62 | 1338 | 0.706 | -0.348 |
| TV | ACAGTG | 2820.61 | 2280 | 0.808 | -0.213 |
| TV | ACAGTT | 2438.33 | 2476 | 1.015 | 0.015 |
| TY | ACATAC | 1976.56 | 1416 | 0.716 | -0.334 |
| TY | ACATAT | 1464.73 | 1612 | 1.101 | 0.096 |
| TS | ACATCA | 1754.22 | 2720 | 1.551 | 0.439 |
| TS | ACATCC | 2068.71 | 2300 | 1.112 | 0.106 |
| TS | ACATCG | 2479.19 | 2810 | 1.133 | 0.125 |
| TS | ACATCT | 1429.95 | 1952 | 1.365 | 0.311 |
| TC | ACATGC | 1498.8 | 1265 | 0.844 | -0.170 |
| TW | ACATGG | 1492.34 | 1500 | 1.005 | 0.005 |
| TC | ACATGT | 1387.07 | 1420 | 1.024 | 0.023 |
| TL | ACATTA | 1147.39 | 1443 | 1.258 | 0.229 |
| TF | ACATTC | 2883.71 | 3219 | 1.116 | 0.110 |
| TL | ACATTG | 2412.99 | 2504 | 1.038 | 0.037 |
| TF | ACATTT | 2207.73 | 2803 | 1.270 | 0.239 |
| TK | ACCAAA | 4408.88 | 5793 | 1.314 | 0.273 |
| TN | ACCAAC | 3922.36 | 5925 | 1.511 | 0.412 |
| TK | ACCAAG | 4188.92 | 5485 | 1.309 | 0.270 |
| TN | ACCAAT | 3388.76 | 4168 | 1.230 | 0.207 |
| TT | ACCACA | 2940.79 | 2514 | 0.855 | -0.157 |
| TT | ACCACC | 3494.99 | 4337 | 1.241 | 0.216 |
| TT | ACCACG | 3440.23 | 2364 | 0.687 | -0.375 |
| TT | ACCACT | 2534.78 | 2677 | 1.056 | 0.055 |
| TR | ACCAGA | 1487.65 | 1923 | 1.293 | 0.257 |
| TS | ACCAGC | 2588.49 | 3976 | 1.536 | 0.429 |
| TR | ACCAGG | 1105.07 | 1293 | 1.170 | 0.157 |
| TS | ACCAGT | 2368.95 | 3196 | 1.349 | 0.299 |
| TI | ACCATA | 2028.47 | 1570 | 0.774 | -0.256 |
| TI | ACCATC | 3936.78 | 5145 | 1.307 | 0.268 |
| TM | ACCATG | 3294.54 | 3369 | 1.023 | 0.022 |
| TI | ACCATT | 3408.1 | 3550 | 1.042 | 0.041 |
| TQ | ACCCAA | 2611.89 | 2263 | 0.866 | -0.143 |
| TH | ACCCAC | 1821.04 | 1665 | 0.914 | -0.090 |
| TQ | ACCCAG | 2566.05 | 2352 | 0.917 | -0.087 |
| TH | ACCCAT | 1784.12 | 1577 | 0.884 | -0.123 |
| TP | ACCCCA | 2590.96 | 1539 | 0.594 | -0.521 |
| TP | ACCCCC | 1582.17 | 892 | 0.564 | -0.573 |
| TP | ACCCCG | 2742.05 | 1528 | 0.557 | -0.585 |
| TP | ACCCCT | 1564.34 | 967 | 0.618 | -0.481 |
| TR | ACCCGA | 1971.4 | 1509 | 0.765 | -0.267 |
| TR | ACCCGC | 1273.86 | 1171 | 0.919 | -0.084 |
| TR | ACCCGG | 1671.02 | 1699 | 1.017 | 0.017 |
| TR | ACCCGT | 1340.28 | 1242 | 0.927 | -0.076 |
| TL | ACCCTA | 1402.86 | 1036 | 0.738 | -0.303 |
| TL | ACCCTC | 1642.47 | 1470 | 0.895 | -0.111 |
| TL | ACCCTG | 3631.18 | 2753 | 0.758 | -0.277 |
| TL | ACCCTT | 1649.37 | 1201 | 0.728 | -0.317 |
| TE | ACCGAA | 4877.41 | 5372 | 1.101 | 0.097 |
| TD | ACCGAC | 2773.99 | 3173 | 1.144 | 0.134 |
| TE | ACCGAG | 3276.57 | 4004 | 1.222 | 0.200 |
| TD | ACCGAT | 3667.53 | 4858 | 1.325 | 0.281 |
| TA | ACCGCA | 2612.11 | 1758 | 0.673 | -0.396 |
| TA | ACCGCC | 3068.55 | 2416 | 0.787 | -0.239 |
| TA | ACCGCG | 2137.93 | 1095 | 0.512 | -0.669 |
| TA | ACCGCT | 2549.68 | 2010 | 0.788 | -0.238 |
| TG | ACCGGA | 3292.28 | 4809 | 1.461 | 0.379 |
| TG | ACCGGC | 2121.71 | 2570 | 1.211 | 0.192 |
| TG | ACCGGG | 1265.67 | 1815 | 1.434 | 0.360 |
| TG | ACCGGT | 2196.37 | 3492 | 1.590 | 0.464 |
| TV | ACCGTA | 1842.4 | 1885 | 1.023 | 0.023 |
| TV | ACCGTC | 2251.66 | 2465 | 1.095 | 0.091 |
| TV | ACCGTG | 3352.16 | 2666 | 0.795 | -0.229 |
| TV | ACCGTT | 2897.84 | 3199 | 1.104 | 0.099 |
| TY | ACCTAC | 2349.04 | 3043 | 1.295 | 0.259 |
| TY | ACCTAT | 1740.76 | 1862 | 1.070 | 0.067 |
| TS | ACCTCA | 2084.81 | 1336 | 0.641 | -0.445 |
| TS | ACCTCC | 2458.56 | 1773 | 0.721 | -0.327 |
| TS | ACCTCG | 2946.39 | 2008 | 0.682 | -0.383 |
| TS | ACCTCT | 1699.42 | 1054 | 0.620 | -0.478 |
| TC | ACCTGC | 1781.25 | 2048 | 1.150 | 0.140 |
| TW | ACCTGG | 1773.57 | 1755 | 0.990 | -0.011 |
| TC | ACCTGT | 1648.47 | 1705 | 1.034 | 0.034 |
| TL | ACCTTA | 1363.61 | 936 | 0.686 | -0.376 |
| TF | ACCTTC | 3427.15 | 3350 | 0.977 | -0.023 |
| TL | ACCTTG | 2867.72 | 1841 | 0.642 | -0.443 |
| TF | ACCTTT | 2623.78 | 1663 | 0.634 | -0.456 |
| TK | ACGAAA | 4339.81 | 4323 | 0.996 | -0.004 |
| TN | ACGAAC | 3860.91 | 3191 | 0.826 | -0.191 |
| TK | ACGAAG | 4123.29 | 4029 | 0.977 | -0.023 |
| TN | ACGAAT | 3335.67 | 2933 | 0.879 | -0.129 |
| TT | ACGACA | 2894.72 | 2805 | 0.969 | -0.031 |
| TT | ACGACC | 3440.23 | 2773 | 0.806 | -0.216 |
| TT | ACGACG | 3386.33 | 3640 | 1.075 | 0.072 |
| TT | ACGACT | 2495.06 | 1940 | 0.778 | -0.252 |
| TR | ACGAGA | 1464.35 | 1894 | 1.293 | 0.257 |
| TS | ACGAGC | 2547.94 | 1907 | 0.748 | -0.290 |
| TR | ACGAGG | 1087.75 | 1605 | 1.476 | 0.389 |
| TS | ACGAGT | 2331.83 | 1806 | 0.774 | -0.256 |
| TI | ACGATA | 1996.69 | 2404 | 1.204 | 0.186 |
| TI | ACGATC | 3875.1 | 4334 | 1.118 | 0.112 |
| TM | ACGATG | 3242.93 | 4097 | 1.263 | 0.234 |
| TI | ACGATT | 3354.71 | 3475 | 1.036 | 0.035 |
| TQ | ACGCAA | 2570.97 | 2752 | 1.070 | 0.068 |
| TH | ACGCAC | 1792.51 | 1875 | 1.046 | 0.045 |
| TQ | ACGCAG | 2525.85 | 2690 | 1.065 | 0.063 |
| TH | ACGCAT | 1756.17 | 1579 | 0.899 | -0.106 |
| TP | ACGCCA | 2550.37 | 2563 | 1.005 | 0.005 |
| TP | ACGCCC | 1557.39 | 1732 | 1.112 | 0.106 |
| TP | ACGCCG | 2699.09 | 2477 | 0.918 | -0.086 |
| TP | ACGCCT | 1539.83 | 1360 | 0.883 | -0.124 |
| TR | ACGCGA | 1940.51 | 1343 | 0.692 | -0.368 |
| TR | ACGCGC | 1253.9 | 825 | 0.658 | -0.419 |
| TR | ACGCGG | 1644.84 | 1144 | 0.696 | -0.363 |
| TR | ACGCGT | 1319.28 | 906 | 0.687 | -0.376 |
| TL | ACGCTA | 1380.88 | 1457 | 1.055 | 0.054 |
| TL | ACGCTC | 1616.74 | 1967 | 1.217 | 0.196 |
| TL | ACGCTG | 3574.3 | 4607 | 1.289 | 0.254 |
| TL | ACGCTT | 1623.53 | 1955 | 1.204 | 0.186 |
| TE | ACGGAA | 4801 | 5641 | 1.175 | 0.161 |
| TD | ACGGAC | 2730.53 | 2834 | 1.038 | 0.037 |
| TE | ACGGAG | 3225.24 | 3796 | 1.177 | 0.163 |
| TD | ACGGAT | 3610.07 | 4101 | 1.136 | 0.128 |
| TA | ACGGCA | 2571.19 | 3096 | 1.204 | 0.186 |
| TA | ACGGCC | 3020.47 | 3718 | 1.231 | 0.208 |
| TA | ACGGCG | 2104.44 | 2652 | 1.260 | 0.231 |
| TA | ACGGCT | 2509.73 | 2537 | 1.011 | 0.011 |
| TG | ACGGGA | 3240.7 | 2318 | 0.715 | -0.335 |
| TG | ACGGGC | 2088.47 | 1165 | 0.558 | -0.584 |
| TG | ACGGGG | 1245.84 | 1133 | 0.909 | -0.095 |
| TG | ACGGGT | 2161.96 | 1515 | 0.701 | -0.356 |
| TV | ACGGTA | 1813.53 | 1863 | 1.027 | 0.027 |
| TV | ACGGTC | 2216.39 | 2284 | 1.031 | 0.030 |
| TV | ACGGTG | 3299.64 | 3987 | 1.208 | 0.189 |
| TV | ACGGTT | 2852.44 | 3243 | 1.137 | 0.128 |
| TY | ACGTAC | 2312.24 | 2419 | 1.046 | 0.045 |
| TY | ACGTAT | 1713.49 | 1519 | 0.886 | -0.120 |

-continued

Dataset SI. Mosquito codon pair scores.

| AA pair | Codon Pair | Expected | Ob-served | Observed/Expected | CPS |
|---|---|---|---|---|---|
| TS | ACGTCA | 2052.14 | 1563 | 0.762 | -0.272 |
| TS | ACGTCC | 2420.04 | 2009 | 0.830 | -0.186 |
| TS | ACGTCG | 2900.23 | 2129 | 0.734 | -0.309 |
| TS | ACGTCT | 1672.8 | 1215 | 0.726 | -0.320 |
| TC | ACGTGC | 1753.34 | 1648 | 0.940 | -0.062 |
| TW | ACGTGG | 1745.79 | 1800 | 1.031 | 0.031 |
| TC | ACGTGT | 1622.64 | 1503 | 0.926 | -0.077 |
| TL | ACGTTA | 1342.25 | 1374 | 1.024 | 0.023 |
| TF | ACGTTC | 3373.45 | 3648 | 1.081 | 0.078 |
| TL | ACGTTG | 2822.79 | 3501 | 1.240 | 0.215 |
| TF | ACGTTT | 2582.68 | 2541 | 0.984 | -0.016 |
| TK | ACTAAA | 3197.59 | 2057 | 0.643 | -0.441 |
| TN | ACTAAC | 2844.74 | 1357 | 0.477 | -0.740 |
| ~~TK~~ | ~~ACTAAG~~ | 3038.06 | 1348 | 0.444 | -0.813 |
| ~~TN~~ | ~~ACTAAT~~ | 2457.74 | 1546 | 0.629 | -0.464 |
| TT | ACTACA | 2132.84 | 2272 | 1.065 | 0.063 |
| TT | ACTACC | 2534.78 | 2063 | 0.814 | -0.206 |
| TT | ACTACG | 2495.06 | 2218 | 0.889 | -0.118 |
| TT | ACTACT | 1838.37 | 1993 | 1.084 | 0.081 |
| TR | ACTAGA | 1078.94 | 981 | 0.909 | -0.095 |
| TS | ACTAGC | 1877.33 | 1394 | 0.743 | -0.298 |
| TR | ACTAGG | 801.46 | 603 | 0.752 | -0.285 |
| TS | ACTAGT | 1718.1 | 1553 | 0.904 | -0.101 |
| TI | ACTATA | 1471.17 | 1073 | 0.729 | -0.316 |
| TI | ACTATC | 2855.19 | 1750 | 0.613 | -0.490 |
| TM | ACTATG | 2389.4 | 1557 | 0.652 | -0.428 |
| TI | ACTATT | 2471.76 | 2063 | 0.835 | -0.181 |
| TQ | ACTCAA | 1894.3 | 2351 | 1.241 | 0.216 |
| TH | ACTCAC | 1320.73 | 1316 | 0.996 | -0.004 |
| TQ | ACTCAG | 1861.06 | 1773 | 0.953 | -0.048 |
| TH | ACTCAT | 1293.95 | 1392 | 1.076 | 0.073 |
| TP | ACTCCA | 1879.12 | 2644 | 1.407 | 0.341 |
| TP | ACTCCC | 1147.49 | 1604 | 1.398 | 0.335 |
| TP | ACTCCG | 1988.7 | 2850 | 1.433 | 0.360 |
| TP | ACTCCT | 1134.55 | 1754 | 1.546 | 0.436 |
| TR | ACTCGA | 1429.78 | 1625 | 1.137 | 0.128 |
| TR | ACTCGC | 923.88 | 1175 | 1.272 | 0.240 |
| TR | ACTCGG | 1211.93 | 1234 | 1.018 | 0.018 |
| TR | ACTCGT | 972.05 | 1299 | 1.336 | 0.290 |
| TL | ACTCTA | 1017.44 | 1078 | 1.060 | 0.058 |
| TL | ACTCTC | 1191.22 | 1259 | 1.057 | 0.055 |
| TL | ACTCTG | 2633.56 | 2162 | 0.821 | -0.197 |
| TL | ACTCTT | 1196.22 | 1370 | 1.145 | 0.136 |
| TE | ACTGAA | 3537.39 | 3587 | 1.014 | 0.014 |
| TD | ACTGAC | 2011.87 | 1523 | 0.757 | -0.278 |
| TE | ACTGAG | 2376.37 | 1680 | 0.707 | -0.347 |
| TD | ACTGAT | 2659.91 | 2626 | 0.987 | -0.013 |
| TA | ACTGCA | 1894.46 | 2342 | 1.236 | 0.212 |
| TA | ACTGCC | 2225.5 | 2501 | 1.124 | 0.117 |
| TA | ACTGCG | 1550.56 | 1575 | 1.016 | 0.016 |
| TA | ACTGCT | 1849.18 | 2605 | 1.409 | 0.343 |
| TG | ACTGGA | 2387.76 | 3089 | 1.294 | 0.257 |
| TG | ACTGGC | 1538.79 | 1750 | 1.137 | 0.129 |
| TG | ACTGGG | 917.94 | 1145 | 1.247 | 0.221 |
| TG | ACTGGT | 1592.94 | 1922 | 1.207 | 0.188 |
| TV | ACTGTA | 1336.22 | 1567 | 1.173 | 0.159 |
| TV | ACTGTC | 1633.04 | 1420 | 0.870 | -0.140 |
| TV | ACTGTG | 2431.19 | 2136 | 0.879 | -0.129 |
| TV | ACTGTT | 2101.69 | 2363 | 1.124 | 0.117 |
| TY | ACTTAC | 1703.67 | 1312 | 0.770 | -0.261 |
| TY | ACTTAT | 1262.51 | 1340 | 1.061 | 0.060 |
| TS | ACTTCA | 1512.03 | 2312 | 1.529 | 0.425 |
| TS | ACTTCC | 1783.1 | 2689 | 1.508 | 0.411 |
| TS | ACTTCG | 2136.9 | 2703 | 1.265 | 0.235 |
| TS | ACTTCT | 1232.52 | 1794 | 1.456 | 0.375 |
| TC | ACTTGC | 1291.87 | 1320 | 1.022 | 0.022 |
| TW | ACTTGG | 1286.3 | 1243 | 0.966 | -0.034 |
| TC | ACTTGT | 1195.57 | 1270 | 1.062 | 0.060 |
| TL | ACTTTA | 988.97 | 1323 | 1.338 | 0.291 |
| TF | ACTTTC | 2485.57 | 2150 | 0.865 | -0.145 |
| TL | ACTTTG | 2079.84 | 2792 | 1.342 | 0.294 |
| TF | ACTTTT | 1902.93 | 2113 | 1.110 | 0.105 |
| RK | AGAAAA | 3857.27 | 4792 | 1.242 | 0.217 |
| RN | AGAAAC | 2918.18 | 3029 | 1.038 | 0.037 |
| RK | AGAAAG | 3664.82 | 2937 | 0.801 | -0.221 |
| RN | AGAAAT | 2521.19 | 3364 | 1.334 | 0.288 |
| RT | AGAACA | 1482.92 | 2495 | 1.682 | 0.520 |
| RT | AGAACC | 1762.37 | 1740 | 0.987 | -0.013 |
| RT | AGAACG | 1734.76 | 1775 | 1.023 | 0.023 |
| RT | AGAACT | 1278.18 | 1854 | 1.450 | 0.372 |
| RR | AGAAGA | 1589.65 | 3791 | 2.385 | 0.869 |
| RS | AGAAGC | 1726.29 | 2732 | 1.583 | 0.459 |
| RR | AGAAGG | 1180.84 | 2404 | 2.036 | 0.711 |
| RS | AGAAGT | 1579.87 | 2265 | 1.434 | 0.360 |
| RI | AGAATA | 1249.81 | 1899 | 1.519 | 0.418 |
| RI | AGAATC | 2425.59 | 2211 | 0.912 | -0.093 |
| RM | AGAATG | 2179.55 | 2123 | 0.974 | -0.026 |
| RI | AGAATT | 2099.85 | 2167 | 1.032 | 0.031 |
| RQ | AGACAA | 2114.47 | 1849 | 0.874 | -0.134 |
| RH | AGACAC | 1439.41 | 1003 | 0.697 | -0.361 |
| RQ | AGACAG | 2077.36 | 1287 | 0.620 | -0.479 |
| RH | AGACAT | 1410.23 | 1225 | 0.869 | -0.141 |
| RP | AGACCA | 1441.66 | 1323 | 0.918 | -0.086 |
| RP | AGACCC | 880.35 | 625 | 0.710 | -0.343 |
| RP | AGACCG | 1525.73 | 1116 | 0.731 | -0.313 |
| RP | AGACCT | 870.43 | 842 | 0.967 | -0.033 |
| RR | AGACGA | 2106.57 | 1938 | 0.920 | -0.083 |
| RR | AGACGC | 1361.2 | 802 | 0.589 | -0.529 |
| RR | AGACGG | 1785.6 | 972 | 0.544 | -0.608 |
| RR | AGACGT | 1432.17 | 998 | 0.697 | -0.361 |
| RL | AGACTA | 945.18 | 880 | 0.931 | -0.071 |
| RL | AGACTC | 1106.62 | 669 | 0.605 | -0.503 |
| RL | AGACTG | 2446.53 | 1527 | 0.624 | -0.471 |
| RL | AGACTT | 1111.27 | 1088 | 0.979 | -0.021 |
| RE | AGAGAA | 3073.23 | 2609 | 0.849 | -0.164 |
| RD | AGAGAC | 1724.82 | 1115 | 0.646 | -0.436 |
| RE | AGAGAG | 2064.55 | 1585 | 0.768 | -0.264 |
| RD | AGAGAT | 2280.4 | 2108 | 0.924 | -0.079 |
| RA | AGAGCA | 1277.86 | 1804 | 1.412 | 0.345 |
| RA | AGAGCC | 1501.15 | 929 | 0.619 | -0.480 |
| RA | AGAGCG | 1045.89 | 1085 | 1.037 | 0.037 |
| RA | AGAGCT | 1247.32 | 1399 | 1.122 | 0.115 |
| RG | AGAGGA | 1787.28 | 2120 | 1.186 | 0.171 |
| RG | AGAGGC | 1151.81 | 944 | 0.820 | -0.199 |
| RG | AGAGGG | 687.1 | 650 | 0.946 | -0.056 |
| RG | AGAGGT | 1192.35 | 1005 | 0.843 | -0.171 |
| RV | AGAGTA | 907.43 | 1079 | 1.189 | 0.173 |
| RV | AGAGTC | 1109.01 | 736 | 0.664 | -0.410 |
| RV | AGAGTG | 1651.03 | 1287 | 0.780 | -0.249 |
| RV | AGAGTT | 1427.27 | 1455 | 1.019 | 0.019 |
| RY | AGATAC | 1813.04 | 1068 | 0.589 | -0.529 |
| RY | AGATAT | 1343.56 | 1488 | 1.108 | 0.102 |
| RS | AGATCA | 1390.38 | 1834 | 1.319 | 0.277 |
| RS | AGATCC | 1639.64 | 1214 | 0.740 | -0.301 |
| RS | AGATCG | 1964.97 | 1622 | 0.825 | -0.192 |
| RS | AGATCT | 1133.36 | 1348 | 1.189 | 0.173 |
| RC | AGATGC | 1506.26 | 1243 | 0.825 | -0.192 |
| RW | AGATGG | 1807.86 | 1462 | 0.809 | -0.212 |
| RC | AGATGT | 1393.98 | 1463 | 1.050 | 0.048 |
| RL | AGATTA | 918.74 | 1486 | 1.617 | 0.481 |
| RF | AGATTC | 2533 | 1871 | 0.739 | -0.303 |
| RL | AGATTG | 1932.14 | 1965 | 1.017 | 0.017 |
| RF | AGATTT | 1939.24 | 2312 | 1.192 | 0.176 |
| SK | AGCAAA | 4034.44 | 5639 | 1.398 | 0.335 |
| SN | AGCAAC | 3854.55 | 5123 | 1.329 | 0.284 |
| SK | AGCAAG | 3833.16 | 4217 | 1.100 | 0.095 |
| SN | AGCAAT | 3330.18 | 4821 | 1.448 | 0.370 |
| ST | AGCACA | 2390.44 | 2396 | 1.002 | 0.002 |
| ST | AGCACC | 2840.92 | 3163 | 1.113 | 0.107 |
| ST | AGCACG | 2796.42 | 1797 | 0.643 | -0.442 |
| ST | AGCACT | 2060.41 | 2215 | 1.075 | 0.072 |
| SR | AGCAGA | 1537.97 | 2383 | 1.549 | 0.438 |
| SS | AGCAGC | 3166.66 | 5705 | 1.802 | 0.589 |
| SR | AGCAGG | 1142.45 | 1512 | 1.323 | 0.280 |
| SS | AGCAGT | 2898.08 | 4890 | 1.687 | 0.523 |
| SI | AGCATA | 1730.25 | 1974 | 1.141 | 0.132 |
| SI | AGCATC | 3358.01 | 3327 | 0.991 | -0.009 |

-continued

Dataset SI. Mosquito codon pair scores.

| AA pair | Codon Pair | Expected | Ob-served | Observed/ Expected | CPS |
|---|---|---|---|---|---|
| SM | AGCATG | 2757.26 | 2457 | 0.891 | -0.115 |
| SI | AGCATT | 2907.06 | 3076 | 1.058 | 0.056 |
| SQ | AGCCAA | 2657.07 | 2700 | 1.016 | 0.016 |
| SH | AGCCAC | 1792.58 | 1733 | 0.967 | -0.034 |
| SQ | AGCCAG | 2610.44 | 2163 | 0.829 | -0.188 |
| SH | AGCCAT | 1756.24 | 1775 | 1.011 | 0.011 |
| SP | AGCCCA | 2263.2 | 1522 | 0.672 | -0.397 |
| SP | AGCCCC | 1382.03 | 1085 | 0.785 | -0.242 |
| SP | AGCCCG | 2395.18 | 1269 | 0.530 | -0.635 |
| SP | AGCCCT | 1366.45 | 1119 | 0.819 | -0.200 |
| SR | AGCCGA | 2038.08 | 1769 | 0.868 | -0.142 |
| SR | AGCCGC | 1316.95 | 1138 | 0.864 | -0.146 |
| SR | AGCCGG | 1727.55 | 1562 | 0.904 | -0.101 |
| SR | AGCCGT | 1385.61 | 1288 | 0.930 | -0.073 |
| SL | AGCCTA | 1286.39 | 893 | 0.694 | -0.365 |
| SL | AGCCTC | 1506.11 | 1071 | 0.711 | -0.341 |
| SL | AGCCTG | 3329.71 | 1658 | 0.498 | -0.697 |
| SL | AGCCTT | 1512.43 | 1170 | 0.774 | -0.257 |
| SE | AGCGAA | 4357.73 | 4651 | 1.067 | 0.065 |
| SD | AGCGAC | 2828.43 | 2752 | 0.973 | -0.027 |
| SE | AGCGAG | 2927.46 | 2956 | 1.010 | 0.010 |
| SD | AGCGAT | 3739.49 | 4284 | 1.146 | 0.136 |
| SA | AGCGCA | 2286.49 | 1576 | 0.689 | -0.372 |
| SA | AGCGCC | 2686.03 | 1743 | 0.649 | -0.432 |
| SA | AGCGCG | 1871.42 | 953 | 0.509 | -0.675 |
| SA | AGCGCT | 2231.84 | 1577 | 0.707 | -0.347 |
| SG | AGCGGA | 3398.68 | 3189 | 0.938 | -0.064 |
| SG | AGCGGC | 2190.28 | 1995 | 0.911 | -0.093 |
| SG | AGCGGG | 1306.58 | 1068 | 0.817 | -0.202 |
| SG | AGCGGT | 2267.35 | 2215 | 0.977 | -0.023 |
| SV | AGCGTA | 1572.15 | 1469 | 0.934 | -0.068 |
| SV | AGCGTC | 1921.38 | 1615 | 0.841 | -0.174 |
| SV | AGCGTG | 2860.45 | 1990 | 0.696 | -0.363 |
| SV | AGCGTT | 2472.77 | 2244 | 0.907 | -0.097 |
| SY | AGCTAC | 2310.41 | 3323 | 1.438 | 0.363 |
| SY | AGCTAT | 1712.13 | 2377 | 1.388 | 0.328 |
| SS | AGCTCA | 2550.47 | 1963 | 0.770 | -0.262 |
| SS | AGCTCC | 3007.71 | 2136 | 0.710 | -0.342 |
| SS | AGCTCG | 3604.5 | 2358 | 0.654 | -0.424 |
| SS | AGCTCT | 2079.01 | 1610 | 0.774 | -0.256 |
| SC | AGCTGC | 1787.51 | 2470 | 1.382 | 0.323 |
| SW | AGCTGG | 1861.78 | 2453 | 1.318 | 0.276 |
| SC | AGCTGT | 1654.27 | 2173 | 1.314 | 0.273 |
| SL | AGCTTA | 1250.4 | 1354 | 1.083 | 0.080 |
| SF | AGCTTC | 3332.47 | 3763 | 1.129 | 0.122 |
| SL | AGCTTG | 2629.63 | 2526 | 0.961 | -0.040 |
| SF | AGCTTT | 2551.3 | 2353 | 0.922 | -0.081 |
| RK | AGGAAA | 2865.28 | 4324 | 1.509 | 0.412 |
| RN | AGGAAC | 2167.7 | 2542 | 1.173 | 0.159 |
| RK | AGGAAG | 2722.32 | 3915 | 1.438 | 0.363 |
| RN | AGGAAT | 1872.81 | 2444 | 1.305 | 0.266 |
| RT | AGGACA | 1101.55 | 1701 | 1.544 | 0.434 |
| RT | AGGACC | 1309.14 | 1059 | 0.809 | -0.212 |
| RT | AGGACG | 1288.63 | 1554 | 1.206 | 0.187 |
| RT | AGGACT | 949.47 | 1064 | 1.121 | 0.114 |
| RR | AGGAGA | 1180.84 | 1871 | 1.584 | 0.460 |
| RS | AGGAGC | 1282.33 | 1328 | 1.036 | 0.035 |
| RR | AGGAGG | 877.16 | 1603 | 1.827 | 0.603 |
| RS | AGGAGT | 1173.57 | 1281 | 1.092 | 0.088 |
| RI | AGGATA | 928.39 | 1645 | 1.772 | 0.572 |
| RI | AGGATC | 1801.79 | 1665 | 0.924 | -0.079 |
| RM | AGGATG | 1619.02 | 1961 | 1.211 | 0.192 |
| RI | AGGATT | 1559.83 | 2027 | 1.300 | 0.262 |
| RQ | AGGCAA | 1570.68 | 1626 | 1.035 | 0.035 |
| RH | AGGCAC | 1069.23 | 969 | 0.906 | -0.098 |
| RQ | AGGCAG | 1543.12 | 1339 | 0.868 | -0.142 |
| RH | AGGCAT | 1047.55 | 1108 | 1.058 | 0.056 |
| RP | AGGCCA | 1070.9 | 1345 | 1.256 | 0.228 |
| RP | AGGCCC | 653.95 | 706 | 1.080 | 0.077 |
| RP | AGGCCG | 1133.35 | 992 | 0.875 | -0.133 |
| RP | AGGCCT | 646.58 | 681 | 1.053 | 0.052 |
| RR | AGGCGA | 1564.81 | 1273 | 0.814 | -0.206 |
| RR | AGGCGC | 1011.14 | 607 | 0.600 | -0.510 |
| RR | AGGCGG | 1326.39 | 1021 | 0.770 | -0.262 |

-continued

Dataset SI. Mosquito codon pair scores.

| AA pair | Codon Pair | Expected | Ob-served | Observed/ Expected | CPS |
|---|---|---|---|---|---|
| RR | AGGCGT | 1063.85 | 766 | 0.720 | -0.328 |
| RL | AGGCTA | 702.11 | 776 | 1.105 | 0.100 |
| RL | AGGCTC | 822.03 | 702 | 0.854 | -0.158 |
| RL | AGGCTG | 1817.34 | 1177 | 0.648 | -0.434 |
| RL | AGGCTT | 825.48 | 932 | 1.129 | 0.121 |
| RE | AGGGAA | 2282.87 | 2145 | 0.940 | -0.062 |
| RD | AGGGAC | 1281.24 | 1177 | 0.919 | -0.085 |
| RE | AGGGAG | 1533.6 | 1434 | 0.935 | -0.067 |
| RD | AGGGAT | 1693.94 | 1589 | 0.938 | -0.064 |
| RA | AGGGCA | 949.23 | 1135 | 1.196 | 0.179 |
| RA | AGGGCC | 1115.09 | 770 | 0.691 | -0.370 |
| RA | AGGGCG | 776.91 | 892 | 1.148 | 0.138 |
| RA | AGGGCT | 926.54 | 796 | 0.859 | -0.152 |
| RG | AGGGGA | 1327.64 | 759 | 0.572 | -0.559 |
| RG | AGGGGC | 855.6 | 454 | 0.531 | -0.634 |
| RG | AGGGGG | 510.39 | 333 | 0.652 | -0.427 |
| RG | AGGGGT | 885.7 | 517 | 0.584 | -0.538 |
| RV | AGGGTA | 674.07 | 745 | 1.105 | 0.100 |
| RV | AGGGTC | 823.8 | 645 | 0.783 | -0.245 |
| RV | AGGGTG | 1226.43 | 1072 | 0.874 | -0.135 |
| RV | AGGGTT | 1060.21 | 909 | 0.857 | -0.154 |
| RY | AGGTAC | 1346.78 | 831 | 0.617 | -0.483 |
| RY | AGGTAT | 998.03 | 888 | 0.890 | -0.117 |
| RS | AGGTCA | 1032.81 | 1079 | 1.045 | 0.044 |
| RS | AGGTCC | 1217.96 | 677 | 0.556 | -0.587 |
| RS | AGGTCG | 1459.63 | 879 | 0.602 | -0.507 |
| RS | AGGTCT | 841.89 | 551 | 0.654 | -0.424 |
| RC | AGGTGC | 1118.89 | 909 | 0.812 | -0.208 |
| RW | AGGTGG | 1342.92 | 1187 | 0.884 | -0.123 |
| RC | AGGTGT | 1035.48 | 941 | 0.909 | -0.096 |
| RL | AGGTTA | 682.46 | 863 | 1.265 | 0.235 |
| RF | AGGTTC | 1881.58 | 1325 | 0.704 | -0.351 |
| RL | AGGTTG | 1435.24 | 1302 | 0.907 | -0.097 |
| RF | AGGTTT | 1440.51 | 1435 | 0.996 | -0.004 |
| SK | AGTAAA | 3692.26 | 2833 | 0.767 | -0.265 |
| SN | AGTAAC | 3527.63 | 2040 | 0.578 | -0.548 |
| SK | AGTAAG | 3508.05 | 1786 | 0.509 | -0.675 |
| SN | AGTAAT | 3047.73 | 2435 | 0.799 | -0.224 |
| ST | AGTACA | 2187.7 | 2028 | 0.927 | -0.076 |
| ST | AGTACC | 2599.97 | 1824 | 0.702 | -0.354 |
| ST | AGTACG | 2559.24 | 1971 | 0.770 | -0.261 |
| ST | AGTACT | 1885.66 | 1545 | 0.819 | -0.199 |
| SR | AGTAGA | 1407.53 | 1315 | 0.934 | -0.068 |
| SS | AGTAGC | 2898.08 | 2345 | 0.809 | -0.212 |
| SR | AGTAGG | 1045.55 | 760 | 0.727 | -0.319 |
| SS | AGTAGT | 2652.28 | 2652 | 1.000 | 0.000 |
| SI | AGTATA | 1583.5 | 1445 | 0.913 | -0.092 |
| SI | AGTATC | 3073.2 | 1942 | 0.632 | -0.459 |
| SM | AGTATG | 2523.41 | 1972 | 0.781 | -0.247 |
| SI | AGTATT | 2660.5 | 2468 | 0.928 | -0.075 |
| SQ | AGTCAA | 2431.71 | 2692 | 1.107 | 0.102 |
| SH | AGTCAC | 1640.54 | 1656 | 1.009 | 0.009 |
| SQ | AGTCAG | 2389.04 | 2237 | 0.936 | -0.066 |
| SH | AGTCAT | 1607.28 | 1584 | 0.986 | -0.015 |
| SP | AGTCCA | 2071.25 | 2035 | 0.982 | -0.018 |
| SP | AGTCCC | 1264.81 | 1543 | 1.220 | 0.199 |
| SP | AGTCCG | 2192.03 | 1942 | 0.886 | -0.121 |
| SP | AGTCCT | 1250.56 | 1537 | 1.229 | 0.206 |
| SR | AGTCGA | 1865.22 | 2020 | 1.083 | 0.080 |
| SR | AGTCGC | 1205.25 | 1213 | 1.006 | 0.006 |
| SR | AGTCGG | 1581.02 | 1372 | 0.868 | -0.142 |
| SR | AGTCGT | 1268.09 | 1306 | 1.030 | 0.029 |
| SL | AGTCTA | 1177.28 | 1097 | 0.932 | -0.071 |
| SL | AGTCTC | 1378.37 | 1059 | 0.768 | -0.264 |
| SL | AGTCTG | 3047.3 | 1965 | 0.645 | -0.439 |
| SL | AGTCTT | 1384.16 | 1117 | 0.807 | -0.214 |
| SE | AGTGAA | 3988.13 | 4482 | 1.124 | 0.117 |
| SD | AGTGAC | 2588.53 | 2461 | 0.951 | -0.051 |
| SE | AGTGAG | 2679.17 | 2241 | 0.836 | -0.179 |
| SD | AGTGAT | 3422.33 | 3976 | 1.162 | 0.150 |
| SA | AGTGCA | 2092.57 | 2834 | 1.354 | 0.303 |
| SA | AGTGCC | 2458.21 | 3026 | 1.231 | 0.208 |
| SA | AGTGCG | 1712.7 | 1979 | 1.155 | 0.145 |
| SA | AGTGCT | 2042.55 | 2619 | 1.282 | 0.249 |

-continued

Dataset SI. Mosquito codon pair scores.

| AA pair | Codon Pair | Expected | Ob-served | Observed/ Expected | CPS |
|---|---|---|---|---|---|
| SG | AGTGGA | 3110.42 | 3958 | 1.272 | 0.241 |
| SG | AGTGGC | 2004.51 | 2931 | 1.462 | 0.380 |
| SG | AGTGGG | 1195.76 | 1591 | 1.331 | 0.286 |
| SG | AGTGGT | 2075.05 | 2845 | 1.371 | 0.316 |
| SV | AGTGTA | 1438.81 | 1796 | 1.248 | 0.222 |
| SV | AGTGTC | 1758.42 | 1794 | 1.020 | 0.020 |
| SV | AGTGTG | 2617.84 | 2454 | 0.937 | -0.065 |
| SV | AGTGTT | 2263.04 | 2500 | 1.105 | 0.100 |
| SY | AGTTAC | 2114.45 | 1635 | 0.773 | -0.257 |
| SY | AGTTAT | 1566.92 | 1645 | 1.050 | 0.049 |
| SS | AGTTCA | 2334.15 | 2818 | 1.207 | 0.188 |
| SS | AGTTCC | 2752.61 | 3017 | 1.096 | 0.092 |
| SS | AGTTCG | 3298.78 | 2930 | 0.888 | -0.119 |
| SS | AGTTCT | 1902.67 | 2242 | 1.178 | 0.164 |
| SC | AGTTGC | 1635.9 | 1511 | 0.924 | -0.079 |
| SW | AGTTGG | 1703.87 | 1716 | 1.007 | 0.007 |
| SC | AGTTGT | 1513.96 | 1794 | 1.185 | 0.170 |
| SL | AGTTTA | 1144.35 | 2288 | 1.999 | 0.693 |
| SF | AGTTTC | 3049.83 | 2947 | 0.966 | -0.034 |
| SL | AGTTTG | 2406.6 | 4161 | 1.729 | 0.548 |
| SF | AGTTTT | 2334.91 | 3437 | 1.472 | 0.387 |
| IK | ATAAAA | 3131.97 | 4194 | 1.339 | 0.292 |
| IN | ATAAAC | 2842.74 | 2425 | 0.853 | -0.159 |
| IK | ATAAAG | 2975.71 | 2365 | 0.795 | -0.230 |
| IN | ATAAAT | 2456.01 | 3273 | 1.333 | 0.287 |
| IT | ATAACA | 1484.32 | 1832 | 1.234 | 0.210 |
| IT | ATAACC | 1764.04 | 1708 | 0.968 | -0.032 |
| IT | ATAACG | 1736.4 | 2208 | 1.272 | 0.240 |
| IT | ATAACT | 1279.39 | 1655 | 1.294 | 0.257 |
| IR | ATAAGA | 1217.14 | 1569 | 1.289 | 0.254 |
| IS | ATAAGC | 1694.02 | 1576 | 0.930 | -0.072 |
| IR | ATAAGG | 904.12 | 1113 | 1.231 | 0.208 |
| IS | ATAAGT | 1550.34 | 1558 | 1.005 | 0.005 |
| II | ATAATA | 1394.72 | 2021 | 1.449 | 0.371 |
| II | ATAATC | 2706.82 | 2371 | 0.876 | -0.132 |
| IM | ATAATG | 2053.71 | 2322 | 1.131 | 0.123 |
| II | ATAATT | 2343.31 | 2773 | 1.183 | 0.168 |
| IQ | ATACAA | 2308.12 | 2471 | 1.071 | 0.068 |
| IH | ATACAC | 1506.43 | 1398 | 0.928 | -0.075 |
| IQ | ATACAG | 2267.61 | 2022 | 0.892 | -0.115 |
| IH | ATACAT | 1475.89 | 1553 | 1.052 | 0.051 |
| IP | ATACCA | 1786.88 | 1650 | 0.923 | -0.080 |
| IP | ATACCC | 1091.16 | 840 | 0.770 | -0.262 |
| IP | ATACCG | 1891.08 | 1983 | 1.049 | 0.047 |
| IP | ATACCT | 1078.86 | 1140 | 1.057 | 0.055 |
| IR | ATACGA | 1612.92 | 1681 | 1.042 | 0.041 |
| IR | ATACGC | 1042.23 | 839 | 0.805 | -0.217 |
| IR | ATACGG | 1367.17 | 1346 | 0.985 | -0.016 |
| IR | ATACGT | 1096.56 | 990 | 0.903 | -0.102 |
| IL | ATACTA | 1128.78 | 1103 | 0.977 | -0.023 |
| IL | ATACTC | 1321.58 | 1037 | 0.785 | -0.242 |
| IL | ATACTG | 2921.75 | 2690 | 0.921 | -0.083 |
| IL | ATACTT | 1327.13 | 1433 | 1.080 | 0.077 |
| IE | ATAGAA | 3625.69 | 2830 | 0.781 | -0.248 |
| ID | ATAGAC | 2324.09 | 1466 | 0.631 | -0.461 |
| IE | ATAGAG | 2435.68 | 1686 | 0.692 | -0.368 |
| ID | ATAGAT | 3072.7 | 2125 | 0.692 | -0.369 |
| IA | ATAGCA | 1685.01 | 1779 | 1.056 | 0.054 |
| IA | ATAGCC | 1979.44 | 1549 | 0.783 | -0.245 |
| IA | ATAGCG | 1379.13 | 1593 | 1.155 | 0.144 |
| IA | ATAGCT | 1644.73 | 1601 | 0.973 | -0.027 |
| IG | ATAGGA | 2148.26 | 1516 | 0.706 | -0.349 |
| IG | ATAGGC | 1384.44 | 736 | 0.532 | -0.632 |
| IG | ATAGGG | 825.87 | 660 | 0.799 | -0.224 |
| IG | ATAGGT | 1433.16 | 878 | 0.613 | -0.490 |
| IV | ATAGTA | 1315.8 | 1301 | 0.989 | -0.011 |
| IV | ATAGTC | 1608.09 | 1093 | 0.680 | -0.386 |
| IV | ATAGTG | 2394.04 | 2286 | 0.955 | -0.046 |
| IV | ATAGTT | 2069.58 | 1903 | 0.920 | -0.084 |
| IY | ATATAC | 2173.59 | 1322 | 0.608 | -0.497 |
| IY | ATATAT | 1610.74 | 1766 | 1.096 | 0.092 |
| IS | ATATCA | 1364.39 | 1866 | 1.368 | 0.313 |
| IS | ATATCC | 1608.99 | 1823 | 1.133 | 0.125 |
| IS | ATATCG | 1928.24 | 2399 | 1.244 | 0.218 |

-continued

Dataset SI. Mosquito codon pair scores.

| AA pair | Codon Pair | Expected | Ob-served | Observed/ Expected | CPS |
|---|---|---|---|---|---|
| IS | ATATCT | 1112.17 | 1636 | 1.471 | 0.386 |
| IC | ATATGC | 1699.27 | 1459 | 0.859 | -0.152 |
| IW | ATATGG | 1411.63 | 1343 | 0.951 | -0.050 |
| IC | ATATGT | 1572.6 | 1624 | 1.033 | 0.032 |
| IL | ATATTA | 1097.2 | 1699 | 1.548 | 0.437 |
| IF | ATATTC | 2892.28 | 3165 | 1.094 | 0.090 |
| IL | ATATTG | 2307.44 | 2600 | 1.127 | 0.119 |
| IF | ATATTT | 2214.3 | 3562 | 1.609 | 0.475 |
| IK | ATCAAA | 6078.42 | 8329 | 1.370 | 0.315 |
| IN | ATCAAC | 5517.09 | 8961 | 1.624 | 0.485 |
| IK | ATCAAG | 5775.15 | 8146 | 1.411 | 0.344 |
| IN | ATCAAT | 4766.54 | 5711 | 1.198 | 0.181 |
| IT | ATCACA | 2880.71 | 2694 | 0.935 | -0.067 |
| IT | ATCACC | 3423.58 | 4797 | 1.401 | 0.337 |
| IT | ATCACG | 3369.95 | 2764 | 0.820 | -0.198 |
| IT | ATCACT | 2482.99 | 2477 | 0.998 | -0.002 |
| IR | ATCAGA | 2362.19 | 1957 | 0.828 | -0.188 |
| IS | ATCAGC | 3287.69 | 4182 | 1.272 | 0.241 |
| IR | ATCAGG | 1754.69 | 1344 | 0.766 | -0.267 |
| IS | ATCAGT | 3008.85 | 3281 | 1.090 | 0.087 |
| II | ATCATA | 2706.82 | 2292 | 0.847 | -0.166 |
| II | ATCATC | 5253.29 | 7547 | 1.437 | 0.362 |
| IM | ATCATG | 3985.77 | 4455 | 1.118 | 0.111 |
| II | ATCATT | 4547.82 | 4603 | 1.012 | 0.012 |
| IQ | ATCCAA | 4479.52 | 3406 | 0.760 | -0.274 |
| IH | ATCCAC | 2923.62 | 3261 | 1.115 | 0.109 |
| IQ | ATCCAG | 4400.9 | 4577 | 1.040 | 0.039 |
| IH | ATCCAT | 2864.35 | 2338 | 0.816 | -0.203 |
| IP | ATCCCA | 3467.92 | 2270 | 0.655 | -0.424 |
| IP | ATCCCC | 2117.69 | 1458 | 0.688 | -0.373 |
| IP | ATCCCG | 3670.15 | 2389 | 0.651 | -0.429 |
| IP | ATCCCT | 2093.82 | 1342 | 0.641 | -0.445 |
| IR | ATCCGA | 3130.3 | 2631 | 0.840 | -0.174 |
| IR | ATCCGC | 2022.71 | 1980 | 0.979 | -0.021 |
| IR | ATCCGG | 2653.35 | 3205 | 1.208 | 0.189 |
| IR | ATCCGT | 2128.17 | 1991 | 0.936 | -0.067 |
| IL | ATCCTA | 2190.69 | 1612 | 0.736 | -0.307 |
| IL | ATCCTC | 2564.87 | 2505 | 0.977 | -0.024 |
| IL | ATCCTG | 5670.43 | 4953 | 0.873 | -0.135 |
| IL | ATCCTT | 2575.64 | 1961 | 0.761 | -0.273 |
| IE | ATCGAA | 7036.61 | 8036 | 1.142 | 0.133 |
| ID | ATCGAC | 4510.5 | 6012 | 1.333 | 0.287 |
| IE | ATCGAG | 4727.09 | 6240 | 1.320 | 0.278 |
| ID | ATCGAT | 5963.38 | 7939 | 1.331 | 0.286 |
| IA | ATCGCA | 3270.2 | 2448 | 0.749 | -0.290 |
| IA | ATCGCC | 3841.63 | 3594 | 0.936 | -0.067 |
| IA | ATCGCG | 2676.56 | 1689 | 0.631 | -0.460 |
| IA | ATCGCT | 3192.03 | 2839 | 0.889 | -0.117 |
| IG | ATCGGA | 4169.26 | 4195 | 1.006 | 0.006 |
| IG | ATCGGC | 2686.88 | 2638 | 0.982 | -0.018 |
| IG | ATCGGG | 1602.82 | 1982 | 1.237 | 0.212 |
| IG | ATCGGT | 2781.43 | 3450 | 1.240 | 0.215 |
| IV | ATCGTA | 2553.67 | 2458 | 0.963 | -0.038 |
| IV | ATCGTC | 3120.93 | 3797 | 1.217 | 0.196 |
| IV | ATCGTG | 4646.28 | 4242 | 0.913 | -0.091 |
| IV | ATCGTT | 4016.56 | 3971 | 0.989 | -0.011 |
| IY | ATCTAC | 4218.42 | 6145 | 1.457 | 0.376 |
| IY | ATCTAT | 3126.07 | 2600 | 0.832 | -0.184 |
| IS | ATCTCA | 2647.95 | 1768 | 0.668 | -0.404 |
| IS | ATCTCC | 3122.67 | 2753 | 0.882 | -0.126 |
| IS | ATCTCG | 3742.27 | 2416 | 0.646 | -0.438 |
| IS | ATCTCT | 2158.47 | 1365 | 0.632 | -0.458 |
| IC | ATCTGC | 3297.88 | 3293 | 0.999 | -0.001 |
| IW | ATCTGG | 2739.64 | 2513 | 0.917 | -0.086 |
| IC | ATCTGT | 3052.05 | 2489 | 0.816 | -0.204 |
| IL | ATCTTA | 2129.41 | 1059 | 0.497 | -0.699 |
| IF | ATCTTC | 5613.24 | 5272 | 0.939 | -0.063 |
| IL | ATCTTG | 4478.2 | 2303 | 0.514 | -0.665 |
| IF | ATCTTT | 4297.43 | 2298 | 0.535 | -0.626 |
| MK | ATGAAA | 6639.12 | 6007 | 0.905 | -0.100 |
| MN | ATGAAC | 5176.08 | 5567 | 1.076 | 0.073 |
| MK | ATGAAG | 6307.88 | 6940 | 1.100 | 0.096 |
| MN | ATGAAT | 4471.92 | 4081 | 0.913 | -0.091 |
| MT | ATGACA | 2493 | 2094 | 0.840 | -0.174 |

-continued

Dataset SI. Mosquito codon pair scores.

| AA pair | Codon Pair | Expected | Ob-served | Observed/Expected | CPS |
|---|---|---|---|---|---|
| MT | ATGACC | 2962.81 | 3505 | 1.183 | 0.168 |
| MT | ATGACG | 2916.39 | 2905 | 0.996 | -0.004 |
| MT | ATGACT | 2148.81 | 2017 | 0.939 | -0.063 |
| MR | ATGAGA | 1914.94 | 1881 | 0.982 | -0.018 |
| MS | ATGAGC | 2629.55 | 2737 | 1.041 | 0.040 |
| MR | ATGAGG | 1422.47 | 1424 | 1.001 | 0.001 |
| MS | ATGAGT | 2406.52 | 2358 | 0.980 | -0.020 |
| MI | ATGATA | 2429.4 | 2489 | 1.025 | 0.024 |
| MI | ATGATC | 4714.89 | 4746 | 1.007 | 0.007 |
| MM | ATGATG | 5703 | 5703 | 1.000 | 0.000 |
| MI | ATGATT | 4081.72 | 3991 | 0.978 | -0.022 |
| MQ | ATGCAA | 4138.31 | 3920 | 0.947 | -0.054 |
| MH | ATGCAC | 2485.19 | 2586 | 1.041 | 0.040 |
| MQ | ATGCAG | 4065.69 | 4284 | 1.054 | 0.052 |
| MH | ATGCAT | 2434.81 | 2334 | 0.959 | -0.042 |
| MP | ATGCCA | 2848.38 | 3014 | 1.058 | 0.057 |
| MP | ATGCCC | 1739.37 | 2042 | 1.174 | 0.160 |
| MP | ATGCCG | 3014.48 | 2578 | 0.855 | -0.156 |
| MP | ATGCCT | 1719.76 | 1688 | 0.982 | -0.019 |
| MR | ATGCGA | 2537.63 | 2749 | 1.083 | 0.080 |
| MR | ATGCGC | 1639.74 | 1800 | 1.098 | 0.093 |
| MR | ATGCGG | 2150.98 | 1831 | 0.851 | -0.161 |
| MR | ATGCGT | 1725.24 | 1706 | 0.989 | -0.011 |
| ML | ATGCTA | 2073.36 | 1989 | 0.959 | -0.042 |
| ML | ATGCTC | 2427.5 | 2399 | 0.988 | -0.012 |
| ML | ATGCTG | 5366.73 | 5889 | 1.097 | 0.093 |
| ML | ATGCTT | 2437.7 | 2463 | 1.010 | 0.010 |
| ME | ATGGAA | 7311.94 | 7287 | 0.997 | -0.003 |
| MD | ATGGAC | 4458.45 | 4926 | 1.105 | 0.100 |
| ME | ATGGAG | 4912.06 | 4937 | 1.005 | 0.005 |
| MD | ATGGAT | 5894.55 | 5427 | 0.921 | -0.083 |
| MA | ATGGCA | 3361.8 | 3344 | 0.995 | -0.005 |
| MA | ATGGCC | 3949.23 | 4512 | 1.143 | 0.133 |
| MA | ATGGCG | 2751.53 | 2574 | 0.935 | -0.067 |
| MA | ATGGCT | 3281.44 | 2914 | 0.888 | -0.119 |
| MG | ATGGGA | 3606.81 | 3601 | 0.998 | -0.002 |
| MG | ATGGGC | 2324.4 | 2505 | 1.078 | 0.075 |
| MG | ATGGGG | 1386.59 | 1077 | 0.777 | -0.253 |
| MG | ATGGGT | 2406.2 | 2541 | 1.056 | 0.055 |
| MV | ATGGTA | 2064.14 | 1955 | 0.947 | -0.054 |
| MV | ATGGTC | 2522.66 | 2574 | 1.020 | 0.020 |
| MV | ATGGTG | 3755.6 | 3972 | 1.058 | 0.056 |
| MV | ATGGTT | 3246.6 | 3088 | 0.951 | -0.050 |
| MY | ATGTAC | 3416.9 | 3618 | 1.059 | 0.057 |
| MY | ATGTAT | 2532.1 | 2331 | 0.921 | -0.083 |
| MS | ATGTCA | 2117.87 | 1608 | 0.759 | -0.275 |
| MS | ATGTCC | 2497.56 | 3381 | 1.354 | 0.303 |
| MS | ATGTCG | 2993.12 | 2562 | 0.856 | -0.156 |
| MS | ATGTCT | 1726.38 | 1725 | 0.999 | -0.001 |
| MC | ATGTGC | 2346.46 | 2494 | 1.063 | 0.061 |
| MW | ATGTGG | 2401 | 2401 | 1.000 | 0.000 |
| MC | ATGTGT | 2171.54 | 2024 | 0.932 | -0.070 |
| ML | ATGTTA | 2015.36 | 1675 | 0.831 | -0.185 |
| MF | ATGTTC | 4784.81 | 5098 | 1.065 | 0.063 |
| ML | ATGTTG | 4238.36 | 4144 | 0.978 | -0.023 |
| MF | ATGTTT | 3663.19 | 3350 | 0.915 | -0.089 |
| IK | ATTAAA | 5262.14 | 2929 | 0.557 | -0.586 |
| IN | ATTAAC | 4776.19 | 1998 | 0.418 | -0.871 |
| IK | ATTAAG | 4999.6 | 2260 | 0.452 | -0.794 |
| IN | ATTAAT | 4126.43 | 2117 | 0.513 | -0.667 |
| IT | ATTACA | 2493.86 | 2091 | 0.838 | -0.176 |
| IT | ATTACC | 2963.83 | 2522 | 0.851 | -0.161 |
| IT | ATTACG | 2917.39 | 2404 | 0.824 | -0.194 |
| IT | ATTACT | 2149.55 | 1794 | 0.835 | -0.181 |
| IR | ATTAGA | 2044.97 | 1265 | 0.619 | -0.480 |
| IS | ATTAGC | 2846.18 | 1549 | 0.544 | -0.608 |
| IR | ATTAGG | 1519.05 | 921 | 0.606 | -0.500 |
| IS | ATTAGT | 2604.78 | 1587 | 0.609 | -0.496 |
| II | ATTATA | 2343.31 | 1849 | 0.789 | -0.237 |
| II | ATTATC | 4547.82 | 2848 | 0.626 | -0.468 |
| IM | ATTATG | 3450.52 | 2713 | 0.786 | -0.240 |
| II | ATTATT | 3937.09 | 3477 | 0.883 | -0.124 |
| IQ | ATTCAA | 3877.96 | 4588 | 1.183 | 0.168 |
| IH | ATTCAC | 2531.01 | 2559 | 1.011 | 0.011 |

-continued

Dataset SI. Mosquito codon pair scores.

| AA pair | Codon Pair | Expected | Ob-served | Observed/Expected | CPS |
|---|---|---|---|---|---|
| IQ | ATTCAG | 3809.9 | 4080 | 1.071 | 0.068 |
| IH | ATTCAT | 2479.7 | 2672 | 1.078 | 0.075 |
| IP | ATTCCA | 3002.21 | 4088 | 1.362 | 0.309 |
| IP | ATTCCC | 1833.3 | 2665 | 1.454 | 0.374 |
| IP | ATTCCG | 3177.28 | 4551 | 1.432 | 0.359 |
| IP | ATTCCT | 1812.64 | 2647 | 1.460 | 0.379 |
| IR | ATTCGA | 2709.93 | 3245 | 1.197 | 0.180 |
| IR | ATTCGC | 1751.08 | 2200 | 1.256 | 0.228 |
| IR | ATTCGG | 2297.03 | 2698 | 1.175 | 0.161 |
| IR | ATTCGT | 1842.38 | 2481 | 1.347 | 0.298 |
| IL | ATTCTA | 1896.5 | 2534 | 1.336 | 0.290 |
| IL | ATTCTC | 2220.43 | 2571 | 1.158 | 0.147 |
| IL | ATTCTG | 4908.94 | 5627 | 1.146 | 0.137 |
| IL | ATTCTT | 2229.76 | 2649 | 1.188 | 0.172 |
| IE | ATTGAA | 6091.65 | 5975 | 0.981 | -0.019 |
| ID | ATTGAC | 3904.78 | 2940 | 0.753 | -0.284 |
| IE | ATTGAG | 4092.28 | 3242 | 0.792 | -0.233 |
| ID | ATTGAT | 5162.55 | 4456 | 0.863 | -0.147 |
| IA | ATTGCA | 2831.04 | 3227 | 1.140 | 0.131 |
| IA | ATTGCC | 3325.73 | 4692 | 1.411 | 0.344 |
| IA | ATTGCG | 2317.12 | 2607 | 1.125 | 0.118 |
| IA | ATTGCT | 2763.37 | 3288 | 1.190 | 0.174 |
| IG | ATTGGA | 3609.37 | 4030 | 1.117 | 0.110 |
| IG | ATTGGC | 2326.05 | 2682 | 1.153 | 0.142 |
| IG | ATTGGG | 1387.57 | 1606 | 1.157 | 0.146 |
| IG | ATTGGT | 2407.9 | 2390 | 0.993 | -0.007 |
| IV | ATTGTA | 2210.73 | 2592 | 1.172 | 0.159 |
| IV | ATTGTC | 2701.82 | 2514 | 0.930 | -0.072 |
| IV | ATTGTG | 4022.32 | 4491 | 1.117 | 0.110 |
| IV | ATTGTT | 3477.17 | 3489 | 1.003 | 0.003 |
| IY | ATTTAC | 3651.92 | 2496 | 0.683 | -0.381 |
| IY | ATTTAT | 2706.26 | 3158 | 1.167 | 0.154 |
| IS | ATTTCA | 2292.36 | 2976 | 1.298 | 0.261 |
| IS | ATTTCC | 2703.32 | 3847 | 1.423 | 0.353 |
| IS | ATTTCG | 3239.71 | 3607 | 1.113 | 0.107 |
| IS | ATTTCT | 1868.6 | 2592 | 1.387 | 0.327 |
| IC | ATTTGC | 2855.01 | 3189 | 1.117 | 0.111 |
| IW | ATTTGG | 2371.73 | 2667 | 1.124 | 0.117 |
| IC | ATTTGT | 2642.19 | 3065 | 1.160 | 0.148 |
| IL | ATTTTA | 1843.44 | 3228 | 1.751 | 0.560 |
| IF | ATTTTC | 4859.43 | 5035 | 1.036 | 0.035 |
| IL | ATTTTG | 3876.82 | 5125 | 1.322 | 0.279 |
| IF | ATTTTT | 3720.32 | 4265 | 1.146 | 0.137 |
| QK | CAAAAA | 6216.52 | 5479 | 0.881 | -0.126 |
| QN | CAAAAC | 5469.25 | 5174 | 0.946 | -0.055 |
| QK | CAAAAG | 5906.36 | 4681 | 0.793 | -0.233 |
| QN | CAAAAT | 4725.21 | 5292 | 1.120 | 0.113 |
| QT | CAAACA | 2679.9 | 3759 | 1.403 | 0.338 |
| QT | CAAACC | 3184.92 | 4173 | 1.310 | 0.270 |
| QT | CAAACG | 3135.03 | 4177 | 1.332 | 0.287 |
| QT | CAAACT | 2309.9 | 3178 | 1.376 | 0.319 |
| QR | CAAAGA | 2322.74 | 2627 | 1.131 | 0.123 |
| QS | CAAAGC | 2831.33 | 3093 | 1.092 | 0.088 |
| QR | CAAAGG | 1725.39 | 1762 | 1.021 | 0.021 |
| QS | CAAAGT | 2591.19 | 3098 | 1.196 | 0.179 |
| QI | CAAATA | 2475.14 | 2871 | 1.160 | 0.148 |
| QI | CAAATC | 4803.66 | 5112 | 1.064 | 0.062 |
| QM | CAAATG | 4357.24 | 4101 | 0.941 | -0.061 |
| QI | CAAATT | 4158.57 | 4383 | 1.054 | 0.053 |
| QQ | CAACAA | 8664.39 | 7078 | 0.817 | -0.202 |
| QH | CAACAC | 3398.98 | 2653 | 0.781 | -0.248 |
| QQ | CAACAG | 8512.33 | 7666 | 0.901 | -0.105 |
| QH | CAACAT | 3330.07 | 3282 | 0.986 | -0.015 |
| QP | CAACCA | 3232.41 | 3656 | 1.131 | 0.123 |
| QP | CAACCC | 1973.88 | 2095 | 1.061 | 0.060 |
| QP | CAACCG | 3420.91 | 4604 | 1.346 | 0.297 |
| QP | CAACCT | 1951.63 | 2310 | 1.184 | 0.169 |
| QR | CAACGA | 3078.03 | 3520 | 1.144 | 0.134 |
| QR | CAACGC | 1988.93 | 2062 | 1.037 | 0.036 |
| QR | CAACGG | 2609.03 | 3033 | 1.163 | 0.151 |
| QR | CAACGT | 2092.63 | 2174 | 1.039 | 0.038 |
| QL | CAACTA | 2125.58 | 2208 | 1.039 | 0.038 |
| QL | CAACTC | 2488.64 | 2118 | 0.851 | -0.161 |
| QL | CAACTG | 5501.9 | 4969 | 0.903 | -0.102 |

-continued

Dataset SI. Mosquito codon pair scores.

| AA pair | Codon Pair | Expected | Ob-served | Observed/ Expected | CPS |
|---|---|---|---|---|---|
| QL | CAACTT | 2499.1 | 2506 | 1.003 | 0.003 |
| QE | CAAGAA | 6703.82 | 5898 | 0.880 | -0.128 |
| QD | CAAGAC | 3230.39 | 2540 | 0.786 | -0.240 |
| QE | CAAGAG | 4503.53 | 3316 | 0.736 | -0.306 |
| QD | CAAGAT | 4270.93 | 3634 | 0.851 | -0.161 |
| QA | CAAGCA | 2654.74 | 3340 | 1.258 | 0.230 |
| QA | CAAGCC | 3118.62 | 2951 | 0.946 | -0.055 |
| QA | CAAGCG | 2172.82 | 2849 | 1.311 | 0.271 |
| QA | CAAGCT | 2591.28 | 3267 | 1.261 | 0.232 |
| QG | CAAGGA | 3161.26 | 4102 | 1.298 | 0.261 |
| QG | CAAGGC | 2037.27 | 2362 | 1.159 | 0.148 |
| QG | CAAGGG | 1215.3 | 1448 | 1.191 | 0.175 |
| QG | CAAGGT | 2108.96 | 2431 | 1.153 | 0.142 |
| QV | CAAGTA | 1741.09 | 1886 | 1.083 | 0.080 |
| QV | CAAGTC | 2127.86 | 1867 | 0.877 | -0.131 |
| QV | CAAGTG | 3167.84 | 3330 | 1.051 | 0.050 |
| QV | CAAGTT | 2738.5 | 2868 | 1.047 | 0.046 |
| QY | CAATAC | 3476.7 | 2353 | 0.677 | -0.390 |
| QY | CAATAT | 2576.42 | 2332 | 0.905 | -0.100 |
| QS | CAATCA | 2280.39 | 2930 | 1.285 | 0.251 |
| QS | CAATCC | 2689.21 | 2916 | 1.084 | 0.081 |
| QS | CAATCG | 3222.81 | 4146 | 1.286 | 0.252 |
| QS | CAATCT | 1858.85 | 2119 | 1.140 | 0.131 |
| QC | CAATGC | 2474.12 | 2017 | 0.815 | -0.204 |
| QW | CAATGG | 2435.88 | 2159 | 0.886 | -0.121 |
| QC | CAATGT | 2289.69 | 2056 | 0.898 | -0.108 |
| QL | CAATTA | 2066.12 | 1534 | 0.742 | -0.298 |
| QF | CAATTC | 4331.76 | 2910 | 0.672 | -0.398 |
| QL | CAATTG | 4345.11 | 2770 | 0.637 | -0.450 |
| QF | CAATTT | 3316.35 | 3066 | 0.925 | -0.078 |
| HK | CACAAA | 3074.85 | 4247 | 1.381 | 0.323 |
| HN | CACAAC | 2746.24 | 3820 | 1.391 | 0.330 |
| HK | CACAAG | 2921.44 | 3930 | 1.345 | 0.297 |
| HN | CACAAT | 2372.64 | 3089 | 1.302 | 0.264 |
| HT | CACACA | 1539.1 | 1865 | 1.212 | 0.192 |
| HT | CACACC | 1829.14 | 2446 | 1.337 | 0.291 |
| HT | CACACG | 1800.49 | 2117 | 1.176 | 0.162 |
| HT | CACACT | 1326.61 | 1368 | 1.031 | 0.031 |
| HR | CACAGA | 1695.09 | 1244 | 0.734 | -0.309 |
| HS | CACAGC | 1969.3 | 2405 | 1.221 | 0.200 |
| HR | CACAGG | 1259.16 | 940 | 0.747 | -0.292 |
| HS | CACAGT | 1802.27 | 1940 | 1.076 | 0.074 |
| HI | CACATA | 1411.55 | 1507 | 1.068 | 0.065 |
| HI | CACATC | 2739.48 | 3906 | 1.426 | 0.355 |
| HM | CACATG | 2519.03 | 3296 | 1.308 | 0.269 |
| HI | CACATT | 2371.59 | 3052 | 1.287 | 0.252 |
| HQ | CACCAA | 3598.74 | 2930 | 0.814 | -0.206 |
| HH | CACCAC | 3333.23 | 3027 | 0.908 | -0.096 |
| HQ | CACCAG | 3535.58 | 3198 | 0.905 | -0.100 |
| HH | CACCAT | 3265.66 | 2729 | 0.836 | -0.180 |
| HP | CACCCA | 2303.24 | 1416 | 0.615 | -0.486 |
| HP | CACCCC | 1406.48 | 854 | 0.607 | -0.499 |
| HP | CACCCG | 2437.56 | 1808 | 0.742 | -0.299 |
| HP | CACCCT | 1390.63 | 845 | 0.608 | -0.498 |
| HR | CACCGA | 2246.29 | 2058 | 0.916 | -0.088 |
| HR | CACCGC | 1451.49 | 1255 | 0.865 | -0.145 |
| HR | CACCGG | 1904.03 | 2270 | 1.192 | 0.176 |
| HR | CACCGT | 1527.16 | 1350 | 0.884 | -0.123 |
| HL | CACCTA | 1309.36 | 913 | 0.697 | -0.361 |
| HL | CACCTC | 1533 | 1274 | 0.831 | -0.185 |
| HL | CACCTG | 3389.17 | 2804 | 0.827 | -0.190 |
| HL | CACCTT | 1539.44 | 1108 | 0.720 | -0.329 |
| HE | CACGAA | 3497.92 | 3674 | 1.050 | 0.049 |
| HD | CACGAC | 2115.01 | 2459 | 1.163 | 0.151 |
| HE | CACGAG | 2349.85 | 3178 | 1.352 | 0.302 |
| HD | CACGAT | 2796.27 | 3286 | 1.175 | 0.161 |
| HA | CACGCA | 1506.34 | 1161 | 0.771 | -0.260 |
| HA | CACGCC | 1769.55 | 1812 | 1.024 | 0.024 |
| HA | CACGCG | 1232.89 | 1013 | 0.822 | -0.196 |
| HA | CACGCT | 1470.33 | 1288 | 0.876 | -0.132 |
| HG | CACGGA | 2577.11 | 2174 | 0.844 | -0.170 |
| HG | CACGGC | 1660.82 | 1541 | 0.928 | -0.075 |
| HG | CACGGG | 990.74 | 1034 | 1.044 | 0.043 |
| HG | CACGGT | 1719.26 | 1822 | 1.060 | 0.058 |

-continued

Dataset SI. Mosquito codon pair scores.

| AA pair | Codon Pair | Expected | Ob-served | Observed/ Expected | CPS |
|---|---|---|---|---|---|
| HV | CACGTA | 1230.04 | 1071 | 0.871 | -0.138 |
| HV | CACGTC | 1503.28 | 1682 | 1.119 | 0.112 |
| HV | CACGTG | 2238 | 2843 | 1.270 | 0.239 |
| HV | CACGTT | 1934.68 | 1934 | 1.000 | 0.000 |
| HY | CACTAC | 2359.28 | 2797 | 1.186 | 0.170 |
| HY | CACTAT | 1748.35 | 1680 | 0.961 | -0.040 |
| HS | CACTCA | 1586.1 | 1184 | 0.746 | -0.292 |
| HS | CACTCC | 1870.45 | 1390 | 0.743 | -0.297 |
| HS | CACTCG | 2241.58 | 2524 | 1.126 | 0.119 |
| HS | CACTCT | 1292.9 | 952 | 0.736 | -0.306 |
| HC | CACTGC | 1852.11 | 1918 | 1.036 | 0.035 |
| HW | CACTGG | 1644.17 | 1746 | 1.062 | 0.060 |
| HC | CACTGT | 1714.04 | 1667 | 0.973 | -0.028 |
| HL | CACTTA | 1272.73 | 661 | 0.519 | -0.655 |
| HF | CACTTC | 3282.62 | 3087 | 0.940 | -0.061 |
| HL | CACTTG | 2676.59 | 1856 | 0.693 | -0.366 |
| HF | CACTTT | 2513.13 | 2242 | 0.892 | -0.114 |
| QK | CAGAAA | 6107.42 | 5902 | 0.966 | -0.034 |
| QN | CAGAAC | 5373.26 | 5650 | 1.052 | 0.050 |
| QK | CAGAAG | 5802.7 | 7971 | 1.374 | 0.317 |
| QN | CAGAAT | 4642.28 | 4094 | 0.882 | -0.126 |
| QT | CAGACA | 2632.86 | 1603 | 0.609 | -0.496 |
| QT | CAGACC | 3129.03 | 1798 | 0.575 | -0.554 |
| QT | CAGACG | 3080.01 | 2465 | 0.800 | -0.223 |
| QT | CAGACT | 2269.36 | 1268 | 0.559 | -0.582 |
| QR | CAGAGA | 2281.97 | 1516 | 0.664 | -0.409 |
| QS | CAGAGC | 2781.64 | 2589 | 0.931 | -0.072 |
| QR | CAGAGG | 1695.11 | 1365 | 0.805 | -0.217 |
| QS | CAGAGT | 2545.71 | 2028 | 0.797 | -0.227 |
| QI | CAGATA | 2431.7 | 2067 | 0.850 | -0.162 |
| QI | CAGATC | 4719.35 | 4457 | 0.944 | -0.057 |
| QM | CAGATG | 4280.76 | 4537 | 1.060 | 0.058 |
| QI | CAGATT | 4085.58 | 3784 | 0.926 | -0.077 |
| QQ | CAGCAA | 8512.33 | 8274 | 0.972 | -0.028 |
| QH | CAGCAC | 3339.32 | 3953 | 1.184 | 0.169 |
| QQ | CAGCAG | 8362.94 | 11034 | 1.319 | 0.277 |
| QH | CAGCAT | 3271.63 | 3452 | 1.055 | 0.054 |
| QP | CAGCCA | 3175.68 | 2716 | 0.855 | -0.156 |
| QP | CAGCCC | 1939.24 | 1551 | 0.800 | -0.223 |
| QP | CAGCCG | 3360.87 | 2674 | 0.796 | -0.229 |
| QP | CAGCCT | 1917.38 | 1366 | 0.712 | -0.339 |
| QR | CAGCGA | 3024.01 | 3029 | 1.002 | 0.002 |
| QR | CAGCGC | 1954.03 | 1831 | 0.937 | -0.065 |
| QR | CAGCGG | 2563.25 | 2718 | 1.060 | 0.059 |
| QR | CAGCGT | 2055.9 | 1754 | 0.853 | -0.159 |
| QL | CAGCTA | 2088.28 | 2373 | 1.136 | 0.128 |
| QL | CAGCTC | 2444.97 | 2650 | 1.084 | 0.081 |
| QL | CAGCTG | 5405.34 | 7838 | 1.450 | 0.372 |
| QL | CAGCTT | 2455.24 | 2657 | 1.082 | 0.079 |
| QE | CAGGAA | 6586.16 | 7469 | 1.134 | 0.126 |
| QD | CAGGAC | 3173.7 | 4371 | 1.377 | 0.320 |
| QE | CAGGAG | 4424.49 | 5535 | 1.251 | 0.224 |
| QD | CAGGAT | 4195.98 | 4326 | 1.031 | 0.031 |
| QA | CAGGCA | 2608.15 | 1934 | 0.742 | -0.299 |
| QA | CAGGCC | 3063.89 | 2594 | 0.847 | -0.166 |
| QA | CAGGCG | 2134.69 | 2058 | 0.964 | -0.037 |
| QA | CAGGCT | 2545.81 | 1897 | 0.745 | -0.294 |
| QG | CAGGGA | 3105.78 | 2241 | 0.722 | -0.326 |
| QG | CAGGGC | 2001.51 | 1952 | 0.975 | -0.025 |
| QG | CAGGGG | 1193.97 | 691 | 0.579 | -0.547 |
| QG | CAGGGT | 2071.95 | 1669 | 0.806 | -0.216 |
| QV | CAGGTA | 1710.54 | 1113 | 0.651 | -0.430 |
| QV | CAGGTC | 2090.51 | 2379 | 1.138 | 0.129 |
| QV | CAGGTG | 3112.24 | 3558 | 1.143 | 0.134 |
| QV | CAGGTT | 2690.43 | 2378 | 0.884 | -0.123 |
| QY | CAGTAC | 3415.68 | 4491 | 1.315 | 0.274 |
| QY | CAGTAT | 2531.2 | 2824 | 1.116 | 0.109 |
| QS | CAGTCA | 2240.37 | 1748 | 0.780 | -0.248 |
| QS | CAGTCC | 2642.02 | 2074 | 0.785 | -0.242 |
| QS | CAGTCG | 3166.24 | 2706 | 0.855 | -0.157 |
| QS | CAGTCT | 1826.23 | 1229 | 0.673 | -0.396 |
| QC | CAGTGC | 2430.69 | 3018 | 1.242 | 0.216 |
| QW | CAGTGG | 2393.12 | 2670 | 1.116 | 0.109 |
| QC | CAGTGT | 2249.5 | 2353 | 1.046 | 0.045 |

-continued

Dataset SI. Mosquito codon pair scores.

| AA pair | Codon Pair | Expected | Ob-served | Observed/ Expected | CPS |
|---|---|---|---|---|---|
| QL | CAGTTA | 2029.86 | 1446 | 0.712 | -0.339 |
| QF | CAGTTC | 4255.74 | 5297 | 1.245 | 0.219 |
| QL | CAGTTG | 4268.86 | 4650 | 1.089 | 0.086 |
| QF | CAGTTT | 3258.15 | 3889 | 1.194 | 0.177 |
| HK | CATAAA | 3012.51 | 2118 | 0.703 | -0.352 |
| HN | CATAAC | 2690.57 | 1483 | 0.551 | -0.596 |
| HK | CATAAG | 2862.21 | 1576 | 0.551 | -0.597 |
| HN | CATAAT | 2324.54 | 1742 | 0.749 | -0.288 |
| HT | CATACA | 1507.9 | 1340 | 0.889 | -0.118 |
| HT | CATACC | 1792.06 | 1457 | 0.813 | -0.207 |
| HT | CATACG | 1763.99 | 1254 | 0.711 | -0.341 |
| HT | CATACT | 1299.71 | 1012 | 0.779 | -0.250 |
| HR | CATAGA | 1660.73 | 807 | 0.486 | -0.722 |
| HS | CATAGC | 1929.37 | 1029 | 0.533 | -0.629 |
| HR | CATAGG | 1233.63 | 571 | 0.463 | -0.770 |
| HS | CATAGT | 1765.73 | 1047 | 0.593 | -0.523 |
| HI | CATATA | 1382.93 | 1061 | 0.767 | -0.265 |
| HI | CATATC | 2683.94 | 1499 | 0.559 | -0.582 |
| HM | CATATG | 2467.97 | 1691 | 0.685 | -0.378 |
| HI | CATATT | 2323.51 | 1888 | 0.813 | -0.208 |
| HQ | CATCAA | 3525.78 | 4316 | 1.224 | 0.202 |
| HH | CATCAC | 3265.66 | 3408 | 1.044 | 0.043 |
| HQ | CATCAG | 3463.9 | 3680 | 1.062 | 0.061 |
| HH | CATCAT | 3199.45 | 3900 | 1.219 | 0.198 |
| HP | CATCCA | 2256.55 | 2753 | 1.220 | 0.199 |
| HP | CATCCC | 1377.97 | 1912 | 1.388 | 0.328 |
| HP | CATCCG | 2388.14 | 3513 | 1.471 | 0.386 |
| HP | CATCCT | 1362.43 | 1822 | 1.337 | 0.291 |
| HR | CATCGA | 2200.75 | 3064 | 1.392 | 0.331 |
| HR | CATCGC | 1422.06 | 1838 | 1.292 | 0.257 |
| HR | CATCGG | 1865.43 | 2486 | 1.333 | 0.287 |
| HR | CATCGT | 1496.2 | 2079 | 1.390 | 0.329 |
| HL | CATCTA | 1282.82 | 1688 | 1.316 | 0.274 |
| HL | CATCTC | 1501.93 | 1810 | 1.205 | 0.187 |
| HL | CATCTG | 3320.46 | 4068 | 1.225 | 0.203 |
| HL | CATCTT | 1508.23 | 1872 | 1.241 | 0.216 |
| HE | CATGAA | 3427.01 | 3079 | 0.898 | -0.107 |
| HD | CATGAC | 2072.13 | 1756 | 0.847 | -0.166 |
| HE | CATGAG | 2302.21 | 1646 | 0.715 | -0.336 |
| HD | CATGAT | 2739.59 | 2222 | 0.811 | -0.209 |
| HA | CATGCA | 1475.8 | 1532 | 1.038 | 0.037 |
| HA | CATGCC | 1733.68 | 2004 | 1.156 | 0.145 |
| HA | CATGCG | 1207.9 | 1233 | 1.021 | 0.021 |
| HA | CATGCT | 1440.52 | 1794 | 1.245 | 0.219 |
| HG | CATGGA | 2524.87 | 2591 | 1.026 | 0.026 |
| HG | CATGGC | 1627.15 | 1762 | 1.083 | 0.080 |
| HG | CATGGG | 970.65 | 1185 | 1.221 | 0.200 |
| HG | CATGGT | 1684.41 | 1646 | 0.977 | -0.023 |
| HV | CATGTA | 1205.1 | 1063 | 0.882 | -0.125 |
| HV | CATGTC | 1472.8 | 1437 | 0.976 | -0.025 |
| HV | CATGTG | 2192.63 | 1836 | 0.837 | -0.178 |
| HV | CATGTT | 1895.46 | 1806 | 0.953 | -0.048 |
| HY | CATTAC | 2311.45 | 1917 | 0.829 | -0.187 |
| HY | CATTAT | 1712.91 | 1738 | 1.015 | 0.015 |
| HS | CATTCA | 1553.94 | 1993 | 1.283 | 0.249 |
| HS | CATTCC | 1832.53 | 2425 | 1.323 | 0.280 |
| HS | CATTCG | 2196.14 | 2623 | 1.194 | 0.178 |
| HS | CATTCT | 1266.69 | 1795 | 1.417 | 0.349 |
| HC | CATTGC | 1814.56 | 1778 | 0.980 | -0.020 |
| HW | CATTGG | 1610.83 | 1509 | 0.937 | -0.065 |
| HC | CATTGT | 1679.29 | 1697 | 1.011 | 0.010 |
| HL | CATTTA | 1246.93 | 1703 | 1.366 | 0.312 |
| HF | CATTTC | 3216.07 | 3092 | 0.961 | -0.039 |
| HL | CATTTG | 2622.33 | 3446 | 1.314 | 0.273 |
| HF | CATTTT | 2462.18 | 3053 | 1.240 | 0.215 |
| PK | CCAAAA | 4267.03 | 3977 | 0.932 | -0.070 |
| PN | CCAAAC | 3518.71 | 3292 | 0.936 | -0.067 |
| PK | CCAAAG | 4054.14 | 3777 | 0.932 | -0.071 |
| PN | CCAAAT | 3040.03 | 3298 | 1.085 | 0.081 |
| PT | CCAACA | 2267 | 3200 | 1.412 | 0.345 |
| PT | CCAACC | 2694.22 | 2778 | 1.031 | 0.031 |
| PT | CCAACG | 2652.01 | 3837 | 1.447 | 0.369 |
| PT | CCAACT | 1954.01 | 2491 | 1.275 | 0.243 |
| PR | CCAAGA | 1386.85 | 2084 | 1.503 | 0.407 |
| PS | CCAAGC | 2497.18 | 2181 | 0.873 | -0.135 |
| PR | CCAAGG | 1030.19 | 1875 | 1.820 | 0.599 |
| PS | CCAAGT | 2285.39 | 2183 | 0.955 | -0.046 |
| PI | CCAATA | 1637.11 | 1586 | 0.969 | -0.032 |
| PI | CCAATC | 3177.25 | 3121 | 0.982 | -0.018 |
| PM | CCAATG | 2775.36 | 2619 | 0.944 | -0.058 |
| PI | CCAATT | 2750.57 | 2453 | 0.892 | -0.114 |
| PQ | CCACAA | 3016.94 | 2917 | 0.967 | -0.034 |
| PH | CCACAC | 1706.25 | 1528 | 0.896 | -0.110 |
| PQ | CCACAG | 2963.99 | 2838 | 0.957 | -0.043 |
| PH | CCACAT | 1671.66 | 1780 | 1.065 | 0.063 |
| PP | CCACCA | 3244.77 | 4385 | 1.351 | 0.301 |
| PP | CCACCC | 1981.42 | 1992 | 1.005 | 0.005 |
| PP | CCACCG | 3433.98 | 4780 | 1.392 | 0.331 |
| PP | CCACCT | 1959.09 | 2208 | 1.127 | 0.120 |
| PR | CCACGA | 1837.82 | 1699 | 0.924 | -0.079 |
| PR | CCACGC | 1187.55 | 988 | 0.832 | -0.184 |
| PR | CCACGG | 1557.8 | 1408 | 0.904 | -0.101 |
| PR | CCACGT | 1249.46 | 1226 | 0.981 | -0.019 |
| PL | CCACTA | 1232.61 | 1279 | 1.038 | 0.037 |
| PL | CCACTC | 1443.14 | 1208 | 0.837 | -0.178 |
| PL | CCACTG | 3190.51 | 3278 | 1.027 | 0.027 |
| PL | CCACTT | 1449.2 | 1644 | 1.134 | 0.126 |
| PE | CCAGAA | 5306.23 | 4157 | 0.783 | -0.244 |
| PD | CCAGAC | 2733.94 | 1742 | 0.637 | -0.451 |
| PE | CCAGAG | 3564.65 | 2517 | 0.706 | -0.348 |
| PD | CCAGAT | 3614.57 | 2942 | 0.814 | -0.206 |
| PA | CCAGCA | 2454.95 | 3238 | 1.319 | 0.277 |
| PA | CCAGCC | 2883.93 | 2157 | 0.748 | -0.290 |
| PA | CCAGCG | 2009.3 | 2216 | 1.103 | 0.098 |
| PA | CCAGCT | 2396.27 | 2837 | 1.184 | 0.169 |
| PG | CCAGGA | 2970.76 | 2564 | 0.863 | -0.147 |
| PG | CCAGGC | 1914.5 | 1169 | 0.611 | -0.493 |
| PG | CCAGGG | 1142.07 | 942 | 0.825 | -0.193 |
| PG | CCAGGT | 1981.87 | 1400 | 0.706 | -0.348 |
| PV | CCAGTA | 1708.01 | 1656 | 0.970 | -0.031 |
| PV | CCAGTC | 2087.42 | 1567 | 0.751 | -0.287 |
| PV | CCAGTG | 3107.64 | 2905 | 0.935 | -0.067 |
| PV | CCAGTT | 2686.46 | 2772 | 1.032 | 0.031 |
| PY | CCATAC | 2205.33 | 1698 | 0.770 | -0.261 |
| PY | CCATAT | 1634.27 | 1356 | 0.830 | -0.187 |
| PS | CCATCA | 2011.27 | 2834 | 1.409 | 0.343 |
| PS | CCATCC | 2371.84 | 2438 | 1.028 | 0.028 |
| PS | CCATCG | 2842.46 | 3959 | 1.393 | 0.331 |
| PS | CCATCT | 1639.48 | 1927 | 1.175 | 0.162 |
| PC | CCATGC | 1357.61 | 1154 | 0.850 | -0.162 |
| PW | CCATGG | 1704.69 | 1590 | 0.933 | -0.070 |
| PC | CCATGT | 1256.41 | 1178 | 0.938 | -0.064 |
| PL | CCATTA | 1198.13 | 1055 | 0.881 | -0.127 |
| PF | CCATTC | 2903.1 | 3049 | 1.050 | 0.049 |
| PL | CCATTG | 2519.69 | 2405 | 0.954 | -0.047 |
| PF | CCATTT | 2222.58 | 2228 | 1.002 | 0.002 |
| PK | CCCAAA | 2605.67 | 3418 | 1.312 | 0.271 |
| PN | CCCAAC | 2148.71 | 3241 | 1.508 | 0.411 |
| PK | CCCAAG | 2475.67 | 3491 | 1.410 | 0.344 |
| PN | CCCAAT | 1856.4 | 2327 | 1.254 | 0.226 |
| PT | CCCACA | 1384.35 | 1441 | 1.041 | 0.040 |
| PT | CCCACC | 1645.23 | 1851 | 1.125 | 0.118 |
| PT | CCCACG | 1619.45 | 1631 | 1.007 | 0.007 |
| PT | CCCACT | 1193.22 | 1234 | 1.034 | 0.034 |
| PR | CCCAGA | 846.89 | 1152 | 1.360 | 0.308 |
| PS | CCCAGC | 1524.91 | 2184 | 1.432 | 0.359 |
| PR | CCCAGG | 629.09 | 845 | 1.343 | 0.295 |
| PS | CCCAGT | 1395.57 | 1808 | 1.296 | 0.259 |
| PI | CCCATA | 999.7 | 1034 | 1.034 | 0.034 |
| PI | CCCATC | 1940.19 | 2872 | 1.480 | 0.392 |
| PM | CCCATG | 1694.78 | 1600 | 0.944 | -0.058 |
| PI | CCCATT | 1679.64 | 1934 | 1.151 | 0.141 |
| PQ | CCCCAA | 1842.3 | 1689 | 0.917 | -0.087 |
| PH | CCCCAC | 1041.92 | 1067 | 1.024 | 0.024 |
| PQ | CCCCAG | 1809.97 | 1828 | 1.010 | 0.010 |
| PH | CCCCAT | 1020.8 | 1092 | 1.070 | 0.067 |
| PP | CCCCCA | 1981.42 | 1194 | 0.603 | -0.507 |
| PP | CCCCCC | 1209.96 | 436 | 0.360 | -1.021 |

-continued

Dataset SI. Mosquito codon pair scores.

| AA pair | Codon Pair | Expected | Ob-served | Observed/ Expected | CPS |
|---|---|---|---|---|---|
| PP | CCCCCG | 2096.97 | 1193 | 0.569 | -0.564 |
| PP | CCCCCT | 1196.32 | 723 | 0.604 | -0.504 |
| PR | CCCCGA | 1122.27 | 1050 | 0.936 | -0.067 |
| PR | CCCCGC | 725.18 | 767 | 1.058 | 0.056 |
| PR | CCCCGG | 951.27 | 1122 | 1.179 | 0.165 |
| PR | CCCCGT | 762.99 | 758 | 0.993 | -0.007 |
| PL | CCCCTA | 752.69 | 566 | 0.752 | -0.285 |
| PL | CCCCTC | 881.26 | 879 | 0.997 | -0.003 |
| PL | CCCCTG | 1948.29 | 1541 | 0.791 | -0.235 |
| PL | CCCCTT | 884.96 | 717 | 0.810 | -0.210 |
| PE | CCCGAA | 3240.26 | 2695 | 0.832 | -0.184 |
| PD | CCCGAC | 1669.49 | 1334 | 0.799 | -0.224 |
| PE | CCCGAG | 2176.76 | 1813 | 0.833 | -0.183 |
| PD | CCCGAT | 2207.24 | 2231 | 1.011 | 0.011 |
| PA | CCCGCA | 1499.12 | 1120 | 0.747 | -0.292 |
| PA | CCCGCC | 1761.07 | 1349 | 0.766 | -0.267 |
| PA | CCCGCG | 1226.98 | 686 | 0.559 | -0.581 |
| PA | CCCGCT | 1463.29 | 977 | 0.668 | -0.404 |
| PG | CCCGGA | 1814.1 | 2556 | 1.409 | 0.343 |
| PG | CCCGGC | 1169.09 | 1528 | 1.307 | 0.268 |
| PG | CCCGGG | 697.41 | 952 | 1.365 | 0.311 |
| PG | CCCGGT | 1210.23 | 1815 | 1.500 | 0.405 |
| PV | CCCGTA | 1043 | 965 | 0.925 | -0.078 |
| PV | CCCGTC | 1274.69 | 1356 | 1.064 | 0.062 |
| PV | CCCGTG | 1897.69 | 1252 | 0.660 | -0.416 |
| PV | CCCGTT | 1640.49 | 1543 | 0.941 | -0.061 |
| PY | CCCTAC | 1346.69 | 1611 | 1.196 | 0.179 |
| PY | CCCTAT | 997.97 | 985 | 0.987 | -0.013 |
| PS | CCCTCA | 1228.18 | 984 | 0.801 | -0.222 |
| PS | CCCTCC | 1448.37 | 1051 | 0.726 | -0.321 |
| PS | CCCTCG | 1735.75 | 1881 | 1.084 | 0.080 |
| PS | CCCTCT | 1001.15 | 723 | 0.722 | -0.325 |
| PC | CCCTGC | 829.03 | 1094 | 1.320 | 0.277 |
| PW | CCCTGG | 1040.97 | 1189 | 1.142 | 0.133 |
| PC | CCCTGT | 767.23 | 829 | 1.081 | 0.077 |
| PL | CCCTTA | 731.64 | 499 | 0.682 | -0.383 |
| PF | CCCTTC | 1772.78 | 1936 | 1.092 | 0.088 |
| PL | CCCTTG | 1538.66 | 1127 | 0.732 | -0.311 |
| PF | CCCTTT | 1357.22 | 882 | 0.650 | -0.431 |
| PK | CCGAAA | 4515.86 | 4570 | 1.012 | 0.012 |
| PN | CCGAAC | 3723.9 | 4086 | 1.097 | 0.093 |
| PK | CCGAAG | 4290.56 | 5440 | 1.268 | 0.237 |
| PN | CCGAAT | 3217.3 | 3069 | 0.954 | -0.047 |
| PT | CCGACA | 2399.2 | 1627 | 0.678 | -0.388 |
| PT | CCGACC | 2851.33 | 2125 | 0.745 | -0.294 |
| PT | CCGACG | 2806.66 | 2732 | 0.973 | -0.027 |
| PT | CCGACT | 2067.96 | 1298 | 0.628 | -0.466 |
| PR | CCGAGA | 1467.73 | 1319 | 0.899 | -0.107 |
| PS | CCGAGC | 2642.81 | 1964 | 0.743 | -0.297 |
| PR | CCGAGG | 1090.27 | 1533 | 1.406 | 0.341 |
| PS | CCGAGT | 2418.66 | 1618 | 0.669 | -0.402 |
| PI | CCGATA | 1732.58 | 1640 | 0.947 | -0.055 |
| PI | CCGATC | 3362.53 | 3880 | 1.154 | 0.143 |
| PM | CCGATG | 2937.2 | 3868 | 1.317 | 0.275 |
| PI | CCGATT | 2910.97 | 3113 | 1.069 | 0.067 |
| PQ | CCGCAA | 3192.87 | 2544 | 0.797 | -0.227 |
| PH | CCGCAC | 1805.75 | 1858 | 1.029 | 0.029 |
| PQ | CCGCAG | 3136.83 | 3290 | 1.049 | 0.048 |
| PH | CCGCAT | 1769.14 | 1371 | 0.775 | -0.255 |
| PP | CCGCCA | 3433.98 | 2763 | 0.805 | -0.217 |
| PP | CCGCCC | 2096.97 | 1405 | 0.670 | -0.400 |
| PP | CCGCCG | 3634.23 | 2834 | 0.780 | -0.249 |
| PP | CCGCCT | 2073.33 | 1359 | 0.655 | -0.422 |
| PR | CCGCGA | 1944.99 | 1138 | 0.585 | -0.536 |
| PR | CCGCGC | 1256.8 | 636 | 0.506 | -0.681 |
| PR | CCGCGG | 1648.64 | 1100 | 0.667 | -0.405 |
| PR | CCGCGT | 1322.32 | 608 | 0.460 | -0.777 |
| PL | CCGCTA | 1304.49 | 1160 | 0.889 | -0.117 |
| PL | CCGCTC | 1527.3 | 1401 | 0.917 | -0.086 |
| PL | CCGCTG | 3376.56 | 4156 | 1.231 | 0.208 |
| PL | CCGCTT | 1533.71 | 1413 | 0.921 | -0.082 |
| PE | CCGGAA | 5615.65 | 8041 | 1.432 | 0.359 |
| PD | CCGGAC | 2893.37 | 4394 | 1.519 | 0.418 |
| PE | CCGGAG | 3772.51 | 6048 | 1.603 | 0.472 |

-continued

Dataset SI. Mosquito codon pair scores.

| AA pair | Codon Pair | Expected | Ob-served | Observed/ Expected | CPS |
|---|---|---|---|---|---|
| PD | CCGGAT | 3825.35 | 5359 | 1.401 | 0.337 |
| PA | CCGGCA | 2598.11 | 2589 | 0.996 | -0.004 |
| PA | CCGGCC | 3052.1 | 3185 | 1.044 | 0.043 |
| PA | CCGGCG | 2126.47 | 2518 | 1.184 | 0.169 |
| PA | CCGGCT | 2536.01 | 2233 | 0.881 | -0.127 |
| PG | CCGGGA | 3144 | 2717 | 0.864 | -0.146 |
| PG | CCGGGC | 2026.15 | 1680 | 0.829 | -0.187 |
| PG | CCGGGG | 1208.67 | 1000 | 0.827 | -0.190 |
| PG | CCGGGT | 2097.45 | 1565 | 0.746 | -0.293 |
| PV | CCGGTA | 1807.61 | 1935 | 1.070 | 0.068 |
| PV | CCGGTC | 2209.15 | 2394 | 1.084 | 0.080 |
| PV | CCGGTG | 3288.86 | 4614 | 1.403 | 0.339 |
| PV | CCGGTT | 2843.12 | 2954 | 1.039 | 0.038 |
| PY | CCGTAC | 2333.94 | 3095 | 1.326 | 0.282 |
| PY | CCGTAT | 1729.57 | 1547 | 0.894 | -0.112 |
| PS | CCGTCA | 2128.55 | 1531 | 0.719 | -0.330 |
| PS | CCGTCC | 2510.15 | 1733 | 0.690 | -0.370 |
| PS | CCGTCG | 3008.21 | 2733 | 0.909 | -0.096 |
| PS | CCGTCT | 1735.08 | 1095 | 0.631 | -0.460 |
| PC | CCGTGC | 1436.78 | 1268 | 0.883 | -0.125 |
| PW | CCGTGG | 1804.1 | 1655 | 0.917 | -0.086 |
| PC | CCGTGT | 1329.68 | 1098 | 0.826 | -0.191 |
| PL | CCGTTA | 1267.99 | 989 | 0.780 | -0.248 |
| PF | CCGTTC | 3072.39 | 3567 | 1.161 | 0.149 |
| PL | CCGTTG | 2666.63 | 3348 | 1.256 | 0.228 |
| PF | CCGTTT | 2352.19 | 2269 | 0.965 | -0.036 |
| PK | CCTAAA | 2576.3 | 1458 | 0.566 | -0.569 |
| PN | CCTAAC | 2124.49 | 1032 | 0.486 | -0.722 |
| PK | CCTAAG | 2447.76 | 1102 | 0.450 | -0.798 |
| PN | CCTAAT | 1835.47 | 1120 | 0.610 | -0.494 |
| PT | CCTACA | 1368.74 | 1337 | 0.977 | -0.023 |
| PT | CCTACC | 1626.68 | 1262 | 0.776 | -0.254 |
| PT | CCTACG | 1601.2 | 1326 | 0.828 | -0.189 |
| PT | CCTACT | 1179.77 | 1141 | 0.967 | -0.033 |
| PR | CCTAGA | 837.34 | 635 | 0.758 | -0.277 |
| PS | CCTAGC | 1507.72 | 935 | 0.620 | -0.478 |
| PR | CCTAGG | 622 | 461 | 0.741 | -0.300 |
| PS | CCTAGT | 1379.84 | 993 | 0.720 | -0.329 |
| PI | CCTATA | 988.44 | 557 | 0.564 | -0.574 |
| PI | CCTATC | 1918.32 | 1340 | 0.699 | -0.359 |
| PM | CCTATG | 1675.67 | 996 | 0.594 | -0.520 |
| PI | CCTATT | 1660.71 | 1228 | 0.739 | -0.302 |
| PQ | CCTCAA | 1821.53 | 2371 | 1.302 | 0.264 |
| PH | CCTCAC | 1030.18 | 1161 | 1.127 | 0.120 |
| PQ | CCTCAG | 1789.56 | 2097 | 1.172 | 0.159 |
| PH | CCTCAT | 1009.29 | 1198 | 1.187 | 0.171 |
| PP | CCTCCA | 1959.09 | 3013 | 1.538 | 0.430 |
| PP | CCTCCC | 1196.32 | 1529 | 1.278 | 0.245 |
| PP | CCTCCG | 2073.33 | 3212 | 1.549 | 0.438 |
| PP | CCTCCT | 1182.83 | 1728 | 1.461 | 0.379 |
| PR | CCTCGA | 1109.62 | 1343 | 1.210 | 0.191 |
| PR | CCTCGC | 717 | 902 | 1.258 | 0.230 |
| PR | CCTCGG | 940.55 | 1305 | 1.387 | 0.327 |
| PR | CCTCGT | 754.39 | 1045 | 1.385 | 0.326 |
| PL | CCTCTA | 744.21 | 920 | 1.236 | 0.212 |
| PL | CCTCTC | 871.32 | 1076 | 1.235 | 0.211 |
| PL | CCTCTG | 1926.33 | 1959 | 1.017 | 0.017 |
| PL | CCTCTT | 874.98 | 995 | 1.137 | 0.129 |
| PE | CCTGAA | 3203.73 | 2529 | 0.789 | -0.236 |
| PD | CCTGAC | 1650.67 | 1023 | 0.620 | -0.178 |
| PE | CCTGAG | 2152.22 | 1232 | 0.572 | -0.558 |
| PD | CCTGAT | 2182.36 | 1752 | 0.803 | -0.220 |
| PA | CCTGCA | 1482.22 | 1761 | 1.188 | 0.172 |
| PA | CCTGCC | 1741.22 | 1801 | 1.034 | 0.034 |
| PA | CCTGCG | 1213.15 | 1254 | 1.034 | 0.033 |
| PA | CCTGCT | 1446.79 | 1970 | 1.362 | 0.309 |
| PG | CCTGGA | 1793.65 | 2532 | 1.412 | 0.345 |
| PG | CCTGGC | 1155.92 | 1371 | 1.186 | 0.171 |
| PG | CCTGGG | 689.54 | 876 | 1.270 | 0.239 |
| PG | CCTGGT | 1196.59 | 1545 | 1.291 | 0.256 |
| PV | CCTGTA | 1031.24 | 1115 | 1.081 | 0.078 |
| PV | CCTGTC | 1260.32 | 1145 | 0.908 | -0.096 |
| PV | CCTGTG | 1876.3 | 1498 | 0.798 | -0.225 |
| PV | CCTGTT | 1622 | 1713 | 1.056 | 0.055 |

-continued

Dataset SI. Mosquito codon pair scores.

| AA pair | Codon Pair | Expected | Ob-served | Observed/Expected | CPS |
|---|---|---|---|---|---|
| PY | CCTTAC | 1331.51 | 1289 | 0.968 | -0.032 |
| PY | CCTTAT | 986.72 | 985 | 0.998 | -0.002 |
| PS | CCTTCA | 1214.34 | 1849 | 1.523 | 0.420 |
| PS | CCTTCC | 1432.04 | 1958 | 1.367 | 0.313 |
| PS | CCTTCG | 1716.19 | 2730 | 1.591 | 0.464 |
| PS | CCTTCT | 989.86 | 1373 | 1.387 | 0.327 |
| PC | CCTTGC | 819.68 | 1010 | 1.232 | 0.209 |
| PW | CCTTGG | 1029.24 | 1145 | 1.112 | 0.107 |
| PC | CCTTGT | 758.58 | 924 | 1.218 | 0.197 |
| PL | CCTTTA | 723.39 | 702 | 0.970 | -0.030 |
| PF | CCTTTC | 1752.8 | 1630 | 0.930 | -0.073 |
| PL | CCTTTG | 1521.31 | 1792 | 1.178 | 0.164 |
| PF | CCTTTT | 1341.92 | 1214 | 0.905 | -0.100 |
| RK | CGAAAA | 5111.55 | 4039 | 0.790 | -0.236 |
| RN | CGAAAC | 3867.09 | 3445 | 0.891 | -0.116 |
| RK | CGAAAG | 4856.52 | 3611 | 0.744 | -0.296 |
| RN | CGAAAT | 3341.01 | 3137 | 0.939 | -0.063 |
| RT | CGAACA | 1965.12 | 2336 | 1.189 | 0.173 |
| RT | CGAACC | 2335.45 | 2309 | 0.989 | -0.011 |
| RT | CGAACG | 2298.86 | 2820 | 1.227 | 0.204 |
| RT | CGAACT | 1693.81 | 1780 | 1.051 | 0.050 |
| RR | CGAAGA | 2106.57 | 3264 | 1.549 | 0.438 |
| RS | CGAAGC | 2287.63 | 2551 | 1.115 | 0.109 |
| RR | CGAAGG | 1564.81 | 2250 | 1.438 | 0.363 |
| RS | CGAAGT | 2093.6 | 2263 | 1.081 | 0.078 |
| RI | CGAATA | 1656.22 | 1776 | 1.072 | 0.070 |
| RI | CGAATC | 3214.33 | 3150 | 0.980 | -0.020 |
| RM | CGAATG | 2888.28 | 2982 | 1.032 | 0.032 |
| RI | CGAATT | 2782.67 | 2203 | 0.792 | -0.234 |
| RQ | CGACAA | 2802.04 | 2599 | 0.928 | -0.075 |
| RH | CGACAC | 1907.46 | 1589 | 0.833 | -0.183 |
| RQ | CGACAG | 2752.86 | 2478 | 0.900 | -0.105 |
| RH | CGACAT | 1868.79 | 1806 | 0.966 | -0.034 |
| RP | CGACCA | 1910.45 | 1903 | 0.996 | -0.004 |
| RP | CGACCC | 1166.62 | 1118 | 0.958 | -0.043 |
| RP | CGACCG | 2021.86 | 2300 | 1.138 | 0.129 |
| RP | CGACCT | 1153.47 | 1252 | 1.085 | 0.082 |
| RR | CGACGA | 2791.56 | 2956 | 1.059 | 0.057 |
| RR | CGACGC | 1803.83 | 1216 | 0.674 | -0.394 |
| RR | CGACGG | 2366.22 | 1899 | 0.803 | -0.220 |
| RR | CGACGT | 1897.88 | 1245 | 0.656 | -0.422 |
| RL | CGACTA | 1252.53 | 1075 | 0.858 | -0.153 |
| RL | CGACTC | 1466.47 | 1134 | 0.773 | -0.257 |
| RL | CGACTG | 3242.07 | 2650 | 0.817 | -0.202 |
| RL | CGACTT | 1472.63 | 1259 | 0.855 | -0.157 |
| RE | CGAGAA | 4072.56 | 3760 | 0.923 | -0.080 |
| RD | CGAGAC | 2285.69 | 1674 | 0.732 | -0.311 |
| RE | CGAGAG | 2735.89 | 2494 | 0.912 | -0.093 |
| RD | CGAGAT | 3021.93 | 2625 | 0.869 | -0.141 |
| RA | CGAGCA | 1693.39 | 1970 | 1.163 | 0.151 |
| RA | CGAGCC | 1989.29 | 1695 | 0.852 | -0.160 |
| RA | CGAGCG | 1385.98 | 1924 | 1.388 | 0.328 |
| RA | CGAGCT | 1652.91 | 1944 | 1.176 | 0.162 |
| RG | CGAGGA | 2368.46 | 3207 | 1.354 | 0.303 |
| RG | CGAGGC | 1526.35 | 1552 | 1.017 | 0.017 |
| RG | CGAGGG | 910.52 | 1127 | 1.238 | 0.213 |
| RG | CGAGGT | 1580.06 | 1560 | 0.987 | -0.013 |
| RV | CGAGTA | 1202.51 | 1337 | 1.112 | 0.106 |
| RV | CGAGTC | 1469.63 | 1313 | 0.893 | -0.113 |
| RV | CGAGTG | 2187.91 | 2550 | 1.165 | 0.153 |
| RV | CGAGTT | 1891.38 | 2040 | 1.079 | 0.076 |
| RY | CGATAC | 2402.6 | 2223 | 0.925 | -0.078 |
| RY | CGATAT | 1780.45 | 1848 | 1.038 | 0.037 |
| RS | CGATCA | 1842.49 | 2476 | 1.344 | 0.296 |
| RS | CGATCC | 2172.8 | 2133 | 0.982 | -0.018 |
| RS | CGATCG | 2603.93 | 3533 | 1.357 | 0.305 |
| RS | CGATCT | 1501.9 | 1707 | 1.137 | 0.128 |
| RC | CGATGC | 1996.05 | 1950 | 0.977 | -0.023 |
| RW | CGATGG | 2395.72 | 2310 | 0.964 | -0.036 |
| RC | CGATGT | 1847.26 | 1718 | 0.930 | -0.073 |
| RL | CGATTA | 1217.49 | 1496 | 1.229 | 0.206 |
| RF | CGATTC | 3356.66 | 3262 | 0.972 | -0.029 |
| RL | CGATTG | 2560.42 | 3431 | 1.340 | 0.293 |
| RF | CGATTT | 2569.82 | 2527 | 0.983 | -0.017 |

-continued

Dataset SI. Mosquito codon pair scores.

| AA pair | Codon Pair | Expected | Ob-served | Observed/Expected | CPS |
|---|---|---|---|---|---|
| RK | CGCAAA | 3302.94 | 3442 | 1.042 | 0.041 |
| RN | CGCAAC | 2498.81 | 2824 | 1.130 | 0.122 |
| RK | CGCAAG | 3138.15 | 3700 | 1.179 | 0.165 |
| RN | CGCAAT | 2158.87 | 2261 | 1.047 | 0.046 |
| RT | CGCACA | 1269.81 | 1140 | 0.898 | -0.108 |
| RT | CGCACC | 1509.1 | 1641 | 1.087 | 0.084 |
| RT | CGCACG | 1485.46 | 962 | 0.648 | -0.434 |
| RT | CGCACT | 1094.49 | 967 | 0.884 | -0.124 |
| RR | CGCAGA | 1361.2 | 1163 | 0.854 | -0.157 |
| RS | CGCAGC | 1478.2 | 1911 | 1.293 | 0.257 |
| RR | CGCAGG | 1011.14 | 844 | 0.835 | -0.181 |
| RS | CGCAGT | 1352.83 | 1551 | 1.146 | 0.137 |
| RI | CGCATA | 1070.2 | 861 | 0.805 | -0.218 |
| RI | CGCATC | 2077.01 | 2455 | 1.182 | 0.167 |
| RM | CGCATG | 1866.32 | 1523 | 0.816 | -0.203 |
| RI | CGCATT | 1798.08 | 1683 | 0.936 | -0.066 |
| RQ | CGCCAA | 1810.6 | 2421 | 1.337 | 0.291 |
| RH | CGCCAC | 1232.55 | 1642 | 1.332 | 0.287 |
| RQ | CGCCAG | 1778.82 | 2092 | 1.176 | 0.162 |
| RH | CGCCAT | 1207.56 | 1539 | 1.274 | 0.243 |
| RP | CGCCCA | 1234.48 | 1051 | 0.851 | -0.161 |
| RP | CGCCCC | 753.84 | 611 | 0.811 | -0.210 |
| RP | CGCCCG | 1306.47 | 853 | 0.653 | -0.426 |
| RP | CGCCCT | 745.34 | 729 | 0.978 | -0.022 |
| RR | CGCCGA | 1803.83 | 1686 | 0.935 | -0.068 |
| RR | CGCCGC | 1165.58 | 1236 | 1.060 | 0.059 |
| RR | CGCCGG | 1528.98 | 1462 | 0.956 | -0.045 |
| RR | CGCCGT | 1226.35 | 1244 | 1.014 | 0.014 |
| RL | CGCCTA | 809.35 | 730 | 0.902 | -0.103 |
| RL | CGCCTC | 947.59 | 1057 | 1.115 | 0.109 |
| RL | CGCCTG | 2094.93 | 1299 | 0.620 | -0.478 |
| RL | CGCCTT | 951.57 | 882 | 0.927 | -0.076 |
| RE | CGCGAA | 2631.57 | 2726 | 1.036 | 0.035 |
| RD | CGCGAC | 1476.94 | 1424 | 0.964 | -0.037 |
| RE | CGCGAG | 1767.85 | 2154 | 1.218 | 0.198 |
| RD | CGCGAT | 1952.68 | 2493 | 1.277 | 0.244 |
| RA | CGCGCA | 1094.22 | 684 | 0.625 | -0.470 |
| RA | CGCGCC | 1285.42 | 1105 | 0.860 | -0.151 |
| RA | CGCGCG | 895.58 | 507 | 0.566 | -0.569 |
| RA | CGCGCT | 1068.06 | 787 | 0.737 | -0.305 |
| RG | CGCGGA | 1530.43 | 1386 | 0.906 | -0.099 |
| RG | CGCGGC | 986.29 | 924 | 0.937 | -0.065 |
| RG | CGCGGG | 588.35 | 512 | 0.870 | -0.139 |
| RG | CGCGGT | 1020.99 | 1079 | 1.057 | 0.055 |
| RV | CGCGTA | 777.03 | 704 | 0.906 | -0.099 |
| RV | CGCGTC | 949.63 | 1204 | 1.268 | 0.237 |
| RV | CGCGTG | 1413.76 | 1000 | 0.707 | -0.346 |
| RV | CGCGTT | 1222.15 | 1301 | 1.065 | 0.063 |
| RY | CGCTAC | 1552.49 | 2208 | 1.422 | 0.352 |
| RY | CGCTAT | 1150.48 | 1334 | 1.160 | 0.148 |
| RS | CGCTCA | 1190.56 | 957 | 0.804 | -0.218 |
| RS | CGCTCC | 1404 | 1170 | 0.833 | -0.182 |
| RS | CGCTCG | 1682.59 | 1559 | 0.927 | -0.076 |
| RS | CGCTCT | 970.48 | 780 | 0.804 | -0.218 |
| RC | CGCTGC | 1289.79 | 1749 | 1.356 | 0.305 |
| RW | CGCTGG | 1548.05 | 1736 | 1.121 | 0.115 |
| RC | CGCTGT | 1193.65 | 1347 | 1.128 | 0.121 |
| RL | CGCTTA | 786.71 | 670 | 0.852 | -0.161 |
| RF | CGCTTC | 2168.98 | 2859 | 1.318 | 0.276 |
| RL | CGCTTG | 1654.47 | 1340 | 0.810 | -0.211 |
| RF | CGCTTT | 1660.54 | 1297 | 0.781 | -0.247 |
| RK | CGGAAA | 4332.71 | 4594 | 1.060 | 0.059 |
| RN | CGGAAC | 3277.88 | 3599 | 1.098 | 0.093 |
| RK | CGGAAG | 4116.55 | 5777 | 1.403 | 0.339 |
| RN | CGGAAT | 2831.95 | 2771 | 0.978 | -0.022 |
| RT | CGGACA | 1665.7 | 1512 | 0.908 | -0.097 |
| RT | CGGACC | 1979.6 | 1122 | 0.567 | -0.568 |
| RT | CGGACG | 1948.59 | 2052 | 1.053 | 0.052 |
| RT | CGGACT | 1435.73 | 843 | 0.587 | -0.532 |
| RR | CGGAGA | 1785.6 | 1994 | 1.117 | 0.110 |
| RS | CGGAGC | 1939.07 | 1432 | 0.738 | -0.303 |
| RR | CGGAGG | 1326.39 | 1991 | 1.501 | 0.406 |
| RS | CGGAGT | 1774.61 | 1365 | 0.769 | -0.262 |
| RI | CGGATA | 1403.86 | 2091 | 1.489 | 0.398 |

-continued

Dataset SI. Mosquito codon pair scores.

| AA pair | Codon Pair | Expected | Ob-served | Observed/ Expected | CPS |
|---|---|---|---|---|---|
| RI | CGGATC | 2724.57 | 2467 | 0.905 | -0.099 |
| RM | CGGATG | 2448.2 | 3199 | 1.307 | 0.267 |
| RI | CGGATT | 2358.68 | 2299 | 0.975 | -0.026 |
| RQ | CGGCAA | 2375.1 | 2347 | 0.988 | -0.012 |
| RH | CGGCAC | 1616.83 | 1752 | 1.084 | 0.080 |
| RQ | CGGCAG | 2333.41 | 2914 | 1.249 | 0.222 |
| RH | CGGCAT | 1584.05 | 1436 | 0.907 | -0.098 |
| RP | CGGCCA | 1619.36 | 1842 | 1.137 | 0.129 |
| RP | CGGCCC | 988.87 | 895 | 0.905 | -0.100 |
| RP | CGGCCG | 1713.79 | 1764 | 1.029 | 0.029 |
| RP | CGGCCT | 977.72 | 788 | 0.806 | -0.216 |
| RR | CGGCGA | 2366.22 | 1706 | 0.721 | -0.327 |
| RR | CGGCGC | 1528.98 | 1033 | 0.676 | -0.392 |
| RR | CGGCGG | 2005.69 | 1872 | 0.933 | -0.069 |
| RR | CGGCGT | 1608.7 | 881 | 0.548 | -0.602 |
| RL | CGGCTA | 1061.68 | 1117 | 1.052 | 0.051 |
| RL | CGGCTC | 1243.02 | 1395 | 1.122 | 0.115 |
| RL | CGGCTG | 2748.09 | 2782 | 1.012 | 0.012 |
| RL | CGGCTT | 1248.25 | 1181 | 0.946 | -0.055 |
| RE | CGGGAA | 3452.04 | 3910 | 1.133 | 0.125 |
| RD | CGGGAC | 1937.42 | 2743 | 1.416 | 0.348 |
| RE | CGGGAG | 2319.03 | 3192 | 1.376 | 0.319 |
| RD | CGGGAT | 2561.49 | 2596 | 1.013 | 0.013 |
| RA | CGGGCA | 1435.37 | 1243 | 0.866 | -0.144 |
| RA | CGGGCC | 1686.18 | 1475 | 0.875 | -0.134 |
| RA | CGGGCG | 1174.81 | 1326 | 1.129 | 0.121 |
| RA | CGGGCT | 1401.06 | 926 | 0.661 | -0.414 |
| RG | CGGGGA | 2007.58 | 1379 | 0.687 | -0.376 |
| RG | CGGGGC | 1293.79 | 1064 | 0.822 | -0.196 |
| RG | CGGGGG | 771.79 | 664 | 0.860 | -0.150 |
| RG | CGGGGT | 1339.31 | 799 | 0.597 | -0.517 |
| RV | CGGGTA | 1019.28 | 905 | 0.888 | -0.119 |
| RV | CGGGTC | 1245.71 | 1142 | 0.917 | -0.087 |
| RV | CGGGTG | 1854.54 | 2226 | 1.200 | 0.183 |
| RV | CGGGTT | 1603.19 | 1313 | 0.819 | -0.200 |
| RY | CGGTAC | 2036.52 | 2310 | 1.134 | 0.126 |
| RY | CGGTAT | 1509.17 | 1677 | 1.111 | 0.105 |
| RS | CGGTCA | 1561.75 | 1354 | 0.867 | -0.143 |
| RS | CGGTCC | 1841.74 | 1310 | 0.711 | -0.341 |
| RS | CGGTCG | 2207.18 | 1618 | 0.733 | -0.311 |
| RS | CGGTCT | 1273.06 | 789 | 0.620 | -0.478 |
| RC | CGGTGC | 1691.92 | 1778 | 1.051 | 0.050 |
| RW | CGGTGG | 2030.69 | 2296 | 1.131 | 0.123 |
| RC | CGGTGT | 1565.8 | 1295 | 0.827 | -0.190 |
| RL | CGGTTA | 1031.98 | 1420 | 1.376 | 0.319 |
| RF | CGGTTC | 2845.22 | 3236 | 1.137 | 0.129 |
| RL | CGGTTG | 2170.29 | 3215 | 1.481 | 0.393 |
| RF | CGGTTT | 2178.26 | 2102 | 0.965 | -0.036 |
| RK | CGTAAA | 3475.14 | 1924 | 0.554 | -0.591 |
| RN | CGTAAC | 2629.09 | 1531 | 0.582 | -0.541 |
| RK | CGTAAG | 3301.76 | 1690 | 0.512 | -0.670 |
| RN | CGTAAT | 2271.42 | 1409 | 0.620 | -0.478 |
| RT | CGTACA | 1336.01 | 1040 | 0.778 | -0.250 |
| RT | CGTACC | 1587.78 | 1270 | 0.800 | -0.223 |
| RT | CGTACG | 1562.91 | 1206 | 0.772 | -0.259 |
| RT | CGTACT | 1151.56 | 985 | 0.855 | -0.156 |
| RR | CGTAGA | 1432.17 | 978 | 0.683 | -0.381 |
| RS | CGTAGC | 1555.27 | 982 | 0.631 | -0.460 |
| RR | CGTAGG | 1063.85 | 466 | 0.438 | -0.825 |
| RS | CGTAGT | 1423.36 | 929 | 0.653 | -0.427 |
| RI | CGTATA | 1126 | 655 | 0.582 | -0.542 |
| RI | CGTATC | 2185.29 | 1612 | 0.738 | -0.304 |
| RM | CGTATG | 1963.63 | 1177 | 0.599 | -0.512 |
| RI | CGTATT | 1891.83 | 1488 | 0.787 | -0.240 |
| RQ | CGTCAA | 1904.99 | 2257 | 1.185 | 0.170 |
| RH | CGTCAC | 1296.81 | 1436 | 1.107 | 0.102 |
| RQ | CGTCAG | 1871.56 | 1726 | 0.922 | -0.081 |
| RH | CGTCAT | 1270.52 | 1446 | 1.138 | 0.129 |
| RP | CGTCCA | 1298.84 | 1698 | 1.307 | 0.268 |
| RP | CGTCCC | 793.14 | 1080 | 1.362 | 0.309 |
| RP | CGTCCG | 1374.58 | 1496 | 1.088 | 0.085 |
| RP | CGTCCT | 784.2 | 1056 | 1.347 | 0.298 |
| RR | CGTCGA | 1897.88 | 2044 | 1.077 | 0.074 |
| RR | CGTCGC | 1226.35 | 1466 | 1.195 | 0.178 |

-continued

Dataset SI. Mosquito codon pair scores.

| AA pair | Codon Pair | Expected | Ob-served | Observed/ Expected | CPS |
|---|---|---|---|---|---|
| RR | CGTCGG | 1608.7 | 1368 | 0.850 | -0.162 |
| RR | CGTCGT | 1290.29 | 1939 | 1.503 | 0.407 |
| RL | CGTCTA | 851.55 | 896 | 1.052 | 0.051 |
| RL | CGTCTC | 996.99 | 1069 | 1.072 | 0.070 |
| RL | CGTCTG | 2204.16 | 1836 | 0.833 | -0.183 |
| RL | CGTCTT | 1001.18 | 1014 | 1.013 | 0.013 |
| RE | CGTGAA | 2768.78 | 2921 | 1.055 | 0.054 |
| RD | CGTGAC | 1553.95 | 1847 | 1.189 | 0.173 |
| RE | CGTGAG | 1860.02 | 1632 | 0.877 | -0.131 |
| RD | CGTGAT | 2054.49 | 2434 | 1.185 | 0.170 |
| RA | CGTGCA | 1151.27 | 1293 | 1.123 | 0.116 |
| RA | CGTGCC | 1352.44 | 2036 | 1.505 | 0.409 |
| RA | CGTGCG | 942.28 | 951 | 1.009 | 0.009 |
| RA | CGTGCT | 1123.75 | 1496 | 1.331 | 0.286 |
| RG | CGTGGA | 1610.22 | 2330 | 1.447 | 0.369 |
| RG | CGTGGC | 1037.71 | 1852 | 1.785 | 0.579 |
| RG | CGTGGG | 619.03 | 766 | 1.237 | 0.213 |
| RG | CGTGGT | 1074.22 | 1680 | 1.564 | 0.447 |
| RV | CGTGTA | 817.54 | 985 | 1.205 | 0.186 |
| RV | CGTGTC | 999.14 | 1293 | 1.294 | 0.258 |
| RV | CGTGTG | 1487.47 | 1517 | 1.020 | 0.020 |
| RV | CGTGTT | 1285.87 | 1548 | 1.204 | 0.186 |
| RY | CGTTAC | 1633.43 | 1630 | 0.998 | -0.002 |
| RY | CGTTAT | 1210.46 | 1272 | 1.051 | 0.050 |
| RS | CGTTCA | 1252.64 | 1584 | 1.265 | 0.235 |
| RS | CGTTCC | 1477.2 | 1936 | 1.311 | 0.270 |
| RS | CGTTCG | 1770.31 | 2180 | 1.231 | 0.208 |
| RS | CGTTCT | 1021.08 | 1241 | 1.215 | 0.195 |
| RC | CGTTGC | 1357.04 | 1577 | 1.162 | 0.150 |
| RW | CGTTGG | 1628.76 | 1763 | 1.082 | 0.079 |
| RC | CGTTGT | 1255.88 | 1282 | 1.021 | 0.021 |
| RL | CGTTTA | 827.72 | 1193 | 1.441 | 0.366 |
| RF | CGTTTC | 2282.06 | 2489 | 1.091 | 0.087 |
| RL | CGTTTG | 1740.73 | 2819 | 1.619 | 0.482 |
| RF | CGTTTT | 1747.12 | 1888 | 1.081 | 0.078 |
| LK | CTAAAA | 2808.19 | 2127 | 0.757 | -0.278 |
| LN | CTAAAC | 2254.71 | 1789 | 0.793 | -0.231 |
| LK | CTAAAG | 2668.08 | 1674 | 0.627 | -0.466 |
| LN | CTAAAT | 1947.98 | 1632 | 0.838 | -0.177 |
| LT | CTAACA | 1091.73 | 1235 | 1.131 | 0.123 |
| LT | CTAACC | 1297.47 | 1460 | 1.125 | 0.118 |
| LT | CTAACG | 1277.14 | 1948 | 1.525 | 0.422 |
| LT | CTAACT | 941 | 1080 | 1.148 | 0.138 |
| LR | CTAAGA | 1016.96 | 857 | 0.843 | -0.171 |
| LS | CTAAGC | 1305.15 | 1129 | 0.865 | -0.145 |
| LR | CTAAGG | 755.43 | 758 | 1.003 | 0.003 |
| LS | CTAAGT | 1194.46 | 984 | 0.824 | -0.194 |
| LI | CTAATA | 1026.53 | 1108 | 1.079 | 0.076 |
| LI | CTAATC | 1992.26 | 1620 | 0.813 | -0.207 |
| LM | CTAATG | 1794.07 | 1494 | 0.833 | -0.183 |
| LI | CTAATT | 1724.72 | 1407 | 0.816 | -0.204 |
| LQ | CTACAA | 2198.84 | 2832 | 1.288 | 0.253 |
| LH | CTACAC | 1312.46 | 1602 | 1.221 | 0.199 |
| LQ | CTACAG | 2160.25 | 2550 | 1.180 | 0.166 |
| LH | CTACAT | 1285.86 | 1693 | 1.317 | 0.275 |
| LP | CTACCA | 1511.33 | 2108 | 1.395 | 0.333 |
| LP | CTACCC | 922.89 | 1073 | 1.163 | 0.151 |
| LP | CTACCG | 1599.46 | 2491 | 1.557 | 0.443 |
| LP | CTACCT | 912.49 | 1152 | 1.262 | 0.233 |
| LR | CTACGA | 1347.65 | 2043 | 1.516 | 0.416 |
| LR | CTACGC | 870.81 | 1187 | 1.363 | 0.310 |
| LR | CTACGG | 1142.31 | 1463 | 1.281 | 0.247 |
| LR | CTACGT | 916.22 | 1215 | 1.326 | 0.282 |
| LL | CTACTA | 1009.68 | 1367 | 1.354 | 0.303 |
| LL | CTACTC | 1182.14 | 1374 | 1.162 | 0.150 |
| LL | CTACTG | 2613.48 | 2732 | 1.045 | 0.044 |
| LL | CTACTT | 1187.1 | 1416 | 1.193 | 0.176 |
| LE | CTAGAA | 3147.26 | 2422 | 0.770 | -0.262 |
| LD | CTAGAC | 1798.22 | 1321 | 0.735 | -0.308 |
| LE | CTAGAG | 2114.29 | 1623 | 0.768 | -0.264 |
| LD | CTAGAT | 2377.44 | 1829 | 0.769 | -0.262 |
| LA | CTAGCA | 1367.72 | 1422 | 1.040 | 0.039 |
| LA | CTAGCC | 1606.71 | 1333 | 0.830 | -0.187 |
| LA | CTAGCG | 1119.44 | 1343 | 1.200 | 0.182 |

-continued

Dataset SI. Mosquito codon pair scores.

| AA pair | Codon Pair | Expected | Ob-served | Observed/Expected | CPS |
|---|---|---|---|---|---|
| LA | CTAGCT | 1335.03 | 1253 | 0.939 | -0.063 |
| LG | CTAGGA | 1615.17 | 1379 | 0.854 | -0.158 |
| LG | CTAGGC | 1040.89 | 719 | 0.691 | -0.370 |
| LG | CTAGGG | 620.93 | 631 | 1.016 | 0.016 |
| LG | CTAGGT | 1077.52 | 798 | 0.741 | -0.300 |
| LV | CTAGTA | 952.82 | 883 | 0.927 | -0.076 |
| LV | CTAGTC | 1164.48 | 1131 | 0.971 | -0.029 |
| LV | CTAGTG | 1733.62 | 1713 | 0.988 | -0.012 |
| LV | CTAGTT | 1498.66 | 1277 | 0.852 | -0.160 |
| LY | CTATAC | 1566.43 | 941 | 0.601 | -0.510 |
| LY | CTATAT | 1160.81 | 911 | 0.785 | -0.242 |
| LS | CTATCA | 1051.19 | 1510 | 1.436 | 0.362 |
| LS | CTATCC | 1239.64 | 1560 | 1.258 | 0.230 |
| LS | CTATCG | 1485.61 | 2341 | 1.576 | 0.455 |
| LS | CTATCT | 856.87 | 1229 | 1.434 | 0.361 |
| LC | CTATGC | 1147.78 | 997 | 0.869 | -0.141 |
| LW | CTATGG | 1067.68 | 969 | 0.908 | -0.097 |
| LC | CTATGT | 1062.22 | 900 | 0.847 | -0.166 |
| LL | CTATTA | 981.43 | 999 | 1.018 | 0.018 |
| LF | CTATTC | 2209.81 | 1729 | 0.782 | -0.245 |
| LL | CTATTG | 2063.99 | 1661 | 0.805 | -0.217 |
| LF | CTATTT | 1691.8 | 1840 | 1.088 | 0.084 |
| LK | CTCAAA | 3287.84 | 4426 | 1.346 | 0.297 |
| LN | CTCAAC | 2639.83 | 4248 | 1.609 | 0.476 |
| LK | CTCAAG | 3123.8 | 4447 | 1.424 | 0.353 |
| LN | CTCAAT | 2280.7 | 2579 | 1.131 | 0.123 |
| LT | CTCACA | 1278.2 | 1384 | 1.083 | 0.080 |
| LT | CTCACC | 1519.08 | 2473 | 1.628 | 0.487 |
| LT | CTCACG | 1495.28 | 1508 | 1.009 | 0.008 |
| LT | CTCACT | 1101.73 | 1202 | 1.091 | 0.087 |
| LR | CTCAGA | 1190.66 | 1028 | 0.863 | -0.147 |
| LS | CTCAGC | 1528.08 | 2589 | 1.694 | 0.527 |
| LR | CTCAGG | 884.46 | 799 | 0.903 | -0.102 |
| LS | CTCAGT | 1398.47 | 1882 | 1.346 | 0.297 |
| LI | CTCATA | 1201.87 | 1087 | 0.904 | -0.100 |
| LI | CTCATC | 2332.55 | 3142 | 1.347 | 0.298 |
| LM | CTCATG | 2100.5 | 1756 | 0.836 | -0.179 |
| LI | CTCATT | 2019.31 | 1709 | 0.846 | -0.167 |
| LQ | CTCCAA | 2574.41 | 2153 | 0.836 | -0.179 |
| LH | CTCCAC | 1536.64 | 1374 | 0.894 | -0.112 |
| LQ | CTCCAG | 2529.23 | 2635 | 1.042 | 0.041 |
| LH | CTCCAT | 1505.49 | 1249 | 0.830 | -0.187 |
| LP | CTCCCA | 1769.47 | 1203 | 0.680 | -0.386 |
| LP | CTCCCC | 1080.53 | 775 | 0.717 | -0.332 |
| LP | CTCCCG | 1872.65 | 1419 | 0.758 | -0.277 |
| LP | CTCCCT | 1068.35 | 658 | 0.616 | -0.485 |
| LR | CTCCGA | 1577.83 | 1608 | 1.019 | 0.019 |
| LR | CTCCGC | 1019.55 | 1173 | 1.151 | 0.140 |
| LR | CTCCGG | 1337.42 | 1958 | 1.464 | 0.381 |
| LR | CTCCGT | 1072.71 | 1079 | 1.006 | 0.006 |
| LL | CTCCTA | 1182.14 | 804 | 0.680 | -0.385 |
| LL | CTCCTC | 1384.05 | 1252 | 0.905 | -0.100 |
| LL | CTCCTG | 3059.87 | 2006 | 0.656 | -0.422 |
| LL | CTCCTT | 1389.86 | 813 | 0.585 | -0.536 |
| LE | CTCGAA | 3684.83 | 3028 | 0.822 | -0.196 |
| LD | CTCGAC | 2105.36 | 1680 | 0.798 | -0.226 |
| LE | CTCGAG | 2475.41 | 2361 | 0.954 | -0.047 |
| LD | CTCGAT | 2783.52 | 2704 | 0.971 | -0.029 |
| LA | CTCGCA | 1601.33 | 1176 | 0.734 | -0.309 |
| LA | CTCGCC | 1881.15 | 1546 | 0.822 | -0.196 |
| LA | CTCGCG | 1310.64 | 835 | 0.637 | -0.451 |
| LA | CTCGCT | 1563.06 | 1295 | 0.829 | -0.188 |
| LG | CTCGGA | 1891.05 | 2526 | 1.336 | 0.290 |
| LG | CTCGGC | 1218.68 | 1994 | 1.636 | 0.492 |
| LG | CTCGGG | 726.99 | 1150 | 1.582 | 0.459 |
| LG | CTCGGT | 1261.57 | 1869 | 1.481 | 0.393 |
| LV | CTCGTA | 1115.57 | 933 | 0.836 | -0.179 |
| LV | CTCGTC | 1363.38 | 1710 | 1.254 | 0.227 |
| LV | CTCGTG | 2029.73 | 1338 | 0.659 | -0.417 |
| LV | CTCGTT | 1754.64 | 1512 | 0.862 | -0.149 |
| LY | CTCTAC | 1833.99 | 2579 | 1.406 | 0.341 |
| LY | CTCTAT | 1359.08 | 1313 | 0.966 | -0.034 |
| LS | CTCTCA | 1230.74 | 1059 | 0.860 | -0.150 |
| LS | CTCTCC | 1451.38 | 1512 | 1.042 | 0.041 |

-continued

Dataset SI. Mosquito codon pair scores.

| AA pair | Codon Pair | Expected | Ob-served | Observed/Expected | CPS |
|---|---|---|---|---|---|
| LS | CTCTCG | 1739.36 | 2141 | 1.231 | 0.208 |
| LS | CTCTCT | 1003.23 | 950 | 0.947 | -0.055 |
| LC | CTCTGC | 1343.82 | 1722 | 1.281 | 0.248 |
| LW | CTCTGG | 1250.05 | 1288 | 1.030 | 0.030 |
| LC | CTCTGT | 1243.65 | 1304 | 1.049 | 0.047 |
| LL | CTCTTA | 1149.07 | 591 | 0.514 | -0.665 |
| LF | CTCTTC | 2587.25 | 2390 | 0.924 | -0.079 |
| LL | CTCTTG | 2416.52 | 1084 | 0.449 | -0.802 |
| LF | CTCTTT | 1980.77 | 1185 | 0.598 | -0.514 |
| LK | CTGAAA | 7268.77 | 6329 | 0.871 | -0.138 |
| LN | CTGAAC | 5836.14 | 6852 | 1.174 | 0.160 |
| LK | CTGAAG | 6906.11 | 9634 | 1.395 | 0.333 |
| LN | CTGAAT | 5042.19 | 4039 | 0.801 | -0.222 |
| LT | CTGACA | 2825.85 | 1580 | 0.559 | -0.581 |
| LT | CTGACC | 3358.38 | 3572 | 1.064 | 0.062 |
| LT | CTGACG | 3305.77 | 3871 | 1.171 | 0.158 |
| LT | CTGACT | 2435.7 | 1543 | 0.633 | -0.457 |
| LR | CTGAGA | 2632.32 | 1584 | 0.602 | -0.508 |
| LS | CTGAGC | 3378.28 | 2741 | 0.811 | -0.209 |
| LR | CTGAGG | 1955.36 | 1790 | 0.915 | -0.088 |
| LS | CTGAGT | 3091.76 | 1878 | 0.607 | -0.499 |
| LI | CTGATA | 2657.1 | 2565 | 0.965 | -0.035 |
| LI | CTGATC | 5156.81 | 5628 | 1.091 | 0.087 |
| LM | CTGATG | 4643.8 | 6045 | 1.302 | 0.264 |
| LI | CTGATT | 4464.29 | 3959 | 0.887 | -0.120 |
| LQ | CTGCAA | 5691.53 | 4407 | 0.774 | -0.256 |
| LH | CTGCAC | 3397.21 | 3875 | 1.141 | 0.132 |
| LQ | CTGCAG | 5591.64 | 7308 | 1.307 | 0.268 |
| LH | CTGCAT | 3328.34 | 2424 | 0.728 | -0.317 |
| LP | CTGCCA | 3911.95 | 3027 | 0.774 | -0.256 |
| LP | CTGCCC | 2388.84 | 2136 | 0.894 | -0.112 |
| LP | CTGCCG | 4140.07 | 3755 | 0.907 | -0.098 |
| LP | CTGCCT | 2361.91 | 1316 | 0.557 | -0.585 |
| LR | CTGCGA | 3488.28 | 2731 | 0.783 | -0.245 |
| LR | CTGCGC | 2254.03 | 2036 | 0.903 | -0.102 |
| LR | CTGCGG | 2956.78 | 3096 | 1.047 | 0.046 |
| LR | CTGCGT | 2371.55 | 1511 | 0.637 | -0.451 |
| LL | CTGCTA | 2613.48 | 2290 | 0.876 | -0.132 |
| LL | CTGCTC | 3059.87 | 3841 | 1.255 | 0.227 |
| LL | CTGCTG | 6764.77 | 10254 | 1.516 | 0.416 |
| LL | CTGCTT | 3072.72 | 2221 | 0.723 | -0.325 |
| LE | CTGGAA | 8146.44 | 9046 | 1.110 | 0.105 |
| LD | CTGGAC | 4654.54 | 7140 | 1.534 | 0.428 |
| LE | CTGGAG | 5472.66 | 8606 | 1.573 | 0.453 |
| LD | CTGGAT | 6153.81 | 6316 | 1.026 | 0.026 |
| LA | CTGGCA | 3540.24 | 3017 | 0.852 | -0.160 |
| LA | CTGGCC | 4158.85 | 5564 | 1.338 | 0.291 |
| LA | CTGGCG | 2897.57 | 3685 | 1.272 | 0.240 |
| LA | CTGGCT | 3455.61 | 2519 | 0.729 | -0.316 |
| LG | CTGGGA | 4180.73 | 3428 | 0.820 | -0.199 |
| LG | CTGGGC | 2694.27 | 2566 | 0.952 | -0.049 |
| LG | CTGGGG | 1607.23 | 1565 | 0.974 | -0.027 |
| LG | CTGGGT | 2789.08 | 1882 | 0.675 | -0.393 |
| LV | CTGGTA | 2466.31 | 2038 | 0.826 | -0.191 |
| LV | CTGGTC | 3014.17 | 3697 | 1.227 | 0.204 |
| LV | CTGGTG | 4487.33 | 6381 | 1.422 | 0.352 |
| LV | CTGGTT | 3879.16 | 2964 | 0.764 | -0.269 |
| LY | CTGTAC | 4054.59 | 5151 | 1.270 | 0.239 |
| LY | CTGTAT | 3004.66 | 2445 | 0.814 | -0.206 |
| LS | CTGTCA | 2720.92 | 1394 | 0.512 | -0.669 |
| LS | CTGTCC | 3208.71 | 3492 | 1.088 | 0.085 |
| LS | CTGTCG | 3845.38 | 3974 | 1.033 | 0.033 |
| LS | CTGTCT | 2217.95 | 1320 | 0.595 | -0.519 |
| LC | CTGTGC | 2970.92 | 3053 | 1.028 | 0.027 |
| LW | CTGTGG | 2763.61 | 2861 | 1.035 | 0.035 |
| LC | CTGTGT | 2749.46 | 1849 | 0.672 | -0.397 |
| LL | CTGTTA | 2540.36 | 1345 | 0.529 | -0.636 |
| LF | CTGTTC | 5719.91 | 7055 | 1.233 | 0.210 |
| LL | CTGTTG | 5342.46 | 5432 | 1.017 | 0.017 |
| LF | CTGTTT | 4379.1 | 3716 | 0.849 | -0.164 |
| LK | CTTAAA | 3301.65 | 1801 | 0.545 | -0.606 |
| LN | CTTAAC | 2650.91 | 1212 | 0.457 | -0.783 |
| LK | CTTAAG | 3136.92 | 1416 | 0.451 | -0.795 |
| LN | CTTAAT | 2290.28 | 1219 | 0.532 | -0.631 |

-continued

Dataset SI. Mosquito codon pair scores.

| AA pair | Codon Pair | Expected | Ob-served | Observed/Expected | CPS |
|---|---|---|---|---|---|
| LT | CTTACA | 1283.57 | 1080 | 0.841 | -0.173 |
| LT | CTTACC | 1525.46 | 1421 | 0.932 | -0.071 |
| LT | CTTACG | 1501.56 | 1201 | 0.800 | -0.223 |
| LT | CTTACT | 1106.36 | 981 | 0.887 | -0.120 |
| LR | CTTAGA | 1195.66 | 704 | 0.589 | -0.530 |
| LS | CTTAGC | 1534.5 | 1060 | 0.691 | -0.370 |
| LR | CTTAGG | 888.17 | 498 | 0.561 | -0.579 |
| LS | CTTAGT | 1404.35 | 924 | 0.658 | -0.419 |
| LI | CTTATA | 1206.92 | 907 | 0.751 | -0.286 |
| LI | CTTATC | 2342.35 | 1587 | 0.678 | -0.389 |
| LM | CTTATG | 2109.32 | 1329 | 0.630 | -0.462 |
| LI | CTTATT | 2027.79 | 1452 | 0.716 | -0.334 |
| LQ | CTTCAA | 2585.23 | 3658 | 1.415 | 0.347 |
| LH | CTTCAC | 1543.09 | 1717 | 1.113 | 0.107 |
| LQ | CTTCAG | 2539.86 | 2889 | 1.137 | 0.129 |
| LH | CTTCAT | 1511.81 | 2118 | 1.401 | 0.337 |
| LP | CTTCCA | 1776.9 | 2852 | 1.605 | 0.473 |
| LP | CTTCCC | 1085.07 | 2007 | 1.850 | 0.615 |
| LP | CTTCCG | 1880.52 | 3493 | 1.857 | 0.619 |
| LP | CTTCCT | 1072.84 | 1915 | 1.785 | 0.579 |
| LR | CTTCGA | 1584.46 | 2451 | 1.547 | 0.436 |
| LR | CTTCGC | 1023.83 | 1622 | 1.584 | 0.460 |
| LR | CTTCGG | 1343.04 | 2139 | 1.593 | 0.465 |
| LR | CTTCGT | 1077.21 | 1727 | 1.603 | 0.472 |
| LL | CTTCTA | 1187.1 | 1595 | 1.344 | 0.295 |
| LL | CTTCTC | 1389.86 | 1735 | 1.248 | 0.222 |
| LL | CTTCTG | 3072.72 | 3286 | 1.069 | 0.067 |
| LL | CTTCTT | 1395.7 | 1855 | 1.329 | 0.284 |
| LE | CTTGAA | 3700.31 | 2713 | 0.733 | -0.310 |
| LD | CTTGAC | 2114.2 | 1191 | 0.563 | -0.574 |
| LE | CTTGAG | 2485.81 | 1489 | 0.599 | -0.512 |
| LD | CTTGAT | 2795.21 | 1856 | 0.664 | -0.409 |
| LA | CTTGCA | 1608.06 | 1489 | 0.926 | -0.077 |
| LA | CTTGCC | 1889.05 | 1972 | 1.044 | 0.043 |
| LA | CTTGCG | 1316.15 | 1094 | 0.831 | -0.185 |
| LA | CTTGCT | 1569.62 | 1475 | 0.940 | -0.062 |
| LG | CTTGGA | 1898.99 | 2414 | 1.271 | 0.240 |
| LG | CTTGGC | 1223.8 | 1644 | 1.343 | 0.295 |
| LG | CTTGGG | 730.04 | 1155 | 1.582 | 0.459 |
| LG | CTTGGT | 1266.87 | 1512 | 1.193 | 0.177 |
| LV | CTTGTA | 1120.26 | 1049 | 0.936 | -0.066 |
| LV | CTTGTC | 1369.11 | 1066 | 0.779 | -0.250 |
| LV | CTTGTG | 2038.25 | 1454 | 0.713 | -0.338 |
| LV | CTTGTT | 1762.01 | 1551 | 0.880 | -0.128 |
| LY | CTTTAC | 1841.69 | 1485 | 0.806 | -0.215 |
| LY | CTTTAT | 1364.79 | 1307 | 0.958 | -0.043 |
| LS | CTTTCA | 1235.91 | 1639 | 1.326 | 0.282 |
| LS | CTTTCC | 1457.47 | 2102 | 1.442 | 0.366 |
| LS | CTTTCG | 1746.67 | 2737 | 1.567 | 0.449 |
| LS | CTTTCT | 1007.44 | 1374 | 1.364 | 0.310 |
| LC | CTTTGC | 1349.46 | 1838 | 1.362 | 0.309 |
| LW | CTTTGG | 1255.3 | 1540 | 1.227 | 0.204 |
| LC | CTTTGT | 1248.87 | 1591 | 1.274 | 0.242 |
| LL | CTTTTA | 1153.89 | 1275 | 1.105 | 0.100 |
| LF | CTTTTC | 2598.12 | 2429 | 0.935 | -0.067 |
| LL | CTTTTG | 2426.67 | 2433 | 1.003 | 0.003 |
| LF | CTTTTT | 1989.09 | 2079 | 1.045 | 0.044 |
| EK | GAAAAA | 11243 | 8379 | 0.745 | -0.294 |
| EN | GAAAAC | 8674.83 | 7793 | 0.898 | -0.107 |
| EK | GAAAAG | 10682.06 | 9503 | 0.890 | -0.117 |
| EN | GAAAAT | 7494.71 | 7777 | 1.038 | 0.037 |
| ET | GAAACA | 4189.05 | 4827 | 1.152 | 0.142 |
| ET | GAAACC | 4978.48 | 5875 | 1.180 | 0.166 |
| ET | GAAACG | 4900.48 | 7141 | 1.457 | 0.377 |
| ET | GAAACT | 3610.7 | 4417 | 1.223 | 0.202 |
| ER | GAAAGA | 3413.22 | 3017 | 0.884 | -0.123 |
| ES | GAAAGC | 4240.29 | 4947 | 1.167 | 0.154 |
| ER | GAAAGG | 2535.42 | 2334 | 0.921 | -0.083 |
| ES | GAAAGT | 3880.65 | 4664 | 1.202 | 0.184 |
| EI | GAAATA | 3936.75 | 4229 | 1.074 | 0.072 |
| EI | GAAATC | 7640.3 | 8170 | 1.069 | 0.067 |
| EM | GAAATG | 7100.79 | 7005 | 0.987 | -0.014 |
| EI | GAAATT | 6614.28 | 6704 | 1.014 | 0.013 |
| EQ | GAACAA | 7255.98 | 6344 | 0.874 | -0.134 |

-continued

Dataset SI. Mosquito codon pair scores.

| AA pair | Codon Pair | Expected | Ob-served | Observed/Expected | CPS |
|---|---|---|---|---|---|
| EH | GAACAC | 3968.66 | 3441 | 0.867 | -0.143 |
| EQ | GAACAG | 7128.64 | 6743 | 0.946 | -0.056 |
| EH | GAACAT | 3888.21 | 3789 | 0.974 | -0.026 |
| EP | GAACCA | 4040.53 | 4475 | 1.108 | 0.102 |
| EP | GAACCC | 2467.36 | 2583 | 1.047 | 0.046 |
| EP | GAACCG | 4276.15 | 5846 | 1.367 | 0.313 |
| EP | GAACCT | 2439.54 | 2678 | 1.098 | 0.093 |
| ER | GAACGA | 4523.1 | 4715 | 1.042 | 0.042 |
| ER | GAACGC | 2922.7 | 3032 | 1.037 | 0.037 |
| ER | GAACGG | 3833.93 | 4237 | 1.105 | 0.100 |
| ER | GAACGT | 3075.08 | 3207 | 1.043 | 0.042 |
| EL | GAACTA | 3008.67 | 2634 | 0.875 | -0.133 |
| EL | GAACTC | 3522.56 | 2766 | 0.785 | -0.242 |
| EL | GAACTG | 7787.69 | 8742 | 1.123 | 0.116 |
| EL | GAACTT | 3537.36 | 3297 | 0.932 | -0.070 |
| EE | GAAGAA | 15244.02 | 13730 | 0.901 | -0.105 |
| ED | GAAGAC | 7476.17 | 7117 | 0.952 | -0.049 |
| EE | GAAGAG | 10240.71 | 9338 | 0.912 | -0.092 |
| ED | GAAGAT | 9884.32 | 9674 | 0.979 | -0.022 |
| EA | GAAGCA | 4839.19 | 5817 | 1.202 | 0.184 |
| EA | GAAGCC | 5684.78 | 5771 | 1.015 | 0.015 |
| EA | GAAGCG | 3960.72 | 5821 | 1.470 | 0.385 |
| EA | GAAGCT | 4723.52 | 5388 | 1.141 | 0.132 |
| EG | GAAGGA | 5593.33 | 6382 | 1.141 | 0.132 |
| EG | GAAGGC | 3604.62 | 4360 | 1.210 | 0.190 |
| EG | GAAGGG | 2150.28 | 2262 | 1.052 | 0.051 |
| EG | GAAGGT | 3731.46 | 4307 | 1.154 | 0.143 |
| EV | GAAGTA | 3104.46 | 2980 | 0.960 | -0.041 |
| EV | GAAGTC | 3794.09 | 3724 | 0.982 | -0.019 |
| EV | GAAGTG | 5648.43 | 6822 | 1.208 | 0.189 |
| EV | GAAGTT | 4882.89 | 4918 | 1.007 | 0.007 |
| EY | GAATAC | 5173.04 | 4005 | 0.774 | -0.256 |
| EY | GAATAT | 3833.5 | 3359 | 0.876 | -0.132 |
| ES | GAATCA | 3415.19 | 3497 | 1.024 | 0.024 |
| ES | GAATCC | 4027.45 | 3842 | 0.954 | -0.047 |
| ES | GAATCG | 4826.58 | 5855 | 1.213 | 0.193 |
| ES | GAATCT | 2783.88 | 3213 | 1.154 | 0.143 |
| EC | GAATGC | 3591.23 | 3125 | 0.870 | -0.139 |
| EW | GAATGG | 3413.72 | 3159 | 0.925 | -0.078 |
| EC | GAATGT | 3323.53 | 3243 | 0.976 | -0.025 |
| EL | GAATTA | 2924.5 | 1843 | 0.630 | -0.462 |
| EF | GAATTC | 6200.87 | 4550 | 0.734 | -0.310 |
| EL | GAATTG | 6150.31 | 4375 | 0.711 | -0.341 |
| EF | GAATTT | 4747.31 | 3838 | 0.808 | -0.213 |
| DK | GACAAA | 4835.96 | 6309 | 1.305 | 0.266 |
| DN | GACAAC | 4135.79 | 5741 | 1.388 | 0.328 |
| DK | GACAAG | 4594.69 | 6226 | 1.355 | 0.304 |
| DN | GACAAT | 3573.15 | 4277 | 1.197 | 0.180 |
| DT | GACACA | 2056.37 | 2057 | 1.000 | 0.000 |
| DT | GACACC | 2443.89 | 3347 | 1.370 | 0.314 |
| DT | GACACG | 2405.6 | 2737 | 1.138 | 0.129 |
| DT | GACACT | 1772.46 | 1985 | 1.120 | 0.113 |
| DR | GACAGA | 1935.42 | 1395 | 0.721 | -0.327 |
| DS | GACAGC | 2758.53 | 3693 | 1.339 | 0.292 |
| DR | GACAGG | 1437.68 | 1080 | 0.751 | -0.286 |
| DS | GACAGT | 2524.57 | 3337 | 1.322 | 0.279 |
| DI | GACATA | 2203.03 | 1835 | 0.833 | -0.183 |
| DI | GACATC | 4275.55 | 6491 | 1.518 | 0.418 |
| DM | GACATG | 3616.11 | 4196 | 1.160 | 0.149 |
| DI | GACATT | 3701.38 | 4808 | 1.299 | 0.262 |
| DQ | GACCAA | 3611.19 | 2829 | 0.783 | -0.244 |
| DH | GACCAC | 2450.43 | 2357 | 0.962 | -0.039 |
| DQ | GACCAG | 3547.81 | 3113 | 0.877 | -0.131 |
| DH | GACCAT | 2400.76 | 2031 | 0.846 | -0.167 |
| DP | GACCCA | 2652.23 | 1503 | 0.567 | -0.568 |
| DP | GACCCC | 1619.59 | 1189 | 0.734 | -0.309 |
| DP | GACCCG | 2806.89 | 1948 | 0.694 | -0.365 |
| DP | GACCCT | 1601.33 | 873 | 0.545 | -0.607 |
| DR | GACCGA | 2564.77 | 1977 | 0.771 | -0.260 |
| DR | GACCGC | 1657.28 | 1402 | 0.846 | -0.167 |
| DR | GACCGG | 2173.98 | 2155 | 0.991 | -0.009 |
| DR | GACCGT | 1743.68 | 1480 | 0.849 | -0.164 |
| DL | GACCTA | 1785.32 | 1098 | 0.615 | -0.486 |
| DL | GACCTC | 2090.26 | 1622 | 0.776 | -0.254 |

Dataset SI. Mosquito codon pair scores.

| AA pair | Codon Pair | Expected | Ob-served | Observed/ Expected | CPS |
|---|---|---|---|---|---|
| DL | GACCTG | 4621.16 | 3616 | 0.782 | -0.245 |
| DL | GACCTT | 2099.04 | 1454 | 0.693 | -0.367 |
| DE | GACGAA | 8181.2 | 9258 | 1.132 | 0.124 |
| DD | GACGAC | 5392.24 | 6898 | 1.279 | 0.246 |
| DE | GACGAG | 5496.01 | 6884 | 1.253 | 0.225 |
| DD | GACGAT | 7129.13 | 8151 | 1.143 | 0.134 |
| DA | GACGCA | 2578.24 | 1790 | 0.694 | -0.365 |
| DA | GACGCC | 3028.75 | 2956 | 0.976 | -0.024 |
| DA | GACGCG | 2110.2 | 1573 | 0.745 | -0.294 |
| DA | GACGCT | 2516.61 | 1880 | 0.747 | -0.292 |
| DG | GACGGA | 4307.85 | 3545 | 0.823 | -0.195 |
| DG | GACGGC | 2776.19 | 2594 | 0.934 | -0.068 |
| DG | GACGGG | 1656.09 | 1519 | 0.917 | -0.086 |
| DG | GACGGT | 2873.88 | 2767 | 0.963 | -0.038 |
| DV | GACGTA | 2023.64 | 1664 | 0.822 | -0.196 |
| DV | GACGTC | 2473.17 | 2947 | 1.192 | 0.175 |
| DV | GACGTG | 3681.92 | 3711 | 1.008 | 0.008 |
| DV | GACGTT | 3182.91 | 3084 | 0.969 | -0.032 |
| DY | GACTAC | 3552.88 | 4724 | 1.330 | 0.285 |
| DY | GACTAT | 2632.87 | 2461 | 0.935 | -0.068 |
| DS | GACTCA | 2221.76 | 1318 | 0.593 | -0.522 |
| DS | GACTCC | 2620.07 | 2050 | 0.782 | -0.245 |
| DS | GACTCG | 3139.95 | 2847 | 0.907 | -0.098 |
| DS | GACTCT | 1811.06 | 1142 | 0.631 | -0.461 |
| DC | GACTGC | 2281.75 | 2365 | 1.036 | 0.036 |
| DW | GACTGG | 2273.79 | 2123 | 0.934 | -0.069 |
| DC | GACTGT | 2111.66 | 1879 | 0.890 | -0.117 |
| DL | GACTTA | 1735.38 | 807 | 0.465 | -0.766 |
| DF | GACTTC | 4470.36 | 4597 | 1.028 | 0.028 |
| DL | GACTTG | 3649.55 | 2655 | 0.727 | -0.318 |
| DF | GACTTT | 3422.46 | 3295 | 0.963 | -0.038 |
| EK | GAGAAA | 7552.88 | 7994 | 1.058 | 0.057 |
| EN | GAGAAC | 5827.63 | 6526 | 1.120 | 0.113 |
| EK | GAGAAG | 7176.05 | 10778 | 1.502 | 0.407 |
| EN | GAGAAT | 5034.83 | 4936 | 0.980 | -0.020 |
| ET | GAGACA | 2814.14 | 1620 | 0.576 | -0.552 |
| ET | GAGACC | 3344.47 | 1702 | 0.509 | -0.676 |
| ET | GAGACG | 3292.07 | 2526 | 0.767 | -0.265 |
| ET | GAGACT | 2425.61 | 1447 | 0.597 | -0.517 |
| ER | GAGAGA | 2292.95 | 1932 | 0.843 | -0.171 |
| ES | GAGAGC | 2848.56 | 2972 | 1.043 | 0.042 |
| ER | GAGAGG | 1703.26 | 1714 | 1.006 | 0.006 |
| ES | GAGAGT | 2606.96 | 2318 | 0.889 | -0.117 |
| EI | GAGATA | 2644.65 | 2159 | 0.816 | -0.203 |
| EI | GAGATC | 5132.64 | 4697 | 0.915 | -0.089 |
| EM | GAGATG | 4770.21 | 4866 | 1.020 | 0.020 |
| EI | GAGATT | 4443.37 | 4453 | 1.002 | 0.002 |
| EQ | GAGCAA | 4874.46 | 4907 | 1.007 | 0.007 |
| EH | GAGCAC | 2666.09 | 3113 | 1.168 | 0.155 |
| EQ | GAGCAG | 4788.92 | 6054 | 1.264 | 0.234 |
| EH | GAGCAT | 2612.04 | 2792 | 1.069 | 0.067 |
| EP | GAGCCA | 2714.37 | 2060 | 0.759 | -0.276 |
| EP | GAGCCC | 1657.53 | 1256 | 0.758 | -0.277 |
| EP | GAGCCG | 2872.66 | 1937 | 0.674 | -0.394 |
| EP | GAGCCT | 1638.85 | 1272 | 0.776 | -0.253 |
| ER | GAGCGA | 3038.55 | 3055 | 1.005 | 0.005 |
| ER | GAGCGC | 1963.43 | 2011 | 1.024 | 0.024 |
| ER | GAGCGG | 2575.58 | 2918 | 1.133 | 0.125 |
| ER | GAGCGT | 2065.79 | 1771 | 0.857 | -0.154 |
| EL | GAGCTA | 2021.18 | 2138 | 1.058 | 0.056 |
| EL | GAGCTC | 2366.4 | 2285 | 0.966 | -0.035 |
| EL | GAGCTG | 5231.66 | 8021 | 1.533 | 0.427 |
| EL | GAGCTT | 2376.34 | 2729 | 1.148 | 0.138 |
| EE | GAGGAA | 10240.71 | 11541 | 1.127 | 0.120 |
| ED | GAGGAC | 5022.38 | 6182 | 1.231 | 0.208 |
| EE | GAGGAG | 6879.56 | 7996 | 1.162 | 0.150 |
| ED | GAGGAT | 6640.14 | 6050 | 0.911 | -0.093 |
| EA | GAGGCA | 3250.9 | 2318 | 0.713 | -0.338 |
| EA | GAGGCC | 3818.95 | 2475 | 0.648 | -0.434 |
| EA | GAGGCG | 2660.76 | 2527 | 0.950 | -0.052 |
| EA | GAGGCT | 3173.19 | 1995 | 0.629 | -0.464 |
| EG | GAGGGA | 3757.52 | 2676 | 0.712 | -0.339 |
| EG | GAGGGC | 2421.53 | 2239 | 0.925 | -0.078 |
| EG | GAGGGG | 1444.53 | 1010 | 0.699 | -0.358 |

Dataset SI. Mosquito codon pair scores.

| AA pair | Codon Pair | Expected | Ob-served | Observed/ Expected | CPS |
|---|---|---|---|---|---|
| EG | GAGGGT | 2506.74 | 1974 | 0.787 | -0.239 |
| EV | GAGGTA | 2085.53 | 1541 | 0.739 | -0.303 |
| EV | GAGGTC | 2548.81 | 2296 | 0.901 | -0.104 |
| EV | GAGGTG | 3794.53 | 4317 | 1.138 | 0.129 |
| EV | GAGGTT | 3280.26 | 2541 | 0.775 | -0.255 |
| EY | GAGTAC | 3475.18 | 4908 | 1.412 | 0.345 |
| EY | GAGTAT | 2575.29 | 2785 | 1.081 | 0.078 |
| ES | GAGTCA | 2294.27 | 1552 | 0.676 | -0.391 |
| ES | GAGTCC | 2705.58 | 2039 | 0.754 | -0.283 |
| ES | GAGTCG | 3242.42 | 2538 | 0.783 | -0.245 |
| ES | GAGTCT | 1870.17 | 1305 | 0.698 | -0.360 |
| EC | GAGTGC | 2412.54 | 2936 | 1.217 | 0.196 |
| EW | GAGTGG | 2293.28 | 2548 | 1.111 | 0.105 |
| EC | GAGTGT | 2232.7 | 2256 | 1.010 | 0.010 |
| EL | GAGTTA | 1964.64 | 1353 | 0.689 | -0.373 |
| EF | GAGTTC | 4165.65 | 5805 | 1.394 | 0.332 |
| EL | GAGTTG | 4131.69 | 4840 | 1.171 | 0.158 |
| EF | GAGTTT | 3189.17 | 4110 | 1.289 | 0.254 |
| DK | GATAAA | 6393.67 | 4503 | 0.704 | -0.351 |
| DN | GATAAC | 5467.96 | 3958 | 0.724 | -0.323 |
| DK | GATAAG | 6074.68 | 4861 | 0.800 | -0.223 |
| DN | GATAAT | 4724.1 | 3925 | 0.831 | -0.185 |
| DT | GATACA | 2718.74 | 2076 | 0.764 | -0.270 |
| DT | GATACC | 3231.09 | 2757 | 0.853 | -0.159 |
| DT | GATACG | 3180.47 | 3283 | 1.032 | 0.032 |
| DT | GATACT | 2343.38 | 1910 | 0.815 | -0.204 |
| DR | GATAGA | 2558.84 | 1628 | 0.636 | -0.452 |
| DS | GATAGC | 3647.09 | 2666 | 0.731 | -0.313 |
| DR | GATAGG | 1900.77 | 1191 | 0.627 | -0.467 |
| DS | GATAGT | 3337.76 | 2508 | 0.751 | -0.286 |
| DI | GATATA | 2912.64 | 1834 | 0.630 | -0.463 |
| DI | GATATC | 5652.75 | 4155 | 0.735 | -0.308 |
| DM | GATATG | 4780.89 | 4201 | 0.879 | -0.129 |
| DI | GATATT | 4893.64 | 4516 | 0.923 | -0.080 |
| DQ | GATCAA | 4774.39 | 5402 | 1.131 | 0.124 |
| DH | GATCAC | 3239.74 | 3480 | 1.074 | 0.072 |
| DQ | GATCAG | 4690.6 | 5280 | 1.126 | 0.118 |
| DH | GATCAT | 3174.06 | 3397 | 1.070 | 0.068 |
| DP | GATCCA | 3506.54 | 3881 | 1.107 | 0.101 |
| DP | GATCCC | 2141.27 | 3100 | 1.448 | 0.370 |
| DP | GATCCG | 3711.02 | 5003 | 1.348 | 0.299 |
| DP | GATCCT | 2117.14 | 2659 | 1.256 | 0.228 |
| DR | GATCGA | 3390.9 | 4434 | 1.308 | 0.268 |
| DR | GATCGC | 2191.1 | 3250 | 1.483 | 0.394 |
| DR | GATCGG | 2874.24 | 3429 | 1.193 | 0.176 |
| DR | GATCGT | 2305.34 | 3313 | 1.437 | 0.363 |
| DL | GATCTA | 2360.39 | 2492 | 1.056 | 0.054 |
| DL | GATCTC | 2763.56 | 3104 | 1.123 | 0.116 |
| DL | GATCTG | 6109.69 | 7197 | 1.178 | 0.164 |
| DL | GATCTT | 2775.17 | 3010 | 1.085 | 0.081 |
| DE | GATGAA | 10816.45 | 9212 | 0.852 | -0.161 |
| DD | GATGAC | 7129.13 | 6134 | 0.860 | -0.150 |
| DE | GATGAG | 7266.33 | 6406 | 0.882 | -0.126 |
| DD | GATGAT | 9425.5 | 7893 | 0.837 | -0.177 |
| DA | GATGCA | 3408.71 | 3506 | 1.029 | 0.028 |
| DA | GATGCC | 4004.34 | 5260 | 1.314 | 0.273 |
| DA | GATGCG | 2789.92 | 3129 | 1.122 | 0.115 |
| DA | GATGCT | 3327.23 | 3670 | 1.103 | 0.098 |
| DG | GATGGA | 5695.45 | 5802 | 1.019 | 0.019 |
| DG | GATGGC | 3670.43 | 4392 | 1.197 | 0.179 |
| DG | GATGGG | 2189.54 | 2817 | 1.287 | 0.252 |
| DG | GATGGT | 3799.59 | 3533 | 0.930 | -0.073 |
| DV | GATGTA | 2675.48 | 2494 | 0.932 | -0.070 |
| DV | GATGTC | 3269.81 | 3261 | 0.997 | -0.003 |
| DV | GATGTG | 4867.91 | 5328 | 1.095 | 0.090 |
| DV | GATGTT | 4208.16 | 3894 | 0.925 | -0.078 |
| DY | GATTAC | 4697.3 | 4081 | 0.869 | -0.141 |
| DY | GATTAT | 3480.95 | 3098 | 0.890 | -0.117 |
| DS | GATTCA | 2937.41 | 3073 | 1.046 | 0.045 |
| DS | GATTCC | 3464.02 | 4409 | 1.273 | 0.241 |
| DS | GATTCG | 4151.35 | 5087 | 1.225 | 0.203 |
| DS | GATTCT | 2394.42 | 2878 | 1.202 | 0.184 |
| DC | GATTGC | 3016.73 | 3025 | 1.003 | 0.003 |
| DW | GATTGG | 3006.21 | 3157 | 1.050 | 0.049 |

-continued

Dataset SI. Mosquito codon pair scores.

| AA pair | Codon Pair | Expected | Ob- served | Observed/ Expected | CPS |
|---|---|---|---|---|---|
| DC | GATTGT | 2791.85 | 2933 | 1.051 | 0.049 |
| DL | GATTTA | 2294.36 | 2529 | 1.102 | 0.097 |
| DF | GATTTC | 5910.31 | 5948 | 1.006 | 0.006 |
| DL | GATTTG | 4825.11 | 7525 | 1.560 | 0.444 |
| DF | GATTTT | 4524.87 | 4488 | 0.992 | -0.008 |
| AK | GCAAAA | 4177.99 | 4180 | 1.000 | 0.000 |
| AN | GCAAAC | 3425.64 | 3451 | 1.007 | 0.007 |
| AK | GCAAAG | 3969.54 | 3187 | 0.803 | -0.220 |
| AN | GCAAAT | 2959.61 | 3282 | 1.109 | 0.103 |
| AT | GCAACA | 2148.37 | 2973 | 1.384 | 0.325 |
| AT | GCAACC | 2553.23 | 2522 | 0.988 | -0.012 |
| AT | GCAACG | 2513.23 | 3207 | 1.276 | 0.244 |
| AT | GCAACT | 1851.76 | 2264 | 1.223 | 0.201 |
| AR | GCAAGA | 1327.75 | 1953 | 1.471 | 0.386 |
| AS | GCAAGC | 2193.33 | 2003 | 0.913 | -0.091 |
| AR | GCAAGG | 986.29 | 1489 | 1.510 | 0.412 |
| AS | GCAAGT | 2007.3 | 1897 | 0.945 | -0.057 |
| AI | GCAATA | 1722.35 | 1801 | 1.046 | 0.045 |
| AI | GCAATC | 3342.68 | 3143 | 0.940 | -0.062 |
| AM | GCAATG | 3039.58 | 3092 | 1.017 | 0.017 |
| AI | GCAATT | 2893.79 | 2542 | 0.878 | -0.130 |
| AQ | GCACAA | 2710.91 | 2677 | 0.987 | -0.013 |
| AH | GCACAC | 1624.94 | 1370 | 0.843 | -0.171 |
| AQ | GCACAG | 2663.33 | 2228 | 0.837 | -0.178 |
| AH | GCACAT | 1592 | 1759 | 1.105 | 0.100 |
| AP | GCACCA | 2056.89 | 2419 | 1.176 | 0.162 |
| AP | GCACCC | 1256.04 | 1341 | 1.068 | 0.065 |
| AP | GCACCG | 2176.84 | 2830 | 1.300 | 0.262 |
| AP | GCACCT | 1241.89 | 1465 | 1.180 | 0.165 |
| AR | GCACGA | 1759.5 | 1568 | 0.891 | -0.115 |
| AR | GCACGC | 1136.94 | 948 | 0.834 | -0.182 |
| AR | GCACGG | 1491.41 | 1186 | 0.795 | -0.229 |
| AR | GCACGT | 1196.22 | 1198 | 1.001 | 0.001 |
| AL | GCACTA | 1329.42 | 1264 | 0.951 | -0.050 |
| AL | GCACTC | 1556.49 | 1372 | 0.881 | -0.126 |
| AL | GCACTG | 3441.09 | 3559 | 1.034 | 0.034 |
| AL | GCACTT | 1563.02 | 1615 | 1.033 | 0.033 |
| AE | GCAGAA | 4994.71 | 4326 | 0.866 | -0.144 |
| AD | GCAGAC | 2688.03 | 1870 | 0.696 | -0.363 |
| AE | GCAGAG | 3355.37 | 2399 | 0.715 | -0.336 |
| AD | GCAGAT | 3553.87 | 3173 | 0.893 | -0.113 |
| AA | GCAGCA | 3063.27 | 4514 | 1.474 | 0.388 |
| AA | GCAGCC | 3598.54 | 3111 | 0.865 | -0.146 |
| AA | GCAGCG | 2507.19 | 2901 | 1.157 | 0.146 |
| AA | GCAGCT | 2990.05 | 3510 | 1.174 | 0.160 |
| AG | GCAGGA | 3220.55 | 2846 | 0.884 | -0.124 |
| AG | GCAGGC | 2075.48 | 1282 | 0.618 | -0.482 |
| AG | GCAGGG | 1238.1 | 990 | 0.800 | -0.224 |
| AG | GCAGGT | 2148.51 | 1530 | 0.712 | -0.340 |
| AV | GCAGTA | 1679.62 | 1880 | 1.119 | 0.113 |
| AV | GCAGTC | 2052.72 | 1672 | 0.815 | -0.205 |
| AV | GCAGTG | 3055.98 | 2691 | 0.881 | -0.127 |
| AV | GCAGTT | 2641.8 | 2761 | 1.045 | 0.044 |
| AY | GCATAC | 1993.99 | 1449 | 0.727 | -0.319 |
| AY | GCATAT | 1477.65 | 1309 | 0.886 | -0.121 |
| AS | GCATCA | 1766.54 | 2223 | 1.258 | 0.230 |
| AS | GCATCC | 2083.24 | 2471 | 1.186 | 0.171 |
| AS | GCATCG | 2496.59 | 3000 | 1.202 | 0.184 |
| AS | GCATCT | 1439.99 | 1699 | 1.180 | 0.165 |
| AC | GCATGC | 1419.78 | 1266 | 0.892 | -0.115 |
| AW | GCATGG | 1413.09 | 1306 | 0.924 | -0.079 |
| AC | GCATGT | 1313.95 | 1244 | 0.947 | -0.055 |
| AL | GCATTA | 1292.23 | 1279 | 0.990 | -0.010 |
| AF | GCATTC | 2979.96 | 3162 | 1.061 | 0.059 |
| AL | GCATTG | 2717.59 | 2714 | 0.999 | -0.001 |
| AF | GCATTT | 2281.42 | 2846 | 1.247 | 0.221 |
| AK | GCCAAA | 4908.04 | 6468 | 1.318 | 0.276 |
| AN | GCCAAC | 4024.23 | 6374 | 1.584 | 0.460 |
| AK | GCCAAG | 4663.17 | 7500 | 1.608 | 0.475 |
| AN | GCCAAT | 3476.77 | 4375 | 1.258 | 0.230 |
| AT | GCCACA | 2523.77 | 2220 | 0.880 | -0.128 |
| AT | GCCACC | 2999.37 | 4605 | 1.535 | 0.429 |
| AT | GCCACG | 2952.38 | 2513 | 0.851 | -0.161 |
| AT | GCCACT | 2175.33 | 2291 | 1.053 | 0.052 |

-continued

Dataset SI. Mosquito codon pair scores.

| AA pair | Codon Pair | Expected | Ob- served | Observed/ Expected | CPS |
|---|---|---|---|---|---|
| AR | GCCAGA | 1559.76 | 1684 | 1.080 | 0.077 |
| AS | GCCAGC | 2576.59 | 3624 | 1.407 | 0.341 |
| AR | GCCAGG | 1158.63 | 1280 | 1.105 | 0.100 |
| AS | GCCAGT | 2358.05 | 3087 | 1.309 | 0.269 |
| AI | GCCATA | 2023.31 | 1603 | 0.792 | -0.233 |
| AI | GCCATC | 3926.78 | 6418 | 1.634 | 0.491 |
| AM | GCCATG | 3570.7 | 3972 | 1.112 | 0.107 |
| AI | GCCATT | 3399.44 | 3835 | 1.128 | 0.121 |
| AQ | GCCCAA | 3184.61 | 2592 | 0.814 | -0.206 |
| AH | GCCCAC | 1908.88 | 1780 | 0.932 | -0.070 |
| AQ | GCCCAG | 3128.72 | 3202 | 1.023 | 0.023 |
| AH | GCCCAT | 1870.18 | 1740 | 0.930 | -0.072 |
| AP | GCCCCA | 2416.31 | 1518 | 0.628 | -0.465 |
| AP | GCCCCC | 1475.52 | 907 | 0.615 | -0.487 |
| AP | GCCCCG | 2557.21 | 1632 | 0.638 | -0.449 |
| AP | GCCCCT | 1458.89 | 885 | 0.607 | -0.500 |
| AR | GCCCGA | 2066.95 | 1398 | 0.676 | -0.391 |
| AR | GCCCGC | 1335.61 | 1352 | 1.012 | 0.012 |
| AR | GCCCGG | 1752.02 | 1881 | 1.074 | 0.071 |
| AR | GCCCGT | 1405.24 | 1163 | 0.828 | -0.189 |
| AL | GCCCTA | 1561.71 | 1143 | 0.732 | -0.312 |
| AL | GCCCTC | 1828.46 | 2123 | 1.161 | 0.149 |
| AL | GCCCTG | 4042.37 | 4027 | 0.996 | -0.004 |
| AL | GCCCTT | 1836.14 | 1309 | 0.713 | -0.338 |
| AE | GCCGAA | 5867.47 | 6159 | 1.050 | 0.048 |
| AD | GCCGAC | 3157.73 | 3320 | 1.051 | 0.050 |
| AE | GCCGAG | 3941.68 | 4533 | 1.150 | 0.140 |
| AD | GCCGAT | 4174.87 | 4735 | 1.134 | 0.126 |
| AA | GCCGCA | 3598.54 | 1974 | 0.549 | -0.600 |
| AA | GCCGCC | 4227.34 | 3811 | 0.902 | -0.104 |
| AA | GCCGCG | 2945.29 | 1396 | 0.474 | -0.747 |
| AA | GCCGCT | 3512.53 | 2595 | 0.739 | -0.303 |
| AG | GCCGGA | 3783.3 | 4286 | 1.133 | 0.125 |
| AG | GCCGGC | 2438.14 | 2602 | 1.067 | 0.065 |
| AG | GCCGGG | 1454.44 | 1649 | 1.134 | 0.126 |
| AG | GCCGGT | 2523.94 | 3153 | 1.249 | 0.223 |
| AV | GCCGTA | 1973.11 | 1813 | 0.919 | -0.085 |
| AV | GCCGTC | 2411.41 | 3287 | 1.363 | 0.310 |
| AV | GCCGTG | 3589.97 | 2941 | 0.819 | -0.199 |
| AV | GCCGTT | 3103.42 | 3399 | 1.095 | 0.091 |
| AY | GCCTAC | 2342.42 | 2630 | 1.123 | 0.116 |
| AY | GCCTAT | 1735.85 | 1659 | 0.956 | -0.045 |
| AS | GCCTCA | 2075.22 | 1106 | 0.533 | -0.629 |
| AS | GCCTCC | 2447.26 | 1873 | 0.765 | -0.267 |
| AS | GCCTCG | 2932.84 | 1970 | 0.672 | -0.398 |
| AS | GCCTCT | 1691.61 | 989 | 0.585 | -0.537 |
| AC | GCCTGC | 1667.87 | 1498 | 0.898 | -0.107 |
| AW | GCCTGG | 1660.01 | 1381 | 0.832 | -0.184 |
| AC | GCCTGT | 1543.54 | 1363 | 0.883 | -0.124 |
| AL | GCCTTA | 1518.02 | 984 | 0.648 | -0.434 |
| AF | GCCTTC | 3500.67 | 3408 | 0.974 | -0.027 |
| AL | GCCTTG | 3192.45 | 2112 | 0.662 | -0.413 |
| AF | GCCTTT | 2680.07 | 1531 | 0.571 | -0.560 |
| AK | GCGAAA | 3419.55 | 3568 | 1.043 | 0.042 |
| AN | GCGAAC | 2803.78 | 2445 | 0.872 | -0.137 |
| AK | GCGAAG | 3248.94 | 3335 | 1.026 | 0.026 |
| AN | GCGAAT | 2422.35 | 2237 | 0.923 | -0.080 |
| AT | GCGACA | 1758.37 | 1554 | 0.884 | -0.124 |
| AT | GCGACC | 2089.74 | 1563 | 0.748 | -0.290 |
| AT | GCGACG | 2057 | 1968 | 0.957 | -0.044 |
| AT | GCGACT | 1515.6 | 1002 | 0.661 | -0.414 |
| AR | GCGAGA | 1086.72 | 1299 | 1.195 | 0.178 |
| AS | GCGAGC | 1795.17 | 1240 | 0.691 | -0.370 |
| AR | GCGAGG | 807.25 | 1148 | 1.422 | 0.352 |
| AS | GCGAGT | 1642.92 | 1372 | 0.835 | -0.180 |
| AI | GCGATA | 1409.69 | 1619 | 1.148 | 0.138 |
| AI | GCGATC | 2735.88 | 3254 | 1.189 | 0.173 |
| AM | GCGATG | 2487.8 | 3114 | 1.252 | 0.225 |
| AI | GCGATT | 2368.48 | 2548 | 1.076 | 0.073 |
| AQ | GCGCAA | 2218.8 | 2253 | 1.015 | 0.015 |
| AH | GCGCAC | 1329.96 | 1393 | 1.047 | 0.046 |
| AQ | GCGCAG | 2179.85 | 2234 | 1.025 | 0.025 |
| AH | GCGCAT | 1303 | 1061 | 0.814 | -0.205 |
| AP | GCGCCA | 1683.5 | 1711 | 1.016 | 0.016 |

-continued

Dataset SI. Mosquito codon pair scores.

| AA pair | Codon Pair | Expected | Observed | Observed/ Expected | CPS |
|---|---|---|---|---|---|
| AP | GCGCCC | 1028.03 | 901 | 0.876 | -0.132 |
| AP | GCGCCG | 1781.67 | 1475 | 0.828 | -0.189 |
| AP | GCGCCT | 1016.44 | 782 | 0.769 | -0.262 |
| AR | GCGCGA | 1440.1 | 1071 | 0.744 | -0.296 |
| AR | GCGCGC | 930.55 | 704 | 0.757 | -0.279 |
| AR | GCGCGG | 1220.67 | 921 | 0.755 | -0.282 |
| AR | GCGCGT | 979.07 | 672 | 0.686 | -0.376 |
| AL | GCGCTA | 1088.09 | 979 | 0.900 | -0.106 |
| AL | GCGCTC | 1273.93 | 1331 | 1.045 | 0.044 |
| AL | GCGCTG | 2816.42 | 3574 | 1.269 | 0.238 |
| AL | GCGCTT | 1279.29 | 1305 | 1.020 | 0.020 |
| AE | GCGGAA | 4088.01 | 5283 | 1.292 | 0.256 |
| AD | GCGGAC | 2200.07 | 2716 | 1.235 | 0.211 |
| AE | GCGGAG | 2746.27 | 3195 | 1.163 | 0.151 |
| AD | GCGGAT | 2908.73 | 3129 | 1.076 | 0.073 |
| AA | GCGGCA | 2507.19 | 2404 | 0.959 | -0.042 |
| AA | GCGGCC | 2945.29 | 3418 | 1.160 | 0.149 |
| AA | GCGGCG | 2052.06 | 2233 | 1.088 | 0.085 |
| AA | GCGGCT | 2447.26 | 1873 | 0.765 | -0.267 |
| AG | GCGGGA | 2635.92 | 1749 | 0.664 | -0.410 |
| AG | GCGGGC | 1698.71 | 886 | 0.522 | -0.651 |
| AG | GCGGGG | 1013.34 | 760 | 0.750 | -0.288 |
| AG | GCGGGT | 1758.49 | 1040 | 0.591 | -0.525 |
| AV | GCGGTA | 1374.71 | 1348 | 0.981 | -0.020 |
| AV | GCGGTC | 1680.09 | 1850 | 1.101 | 0.096 |
| AV | GCGGTG | 2501.22 | 2818 | 1.127 | 0.119 |
| AV | GCGGTT | 2162.23 | 1969 | 0.911 | -0.094 |
| AY | GCGTAC | 1632.02 | 2200 | 1.348 | 0.299 |
| AY | GCGTAT | 1209.41 | 1239 | 1.024 | 0.024 |
| AS | GCGTCA | 1445.86 | 1072 | 0.741 | -0.299 |
| AS | GCGTCC | 1705.06 | 1636 | 0.959 | -0.041 |
| AS | GCGTCG | 2043.38 | 1777 | 0.870 | -0.140 |
| AS | GCGTCT | 1178.58 | 809 | 0.686 | -0.376 |
| AC | GCGTGC | 1162.05 | 1065 | 0.916 | -0.087 |
| AW | GCGTGG | 1156.57 | 1424 | 1.231 | 0.208 |
| AC | GCGTGT | 1075.42 | 1154 | 1.073 | 0.071 |
| AL | GCGTTA | 1057.65 | 954 | 0.902 | -0.103 |
| AF | GCGTTC | 2439 | 3083 | 1.264 | 0.234 |
| AL | GCGTTG | 2224.26 | 3078 | 1.384 | 0.325 |
| AF | GCGTTT | 1867.27 | 2006 | 1.074 | 0.072 |
| AK | GCTAAA | 4078.12 | 2209 | 0.542 | -0.613 |
| AN | GCTAAC | 3343.75 | 1542 | 0.461 | -0.774 |
| AK | GCTAAG | 3874.65 | 1893 | 0.489 | -0.716 |
| AN | GCTAAT | 2888.87 | 1639 | 0.567 | -0.567 |
| AT | GCTACA | 2097.01 | 1689 | 0.805 | -0.216 |
| AT | GCTACC | 2492.2 | 2159 | 0.866 | -0.144 |
| AT | GCTACG | 2453.15 | 1785 | 0.728 | -0.318 |
| AT | GCTACT | 1807.49 | 1673 | 0.926 | -0.077 |
| AR | GCTAGA | 1296.02 | 1157 | 0.893 | -0.113 |
| AS | GCTAGC | 2140.9 | 1378 | 0.644 | -0.441 |
| AR | GCTAGG | 962.71 | 755 | 0.784 | -0.243 |
| AS | GCTAGT | 1959.32 | 1523 | 0.777 | -0.252 |
| AI | GCTATA | 1681.18 | 856 | 0.509 | -0.675 |
| AI | GCTATC | 3262.78 | 2035 | 0.624 | -0.472 |
| AM | GCTATG | 2966.92 | 1887 | 0.636 | -0.453 |
| AI | GCTATT | 2824.62 | 1937 | 0.686 | -0.377 |
| AQ | GCTCAA | 2646.11 | 3315 | 1.253 | 0.225 |
| AH | GCTCAC | 1586.1 | 1894 | 1.194 | 0.177 |
| AQ | GCTCAG | 2599.67 | 2831 | 1.089 | 0.085 |
| AH | GCTCAT | 1553.94 | 1772 | 1.140 | 0.131 |
| AP | GCTCCA | 2007.73 | 2695 | 1.342 | 0.294 |
| AP | GCTCCC | 1226.02 | 1705 | 1.391 | 0.330 |
| AP | GCTCCG | 2124.8 | 2701 | 1.271 | 0.240 |
| AP | GCTCCT | 1212.2 | 1753 | 1.446 | 0.369 |
| AR | GCTCGA | 1717.44 | 1786 | 1.040 | 0.039 |
| AR | GCTCGC | 1109.76 | 1517 | 1.367 | 0.313 |
| AR | GCTCGG | 1455.76 | 1587 | 1.090 | 0.086 |
| AR | GCTCGT | 1167.62 | 1633 | 1.399 | 0.335 |
| AL | GCTCTA | 1297.64 | 1252 | 0.965 | -0.036 |
| AL | GCTCTC | 1519.28 | 1664 | 1.095 | 0.091 |
| AL | GCTCTG | 3358.83 | 3418 | 1.018 | 0.017 |
| AL | GCTCTT | 1525.66 | 1568 | 1.028 | 0.027 |
| AE | GCTGAA | 4875.32 | 4872 | 0.999 | -0.001 |
| AD | GCTGAC | 2623.78 | 2186 | 0.833 | -0.183 |
| AE | GCTGAG | 3275.17 | 2377 | 0.726 | -0.321 |
| AD | GCTGAT | 3468.92 | 3647 | 1.051 | 0.050 |
| AA | GCTGCA | 2990.05 | 3293 | 1.101 | 0.097 |
| AA | GCTGCC | 3512.53 | 4668 | 1.329 | 0.284 |
| AA | GCTGCG | 2447.26 | 2261 | 0.924 | -0.079 |
| AA | GCTGCT | 2918.58 | 4301 | 1.474 | 0.388 |
| AG | GCTGGA | 3143.56 | 4676 | 1.487 | 0.397 |
| AG | GCTGGC | 2025.87 | 2544 | 1.256 | 0.228 |
| AG | GCTGGG | 1208.5 | 1608 | 1.331 | 0.286 |
| AG | GCTGGT | 2097.16 | 2863 | 1.365 | 0.311 |
| AV | GCTGTA | 1639.47 | 1696 | 1.034 | 0.034 |
| AV | GCTGTC | 2003.66 | 1775 | 0.886 | -0.121 |
| AV | GCTGTG | 2982.93 | 2543 | 0.853 | -0.160 |
| AV | GCTGTT | 2578.65 | 2988 | 1.159 | 0.147 |
| AY | GCTTAC | 1946.33 | 1849 | 0.950 | -0.051 |
| AY | GCTTAT | 1442.33 | 1445 | 1.002 | 0.002 |
| AS | GCTTCA | 1724.31 | 2222 | 1.289 | 0.254 |
| AS | GCTTCC | 2033.44 | 3426 | 1.685 | 0.522 |
| AS | GCTTCG | 2436.92 | 3215 | 1.319 | 0.277 |
| AS | GCTTCT | 1405.57 | 1968 | 1.400 | 0.337 |
| AC | GCTTGC | 1385.84 | 1773 | 1.279 | 0.246 |
| AW | GCTTGG | 1379.32 | 1498 | 1.086 | 0.083 |
| AC | GCTTGT | 1282.54 | 1488 | 1.160 | 0.149 |
| AL | GCTTTA | 1261.34 | 1298 | 1.029 | 0.029 |
| AF | GCTTTC | 2908.73 | 2877 | 0.989 | -0.011 |
| AL | GCTTTG | 2652.63 | 3312 | 1.249 | 0.222 |
| AF | GCTTTT | 2226.89 | 1971 | 0.885 | -0.122 |
| GK | GGAAAA | 5632.89 | 5609 | 0.996 | -0.004 |
| GN | GGAAAC | 4916.36 | 5031 | 1.023 | 0.023 |
| GK | GGAAAG | 5351.85 | 4731 | 0.884 | -0.123 |
| GN | GGAAAT | 4247.54 | 4731 | 1.114 | 0.108 |
| GT | GGAACA | 2801.96 | 3364 | 1.201 | 0.183 |
| GT | GGAACC | 3329.99 | 3929 | 1.180 | 0.165 |
| GT | GGAACG | 3277.82 | 4702 | 1.434 | 0.361 |
| GT | GGAACT | 2415.11 | 3029 | 1.254 | 0.226 |
| GR | GGAAGA | 2187.67 | 3383 | 1.546 | 0.436 |
| GS | GGAAGC | 3355.99 | 4742 | 1.413 | 0.346 |
| GR | GGAAGG | 1625.05 | 2110 | 1.298 | 0.261 |
| GS | GGAAGT | 3071.35 | 4035 | 1.314 | 0.273 |
| GI | GGAATA | 2170.97 | 2361 | 1.088 | 0.084 |
| GI | GGAATC | 4213.35 | 4776 | 1.134 | 0.125 |
| GM | GGAATG | 3834.55 | 4574 | 1.193 | 0.176 |
| GI | GGAATT | 3647.53 | 3582 | 0.982 | -0.018 |
| GQ | GGACAA | 3786.92 | 3395 | 0.897 | -0.109 |
| GH | GGACAC | 2711.26 | 2062 | 0.761 | -0.274 |
| GQ | GGACAG | 3720.46 | 2840 | 0.763 | -0.270 |
| GH | GGACAT | 2656.3 | 2264 | 0.852 | -0.160 |
| GP | GGACCA | 2464.26 | 2527 | 1.025 | 0.025 |
| GP | GGACCC | 1504.81 | 1335 | 0.887 | -0.120 |
| GP | GGACCG | 2607.96 | 2540 | 0.974 | -0.026 |
| GP | GGACCT | 1487.84 | 1557 | 1.046 | 0.045 |
| GR | GGACGA | 2899.04 | 3012 | 1.039 | 0.038 |
| GR | GGACGC | 1873.27 | 1365 | 0.729 | -0.317 |
| GR | GGACGG | 2457.32 | 1744 | 0.710 | -0.343 |
| GR | GGACGT | 1970.94 | 1647 | 0.836 | -0.180 |
| GL | GGACTA | 1591.84 | 1250 | 0.785 | -0.242 |
| GL | GGACTC | 1863.73 | 1290 | 0.692 | -0.368 |
| GL | GGACTG | 4120.35 | 3416 | 0.829 | -0.187 |
| GL | GGACTT | 1871.56 | 1761 | 0.941 | -0.061 |
| GE | GGAGAA | 5702.71 | 5220 | 0.915 | -0.088 |
| GD | GGAGAC | 3612.37 | 2582 | 0.715 | -0.336 |
| GE | GGAGAG | 3831 | 3162 | 0.825 | -0.192 |
| GD | GGAGAT | 4775.95 | 4377 | 0.916 | -0.087 |
| GA | GGAGCA | 2821.81 | 3206 | 1.136 | 0.128 |
| GA | GGAGCC | 3314.88 | 2517 | 0.759 | -0.275 |
| GA | GGAGCG | 2309.56 | 2747 | 1.189 | 0.173 |
| GA | GGAGCT | 2754.36 | 2953 | 1.072 | 0.070 |
| GG | GGAGGA | 5729.53 | 6244 | 1.090 | 0.086 |
| GG | GGAGGC | 3692.39 | 2954 | 0.800 | -0.223 |
| GG | GGAGGG | 2202.64 | 1644 | 0.746 | -0.293 |
| GG | GGAGGT | 3822.32 | 3317 | 0.868 | -0.142 |
| GV | GGAGTA | 1918.06 | 1724 | 0.899 | -0.107 |
| GV | GGAGTC | 2344.14 | 2103 | 0.897 | -0.109 |
| GV | GGAGTG | 3489.82 | 3692 | 1.058 | 0.056 |

-continued

Dataset SI. Mosquito codon pair scores.

| AA pair | Codon Pair | Expected | Ob-served | Observed/ Expected | CPS |
|---|---|---|---|---|---|
| GV | GGAGTT | 3016.84 | 3391 | 1.124 | 0.117 |
| GY | GGATAC | 3470.89 | 2873 | 0.828 | -0.189 |
| GY | GGATAT | 2572.11 | 2659 | 1.034 | 0.033 |
| GS | GGATCA | 2702.96 | 2717 | 1.005 | 0.005 |
| GS | GGATCC | 3187.54 | 2553 | 0.801 | -0.222 |
| GS | GGATCG | 3820.01 | 4128 | 1.081 | 0.078 |
| GS | GGATCT | 2203.31 | 2275 | 1.033 | 0.032 |
| GC | GGATGC | 2303 | 2151 | 0.934 | -0.068 |
| GW | GGATGG | 2623.13 | 2494 | 0.951 | -0.050 |
| GC | GGATGT | 2131.33 | 2147 | 1.007 | 0.007 |
| GL | GGATTA | 1547.31 | 1707 | 1.103 | 0.098 |
| GF | GGATTC | 4405.21 | 4799 | 1.089 | 0.086 |
| GL | GGATTG | 3254.03 | 4047 | 1.244 | 0.218 |
| GF | GGATTT | 3372.58 | 3381 | 1.002 | 0.002 |
| GK | GGCAAA | 3630.11 | 4610 | 1.270 | 0.239 |
| GN | GGCAAC | 3168.35 | 3768 | 1.189 | 0.173 |
| GK | GGCAAG | 3449 | 4339 | 1.258 | 0.230 |
| GN | GGCAAT | 2737.32 | 3280 | 1.198 | 0.181 |
| GT | GGCACA | 1805.72 | 1418 | 0.785 | -0.242 |
| GT | GGCACC | 2146.01 | 2173 | 1.013 | 0.012 |
| GT | GGCACG | 2112.39 | 1519 | 0.719 | -0.330 |
| GT | GGCACT | 1556.42 | 1563 | 1.004 | 0.004 |
| GR | GGCAGA | 1409.84 | 1300 | 0.922 | -0.081 |
| GS | GGCAGC | 2162.77 | 3291 | 1.522 | 0.420 |
| GR | GGCAGG | 1047.27 | 820 | 0.783 | -0.245 |
| GS | GGCAGT | 1979.33 | 2731 | 1.380 | 0.322 |
| GI | GGCATA | 1399.08 | 1138 | 0.813 | -0.207 |
| GI | GGCATC | 2715.29 | 3324 | 1.224 | 0.202 |
| GM | GGCATG | 2471.17 | 2187 | 0.885 | -0.122 |
| GI | GGCATT | 2350.65 | 2573 | 1.095 | 0.090 |
| GQ | GGCCAA | 2440.48 | 3076 | 1.260 | 0.231 |
| GH | GGCCAC | 1747.27 | 2129 | 1.218 | 0.198 |
| GQ | GGCCAG | 2397.65 | 2378 | 0.992 | -0.008 |
| GH | GGCCAT | 1711.85 | 2126 | 1.242 | 0.217 |
| GP | GGCCCA | 1588.09 | 1297 | 0.817 | -0.202 |
| GP | GGCCCC | 969.77 | 830 | 0.856 | -0.156 |
| GP | GGCCCG | 1680.7 | 1074 | 0.639 | -0.448 |
| GP | GGCCCT | 958.84 | 968 | 1.010 | 0.010 |
| GR | GGCCGA | 1868.28 | 1778 | 0.952 | -0.050 |
| GR | GGCCGC | 1207.23 | 1487 | 1.232 | 0.208 |
| GR | GGCCGG | 1583.62 | 1484 | 0.937 | -0.065 |
| GR | GGCCGT | 1270.17 | 1331 | 1.048 | 0.047 |
| GL | GGCCTA | 1025.86 | 904 | 0.881 | -0.126 |
| GL | GGCCTC | 1201.08 | 1206 | 1.004 | 0.004 |
| GL | GGCCTG | 2655.35 | 1786 | 0.673 | -0.397 |
| GL | GGCCTT | 1206.13 | 1312 | 1.088 | 0.084 |
| GE | GGCGAA | 3675.11 | 4340 | 1.181 | 0.166 |
| GD | GGCGAC | 2327.99 | 2467 | 1.060 | 0.058 |
| GE | GGCGAG | 2468.88 | 3044 | 1.233 | 0.209 |
| GD | GGCGAT | 3077.86 | 4019 | 1.306 | 0.267 |
| GA | GGCGCA | 1818.51 | 1185 | 0.652 | -0.428 |
| GA | GGCGCC | 2136.27 | 1705 | 0.798 | -0.225 |
| GA | GGCGCG | 1488.4 | 851 | 0.572 | -0.559 |
| GA | GGCGCT | 1775.04 | 1380 | 0.777 | -0.252 |
| GG | GGCGGA | 3692.39 | 3220 | 0.872 | -0.137 |
| GG | GGCGGC | 2379.56 | 2652 | 1.114 | 0.108 |
| GG | GGCGGG | 1419.49 | 962 | 0.678 | -0.389 |
| GG | GGCGGT | 2463.29 | 2782 | 1.129 | 0.122 |
| GV | GGCGTA | 1236.09 | 1245 | 1.007 | 0.007 |
| GV | GGCGTC | 1510.68 | 1930 | 1.278 | 0.245 |
| GV | GGCGTG | 2249.01 | 1649 | 0.733 | -0.310 |
| GV | GGCGTT | 1944.2 | 2221 | 1.142 | 0.133 |
| GY | GGCTAC | 2236.81 | 2878 | 1.287 | 0.252 |
| GY | GGCTAT | 1657.59 | 1864 | 1.125 | 0.117 |
| GS | GGCTCA | 1741.92 | 1103 | 0.633 | -0.457 |
| GS | GGCTCC | 2054.21 | 1280 | 0.623 | -0.173 |
| GS | GGCTCG | 2461.8 | 1656 | 0.673 | -0.396 |
| GS | GGCTCT | 1419.92 | 865 | 0.609 | -0.496 |
| GC | GGCTGC | 1484.17 | 1670 | 1.125 | 0.118 |
| GW | GGCTGG | 1690.48 | 1754 | 1.038 | 0.037 |
| GC | GGCTGT | 1373.53 | 1305 | 0.950 | -0.051 |
| GL | GGCTTA | 997.16 | 732 | 0.734 | -0.309 |
| GF | GGCTTC | 2838.93 | 2912 | 1.026 | 0.025 |
| GL | GGCTTG | 2097.06 | 1651 | 0.787 | -0.239 |

-continued

Dataset SI. Mosquito codon pair scores.

| AA pair | Codon Pair | Expected | Ob-served | Observed/ Expected | CPS |
|---|---|---|---|---|---|
| GF | GGCTTT | 2173.45 | 1423 | 0.655 | -0.424 |
| GK | GGGAAA | 2165.49 | 2894 | 1.336 | 0.290 |
| GN | GGGAAC | 1890.03 | 2133 | 1.129 | 0.121 |
| GK | GGGAAG | 2057.45 | 2861 | 1.391 | 0.330 |
| GN | GGGAAT | 1632.91 | 1804 | 1.105 | 0.100 |
| GT | GGGACA | 1077.17 | 1277 | 1.186 | 0.170 |
| GT | GGGACC | 1280.17 | 968 | 0.756 | -0.280 |
| GT | GGGACG | 1260.11 | 1577 | 1.251 | 0.224 |
| GT | GGGACT | 928.46 | 816 | 0.879 | -0.129 |
| GR | GGGAGA | 841.02 | 1118 | 1.329 | 0.285 |
| GS | GGGAGC | 1290.17 | 1048 | 0.812 | -0.208 |
| GR | GGGAGG | 624.73 | 897 | 1.436 | 0.362 |
| GS | GGGAGT | 1180.74 | 932 | 0.789 | -0.237 |
| GI | GGGATA | 834.6 | 876 | 1.050 | 0.048 |
| GI | GGGATC | 1619.76 | 1600 | 0.988 | -0.012 |
| GM | GGGATG | 1474.14 | 1757 | 1.192 | 0.176 |
| GI | GGGATT | 1402.24 | 1526 | 1.088 | 0.085 |
| GQ | GGGCAA | 1455.83 | 1497 | 1.028 | 0.028 |
| GH | GGGCAC | 1042.31 | 1029 | 0.987 | -0.013 |
| GQ | GGGCAG | 1430.28 | 1546 | 1.081 | 0.078 |
| GH | GGGCAT | 1021.18 | 986 | 0.966 | -0.035 |
| GP | GGGCCA | 947.35 | 1164 | 1.229 | 0.206 |
| GP | GGGCCC | 578.5 | 626 | 1.082 | 0.079 |
| GP | GGGCCG | 1002.6 | 970 | 0.967 | -0.033 |
| GP | GGGCCT | 571.98 | 620 | 1.084 | 0.081 |
| GR | GGGCGA | 1114.5 | 1111 | 0.997 | -0.003 |
| GR | GGGCGC | 720.15 | 803 | 1.115 | 0.109 |
| GR | GGGCGG | 944.68 | 930 | 0.984 | -0.016 |
| GR | GGGCGT | 757.7 | 646 | 0.853 | -0.159 |
| GL | GGGCTA | 611.96 | 591 | 0.966 | -0.035 |
| GL | GGGCTC | 716.49 | 785 | 1.096 | 0.091 |
| GL | GGGCTG | 1584.01 | 2071 | 1.307 | 0.268 |
| GL | GGGCTT | 719.5 | 974 | 1.354 | 0.303 |
| GE | GGGGAA | 2192.33 | 2183 | 0.996 | -0.004 |
| GD | GGGGAC | 1388.73 | 1537 | 1.107 | 0.101 |
| GE | GGGGAG | 1472.78 | 1547 | 1.050 | 0.049 |
| GD | GGGGAT | 1836.05 | 1545 | 0.841 | -0.173 |
| GA | GGGGCA | 1084.81 | 1003 | 0.925 | -0.078 |
| GA | GGGGCC | 1274.36 | 1035 | 0.812 | -0.208 |
| GA | GGGGCG | 887.88 | 1009 | 1.136 | 0.128 |
| GA | GGGGCT | 1058.88 | 891 | 0.841 | -0.173 |
| GG | GGGGGA | 2202.64 | 1098 | 0.498 | -0.696 |
| GG | GGGGGC | 1419.49 | 774 | 0.545 | -0.606 |
| GG | GGGGGG | 846.78 | 285 | 0.337 | -1.089 |
| GG | GGGGGT | 1469.44 | 790 | 0.538 | -0.621 |
| GV | GGGGTA | 737.37 | 507 | 0.688 | -0.375 |
| GV | GGGGTC | 901.17 | 725 | 0.805 | -0.218 |
| GV | GGGGTG | 1341.62 | 1305 | 0.973 | -0.028 |
| GV | GGGGTT | 1159.79 | 883 | 0.761 | -0.273 |
| GY | GGGTAC | 1334.34 | 1317 | 0.987 | -0.013 |
| GY | GGGTAT | 988.81 | 1052 | 1.064 | 0.062 |
| GS | GGGTCA | 1039.12 | 884 | 0.851 | -0.162 |
| GS | GGGTCC | 1225.41 | 861 | 0.703 | -0.353 |
| GS | GGGTCG | 1468.55 | 1125 | 0.766 | -0.266 |
| GS | GGGTCT | 847.03 | 651 | 0.769 | -0.263 |
| GC | GGGTGC | 885.36 | 976 | 1.102 | 0.097 |
| GW | GGGTGG | 1008.43 | 1097 | 1.088 | 0.084 |
| GC | GGGTGT | 819.36 | 747 | 0.912 | -0.092 |
| GL | GGGTTA | 594.84 | 575 | 0.967 | -0.034 |
| GF | GGGTTC | 1693.52 | 2026 | 1.196 | 0.179 |
| GL | GGGTTG | 1250.97 | 1978 | 1.581 | 0.458 |
| GF | GGGTTT | 1296.54 | 1347 | 1.039 | 0.038 |
| GK | GGTAAA | 3757.85 | 2462 | 0.655 | -0.423 |
| GN | GGTAAC | 3279.84 | 2067 | 0.630 | -0.462 |
| GK | GGTAAG | 3570.37 | 2109 | 0.591 | -0.526 |
| GN | GGTAAT | 2833.65 | 1892 | 0.668 | -0.404 |
| GT | GGTACA | 1869.26 | 1309 | 0.700 | -0.356 |
| GT | GGTACC | 2221.52 | 1660 | 0.747 | -0.291 |
| GT | GGTACG | 2186.72 | 1337 | 0.611 | -0.492 |
| GT | GGTACT | 1611.18 | 1239 | 0.769 | -0.263 |
| GR | GGTAGA | 1459.45 | 1075 | 0.737 | -0.306 |
| GS | GGTAGC | 2238.87 | 1749 | 0.781 | -0.247 |
| GR | GGTAGG | 1084.12 | 506 | 0.467 | -0.762 |
| GS | GGTAGT | 2048.98 | 1514 | 0.739 | -0.303 |

-continued

Dataset SI. Mosquito codon pair scores.

| AA pair | Codon Pair | Expected | Ob-served | Observed/ Expected | CPS |
|---|---|---|---|---|---|
| GI | GGTATA | 1448.31 | 908 | 0.627 | -0.467 |
| GI | GGTATC | 2810.84 | 2347 | 0.835 | -0.180 |
| GM | GGTATG | 2558.13 | 1820 | 0.711 | -0.340 |
| GI | GGTATT | 2433.37 | 2035 | 0.836 | -0.179 |
| GQ | GGTCAA | 2526.36 | 3155 | 1.249 | 0.222 |
| GH | GGTCAC | 1808.76 | 1986 | 1.098 | 0.093 |
| GQ | GGTCAG | 2482.02 | 2353 | 0.948 | -0.053 |
| GH | GGTCAT | 1772.09 | 1889 | 1.066 | 0.064 |
| GP | GGTCCA | 1643.98 | 2040 | 1.241 | 0.216 |
| GP | GGTCCC | 1003.9 | 1431 | 1.425 | 0.354 |
| GP | GGTCCG | 1739.84 | 1535 | 0.882 | -0.125 |
| GP | GGTCCT | 992.58 | 1229 | 1.238 | 0.214 |
| GR | GGTCGA | 1934.03 | 1987 | 1.027 | 0.027 |
| GR | GGTCGC | 1249.71 | 1482 | 1.186 | 0.170 |
| GR | GGTCGG | 1639.34 | 1321 | 0.806 | -0.216 |
| GR | GGTCGT | 1314.87 | 1747 | 1.329 | 0.284 |
| GL | GGTCTA | 1061.96 | 1032 | 0.972 | -0.029 |
| GL | GGTCTC | 1243.35 | 1304 | 1.049 | 0.048 |
| GL | GGTCTG | 2748.8 | 2243 | 0.816 | -0.203 |
| GL | GGTCTT | 1248.57 | 1286 | 1.030 | 0.030 |
| GE | GGTGAA | 3804.43 | 4284 | 1.126 | 0.119 |
| GD | GGTGAC | 2409.91 | 2622 | 1.088 | 0.084 |
| GE | GGTGAG | 2555.76 | 1923 | 0.752 | -0.284 |
| GD | GGTGAT | 3186.16 | 3466 | 1.088 | 0.084 |
| GA | GGTGCA | 1882.51 | 2209 | 1.173 | 0.160 |
| GA | GGTGCC | 2211.45 | 3113 | 1.408 | 0.342 |
| GA | GGTGCG | 1540.77 | 1554 | 1.009 | 0.009 |
| GA | GGTGCT | 1837.51 | 2839 | 1.545 | 0.435 |
| GG | GGTGGA | 3822.32 | 5190 | 1.358 | 0.306 |
| GG | GGTGGC | 2463.29 | 4317 | 1.753 | 0.561 |
| GG | GGTGGG | 1469.44 | 1355 | 0.922 | -0.081 |
| GG | GGTGGT | 2549.98 | 4061 | 1.593 | 0.465 |
| GV | GGTGTA | 1279.59 | 1347 | 1.053 | 0.051 |
| GV | GGTGTC | 1563.84 | 1876 | 1.200 | 0.182 |
| GV | GGTGTG | 2328.16 | 2136 | 0.917 | -0.086 |
| GV | GGTGTT | 2012.62 | 2299 | 1.142 | 0.133 |
| GY | GGTTAC | 2315.52 | 2004 | 0.865 | -0.144 |
| GY | GGTTAT | 1715.92 | 1645 | 0.959 | -0.042 |
| GS | GGTTCA | 1803.22 | 2010 | 1.115 | 0.109 |
| GS | GGTTCC | 2126.49 | 2791 | 1.312 | 0.272 |
| GS | GGTTCG | 2548.43 | 2879 | 1.130 | 0.122 |
| GS | GGTTCT | 1469.89 | 1628 | 1.108 | 0.102 |
| GC | GGTTGC | 1536.39 | 1519 | 0.989 | -0.011 |
| GW | GGTTGG | 1749.96 | 1727 | 0.987 | -0.013 |
| GC | GGTTGT | 1421.87 | 1440 | 1.013 | 0.013 |
| GL | GGTTTA | 1032.25 | 1379 | 1.336 | 0.290 |
| GF | GGTTTC | 2938.83 | 3148 | 1.071 | 0.069 |
| GL | GGTTTG | 2170.85 | 3135 | 1.444 | 0.368 |
| GF | GGTTTT | 2249.94 | 1933 | 0.859 | -0.152 |
| VK | GTAAAA | 2781.22 | 2855 | 1.027 | 0.026 |
| VN | GTAAAC | 2246.7 | 1755 | 0.781 | -0.247 |
| VK | GTAAAG | 2642.46 | 1965 | 0.744 | -0.296 |
| VN | GTAAAT | 1941.06 | 2165 | 1.115 | 0.109 |
| VT | GTAACA | 1304.75 | 1660 | 1.272 | 0.241 |
| VT | GTAACC | 1550.63 | 1495 | 0.964 | -0.037 |
| VT | GTAACG | 1526.34 | 2287 | 1.498 | 0.404 |
| VT | GTAACT | 1124.61 | 1446 | 1.286 | 0.251 |
| VR | GTAAGA | 1040.23 | 1074 | 1.032 | 0.032 |
| VS | GTAAGC | 1389.68 | 1169 | 0.841 | -0.173 |
| VR | GTAAGG | 772.71 | 840 | 1.087 | 0.083 |
| VS | GTAAGT | 1271.81 | 1239 | 0.974 | -0.026 |
| VI | GTAATA | 1165.06 | 1423 | 1.221 | 0.200 |
| VI | GTAATC | 2261.1 | 1882 | 0.832 | -0.184 |
| VM | GTAATG | 1870.71 | 1953 | 1.044 | 0.043 |
| VI | GTAATT | 1957.45 | 1917 | 0.979 | -0.021 |
| VQ | GTACAA | 2272.61 | 2857 | 1.257 | 0.229 |
| VH | GTACAC | 1369.58 | 1200 | 0.876 | -0.132 |
| VQ | GTACAG | 2232.73 | 1942 | 0.870 | -0.140 |
| VH | GTACAT | 1341.82 | 1555 | 1.159 | 0.147 |
| VP | GTACCA | 1660.39 | 1718 | 1.035 | 0.034 |
| VP | GTACCC | 1013.92 | 884 | 0.872 | -0.137 |
| VP | GTACCG | 1757.21 | 1914 | 1.089 | 0.085 |
| VP | GTACCT | 1002.49 | 1189 | 1.186 | 0.171 |
| VR | GTACGA | 1378.48 | 1876 | 1.361 | 0.308 |

-continued

Dataset SI. Mosquito codon pair scores.

| AA pair | Codon Pair | Expected | Ob-served | Observed/ Expected | CPS |
|---|---|---|---|---|---|
| VR | GTACGC | 890.74 | 1022 | 1.147 | 0.137 |
| VR | GTACGG | 1168.45 | 1268 | 1.085 | 0.082 |
| VR | GTACGT | 937.18 | 1000 | 1.067 | 0.065 |
| VL | GTACTA | 1035.66 | 1247 | 1.204 | 0.186 |
| VL | GTACTC | 1212.55 | 1063 | 0.877 | -0.132 |
| VL | GTACTG | 2680.72 | 2413 | 0.900 | -0.105 |
| VL | GTACTT | 1217.65 | 1486 | 1.220 | 0.199 |
| VE | GTAGAA | 3463.08 | 2906 | 0.839 | -0.175 |
| VD | GTAGAC | 2089.68 | 1684 | 0.806 | -0.216 |
| VE | GTAGAG | 2326.45 | 1824 | 0.784 | -0.243 |
| VD | GTAGAT | 2762.79 | 2627 | 0.951 | -0.050 |
| VA | GTAGCA | 1623.48 | 1779 | 1.096 | 0.091 |
| VA | GTAGCC | 1907.16 | 1449 | 0.760 | -0.275 |
| VA | GTAGCG | 1328.77 | 1462 | 1.100 | 0.096 |
| VA | GTAGCT | 1584.67 | 1648 | 1.040 | 0.039 |
| VG | GTAGGA | 1929.16 | 1550 | 0.803 | -0.219 |
| VG | GTAGGC | 1243.25 | 827 | 0.665 | -0.408 |
| VG | GTAGGG | 741.64 | 555 | 0.748 | -0.290 |
| VG | GTAGGT | 1287 | 907 | 0.705 | -0.350 |
| VV | GTAGTA | 1196.27 | 1230 | 1.028 | 0.028 |
| VV | GTAGTC | 1462.01 | 1188 | 0.813 | -0.208 |
| VV | GTAGTG | 2176.56 | 2075 | 0.953 | -0.048 |
| VV | GTAGTT | 1881.57 | 1795 | 0.954 | -0.047 |
| VY | GTATAC | 1712.11 | 1066 | 0.623 | -0.474 |
| VY | GTATAT | 1268.77 | 1124 | 0.886 | -0.121 |
| VS | GTATCA | 1119.27 | 1536 | 1.372 | 0.317 |
| VS | GTATCC | 1319.92 | 1535 | 1.163 | 0.151 |
| VS | GTATCG | 1581.82 | 2402 | 1.519 | 0.418 |
| VS | GTATCT | 912.36 | 1315 | 1.441 | 0.366 |
| VC | GTATGC | 1382 | 1167 | 0.844 | -0.169 |
| VW | GTATGG | 1200.12 | 1062 | 0.885 | -0.122 |
| VC | GTATGT | 1278.99 | 1183 | 0.925 | -0.078 |
| VL | GTATTA | 1006.69 | 1313 | 1.304 | 0.266 |
| VF | GTATTC | 2408.2 | 2473 | 1.027 | 0.027 |
| VL | GTATTG | 2117.09 | 1861 | 0.879 | -0.129 |
| VF | GTATTT | 1843.69 | 2492 | 1.352 | 0.301 |
| VK | GTCAAA | 3399.04 | 4702 | 1.383 | 0.324 |
| VN | GTCAAC | 2745.78 | 5009 | 1.824 | 0.601 |
| VK | GTCAAG | 3229.45 | 4944 | 1.531 | 0.426 |
| VN | GTCAAT | 2372.24 | 3251 | 1.370 | 0.315 |
| VT | GTCACA | 1594.58 | 1698 | 1.065 | 0.063 |
| VT | GTCACC | 1895.08 | 2539 | 1.340 | 0.293 |
| VT | GTCACG | 1865.39 | 1798 | 0.964 | -0.037 |
| VT | GTCACT | 1374.43 | 1467 | 1.067 | 0.065 |
| VR | GTCAGA | 1271.3 | 961 | 0.756 | -0.280 |
| VS | GTCAGC | 1698.38 | 2517 | 1.482 | 0.393 |
| VR | GTCAGG | 944.36 | 693 | 0.734 | -0.309 |
| VS | GTCAGT | 1554.33 | 2035 | 1.309 | 0.269 |
| VI | GTCATA | 1423.86 | 1276 | 0.896 | -0.110 |
| VI | GTCATC | 2763.37 | 4217 | 1.526 | 0.423 |
| VM | GTCATG | 2286.26 | 2288 | 1.001 | 0.001 |
| VI | GTCATT | 2392.28 | 2680 | 1.120 | 0.114 |
| VQ | GTCCAA | 2777.44 | 2267 | 0.816 | -0.203 |
| VH | GTCCAC | 1673.82 | 1904 | 1.138 | 0.129 |
| VQ | GTCCAG | 2728.7 | 2593 | 0.950 | -0.051 |
| VH | GTCCAT | 1639.88 | 1476 | 0.900 | -0.105 |
| VP | GTCCCA | 2029.23 | 1480 | 0.729 | -0.316 |
| VP | GTCCCC | 1239.15 | 920 | 0.742 | -0.298 |
| VP | GTCCCG | 2147.56 | 1590 | 0.740 | -0.301 |
| VP | GTCCCT | 1225.18 | 738 | 0.602 | -0.507 |
| VR | GTCCGA | 1684.7 | 1601 | 0.950 | -0.051 |
| VR | GTCCGC | 1088.6 | 1220 | 1.121 | 0.114 |
| VR | GTCCGG | 1428 | 1681 | 1.177 | 0.163 |
| VR | GTCCGT | 1145.36 | 1044 | 0.912 | -0.093 |
| VL | GTCCTA | 1265.72 | 980 | 0.774 | -0.256 |
| VL | GTCCTC | 1481.91 | 1526 | 1.030 | 0.029 |
| VL | GTCCTG | 3276.21 | 2863 | 0.874 | -0.135 |
| VL | GTCCTT | 1488.13 | 1111 | 0.747 | -0.292 |
| VE | GTCGAA | 4232.36 | 4286 | 1.013 | 0.013 |
| VD | GTCGAC | 2553.88 | 2735 | 1.071 | 0.069 |
| VE | GTCGAG | 2843.24 | 3177 | 1.117 | 0.111 |
| VD | GTCGAT | 3376.51 | 3932 | 1.165 | 0.152 |
| VA | GTCGCA | 1984.12 | 1327 | 0.669 | -0.402 |
| VA | GTCGCC | 2330.82 | 1865 | 0.800 | -0.223 |

Dataset SI. Mosquito codon pair scores.

| AA pair | Codon Pair | Expected | Ob-served | Observed/ Expected | CPS |
|---|---|---|---|---|---|
| VA | GTCGCG | 1623.94 | 1091 | 0.672 | -0.398 |
| VA | GTCGCT | 1936.69 | 1592 | 0.822 | -0.196 |
| VG | GTCGGA | 2357.7 | 2777 | 1.178 | 0.164 |
| VG | GTCGGC | 1519.42 | 1959 | 1.289 | 0.254 |
| VG | GTCGGG | 906.39 | 1039 | 1.146 | 0.137 |
| VG | GTCGGT | 1572.89 | 2157 | 1.371 | 0.316 |
| VV | GTCGTA | 1462.01 | 1486 | 1.016 | 0.016 |
| VV | GTCGTC | 1786.78 | 2721 | 1.523 | 0.421 |
| VV | GTCGTG | 2660.06 | 2209 | 0.830 | -0.186 |
| VV | GTCGTT | 2299.54 | 2522 | 1.097 | 0.092 |
| VY | GTCTAC | 2092.44 | 2936 | 1.403 | 0.339 |
| VY | GTCTAT | 1550.61 | 1352 | 0.872 | -0.137 |
| VS | GTCTCA | 1367.9 | 799 | 0.584 | -0.538 |
| VS | GTCTCC | 1613.13 | 1126 | 0.698 | -0.360 |
| VS | GTCTCG | 1933.2 | 1270 | 0.657 | -0.420 |
| VS | GTCTCT | 1115.04 | 686 | 0.615 | -0.486 |
| VC | GTCTGC | 1689 | 1477 | 0.874 | -0.134 |
| VW | GTCTGG | 1466.71 | 1055 | 0.719 | -0.329 |
| VC | GTCTGT | 1563.1 | 1186 | 0.759 | -0.276 |
| VL | GTCTTA | 1230.31 | 548 | 0.445 | -0.809 |
| VF | GTCTTC | 2943.15 | 2164 | 0.735 | -0.308 |
| VL | GTCTTG | 2587.38 | 1078 | 0.417 | -0.876 |
| VF | GTCTTT | 2253.24 | 1111 | 0.493 | -0.707 |
| VK | GTGAAA | 5060.3 | 5479 | 1.083 | 0.079 |
| VN | GTGAAC | 4087.77 | 4323 | 1.058 | 0.056 |
| VK | GTGAAG | 4807.83 | 5603 | 1.165 | 0.153 |
| VN | GTGAAT | 3531.67 | 3352 | 0.949 | -0.052 |
| VT | GTGACA | 2373.93 | 1764 | 0.743 | -0.297 |
| VT | GTGACC | 2821.3 | 2793 | 0.990 | -0.010 |
| VT | GTGACG | 2777.1 | 3262 | 1.175 | 0.161 |
| VT | GTGACT | 2046.18 | 1464 | 0.715 | -0.335 |
| VR | GTGAGA | 1892.65 | 1335 | 0.705 | -0.349 |
| VS | GTGAGC | 2528.45 | 1697 | 0.671 | -0.399 |
| VR | GTGAGG | 1405.91 | 1098 | 0.781 | -0.247 |
| VS | GTGAGT | 2314 | 1452 | 0.627 | -0.466 |
| VI | GTGATA | 2119.76 | 3033 | 1.431 | 0.358 |
| VI | GTGATC | 4113.96 | 4376 | 1.064 | 0.062 |
| VM | GTGATG | 3403.67 | 4302 | 1.264 | 0.234 |
| VI | GTGATT | 3561.49 | 3654 | 1.026 | 0.026 |
| VQ | GTGCAA | 4134.91 | 3565 | 0.862 | -0.148 |
| VH | GTGCAC | 2491.89 | 2557 | 1.026 | 0.026 |
| VQ | GTGCAG | 4062.34 | 3992 | 0.983 | -0.017 |
| VH | GTGCAT | 2441.37 | 1944 | 0.796 | -0.228 |
| VP | GTGCCA | 3021 | 2658 | 0.880 | -0.128 |
| VP | GTGCCC | 1844.78 | 1463 | 0.793 | -0.232 |
| VP | GTGCCG | 3197.17 | 2667 | 0.834 | -0.181 |
| VP | GTGCCT | 1823.98 | 1273 | 0.698 | -0.360 |
| VR | GTGCGA | 2508.08 | 2218 | 0.884 | -0.123 |
| VR | GTGCGC | 1620.65 | 1382 | 0.853 | -0.159 |
| VR | GTGCGG | 2125.93 | 2002 | 0.942 | -0.060 |
| VR | GTGCGT | 1705.15 | 1256 | 0.737 | -0.306 |
| VL | GTGCTA | 1884.33 | 1965 | 1.043 | 0.042 |
| VL | GTGCTC | 2206.19 | 2523 | 1.144 | 0.134 |
| VL | GTGCTG | 4877.45 | 6904 | 1.415 | 0.347 |
| VL | GTGCTT | 2215.45 | 2223 | 1.003 | 0.003 |
| VE | GTGGAA | 6300.91 | 7098 | 1.127 | 0.119 |
| VD | GTGGAC | 3802.08 | 5054 | 1.329 | 0.285 |
| VE | GTGGAG | 4232.86 | 4973 | 1.175 | 0.161 |
| VD | GTGGAT | 5026.77 | 4745 | 0.944 | -0.058 |
| VA | GTGGCA | 2953.85 | 3206 | 1.085 | 0.082 |
| VA | GTGGCC | 3469.99 | 5171 | 1.490 | 0.399 |
| VA | GTGGCG | 2417.63 | 3204 | 1.325 | 0.282 |
| VA | GTGGCT | 2883.24 | 2417 | 0.838 | -0.176 |
| VG | GTGGGA | 3510.02 | 2605 | 0.742 | -0.298 |
| VG | GTGGGC | 2262.03 | 1664 | 0.736 | -0.307 |
| VG | GTGGGG | 1349.38 | 1037 | 0.769 | -0.263 |
| VG | GTGGGT | 2341.63 | 1464 | 0.625 | -0.470 |
| VV | GTGGTA | 2176.56 | 1984 | 0.912 | -0.093 |
| VV | GTGGTC | 2660.06 | 3041 | 1.143 | 0.134 |
| VV | GTGGTG | 3960.15 | 5028 | 1.270 | 0.239 |
| VV | GTGGTT | 3423.43 | 3020 | 0.882 | -0.125 |
| VY | GTGTAC | 3115.11 | 3546 | 1.138 | 0.130 |
| VY | GTGTAT | 2308.46 | 2034 | 0.881 | -0.127 |
| VS | GTGTCA | 2036.45 | 1399 | 0.687 | -0.375 |
| VS | GTGTCC | 2401.54 | 2697 | 1.123 | 0.116 |
| VS | GTGTCG | 2878.05 | 2570 | 0.893 | -0.113 |
| VS | GTGTCT | 1660 | 1305 | 0.786 | -0.241 |
| VC | GTGTGC | 2514.49 | 2305 | 0.917 | -0.087 |
| VW | GTGTGG | 2183.56 | 2164 | 0.991 | -0.009 |
| VC | GTGTGT | 2327.05 | 1771 | 0.761 | -0.273 |
| VL | GTGTTA | 1831.62 | 1258 | 0.687 | -0.376 |
| VF | GTGTTC | 4381.6 | 5675 | 1.295 | 0.259 |
| VL | GTGTTG | 3851.95 | 3553 | 0.922 | -0.081 |
| VF | GTGTTT | 3354.5 | 3566 | 1.063 | 0.061 |
| VK | GTTAAA | 4374.47 | 2490 | 0.569 | -0.564 |
| VN | GTTAAC | 3533.75 | 1923 | 0.544 | -0.608 |
| VK | GTTAAG | 4156.22 | 2413 | 0.581 | -0.544 |
| VN | GTTAAT | 3053.02 | 1734 | 0.568 | -0.566 |
| VT | GTTACA | 2052.19 | 1674 | 0.816 | -0.204 |
| VT | GTTACC | 2438.92 | 2036 | 0.835 | -0.181 |
| VT | GTTACG | 2400.71 | 1994 | 0.831 | -0.186 |
| VT | GTTACT | 1768.86 | 1538 | 0.869 | -0.140 |
| VR | GTTAGA | 1636.14 | 1058 | 0.647 | -0.436 |
| VS | GTTAGC | 2185.77 | 1435 | 0.657 | -0.421 |
| VR | GTTAGG | 1215.36 | 664 | 0.546 | -0.605 |
| VS | GTTAGT | 2000.38 | 1435 | 0.717 | -0.332 |
| VI | GTTATA | 1832.47 | 1275 | 0.696 | -0.363 |
| VI | GTTATC | 3556.39 | 2303 | 0.648 | -0.435 |
| VM | GTTATG | 2942.36 | 1960 | 0.666 | -0.406 |
| VI | GTTATT | 3078.8 | 2190 | 0.711 | -0.341 |
| VQ | GTTCAA | 3574.5 | 4593 | 1.285 | 0.251 |
| VH | GTTCAC | 2154.16 | 2212 | 1.027 | 0.026 |
| VQ | GTTCAG | 3511.77 | 3486 | 0.993 | -0.007 |
| VH | GTTCAT | 2110.49 | 2375 | 1.125 | 0.118 |
| VP | GTTCCA | 2611.56 | 3292 | 1.261 | 0.232 |
| VP | GTTCCC | 1594.75 | 2270 | 1.423 | 0.353 |
| VP | GTTCCG | 2763.85 | 3871 | 1.401 | 0.337 |
| VP | GTTCCT | 1576.78 | 2582 | 1.638 | 0.493 |
| VR | GTTCGA | 2168.16 | 3250 | 1.499 | 0.405 |
| VR | GTTCGC | 1401 | 1981 | 1.414 | 0.346 |
| VR | GTTCGG | 1837.81 | 2109 | 1.148 | 0.138 |
| VR | GTTCGT | 1474.05 | 2108 | 1.430 | 0.358 |
| VL | GTTCTA | 1628.95 | 1961 | 1.204 | 0.186 |
| VL | GTTCTC | 1907.18 | 2051 | 1.075 | 0.073 |
| VL | GTTCTG | 4216.4 | 4098 | 0.972 | -0.028 |
| VL | GTTCTT | 1915.19 | 2220 | 1.159 | 0.148 |
| VE | GTTGAA | 5446.94 | 5245 | 0.963 | -0.038 |
| VD | GTTGAC | 3286.78 | 2584 | 0.786 | -0.241 |
| VE | GTTGAG | 3659.17 | 2996 | 0.819 | -0.200 |
| VD | GTTGAT | 4345.49 | 3883 | 0.894 | -0.113 |
| VA | GTTGCA | 2553.51 | 2378 | 0.931 | -0.071 |
| VA | GTTGCC | 2999.7 | 3168 | 1.056 | 0.055 |
| VA | GTTGCG | 2089.97 | 1792 | 0.857 | -0.154 |
| VA | GTTGCT | 2492.47 | 2631 | 1.056 | 0.054 |
| VG | GTTGGA | 3034.3 | 3988 | 1.314 | 0.273 |
| VG | GTTGGC | 1955.45 | 2596 | 1.328 | 0.283 |
| VG | GTTGGG | 1166.5 | 1608 | 1.378 | 0.321 |
| VG | GTTGGT | 2024.26 | 2468 | 1.219 | 0.198 |
| VV | GTTGTA | 1881.57 | 1888 | 1.003 | 0.003 |
| VV | GTTGTC | 2299.54 | 1848 | 0.804 | -0.219 |
| VV | GTTGTG | 3423.43 | 2848 | 0.832 | -0.184 |
| VV | GTTGTT | 2959.45 | 2826 | 0.955 | -0.046 |
| VY | GTTTAC | 2692.92 | 2416 | 0.897 | -0.109 |
| VY | GTTTAT | 1995.59 | 2262 | 1.133 | 0.125 |
| VS | GTTTCA | 1760.45 | 2408 | 1.368 | 0.313 |
| VS | GTTTCC | 2076.05 | 3052 | 1.470 | 0.385 |
| VS | GTTTCG | 2487.99 | 3488 | 1.402 | 0.338 |
| VS | GTTTCT | 1435.02 | 2074 | 1.445 | 0.368 |
| VC | GTTTGC | 2173.7 | 3119 | 1.435 | 0.361 |
| VW | GTTTGG | 1887.62 | 2457 | 1.302 | 0.264 |
| VC | GTTTGT | 2011.67 | 2732 | 1.358 | 0.306 |
| VL | GTTTTA | 1583.38 | 2236 | 1.412 | 0.345 |
| VF | GTTTTC | 3787.76 | 3511 | 0.927 | -0.076 |
| VL | GTTTTG | 3329.89 | 3567 | 1.071 | 0.069 |
| VF | GTTTTT | 2899.86 | 2880 | 0.993 | -0.007 |
| YK | TACAAA | 4290.42 | 5826 | 1.358 | 0.306 |
| YN | TACAAC | 4181.49 | 5781 | 1.383 | 0.324 |
| YK | TACAAG | 4076.36 | 4988 | 1.224 | 0.202 |

-continued

Dataset SI. Mosquito codon pair scores.

| AA pair | Codon Pair | Expected | Observed | Observed/Expected | CPS |
|---|---|---|---|---|---|
| YN | TACAAT | 3612.64 | 4306 | 1.192 | 0.176 |
| YT | TACACA | 1966.49 | 1996 | 1.015 | 0.015 |
| YT | TACACC | 2337.07 | 3271 | 1.400 | 0.336 |
| YT | TACACG | 2300.46 | 2543 | 1.105 | 0.100 |
| YT | TACACT | 1694.99 | 1980 | 1.168 | 0.155 |
| YR | TACAGA | 1881.31 | 1441 | 0.766 | -0.267 |
| YS | TACAGC | 2330.38 | 3002 | 1.288 | 0.253 |
| YR | TACAGG | 1397.49 | 1055 | 0.755 | -0.281 |
| YS | TACAGT | 2132.73 | 2674 | 1.254 | 0.226 |
| YI | TACATA | 1908.21 | 1852 | 0.971 | -0.030 |
| YI | TACATC | 3703.39 | 4764 | 1.286 | 0.252 |
| YM | TACATG | 3025.76 | 3652 | 1.207 | 0.188 |
| YI | TACATT | 3206.06 | 3856 | 1.203 | 0.185 |
| YQ | TACCAA | 3523.64 | 2847 | 0.808 | -0.213 |
| YH | TACCAC | 2469.82 | 2353 | 0.953 | -0.048 |
| YQ | TACCAG | 3461.8 | 3227 | 0.932 | -0.070 |
| YH | TACCAT | 2419.75 | 1955 | 0.808 | -0.213 |
| YP | TACCCA | 2157.25 | 1274 | 0.591 | -0.527 |
| YP | TACCCC | 1317.33 | 777 | 0.590 | -0.528 |
| YP | TACCCG | 2283.05 | 1783 | 0.781 | -0.247 |
| YP | TACCCT | 1302.48 | 759 | 0.583 | -0.540 |
| YR | TACCGA | 2493.06 | 2177 | 0.873 | -0.136 |
| YR | TACCGC | 1610.94 | 1470 | 0.913 | -0.092 |
| YR | TACCGG | 2113.2 | 2289 | 1.083 | 0.080 |
| YR | TACCGT | 1694.93 | 1555 | 0.917 | -0.086 |
| YL | TACCTA | 1689.57 | 1272 | 0.753 | -0.284 |
| YL | TACCTC | 1978.15 | 1482 | 0.749 | -0.289 |
| YL | TACCTG | 4373.31 | 3321 | 0.759 | -0.275 |
| YL | TACCTT | 1986.46 | 1477 | 0.744 | -0.296 |
| YE | TACGAA | 5173.73 | 5484 | 1.060 | 0.058 |
| YD | TACGAC | 3612.99 | 4789 | 1.325 | 0.282 |
| YE | TACGAG | 3475.64 | 4418 | 1.271 | 0.240 |
| YD | TACGAT | 4776.77 | 5271 | 1.103 | 0.098 |
| YA | TACGCA | 2164.31 | 1606 | 0.742 | -0.298 |
| YA | TACGCC | 2542.49 | 2815 | 1.107 | 0.102 |
| YA | TACGCG | 1771.42 | 1478 | 0.834 | -0.181 |
| YA | TACGCT | 2112.57 | 1953 | 0.924 | -0.079 |
| YG | TACGGA | 3480.05 | 3404 | 0.978 | -0.022 |
| YG | TACGGC | 2242.72 | 2374 | 1.059 | 0.057 |
| YG | TACGGG | 1337.86 | 1284 | 0.960 | -0.041 |
| YG | TACGGT | 2321.63 | 2574 | 1.109 | 0.103 |
| YV | TACGTA | 1695.95 | 1598 | 0.942 | -0.059 |
| YV | TACGTC | 2072.68 | 2371 | 1.144 | 0.134 |
| YV | TACGTG | 3085.7 | 3234 | 1.048 | 0.047 |
| YV | TACGTT | 2667.49 | 2601 | 0.975 | -0.025 |
| YY | TACTAC | 3873.96 | 4529 | 1.169 | 0.156 |
| YY | TACTAT | 2870.81 | 2582 | 0.899 | -0.106 |
| YS | TACTCA | 1876.92 | 1297 | 0.691 | -0.370 |
| YS | TACTCC | 2213.4 | 1715 | 0.775 | -0.255 |
| YS | TACTCG | 2652.59 | 2825 | 1.065 | 0.063 |
| YS | TACTCT | 1529.96 | 1183 | 0.773 | -0.257 |
| YC | TACTGC | 2449.65 | 2533 | 1.034 | 0.033 |
| YW | TACTGG | 2087.24 | 2126 | 1.019 | 0.018 |
| YC | TACTGT | 2267.04 | 2097 | 0.925 | -0.078 |
| YL | TACTTA | 1642.3 | 1148 | 0.699 | -0.358 |
| YF | TACTTC | 4642.84 | 4406 | 0.949 | -0.052 |
| YL | TACTTG | 3453.81 | 2098 | 0.607 | -0.498 |
| YF | TACTTT | 3554.5 | 2882 | 0.811 | -0.210 |
| YK | TATAAA | 3179.42 | 2234 | 0.703 | -0.353 |
| YN | TATAAC | 3098.71 | 1504 | 0.485 | -0.723 |
| YK | TATAAG | 3020.8 | 1519 | 0.503 | -0.687 |
| YN | TATAAT | 2677.16 | 1979 | 0.739 | -0.302 |
| YT | TATACA | 1457.27 | 1260 | 0.865 | -0.145 |
| YT | TATACC | 1731.89 | 1185 | 0.684 | -0.379 |
| YT | TATACG | 1704.76 | 1123 | 0.659 | -0.417 |
| YT | TATACT | 1256.07 | 1091 | 0.869 | -0.141 |
| YR | TATAGA | 1394.15 | 917 | 0.658 | -0.419 |
| YS | TATAGC | 1726.93 | 902 | 0.522 | -0.649 |
| YR | TATAGG | 1035.61 | 601 | 0.580 | -0.544 |
| YS | TATAGT | 1580.46 | 1028 | 0.650 | -0.430 |
| YI | TATATA | 1414.08 | 1265 | 0.895 | -0.111 |
| YI | TATATC | 2744.4 | 1371 | 0.500 | -0.694 |
| YM | TATATG | 2242.24 | 1616 | 0.721 | -0.328 |
| YI | TATATT | 2375.85 | 2244 | 0.945 | -0.057 |

-continued

Dataset SI. Mosquito codon pair scores.

| AA pair | Codon Pair | Expected | Observed | Observed/Expected | CPS |
|---|---|---|---|---|---|
| YQ | TATCAA | 2611.2 | 3164 | 1.212 | 0.192 |
| YH | TATCAC | 1830.27 | 2046 | 1.118 | 0.111 |
| YQ | TATCAG | 2565.37 | 2924 | 1.140 | 0.131 |
| YH | TATCAT | 1793.16 | 2159 | 1.204 | 0.186 |
| YP | TATCCA | 1598.63 | 2224 | 1.391 | 0.330 |
| YP | TATCCC | 976.21 | 1425 | 1.460 | 0.378 |
| YP | TATCCG | 1691.86 | 2519 | 1.489 | 0.398 |
| YP | TATCCT | 965.2 | 1531 | 1.586 | 0.461 |
| YR | TATCGA | 1847.49 | 2487 | 1.346 | 0.297 |
| YR | TATCGC | 1193.79 | 1628 | 1.364 | 0.310 |
| YR | TATCGG | 1565.99 | 2024 | 1.292 | 0.257 |
| YR | TATCGT | 1256.04 | 1840 | 1.465 | 0.382 |
| YL | TATCTA | 1252.06 | 1831 | 1.462 | 0.380 |
| YL | TATCTC | 1465.92 | 1834 | 1.251 | 0.224 |
| YL | TATCTG | 3240.85 | 4458 | 1.376 | 0.319 |
| YL | TATCTT | 1472.07 | 1651 | 1.122 | 0.115 |
| YE | TATGAA | 3834 | 3265 | 0.852 | -0.161 |
| YD | TATGAC | 2677.41 | 1978 | 0.739 | -0.303 |
| YE | TATGAG | 2575.63 | 1892 | 0.735 | -0.308 |
| YD | TATGAT | 3539.83 | 2569 | 0.726 | -0.321 |
| YA | TATGCA | 1603.86 | 1682 | 1.049 | 0.048 |
| YA | TATGCC | 1884.12 | 2084 | 1.106 | 0.101 |
| YA | TATGCG | 1312.71 | 1364 | 1.039 | 0.038 |
| YA | TATGCT | 1565.53 | 1975 | 1.262 | 0.232 |
| YG | TATGGA | 2578.9 | 2546 | 0.987 | -0.013 |
| YG | TATGGC | 1661.97 | 1656 | 0.996 | -0.004 |
| YG | TATGGG | 991.42 | 1058 | 1.067 | 0.065 |
| YG | TATGGT | 1720.45 | 1439 | 0.836 | -0.179 |
| YV | TATGTA | 1256.79 | 1475 | 1.174 | 0.160 |
| YV | TATGTC | 1535.97 | 1199 | 0.781 | -0.248 |
| YV | TATGTG | 2286.67 | 2219 | 0.970 | -0.030 |
| YV | TATGTT | 1976.75 | 1881 | 0.952 | -0.050 |
| YY | TATTAC | 2870.81 | 2342 | 0.816 | -0.204 |
| YY | TATTAT | 2127.42 | 2290 | 1.076 | 0.074 |
| YS | TATTCA | 1390.89 | 1798 | 1.293 | 0.257 |
| YS | TATTCC | 1640.25 | 1944 | 1.185 | 0.170 |
| YS | TATTCG | 1965.71 | 2122 | 1.080 | 0.077 |
| YS | TATTCT | 1133.78 | 1684 | 1.485 | 0.396 |
| YC | TATTGC | 1815.32 | 1677 | 0.924 | -0.079 |
| YW | TATTGG | 1546.76 | 1508 | 0.975 | -0.025 |
| YC | TATTGT | 1680 | 1905 | 1.134 | 0.126 |
| YL | TATTTA | 1217.03 | 2320 | 1.906 | 0.645 |
| YF | TATTTC | 3440.59 | 3224 | 0.937 | -0.065 |
| YL | TATTTG | 2559.46 | 3439 | 1.344 | 0.295 |
| YF | TATTTT | 2634.07 | 3760 | 1.427 | 0.356 |
| SK | TCAAAA | 3249.4 | 3829 | 1.178 | 0.164 |
| SN | TCAAAC | 3104.51 | 3115 | 1.003 | 0.003 |
| SK | TCAAAG | 3087.28 | 2624 | 0.850 | -0.163 |
| SN | TCAAAT | 2682.17 | 3071 | 1.145 | 0.135 |
| ST | TCAACA | 1925.3 | 3008 | 1.562 | 0.446 |
| ST | TCAACC | 2288.12 | 2676 | 1.170 | 0.157 |
| ST | TCAACG | 2252.27 | 3246 | 1.441 | 0.365 |
| ST | TCAACT | 1659.48 | 2492 | 1.502 | 0.407 |
| SR | TCAAGA | 1238.71 | 2018 | 1.629 | 0.488 |
| SS | TCAAGC | 2550.47 | 1996 | 0.783 | -0.245 |
| SR | TCAAGG | 920.14 | 1718 | 1.867 | 0.624 |
| SS | TCAAGT | 2334.15 | 2012 | 0.862 | -0.149 |
| SI | TCAATA | 1393.57 | 1757 | 1.261 | 0.232 |
| SI | TCAATC | 2704.59 | 2532 | 0.936 | -0.066 |
| SM | TCAATG | 2220.74 | 2320 | 1.045 | 0.044 |
| SI | TCAATT | 2341.38 | 2381 | 1.017 | 0.017 |
| SQ | TCACAA | 2140.04 | 2200 | 1.028 | 0.028 |
| SH | TCACAC | 1443.77 | 1361 | 0.943 | -0.059 |
| SQ | TCACAG | 2102.48 | 1736 | 0.826 | -0.192 |
| SH | TCACAT | 1414.5 | 1632 | 1.154 | 0.143 |
| SP | TCACCA | 1822.82 | 2396 | 1.314 | 0.273 |
| SP | TCACCC | 1113.11 | 1474 | 1.324 | 0.281 |
| SP | TCACCG | 1929.11 | 2556 | 1.325 | 0.281 |
| SP | TCACCT | 1100.56 | 1505 | 1.367 | 0.313 |
| SR | TCACGA | 1641.5 | 1412 | 0.860 | -0.151 |
| SR | TCACGC | 1060.69 | 856 | 0.807 | -0.214 |
| SR | TCACGG | 1391.39 | 1006 | 0.723 | -0.324 |
| SR | TCACGT | 1115.99 | 1149 | 1.030 | 0.029 |
| SL | TCACTA | 1036.08 | 1060 | 1.023 | 0.023 |

-continued

Dataset SI. Mosquito codon pair scores.

| AA pair | Codon Pair | Expected | Ob-served | Observed/ Expected | CPS |
|---|---|---|---|---|---|
| SL | TCACTC | 1213.04 | 1184 | 0.976 | -0.024 |
| SL | TCACTG | 2681.8 | 2441 | 0.910 | -0.094 |
| SL | TCACTT | 1218.14 | 1448 | 1.189 | 0.173 |
| SE | TCAGAA | 3509.78 | 2792 | 0.795 | -0.229 |
| SD | TCAGAC | 2278.06 | 1250 | 0.549 | -0.600 |
| SE | TCAGAG | 2357.82 | 1389 | 0.589 | -0.529 |
| SD | TCAGAT | 3011.84 | 2057 | 0.683 | -0.381 |
| SA | TCAGCA | 1841.57 | 2508 | 1.362 | 0.309 |
| SA | TCAGCC | 2163.37 | 1579 | 0.730 | -0.315 |
| SA | TCAGCG | 1507.27 | 1686 | 1.119 | 0.112 |
| SA | TCAGCT | 1797.55 | 2073 | 1.153 | 0.143 |
| SG | TCAGGA | 2737.34 | 1813 | 0.662 | -0.412 |
| SG | TCAGGC | 1764.08 | 824 | 0.467 | -0.761 |
| SG | TCAGGG | 1052.34 | 662 | 0.629 | -0.464 |
| SG | TCAGGT | 1826.16 | 1019 | 0.558 | -0.583 |
| SV | TCAGTA | 1266.23 | 1429 | 1.129 | 0.121 |
| SV | TCAGTC | 1547.51 | 1086 | 0.702 | -0.354 |
| SV | TCAGTG | 2303.85 | 1961 | 0.851 | -0.161 |
| SV | TCAGTT | 1991.61 | 1957 | 0.983 | -0.018 |
| SY | TCATAC | 1860.84 | 1191 | 0.640 | -0.446 |
| SY | TCATAT | 1378.98 | 1231 | 0.893 | -0.114 |
| SS | TCATCA | 2054.18 | 3123 | 1.520 | 0.419 |
| SS | TCATCC | 2422.45 | 2643 | 1.091 | 0.087 |
| SS | TCATCG | 2903.11 | 3548 | 1.222 | 0.201 |
| SS | TCATCT | 1674.46 | 2153 | 1.286 | 0.251 |
| SC | TCATGC | 1439.69 | 930 | 0.646 | -0.437 |
| SW | TCATGG | 1499.5 | 1207 | 0.805 | -0.217 |
| SC | TCATGT | 1332.37 | 1126 | 0.845 | -0.168 |
| SL | TCATTA | 1007.09 | 1277 | 1.268 | 0.237 |
| SF | TCATTC | 2684.02 | 2361 | 0.880 | -0.128 |
| SL | TCATTG | 2117.94 | 2128 | 1.005 | 0.005 |
| SF | TCATTT | 2054.85 | 2311 | 1.125 | 0.117 |
| SK | TCCAAA | 3831.93 | 4736 | 1.236 | 0.212 |
| SN | TCCAAC | 3661.08 | 5167 | 1.411 | 0.345 |
| SK | TCCAAG | 3640.75 | 5190 | 1.426 | 0.355 |
| SN | TCCAAT | 3163.02 | 3615 | 1.143 | 0.134 |
| ST | TCCACA | 2270.46 | 1980 | 0.872 | -0.137 |
| ST | TCCACC | 2698.32 | 3196 | 1.184 | 0.169 |
| ST | TCCACG | 2656.05 | 2121 | 0.799 | -0.225 |
| ST | TCCACT | 1956.99 | 2108 | 1.077 | 0.074 |
| SR | TCCAGA | 1460.78 | 1923 | 1.316 | 0.275 |
| SS | TCCAGC | 3007.71 | 4136 | 1.375 | 0.319 |
| SR | TCCAGG | 1085.1 | 1314 | 1.211 | 0.191 |
| SS | TCCAGT | 2752.61 | 3626 | 1.317 | 0.276 |
| SI | TCCATA | 1643.4 | 1363 | 0.829 | -0.187 |
| SI | TCCATC | 3189.45 | 3547 | 1.112 | 0.106 |
| SM | TCCATG | 2618.86 | 2232 | 0.852 | -0.160 |
| SI | TCCATT | 2761.14 | 2573 | 0.932 | -0.071 |
| SQ | TCCCAA | 2523.7 | 2316 | 0.918 | -0.086 |
| SH | TCCCAC | 1702.6 | 1661 | 0.976 | -0.025 |
| SQ | TCCCAG | 2479.41 | 2488 | 1.003 | 0.003 |
| SH | TCCCAT | 1668.08 | 1601 | 0.960 | -0.041 |
| SP | TCCCCA | 2149.6 | 1472 | 0.685 | -0.379 |
| SP | TCCCCC | 1312.66 | 893 | 0.680 | -0.385 |
| SP | TCCCCG | 2274.96 | 1488 | 0.654 | -0.125 |
| SP | TCCCCT | 1297.86 | 931 | 0.717 | -0.332 |
| SR | TCCCGA | 1935.78 | 1642 | 0.848 | -0.165 |
| SR | TCCCGC | 1250.85 | 1330 | 1.063 | 0.061 |
| SR | TCCCGG | 1640.83 | 1843 | 1.123 | 0.116 |
| SR | TCCCGT | 1316.06 | 1380 | 1.049 | 0.047 |
| SL | TCCCTA | 1221.82 | 956 | 0.782 | -0.245 |
| SL | TCCCTC | 1430.51 | 1510 | 1.056 | 0.054 |
| SL | TCCCTG | 3162.58 | 2102 | 0.665 | -0.408 |
| SL | TCCCTT | 1436.52 | 1221 | 0.850 | -0.163 |
| SE | TCCGAA | 4138.99 | 4004 | 0.967 | -0.033 |
| SD | TCCGAC | 2686.46 | 3057 | 1.138 | 0.129 |
| SE | TCCGAG | 2780.52 | 3090 | 1.111 | 0.106 |
| SD | TCCGAT | 3551.79 | 4107 | 1.156 | 0.145 |
| SA | TCCGCA | 2171.72 | 1703 | 0.784 | -0.243 |
| SA | TCCGCC | 2551.21 | 2320 | 0.909 | -0.095 |
| SA | TCCGCG | 1777.49 | 1146 | 0.645 | -0.439 |
| SA | TCCGCT | 2119.81 | 1903 | 0.898 | -0.108 |
| SG | TCCGGA | 3228.08 | 4571 | 1.416 | 0.348 |
| SG | TCCGGC | 2080.34 | 3098 | 1.489 | 0.398 |

-continued

Dataset SI. Mosquito codon pair scores.

| AA pair | Codon Pair | Expected | Ob-served | Observed/ Expected | CPS |
|---|---|---|---|---|---|
| SG | TCCGGG | 1240.99 | 1707 | 1.376 | 0.319 |
| SG | TCCGGT | 2153.54 | 3643 | 1.692 | 0.526 |
| SV | TCCGTA | 1493.24 | 1576 | 1.055 | 0.054 |
| SV | TCCGTC | 1824.94 | 2064 | 1.131 | 0.123 |
| SV | TCCGTG | 2716.87 | 1969 | 0.725 | -0.322 |
| SV | TCCGTT | 2348.65 | 2522 | 1.074 | 0.071 |
| SY | TCCTAC | 2194.44 | 2513 | 1.145 | 0.136 |
| SY | TCCTAT | 1626.19 | 1446 | 0.889 | -0.117 |
| SS | TCCTCA | 2422.45 | 1580 | 0.652 | -0.427 |
| SS | TCCTCC | 2856.74 | 2354 | 0.824 | -0.194 |
| SS | TCCTCG | 3423.57 | 2453 | 0.717 | -0.333 |
| SS | TCCTCT | 1974.65 | 1378 | 0.698 | -0.360 |
| SC | TCCTGC | 1697.79 | 1914 | 1.127 | 0.120 |
| SW | TCCTGG | 1768.33 | 1896 | 1.072 | 0.070 |
| SC | TCCTGT | 1571.23 | 1634 | 1.040 | 0.039 |
| SL | TCCTTA | 1187.64 | 802 | 0.675 | -0.393 |
| SF | TCCTTC | 3165.2 | 2578 | 0.814 | -0.205 |
| SL | TCCTTG | 2497.64 | 1461 | 0.585 | -0.536 |
| SF | TCCTTT | 2423.24 | 1327 | 0.548 | -0.602 |
| SK | TCGAAA | 4592.27 | 4621 | 1.006 | 0.006 |
| SN | TCGAAC | 4387.51 | 4075 | 0.929 | -0.074 |
| SK | TCGAAG | 4363.15 | 4653 | 1.066 | 0.064 |
| SN | TCGAAT | 3790.63 | 3271 | 0.863 | -0.147 |
| ST | TCGACA | 2720.96 | 2312 | 0.850 | -0.163 |
| ST | TCGACC | 3233.73 | 2365 | 0.731 | -0.313 |
| ST | TCGACG | 3183.06 | 3580 | 1.125 | 0.118 |
| ST | TCGACT | 2345.3 | 1755 | 0.748 | -0.290 |
| SR | TCGAGA | 1750.62 | 1761 | 1.006 | 0.006 |
| SS | TCGAGC | 3604.5 | 2105 | 0.584 | -0.538 |
| SR | TCGAGG | 1300.41 | 1611 | 1.239 | 0.214 |
| SS | TCGAGT | 3298.78 | 2158 | 0.654 | -0.424 |
| SI | TCGATA | 1969.48 | 2444 | 1.241 | 0.216 |
| SI | TCGATC | 3822.31 | 4732 | 1.238 | 0.213 |
| SM | TCGATG | 3138.5 | 4796 | 1.528 | 0.424 |
| SI | TCGATT | 3309 | 4191 | 1.267 | 0.236 |
| SQ | TCGCAA | 3024.45 | 3138 | 1.038 | 0.037 |
| SH | TCGCAC | 2040.43 | 2196 | 1.076 | 0.073 |
| SQ | TCGCAG | 2971.37 | 3371 | 1.134 | 0.126 |
| SH | TCGCAT | 1999.07 | 1736 | 0.868 | -0.141 |
| SP | TCGCCA | 2576.13 | 2676 | 1.039 | 0.038 |
| SP | TCGCCC | 1573.12 | 1678 | 1.067 | 0.065 |
| SP | TCGCCG | 2726.35 | 2985 | 1.095 | 0.091 |
| SP | TCGCCT | 1555.38 | 1445 | 0.929 | -0.074 |
| SR | TCGCGA | 2319.88 | 1637 | 0.706 | -0.349 |
| SR | TCGCGC | 1499.04 | 985 | 0.657 | -0.420 |
| SR | TCGCGG | 1966.41 | 1259 | 0.640 | -0.446 |
| SR | TCGCGT | 1577.2 | 1047 | 0.664 | -0.410 |
| SL | TCGCTA | 1464.25 | 1628 | 1.112 | 0.106 |
| SL | TCGCTC | 1714.35 | 2314 | 1.350 | 0.300 |
| SL | TCGCTG | 3790.1 | 5319 | 1.403 | 0.339 |
| SL | TCGCTT | 1721.55 | 2057 | 1.195 | 0.178 |
| SE | TCGGAA | 4960.25 | 5986 | 1.207 | 0.188 |
| SD | TCGGAC | 3219.5 | 3823 | 1.187 | 0.172 |
| SE | TCGGAG | 3332.23 | 4282 | 1.285 | 0.251 |
| SD | TCGGAT | 4256.54 | 4695 | 1.103 | 0.098 |
| SA | TCGGCA | 2602.64 | 2635 | 1.012 | 0.012 |
| SA | TCGGCC | 3057.42 | 3111 | 1.018 | 0.017 |
| SA | TCGGCG | 2130.18 | 2731 | 1.282 | 0.248 |
| SA | TCGGCT | 2540.43 | 2346 | 0.923 | -0.080 |
| SG | TCGGGA | 3868.6 | 2062 | 0.533 | -0.629 |
| SG | TCGGGC | 2493.12 | 1224 | 0.491 | -0.711 |
| SG | TCGGGG | 1487.23 | 872 | 0.586 | -0.534 |
| SG | TCGGGT | 2580.85 | 1374 | 0.532 | -0.630 |
| SV | TCGGTA | 1789.52 | 2073 | 1.158 | 0.147 |
| SV | TCGGTC | 2187.05 | 2278 | 1.042 | 0.041 |
| SV | TCGGTG | 3255.95 | 4420 | 1.358 | 0.306 |
| SV | TCGGTT | 2814.67 | 3065 | 1.089 | 0.085 |
| SY | TCGTAC | 2629.86 | 2912 | 1.107 | 0.102 |
| SY | TCGTAT | 1948.86 | 1618 | 0.830 | -0.186 |
| SS | TCGTCA | 2903.11 | 2520 | 0.868 | -0.142 |
| SS | TCGTCC | 3423.57 | 3191 | 0.932 | -0.070 |
| SS | TCGTCG | 4102.87 | 4079 | 0.994 | -0.006 |
| SS | TCGTCT | 2366.46 | 1906 | 0.805 | -0.216 |
| SC | TCGTGC | 2034.66 | 1489 | 0.732 | -0.312 |

-continued

Dataset SI. Mosquito codon pair scores.

| AA pair | Codon Pair | Expected | Ob-served | Observed/ Expected | CPS |
|---|---|---|---|---|---|
| SW | TCGTGG | 2119.2 | 1923 | 0.907 | -0.097 |
| SC | TCGTGT | 1882.99 | 1535 | 0.815 | -0.204 |
| SL | TCGTTA | 1423.29 | 1481 | 1.041 | 0.040 |
| SF | TCGTTC | 3793.24 | 4199 | 1.107 | 0.102 |
| SL | TCGTTG | 2993.22 | 4038 | 1.349 | 0.299 |
| SF | TCGTTT | 2904.06 | 3245 | 1.117 | 0.111 |
| SK | TCTAAA | 2648.73 | 1636 | 0.618 | -0.482 |
| SN | TCTAAC | 2530.63 | 1176 | 0.465 | -0.766 |
| SK | TCTAAG | 2516.58 | 1234 | 0.490 | -0.713 |
| SN | TCTAAT | 2186.36 | 1357 | 0.621 | -0.477 |
| ST | TCTACA | 1569.4 | 1986 | 1.265 | 0.235 |
| ST | TCTACC | 1865.15 | 1794 | 0.962 | -0.039 |
| ST | TCTACG | 1835.93 | 2023 | 1.102 | 0.097 |
| ST | TCTACT | 1352.72 | 1553 | 1.148 | 0.138 |
| SR | TCTAGA | 1009.73 | 885 | 0.876 | -0.132 |
| SS | TCTAGC | 2079.01 | 1286 | 0.619 | -0.480 |
| SR | TCTAGG | 750.05 | 578 | 0.771 | -0.261 |
| SS | TCTAGT | 1902.67 | 1527 | 0.803 | -0.220 |
| SI | TCTATA | 1135.96 | 869 | 0.765 | -0.268 |
| SI | TCTATC | 2204.63 | 1473 | 0.668 | -0.403 |
| SM | TCTATG | 1810.23 | 1292 | 0.714 | -0.337 |
| SI | TCTATT | 1908.57 | 1602 | 0.839 | -0.175 |
| SQ | TCTCAA | 1744.45 | 2176 | 1.247 | 0.221 |
| SH | TCTCAC | 1176.88 | 1128 | 0.958 | -0.042 |
| SQ | TCTCAG | 1713.83 | 1571 | 0.917 | -0.087 |
| SH | TCTCAT | 1153.02 | 1332 | 1.155 | 0.144 |
| SP | TCTCCA | 1485.86 | 2126 | 1.431 | 0.358 |
| SP | TCTCCC | 907.34 | 1329 | 1.465 | 0.382 |
| SP | TCTCCG | 1572.51 | 2116 | 1.346 | 0.297 |
| SP | TCTCCT | 897.12 | 1358 | 1.514 | 0.415 |
| SR | TCTCGA | 1338.06 | 1461 | 1.092 | 0.088 |
| SR | TCTCGC | 864.62 | 1150 | 1.330 | 0.285 |
| SR | TCTCGG | 1134.19 | 1188 | 1.047 | 0.046 |
| SR | TCTCGT | 909.7 | 1208 | 1.328 | 0.284 |
| SL | TCTCTA | 844.55 | 995 | 1.178 | 0.164 |
| SL | TCTCTC | 988.81 | 1247 | 1.261 | 0.232 |
| SL | TCTCTG | 2186.06 | 1870 | 0.855 | -0.156 |
| SL | TCTCTT | 992.96 | 1208 | 1.217 | 0.196 |
| SE | TCTGAA | 2860.98 | 2658 | 0.929 | -0.074 |
| SD | TCTGAC | 1856.95 | 1279 | 0.689 | -0.373 |
| SE | TCTGAG | 1921.96 | 1284 | 0.668 | -0.403 |
| SD | TCTGAT | 2455.09 | 2154 | 0.877 | -0.131 |
| SA | TCTGCA | 1501.15 | 2041 | 1.360 | 0.307 |
| SA | TCTGCC | 1763.46 | 1884 | 1.068 | 0.066 |
| SA | TCTGCG | 1228.65 | 1451 | 1.181 | 0.166 |
| SA | TCTGCT | 1465.27 | 2177 | 1.486 | 0.396 |
| SG | TCTGGA | 2231.34 | 2821 | 1.264 | 0.234 |
| SG | TCTGGC | 1437.98 | 1540 | 1.071 | 0.069 |
| SG | TCTGGG | 857.81 | 1104 | 1.287 | 0.252 |
| SG | TCTGGT | 1488.58 | 1951 | 1.311 | 0.271 |
| SV | TCTGTA | 1032.16 | 1271 | 1.231 | 0.208 |
| SV | TCTGTC | 1261.45 | 1203 | 0.954 | -0.047 |
| SV | TCTGTG | 1877.97 | 1582 | 0.842 | -0.172 |
| SV | TCTGTT | 1623.45 | 1922 | 1.184 | 0.169 |
| SY | TCTTAC | 1516.85 | 1071 | 0.706 | -0.348 |
| SY | TCTTAT | 1124.07 | 1022 | 0.909 | -0.095 |
| SS | TCTTCA | 1674.46 | 2429 | 1.451 | 0.372 |
| SS | TCTTCC | 1974.65 | 2645 | 1.339 | 0.292 |
| SS | TCTTCG | 2366.46 | 3123 | 1.320 | 0.277 |
| SS | TCTTCT | 1364.93 | 1946 | 1.426 | 0.355 |
| SC | TCTTGC | 1173.56 | 1087 | 0.926 | -0.077 |
| SW | TCTTGG | 1222.31 | 980 | 0.802 | -0.221 |
| SC | TCTTGT | 1086.07 | 1147 | 1.056 | 0.055 |
| SL | TCTTTA | 820.93 | 950 | 1.157 | 0.146 |
| SF | TCTTTC | 2187.87 | 1836 | 0.839 | -0.175 |
| SL | TCTTTG | 1726.43 | 1874 | 1.085 | 0.082 |
| SF | TCTTTT | 1675.01 | 1799 | 1.074 | 0.071 |
| CK | TGCAAA | 2890.93 | 3650 | 1.263 | 0.233 |
| CN | TGCAAC | 2733.09 | 3280 | 1.200 | 0.182 |
| CK | TGCAAG | 2746.69 | 3317 | 1.208 | 0.189 |
| CN | TGCAAT | 2361.28 | 2975 | 1.260 | 0.231 |
| CT | TGCACA | 1603.03 | 1567 | 0.978 | -0.023 |
| CT | TGCACC | 1905.13 | 2141 | 1.124 | 0.117 |
| CT | TGCACG | 1875.28 | 1476 | 0.787 | -0.239 |

-continued

Dataset SI. Mosquito codon pair scores.

| AA pair | Codon Pair | Expected | Ob-served | Observed/ Expected | CPS |
|---|---|---|---|---|---|
| CT | TGCACT | 1381.71 | 1534 | 1.110 | 0.105 |
| CR | TGCAGA | 1495.87 | 1586 | 1.060 | 0.059 |
| CS | TGCAGC | 2075.26 | 2469 | 1.190 | 0.174 |
| CR | TGCAGG | 1111.17 | 1119 | 1.007 | 0.007 |
| CS | TGCAGT | 1899.25 | 2148 | 1.131 | 0.123 |
| CI | TGCATA | 1305.78 | 1332 | 1.020 | 0.020 |
| CI | TGCATC | 2534.22 | 2827 | 1.116 | 0.109 |
| CM | TGCATG | 1974.08 | 2085 | 1.056 | 0.055 |
| CI | TGCATT | 2193.89 | 2640 | 1.203 | 0.185 |
| CQ | TGCCAA | 2167.08 | 2667 | 1.231 | 0.208 |
| CH | TGCCAC | 1560.12 | 1766 | 1.132 | 0.124 |
| CQ | TGCCAG | 2129.05 | 2327 | 1.093 | 0.089 |
| CH | TGCCAT | 1528.49 | 1864 | 1.220 | 0.198 |
| CP | TGCCCA | 1875.27 | 1322 | 0.705 | -0.350 |
| CP | TGCCCC | 1145.13 | 937 | 0.818 | -0.201 |
| CP | TGCCCG | 1984.62 | 1476 | 0.744 | -0.296 |
| CP | TGCCCT | 1132.23 | 1156 | 1.021 | 0.021 |
| CR | TGCCGA | 1982.29 | 1947 | 0.982 | -0.018 |
| CR | TGCCGC | 1280.9 | 1368 | 1.068 | 0.066 |
| CR | TGCCGG | 1680.25 | 1890 | 1.125 | 0.118 |
| CR | TGCCGT | 1347.68 | 1435 | 1.065 | 0.063 |
| CL | TGCCTA | 1077.51 | 861 | 0.799 | -0.224 |
| CL | TGCCTC | 1261.55 | 1170 | 0.927 | -0.075 |
| CL | TGCCTG | 2789.05 | 1903 | 0.682 | -0.382 |
| CL | TGCCTT | 1266.85 | 1360 | 1.074 | 0.071 |
| CE | TGCGAA | 3524.13 | 3294 | 0.935 | -0.068 |
| CD | TGCGAC | 2461.57 | 2555 | 1.038 | 0.037 |
| CE | TGCGAG | 2367.46 | 2797 | 1.181 | 0.167 |
| CD | TGCGAT | 3254.47 | 3157 | 0.970 | -0.030 |
| CA | TGCGCA | 1611.08 | 1024 | 0.636 | -0.453 |
| CA | TGCGCC | 1892.59 | 1534 | 0.811 | -0.210 |
| CA | TGCGCG | 1318.61 | 791 | 0.600 | -0.511 |
| CA | TGCGCT | 1572.57 | 1421 | 0.904 | -0.101 |
| CG | TGCGGA | 2862.04 | 2309 | 0.807 | -0.215 |
| CG | TGCGGC | 1844.44 | 1791 | 0.971 | -0.029 |
| CG | TGCGGG | 1100.27 | 1073 | 0.975 | -0.025 |
| CG | TGCGGT | 1909.34 | 1847 | 0.967 | -0.033 |
| CV | TGCGTA | 1300.69 | 1128 | 0.867 | -0.142 |
| CV | TGCGTC | 1589.63 | 1729 | 1.088 | 0.084 |
| CV | TGCGTG | 2366.55 | 1793 | 0.758 | -0.278 |
| CV | TGCGTT | 2045.81 | 2019 | 0.987 | -0.013 |
| CY | TGCTAC | 2063.94 | 2554 | 1.237 | 0.213 |
| CY | TGCTAT | 1529.49 | 1546 | 1.011 | 0.011 |
| CS | TGCTCA | 1671.45 | 1453 | 0.869 | -0.140 |
| CS | TGCTCC | 1971.1 | 1712 | 0.869 | -0.141 |
| CS | TGCTCG | 2362.2 | 1919 | 0.812 | -0.208 |
| CS | TGCTCT | 1362.47 | 1179 | 0.865 | -0.145 |
| CC | TGCTGC | 2160.82 | 2737 | 1.267 | 0.236 |
| CW | TGCTGG | 2184.42 | 2490 | 1.140 | 0.131 |
| CC | TGCTGT | 1999.75 | 2057 | 1.029 | 0.028 |
| CL | TGCTTA | 1047.37 | 906 | 0.865 | -0.145 |
| CF | TGCTTC | 3139.52 | 3313 | 1.055 | 0.054 |
| CL | TGCTTG | 2202.65 | 2046 | 0.929 | -0.074 |
| CF | TGCTTT | 2403.58 | 1937 | 0.806 | -0.216 |
| WK | TGGAAA | 4323.35 | 4003 | 0.926 | -0.077 |
| WN | TGGAAC | 3671.22 | 3736 | 1.018 | 0.017 |
| WK | TGGAAG | 4107.65 | 4428 | 1.078 | 0.075 |
| WN | TGGAAT | 3171.78 | 3107 | 0.980 | -0.021 |
| WT | TGGACA | 1895.64 | 2257 | 1.191 | 0.174 |
| WT | TGGACC | 2252.87 | 2034 | 0.903 | -0.102 |
| WT | TGGACG | 2217.57 | 2157 | 0.973 | -0.028 |
| WT | TGGACT | 1633.92 | 1552 | 0.950 | -0.051 |
| WR | TGGAGA | 1620.08 | 2056 | 1.269 | 0.238 |
| WS | TGGAGC | 1715.22 | 2043 | 1.191 | 0.175 |
| WR | TGGAGG | 1203.44 | 1715 | 1.425 | 0.354 |
| WS | TGGAGT | 1569.74 | 1844 | 1.175 | 0.161 |
| WI | TGGATA | 1735.38 | 1774 | 1.022 | 0.022 |
| WI | TGGATC | 3367.96 | 3182 | 0.945 | -0.057 |
| WM | TGGATG | 3057 | 3057 | 1.000 | 0.000 |
| WI | TGGATT | 2915.67 | 3063 | 1.051 | 0.049 |
| WQ | TGGCAA | 2282.03 | 2326 | 1.019 | 0.019 |
| WH | TGGCAC | 1608.81 | 1734 | 1.078 | 0.075 |
| WQ | TGGCAG | 2241.97 | 2198 | 0.980 | -0.020 |
| WH | TGGCAT | 1576.19 | 1451 | 0.921 | -0.083 |

-continued

Dataset SI. Mosquito codon pair scores.

| AA pair | Codon Pair | Expected | Ob-served | Observed/Expected | CPS |
|---|---|---|---|---|---|
| WP | TGGCCA | 1969.91 | 2322 | 1.179 | 0.164 |
| WP | TGGCCC | 1202.93 | 1234 | 1.026 | 0.026 |
| WP | TGGCCG | 2084.79 | 1810 | 0.868 | -0.141 |
| WP | TGGCCT | 1189.37 | 1081 | 0.909 | -0.096 |
| WR | TGGCGA | 2146.88 | 1844 | 0.859 | -0.152 |
| WR | TGGCGC | 1387.25 | 1364 | 0.983 | -0.017 |
| WR | TGGCGG | 1819.77 | 1434 | 0.788 | -0.238 |
| WR | TGGCGT | 1459.58 | 1224 | 0.839 | -0.176 |
| WL | TGGCTA | 1151.69 | 1152 | 1.000 | 0.000 |
| WL | TGGCTC | 1348.41 | 1472 | 1.092 | 0.088 |
| WL | TGGCTG | 2981.07 | 2675 | 0.897 | -0.108 |
| WL | TGGCTT | 1354.07 | 1444 | 1.066 | 0.064 |
| WE | TGGGAA | 3181.03 | 3097 | 0.974 | -0.027 |
| WD | TGGGAC | 2032.2 | 2228 | 1.096 | 0.092 |
| WE | TGGGAG | 2136.97 | 2221 | 1.039 | 0.039 |
| WD | TGGGAT | 2686.8 | 2491 | 0.927 | -0.076 |
| WA | TGGGCA | 1312.32 | 1325 | 1.010 | 0.010 |
| WA | TGGGCC | 1541.63 | 1485 | 0.963 | -0.037 |
| WA | TGGGCG | 1074.09 | 1089 | 1.014 | 0.014 |
| WA | TGGGCT | 1280.95 | 1310 | 1.023 | 0.022 |
| WG | TGGGGA | 1771.88 | 1634 | 0.922 | -0.081 |
| WG | TGGGGC | 1141.88 | 1372 | 1.202 | 0.184 |
| WG | TGGGGG | 681.17 | 402 | 0.590 | -0.527 |
| WG | TGGGGT | 1182.07 | 1369 | 1.158 | 0.147 |
| WV | TGGGTA | 953.79 | 795 | 0.834 | -0.182 |
| WV | TGGGTC | 1165.66 | 1220 | 1.047 | 0.046 |
| WV | TGGGTG | 1735.37 | 1720 | 0.991 | -0.009 |
| WV | TGGGTT | 1500.18 | 1620 | 1.080 | 0.077 |
| WY | TGGTAC | 1878.17 | 1940 | 1.033 | 0.032 |
| WY | TGGTAT | 1391.83 | 1330 | 0.956 | -0.045 |
| WS | TGGTCA | 1381.46 | 1582 | 1.145 | 0.136 |
| WS | TGGTCC | 1629.12 | 1592 | 0.977 | -0.023 |
| WS | TGGTCG | 1952.37 | 1424 | 0.729 | -0.316 |
| WS | TGGTCT | 1126.09 | 889 | 0.789 | -0.236 |
| WC | TGGTGC | 1695.7 | 1803 | 1.063 | 0.061 |
| WW | TGGTGG | 2589 | 2589 | 1.000 | 0.000 |
| WC | TGGTGT | 1569.3 | 1462 | 0.932 | -0.071 |
| WL | TGGTTA | 1119.47 | 1086 | 0.970 | -0.030 |
| WF | TGGTTC | 2741.3 | 2980 | 1.087 | 0.083 |
| WL | TGGTTG | 2354.29 | 2480 | 1.053 | 0.052 |
| WF | TGGTTT | 2098.7 | 1860 | 0.886 | -0.121 |
| CK | TGTAAA | 2675.43 | 2297 | 0.859 | -0.153 |
| CN | TGTAAC | 2529.36 | 1642 | 0.649 | -0.432 |
| CK | TGTAAG | 2541.95 | 1591 | 0.626 | -0.469 |
| CN | TGTAAT | 2185.26 | 1912 | 0.875 | -0.134 |
| CT | TGTACA | 1483.54 | 1741 | 1.174 | 0.160 |
| CT | TGTACC | 1763.11 | 1548 | 0.878 | -0.130 |
| CT | TGTACG | 1735.49 | 1751 | 1.009 | 0.009 |
| CT | TGTACT | 1278.72 | 1268 | 0.992 | -0.008 |
| CR | TGTAGA | 1384.36 | 1086 | 0.784 | -0.243 |
| CS | TGTAGC | 1920.57 | 996 | 0.519 | -0.657 |
| CR | TGTAGG | 1028.34 | 598 | 0.582 | -0.542 |
| CS | TGTAGT | 1757.67 | 1254 | 0.713 | -0.338 |
| CI | TGTATA | 1208.45 | 1249 | 1.034 | 0.033 |
| CI | TGTATC | 2345.31 | 1662 | 0.709 | -0.344 |
| CM | TGTATG | 1826.92 | 1716 | 0.939 | -0.063 |
| CI | TGTATT | 2030.35 | 1908 | 0.940 | -0.062 |
| CQ | TGTCAA | 2005.54 | 1702 | 0.849 | -0.164 |
| CH | TGTCAC | 1443.83 | 1149 | 0.796 | -0.228 |
| CQ | TGTCAG | 1970.34 | 1576 | 0.800 | -0.223 |
| CH | TGTCAT | 1414.56 | 1168 | 0.826 | -0.192 |
| CP | TGTCCA | 1735.48 | 2055 | 1.184 | 0.169 |
| CP | TGTCCC | 1059.77 | 1492 | 1.408 | 0.342 |
| CP | TGTCCG | 1836.68 | 2088 | 1.137 | 0.128 |
| CP | TGTCCT | 1047.83 | 1291 | 1.232 | 0.209 |
| CR | TGTCGA | 1834.52 | 1873 | 1.021 | 0.021 |
| CR | TGTCGC | 1185.41 | 1298 | 1.095 | 0.091 |
| CR | TGTCGG | 1555 | 1491 | 0.959 | -0.042 |
| CR | TGTCGT | 1247.22 | 1442 | 1.156 | 0.145 |
| CL | TGTCTA | 997.19 | 1022 | 1.025 | 0.025 |
| CL | TGTCTC | 1167.51 | 1100 | 0.942 | -0.060 |
| CL | TGTCTG | 2581.15 | 2158 | 0.836 | -0.179 |
| CL | TGTCTT | 1172.42 | 1130 | 0.964 | -0.037 |
| CE | TGTGAA | 3261.43 | 3443 | 1.056 | 0.054 |

-continued

Dataset SI. Mosquito codon pair scores.

| AA pair | Codon Pair | Expected | Ob-served | Observed/Expected | CPS |
|---|---|---|---|---|---|
| CD | TGTGAC | 2278.08 | 2000 | 0.878 | -0.130 |
| CE | TGTGAG | 2190.98 | 1810 | 0.826 | -0.191 |
| CD | TGTGAT | 3011.87 | 3294 | 1.094 | 0.090 |
| CA | TGTGCA | 1490.98 | 1890 | 1.268 | 0.237 |
| CA | TGTGCC | 1751.51 | 2154 | 1.230 | 0.207 |
| CA | TGTGCG | 1220.32 | 1625 | 1.332 | 0.286 |
| CA | TGTGCT | 1455.34 | 1874 | 1.288 | 0.253 |
| CG | TGTGGA | 2648.69 | 2791 | 1.054 | 0.052 |
| CG | TGTGGC | 1706.95 | 2112 | 1.237 | 0.213 |
| CG | TGTGGG | 1018.25 | 1151 | 1.130 | 0.123 |
| CG | TGTGGT | 1767.01 | 1783 | 1.009 | 0.009 |
| CV | TGTGTA | 1203.74 | 1565 | 1.300 | 0.262 |
| CV | TGTGTC | 1471.13 | 1450 | 0.986 | -0.014 |
| CV | TGTGTG | 2190.14 | 2151 | 0.982 | -0.018 |
| CV | TGTGTT | 1893.31 | 2226 | 1.176 | 0.162 |
| CY | TGTTAC | 1910.09 | 1419 | 0.743 | -0.297 |
| CY | TGTTAT | 1415.48 | 1400 | 0.989 | -0.011 |
| CS | TGTTCA | 1546.85 | 2160 | 1.396 | 0.334 |
| CS | TGTTCC | 1824.16 | 2268 | 1.243 | 0.218 |
| CS | TGTTCG | 2186.11 | 2494 | 1.141 | 0.132 |
| CS | TGTTCT | 1260.91 | 1786 | 1.416 | 0.348 |
| CC | TGTTGC | 1999.75 | 1562 | 0.781 | -0.247 |
| CW | TGTTGG | 2021.58 | 1716 | 0.849 | -0.164 |
| CC | TGTTGT | 1850.68 | 1655 | 0.894 | -0.112 |
| CL | TGTTTA | 969.29 | 1529 | 1.577 | 0.456 |
| CF | TGTTTC | 2905.49 | 2701 | 0.930 | -0.073 |
| CL | TGTTTG | 2038.45 | 3386 | 1.661 | 0.507 |
| CF | TGTTTT | 2224.41 | 2722 | 1.224 | 0.202 |
| LK | TTAAAA | 2729.63 | 2610 | 0.956 | -0.045 |
| LN | TTAAAC | 2191.64 | 1606 | 0.733 | -0.311 |
| LK | TTAAAG | 2593.44 | 1401 | 0.540 | -0.616 |
| LN | TTAAAT | 1893.48 | 2157 | 1.139 | 0.130 |
| LT | TTAACA | 1061.19 | 1384 | 1.304 | 0.266 |
| LT | TTAACC | 1261.17 | 1044 | 0.828 | -0.189 |
| LT | TTAACG | 1241.41 | 1222 | 0.984 | -0.016 |
| LT | TTAACT | 914.68 | 1110 | 1.214 | 0.194 |
| LR | TTAAGA | 988.51 | 1225 | 1.239 | 0.214 |
| LS | TTAAGC | 1268.64 | 1144 | 0.902 | -0.103 |
| LR | TTAAGG | 734.29 | 963 | 1.311 | 0.271 |
| LS | TTAAGT | 1161.04 | 1344 | 1.158 | 0.146 |
| LI | TTAATA | 997.82 | 1437 | 1.440 | 0.365 |
| LI | TTAATC | 1936.53 | 1298 | 0.670 | -0.400 |
| LM | TTAATG | 1743.88 | 1230 | 0.705 | -0.349 |
| LI | TTAATT | 1676.47 | 1994 | 1.189 | 0.173 |
| LQ | TTACAA | 2137.33 | 2138 | 1.000 | 0.000 |
| LH | TTACAC | 1275.75 | 1191 | 0.934 | -0.069 |
| LQ | TTACAG | 2099.82 | 1491 | 0.710 | -0.342 |
| LH | TTACAT | 1249.88 | 1441 | 1.153 | 0.142 |
| LP | TTACCA | 1469.05 | 1644 | 1.119 | 0.113 |
| LP | TTACCC | 897.08 | 866 | 0.965 | -0.035 |
| LP | TTACCG | 1554.71 | 1444 | 0.929 | -0.074 |
| LP | TTACCT | 886.96 | 1020 | 1.150 | 0.140 |
| LR | TTACGA | 1309.95 | 1566 | 1.195 | 0.179 |
| LR | TTACGC | 846.45 | 820 | 0.969 | -0.032 |
| LR | TTACGG | 1110.36 | 1037 | 0.934 | -0.068 |
| LR | TTACGT | 890.58 | 1067 | 1.198 | 0.181 |
| LL | TTACTA | 981.43 | 1324 | 1.349 | 0.299 |
| LL | TTACTC | 1149.07 | 1189 | 1.035 | 0.034 |
| LL | TTACTG | 2540.36 | 1904 | 0.750 | -0.288 |
| LL | TTACTT | 1153.89 | 1484 | 1.286 | 0.252 |
| LE | TTAGAA | 3059.22 | 2200 | 0.719 | -0.330 |
| LD | TTAGAC | 1747.91 | 999 | 0.572 | -0.559 |
| LE | TTAGAG | 2055.14 | 1252 | 0.609 | -0.496 |
| LD | TTAGAT | 2310.93 | 2043 | 0.884 | -0.123 |
| LA | TTAGCA | 1329.46 | 1363 | 1.025 | 0.025 |
| LA | TTAGCC | 1561.77 | 879 | 0.563 | -0.575 |
| LA | TTAGCG | 1088.12 | 922 | 0.847 | -0.166 |
| LA | TTAGCT | 1297.68 | 1290 | 0.994 | -0.006 |
| LG | TTAGGA | 1569.98 | 1383 | 0.881 | -0.127 |
| LG | TTAGGC | 1011.78 | 639 | 0.632 | -0.460 |
| LG | TTAGGG | 603.56 | 536 | 0.888 | -0.119 |
| LG | TTAGGT | 1047.38 | 978 | 0.934 | -0.069 |
| LV | TTAGTA | 926.17 | 1084 | 1.170 | 0.157 |
| LV | TTAGTC | 1131.91 | 810 | 0.716 | -0.335 |

-continued

Dataset SI. Mosquito codon pair scores.

| AA pair | Codon Pair | Expected | Ob-served | Observed/ Expected | CPS |
|---|---|---|---|---|---|
| LV | TTAGTG | 1685.12 | 1490 | 0.884 | -0.123 |
| LV | TTAGTT | 1456.73 | 1720 | 1.181 | 0.166 |
| LY | TTATAC | 1522.61 | 1112 | 0.730 | -0.314 |
| LY | TTATAT | 1128.33 | 1485 | 1.316 | 0.275 |
| LS | TTATCA | 1021.78 | 1860 | 1.820 | 0.599 |
| LS | TTATCC | 1204.96 | 1233 | 1.023 | 0.023 |
| LS | TTATCG | 1444.05 | 1738 | 1.204 | 0.185 |
| LS | TTATCT | 832.9 | 1410 | 1.693 | 0.526 |
| LC | TTATGC | 1115.67 | 1044 | 0.936 | -0.066 |
| LW | TTATGG | 1037.81 | 961 | 0.926 | -0.077 |
| LC | TTATGT | 1032.5 | 1446 | 1.400 | 0.337 |
| LL | TTATTA | 953.98 | 1848 | 1.937 | 0.661 |
| LF | TTATTC | 2147.99 | 1874 | 0.872 | -0.136 |
| LL | TTATTG | 2006.25 | 2038 | 1.016 | 0.016 |
| LF | TTATTT | 1644.48 | 3111 | 1.892 | 0.638 |
| FK | TTCAAA | 5513.37 | 7275 | 1.320 | 0.277 |
| FN | TTCAAC | 5213.94 | 8234 | 1.579 | 0.457 |
| FK | TTCAAG | 5238.29 | 6897 | 1.317 | 0.275 |
| FN | TTCAAT | 4504.63 | 4950 | 1.099 | 0.094 |
| FT | TTCACA | 2638.78 | 2384 | 0.903 | -0.102 |
| FT | TTCACC | 3136.06 | 4636 | 1.478 | 0.391 |
| FT | TTCACG | 3086.93 | 2733 | 0.885 | -0.122 |
| FT | TTCACT | 2274.46 | 2156 | 0.948 | -0.053 |
| FR | TTCAGA | 2438.93 | 1828 | 0.750 | -0.288 |
| FS | TTCAGC | 3321.49 | 3967 | 1.194 | 0.178 |
| FR | TTCAGG | 1811.7 | 1331 | 0.735 | -0.308 |
| FS | TTCAGT | 3039.78 | 3227 | 1.062 | 0.060 |
| FI | TTCATA | 2613.19 | 2388 | 0.914 | -0.090 |
| FI | TTCATC | 5071.59 | 6699 | 1.321 | 0.278 |
| FM | TTCATG | 3784.57 | 4084 | 1.079 | 0.076 |
| FI | TTCATT | 4390.52 | 4059 | 0.924 | -0.079 |
| FQ | TTCCAA | 4344.05 | 4242 | 0.977 | -0.024 |
| FH | TTCCAC | 3032 | 3726 | 1.229 | 0.206 |
| FQ | TTCCAG | 4267.81 | 5228 | 1.225 | 0.203 |
| FH | TTCCAT | 2970.53 | 2743 | 0.923 | -0.080 |
| FP | TTCCCA | 3161.14 | 2495 | 0.789 | -0.237 |
| FP | TTCCCC | 1930.35 | 2134 | 1.105 | 0.100 |
| FP | TTCCCG | 3345.48 | 3068 | 0.917 | -0.087 |
| FP | TTCCCT | 1908.59 | 1494 | 0.783 | -0.245 |
| FR | TTCCGA | 3232 | 3230 | 0.999 | -0.001 |
| FR | TTCCGC | 2088.43 | 2818 | 1.349 | 0.300 |
| FR | TTCCGG | 2739.55 | 3748 | 1.368 | 0.313 |
| FR | TTCCGT | 2197.31 | 2471 | 1.125 | 0.117 |
| FL | TTCCTA | 2284.85 | 2136 | 0.935 | -0.067 |
| FL | TTCCTC | 2675.12 | 3401 | 1.271 | 0.240 |
| FL | TTCCTG | 5914.16 | 6573 | 1.111 | 0.106 |
| FL | TTCCTT | 2686.35 | 2318 | 0.863 | -0.147 |
| FE | TTCGAA | 6685 | 6003 | 0.898 | -0.108 |
| FD | TTCGAC | 4525.73 | 5240 | 1.158 | 0.147 |
| FE | TTCGAG | 4490.88 | 5480 | 1.220 | 0.199 |
| FD | TTCGAT | 5983.51 | 6652 | 1.112 | 0.106 |
| FA | TTCGCA | 3059.58 | 1815 | 0.593 | -0.522 |
| FA | TTCGCC | 3594.2 | 3163 | 0.880 | -0.128 |
| FA | TTCGCG | 2504.17 | 1535 | 0.613 | -0.489 |
| FA | TTCGCT | 2986.44 | 2234 | 0.748 | -0.290 |
| FG | TTCGGA | 5032.72 | 4383 | 0.871 | -0.138 |
| FG | TTCGGC | 3243.33 | 3085 | 0.951 | -0.050 |
| FG | TTCGGG | 1934.76 | 1901 | 0.983 | -0.018 |
| FG | TTCGGT | 3357.46 | 3371 | 1.004 | 0.004 |
| FV | TTCGTA | 2623.47 | 2002 | 0.763 | -0.270 |
| FV | TTCGTC | 3206.25 | 3544 | 1.105 | 0.100 |
| FV | TTCGTG | 4773.29 | 3794 | 0.795 | -0.230 |
| FV | TTCGTT | 4126.36 | 3339 | 0.809 | -0.212 |
| FY | TTCTAC | 4503.28 | 5884 | 1.307 | 0.267 |
| FY | TTCTAT | 3337.17 | 2699 | 0.809 | -0.212 |
| FS | TTCTCA | 2675.17 | 1720 | 0.643 | -0.442 |
| FS | TTCTCC | 3154.77 | 3217 | 1.020 | 0.020 |
| FS | TTCTCG | 3780.73 | 3163 | 0.837 | -0.178 |
| FS | TTCTCT | 2180.66 | 1660 | 0.761 | -0.273 |
| FC | TTCTGC | 3170.7 | 3064 | 0.966 | -0.034 |
| FW | TTCTGG | 3058.47 | 2938 | 0.961 | -0.040 |
| FC | TTCTGT | 2934.35 | 2401 | 0.818 | -0.201 |
| FL | TTCTTA | 2220.93 | 1273 | 0.573 | -0.557 |
| FF | TTCTTC | 5964.45 | 7118 | 1.193 | 0.177 |

-continued

Dataset SI. Mosquito codon pair scores.

| AA pair | Codon Pair | Expected | Ob-served | Observed/ Expected | CPS |
|---|---|---|---|---|---|
| FL | TTCTTG | 4670.69 | 2968 | 0.635 | -0.453 |
| FF | TTCTTT | 4566.32 | 2740 | 0.600 | -0.511 |
| LK | TTGAAA | 5740.49 | 6450 | 1.124 | 0.117 |
| LN | TTGAAC | 4609.08 | 5761 | 1.250 | 0.223 |
| LK | TTGAAG | 5454.09 | 6704 | 1.229 | 0.206 |
| LN | TTGAAT | 3982.06 | 4525 | 1.136 | 0.128 |
| LT | TTGACA | 2231.71 | 1652 | 0.740 | -0.301 |
| LT | TTGACC | 2652.27 | 2846 | 1.073 | 0.070 |
| LT | TTGACG | 2610.72 | 2648 | 1.014 | 0.014 |
| LT | TTGACT | 1923.59 | 1796 | 0.934 | -0.069 |
| LR | TTGAGA | 2078.87 | 1922 | 0.925 | -0.078 |
| LS | TTGAGC | 2667.99 | 2359 | 0.884 | -0.123 |
| LR | TTGAGG | 1544.24 | 1682 | 1.089 | 0.085 |
| LS | TTGAGT | 2441.71 | 2206 | 0.903 | -0.102 |
| LI | TTGATA | 2098.44 | 2540 | 1.210 | 0.191 |
| LI | TTGATC | 4072.58 | 4571 | 1.122 | 0.115 |
| LM | TTGATG | 3667.43 | 4205 | 1.147 | 0.137 |
| LI | TTGATT | 3525.67 | 4449 | 1.262 | 0.233 |
| LQ | TTGCAA | 4494.87 | 3407 | 0.758 | -0.277 |
| LH | TTGCAC | 2682.94 | 2290 | 0.854 | -0.158 |
| LQ | TTGCAG | 4415.98 | 3551 | 0.804 | -0.218 |
| LH | TTGCAT | 2628.54 | 2284 | 0.869 | -0.141 |
| LP | TTGCCA | 3089.45 | 2728 | 0.883 | -0.124 |
| LP | TTGCCC | 1886.58 | 1427 | 0.756 | -0.279 |
| LP | TTGCCG | 3269.61 | 2415 | 0.739 | -0.303 |
| LP | TTGCCT | 1865.31 | 1350 | 0.724 | -0.323 |
| LR | TTGCGA | 2754.86 | 2047 | 0.743 | -0.297 |
| LR | TTGCGC | 1780.11 | 1440 | 0.809 | -0.212 |
| LR | TTGCGG | 2335.11 | 1821 | 0.780 | -0.249 |
| LR | TTGCGT | 1872.92 | 1502 | 0.802 | -0.221 |
| LL | TTGCTA | 2063.99 | 1983 | 0.961 | -0.040 |
| LL | TTGCTC | 2416.52 | 2371 | 0.981 | -0.019 |
| LL | TTGCTG | 5342.46 | 5616 | 1.051 | 0.050 |
| LL | TTGCTT | 2426.67 | 2328 | 0.959 | -0.042 |
| LE | TTGGAA | 6433.63 | 7032 | 1.093 | 0.089 |
| LD | TTGGAC | 3675.91 | 4705 | 1.280 | 0.247 |
| LE | TTGGAG | 4322.02 | 5325 | 1.232 | 0.209 |
| LD | TTGGAT | 4859.96 | 5593 | 1.151 | 0.140 |
| LA | TTGGCA | 2795.89 | 3108 | 1.112 | 0.106 |
| LA | TTGGCC | 3284.44 | 4304 | 1.310 | 0.270 |
| LA | TTGGCG | 2288.35 | 2851 | 1.246 | 0.220 |
| LA | TTGGCT | 2729.06 | 2860 | 1.048 | 0.047 |
| LG | TTGGGA | 3301.72 | 3052 | 0.924 | -0.079 |
| LG | TTGGGC | 2127.79 | 1951 | 0.917 | -0.087 |
| LG | TTGGGG | 1269.3 | 1220 | 0.961 | -0.040 |
| LG | TTGGGT | 2202.67 | 1987 | 0.902 | -0.103 |
| LV | TTGGTA | 1947.76 | 2292 | 1.177 | 0.163 |
| LV | TTGGTC | 2380.43 | 2399 | 1.008 | 0.008 |
| LV | TTGGTG | 3543.86 | 4371 | 1.233 | 0.210 |
| LV | TTGGTT | 3063.55 | 3022 | 0.986 | -0.014 |
| LY | TTGTAC | 3202.1 | 3280 | 1.024 | 0.024 |
| LY | TTGTAT | 2372.92 | 2403 | 1.013 | 0.013 |
| LS | TTGTCA | 2148.84 | 1450 | 0.675 | -0.393 |
| LS | TTGTCC | 2534.07 | 2153 | 0.850 | -0.163 |
| LS | TTGTCG | 3036.88 | 2076 | 0.684 | -0.380 |
| LS | TTGTCT | 1751.62 | 1354 | 0.773 | -0.257 |
| LC | TTGTGC | 2346.28 | 1971 | 0.840 | -0.174 |
| LW | TTGTGG | 2182.55 | 1938 | 0.888 | -0.119 |
| LC | TTGTGT | 2171.38 | 2067 | 0.952 | -0.049 |
| LL | TTGTTA | 2006.25 | 1669 | 0.832 | -0.184 |
| LF | TTGTTC | 4517.29 | 4173 | 0.924 | -0.079 |
| LL | TTGTTG | 4219.19 | 3484 | 0.826 | -0.191 |
| LF | TTGTTT | 3458.38 | 3343 | 0.967 | -0.034 |
| FK | TTTAAA | 4220.97 | 2814 | 0.667 | -0.405 |
| FN | TTTAAC | 3991.73 | 1825 | 0.457 | -0.783 |
| FK | TTTAAG | 4010.38 | 1997 | 0.498 | -0.697 |
| FN | TTTAAT | 3448.69 | 2150 | 0.623 | -0.473 |
| FT | TTTACA | 2020.22 | 1837 | 0.909 | -0.095 |
| FT | TTTACC | 2400.93 | 2099 | 0.874 | -0.134 |
| FT | TTTACG | 2363.32 | 2051 | 0.868 | -0.142 |
| FT | TTTACT | 1741.3 | 1766 | 1.014 | 0.014 |
| FR | TTTAGA | 1867.21 | 1326 | 0.710 | -0.342 |
| FS | TTTAGC | 2542.89 | 1543 | 0.607 | -0.500 |
| FR | TTTAGG | 1387.01 | 957 | 0.690 | -0.371 |

-continued

Dataset SI. Mosquito codon pair scores.

| AA pair | Codon Pair | Expected | Ob-served | Observed/ Expected | CPS |
|---|---|---|---|---|---|
| FS | TTTAGT | 2327.22 | 1841 | 0.791 | -0.234 |
| FI | TTTATA | 2000.63 | 2021 | 1.010 | 0.010 |
| FI | TTTATC | 3882.75 | 2577 | 0.664 | -0.410 |
| FM | TTTATG | 2897.43 | 2598 | 0.897 | -0.109 |
| FI | TTTATT | 3361.33 | 3576 | 1.064 | 0.062 |
| FQ | TTTCAA | 3325.75 | 3510 | 1.055 | 0.054 |
| FH | TTTCAC | 2321.26 | 1946 | 0.838 | -0.176 |
| FQ | TTTCAG | 3267.39 | 2225 | 0.681 | -0.384 |
| FH | TTTCAT | 2274.2 | 2183 | 0.960 | -0.041 |
| FP | TTTCCA | 2420.13 | 2528 | 1.045 | 0.044 |
| FP | TTTCCC | 1477.86 | 1873 | 1.267 | 0.237 |
| FP | TTTCCG | 2561.26 | 2567 | 1.002 | 0.002 |
| FP | TTTCCT | 1461.2 | 2107 | 1.442 | 0.366 |
| FR | TTTCGA | 2474.38 | 2447 | 0.989 | -0.011 |
| FR | TTTCGC | 1598.87 | 1570 | 0.982 | -0.018 |
| FR | TTTCGG | 2097.37 | 1945 | 0.927 | -0.075 |
| FR | TTTCGT | 1682.24 | 1944 | 1.156 | 0.145 |
| FL | TTTCTA | 1749.26 | 2021 | 1.155 | 0.144 |
| FL | TTTCTC | 2048.04 | 2376 | 1.160 | 0.149 |
| FL | TTTCTG | 4527.81 | 3638 | 0.803 | -0.219 |
| FL | TTTCTT | 2056.64 | 2480 | 1.206 | 0.187 |
| FE | TTTGAA | 5117.95 | 5288 | 1.033 | 0.033 |
| FD | TTTGAC | 3464.85 | 2870 | 0.828 | -0.188 |
| FE | TTTGAG | 3438.17 | 2961 | 0.861 | -0.149 |
| FD | TTTGAT | 4580.91 | 3793 | 0.828 | -0.189 |
| FA | TTTGCA | 2342.38 | 2738 | 1.169 | 0.156 |
| FA | TTTGCC | 2751.68 | 4312 | 1.567 | 0.449 |
| FA | TTTGCG | 1917.16 | 2581 | 1.346 | 0.297 |
| FA | TTTGCT | 2286.39 | 3064 | 1.340 | 0.293 |
| FG | TTTGGA | 3852.99 | 4133 | 1.073 | 0.070 |
| FG | TTTGGC | 2483.06 | 2764 | 1.113 | 0.107 |
| FG | TTTGGG | 1481.23 | 1836 | 1.240 | 0.215 |
| FG | TTTGGT | 2570.44 | 2483 | 0.966 | -0.035 |
| FV | TTTGTA | 2008.5 | 2662 | 1.325 | 0.282 |
| FV | TTTGTC | 2454.67 | 2666 | 1.086 | 0.083 |
| FV | TTTGTG | 3654.37 | 4264 | 1.167 | 0.154 |
| FV | TTTGTT | 3159.09 | 3735 | 1.182 | 0.167 |
| FY | TTTTAC | 3447.66 | 2338 | 0.678 | -0.388 |
| FY | TTTTAT | 2554.9 | 2922 | 1.144 | 0.134 |
| FS | TTTTCA | 2048.08 | 2651 | 1.294 | 0.258 |
| FS | TTTTCC | 2415.25 | 3253 | 1.347 | 0.298 |
| FS | TTTTCG | 2894.49 | 3185 | 1.100 | 0.096 |
| FS | TTTTCT | 1669.48 | 2623 | 1.571 | 0.452 |
| FC | TTTTGC | 2427.45 | 2357 | 0.971 | -0.029 |
| FW | TTTTGG | 2341.53 | 2462 | 1.051 | 0.050 |
| FC | TTTTGT | 2246.5 | 2957 | 1.316 | 0.275 |
| FL | TTTTTA | 1700.32 | 2755 | 1.620 | 0.483 |
| FF | TTTTTC | 4566.32 | 4260 | 0.933 | -0.069 |
| FL | TTTTTG | 3575.83 | 4171 | 1.166 | 0.154 |
| FF | TTTTTT | 3495.92 | 4475 | 1.280 | 0.247 |

We claim:

1. An attenuated virus comprising a viral genome having one or more modified virus protein-encoding sequences comprising a plurality of rearranged synonymous codons wherein the codon pair bias, relative to a first host, of the one or more modified virus protein-encoding sequence is less than the codon pair bias of the parent nucleic acid sequence from which it is derived, and wherein the codon pair bias of the one or more modified virus protein-encoding sequences is not substantially reduced relative to that of a second host, wherein the first host is a vertebrate and the second host is an arthropod, and wherein the virus is attenuated in the first host, but not attenuated in the second host.

2. The attenuated virus of claim 1, wherein the codon pair bias of the one or more modified virus protein-encoding sequences is reduced relative to the first host by at least 0.05, at least 0.1, at least 0.2, at least 0.3, or at least 0.4.

3. The attenuated virus of claim 1, wherein the codon pair bias of the one or more modified virus protein-encoding sequences is within 0.002, 0.005, 0.010, 0.020, or 0.050 of the parent nucleic acid from which it is derived relative to the second host.

4. The attenuated virus of claim 1, wherein the codon pair bias of the one or more modified virus protein-encoding sequences is reduced relative to the first host by codon rearrangement of the parent nucleic acid without substantially changing the codon usage.

5. The attenuated virus of claim 1, wherein the first host is a mammal.

6. The attenuated virus of claim 5, wherein the first host is a human.

7. The attenuated virus of claim 1, wherein the second host is an insect.

8. The attenuated virus of claim 7, wherein the second host is a mosquito.

9. The attenuated virus of claim 1, wherein the virus is attenuated in the first host, but replicates efficiently in the second host and cell lines derived from the second host.

10. The attenuated virus of claim 1, wherein the codon pair bias of the one or more modified virus protein-encoding sequences is increased relative to the second host.

11. The attenuated virus of claim 1, wherein the attenuated virus is an arbovirus.

12. The attenuated arbovirus of claim 11, wherein the attenuated arbovirus is selected from the group consisting of Bunyaviridae, Flaviviridae, Reoviridae, and Togaviridae.

13. The attenuated virus of claim 12, wherein the virus is a flavavirus.

14. The attenuated virus of claim 13, wherein the virus is a dengue virus.

15. The attenuated virus of claim 14, wherein the one or more modified virus protein-encoding sequences is derived from a nucleic acid sequence encoding the dengue virus protein-encoding sequence, or a portion thereof, selected from one or more of the group consisting of C; prM; E; NS1; 2A; 2B; NS3; 4A; 4B, and NS5.

16. The attenuated virus of claim 15, wherein the modified virus protein-encoding sequence is derived from the nucleic acid sequence encoding the E structural glycoprotein.

17. The attenuated virus of claim 15, wherein the modified virus protein-encoding sequence is derived from the nucleic acid sequence encoding the NS3 multi-functional protease.

18. The attenuated virus of claim 15, wherein the modified virus protein-encoding sequence is derived from the nucleic acid sequence encoding the NS5 multifunctional RNA polymerase.

19. A composition for inducing an immune response in a subject, wherein the composition comprises the attenuated virus of claim 1.

20. A composition for inducing an immune response in a subject comprising the attenuated dengue virus of claim 14, wherein the immune response is against one or more dengue virus serotypes selected from the group consisting of dengue virus serotypes 1 to 5.

21. A method of eliciting an immune response in a subject comprising administering to the subject a prophylactically or therapeutically effective dose of a composition comprising the attenuated virus of claim 1.

22. A method of eliciting an immune response in a subject comprising administering to the subject a prophylactically or therapeutically effective dose of a composition comprising the attenuated arbovirus of claim 11.

* * * * *